(12) United States Patent
Haltli

(10) Patent No.: US 7,595,187 B2
(45) Date of Patent: Sep. 29, 2009

(54) ELAIOPHYLIN BIOSYNTHETIC GENE CLUSTER

(75) Inventor: Bradley A. Haltli, Monroe, NY (US)

(73) Assignee: Wyeth, Madison, NJ (US)

( * ) Notice: Subject to any disclaimer, the term of this patent is extended or adjusted under 35 U.S.C. 154(b) by 225 days.

(21) Appl. No.: 11/274,683

(22) Filed: Nov. 14, 2005

(65) Prior Publication Data

US 2006/0141583 A1 Jun. 29, 2006

Related U.S. Application Data

(60) Provisional application No. 60/627,752, filed on Nov. 12, 2004.

(51) Int. Cl.
| | |
|---|---|
| C12N 1/21 | (2006.01) |
| C12N 15/52 | (2006.01) |
| C12N 15/63 | (2006.01) |
| C12N 15/76 | (2006.01) |
| C12P 17/12 | (2006.01) |

(52) U.S. Cl. ............... 435/252.35; 435/117; 435/320.1; 435/455; 536/23.1

(58) Field of Classification Search .................. None
See application file for complete search history.

(56) References Cited

U.S. PATENT DOCUMENTS

| | | | | |
|---|---|---|---|---|
| 5,096,905 | A * | 3/1992 | Kretzschmar et al. | 514/27 |
| 5,643,774 | A | 7/1997 | Ligon et al. | |
| 6,303,342 | B1 * | 10/2001 | Julien et al. | 435/76 |
| 6,410,301 | B1 * | 6/2002 | Julien et al. | 435/252.3 |
| 6,583,290 | B1 * | 6/2003 | Julien et al. | 548/203 |
| 6,600,029 | B1 * | 7/2003 | Sherman et al. | 536/23.2 |
| 6,858,411 | B1 * | 2/2005 | Julien et al. | 435/76 |
| 6,921,650 | B1 * | 7/2005 | Julien et al. | 435/76 |
| 7,067,286 | B2 * | 6/2006 | Julien et al. | 435/76 |
| 7,129,071 | B1 * | 10/2006 | Julien et al. | 435/193 |
| 7,247,650 | B2 * | 7/2007 | Summers et al. | 514/411 |
| 7,375,088 | B2 * | 5/2008 | Bachmann et al. | 514/25 |
| 7,402,421 | B2 * | 7/2008 | Julien et al. | 435/252.3 |
| 7,416,868 | B2 * | 8/2008 | Zazopoulos et al. | 435/183 |

OTHER PUBLICATIONS

Haydock, et al., *Journal of Biotechnology*, 113:55-68, 2004.
PCT/US2005/41273 International Search Report dated Aug. 11, 2008.
PCT/US2005/41273 Written Opinion dated Aug. 11, 2008.
Alvi, KA et al., "Rapid identification of elaiophylin and geldanamycin in Streptomyces fermentation broths using CPC coupled with a photodiode array detector and LC-MS methodologies", Journal of Industrial Microbiology, 1995, vol. 15:80-84.

* cited by examiner

*Primary Examiner*—Rebecca E Prouty
*Assistant Examiner*—William W Moore
(74) *Attorney, Agent, or Firm*—Choate, Hall & Stewart LLP

(57) ABSTRACT

The present invention relates especially to a DNA fragment that is obtainable from the gene cluster within the genome of streptomycete that is responsible for elaiophylin biosynthesis and that contains at least one gene or a part of a gene that codes for a polypeptide that is involved directly or indirectly in the biosynthesis of elaiophylin and to methods of preparing said DNA fragment. The present invention relates furthermore to recombinant DNA molecules containing one of the DNA fragments according to the invention and to the plasmids and vectors derived therefrom. Also included are host organisms transformed with the said plasmid or vector DNA.

3 Claims, 6 Drawing Sheets

SEQUENCE LISTING

```
<160> NUMBER OF SEQ ID NOS: 55

<210> SEQ ID NO 1
<211> LENGTH: 1446
<212> TYPE: DNA
<213> ORGANISM: Streptomyces sp. NRRL 30748
<220> FEATURE:
<221> NAME/KEY: CDS
<222> LOCATION: (1)..(1446)

<400> SEQUENCE: 1
```

-continued

```
atg gag tgg ttc acc tca tcc gac tac tgg ctg agc cgg ctg gtc ttc      48
Met Glu Trp Phe Thr Ser Ser Asp Tyr Trp Leu Ser Arg Leu Val Phe
1               5                   10                  15 caa cgg ggg ctg gcc gcc gtc tat ctg atc gcc ttt ctg gtg gcg gcc      96
Gln Arg Gly Leu Ala Ala Val Tyr Leu Ile Ala Phe Leu Val Ala Ala
                20                  25                  30 cgg cag ggg cgg gcg cta ctc ggc gag cgg ggg ctg acg ccg gtg ccg     144
Arg Gln Gly Arg Ala Leu Leu Gly Glu Arg Gly Leu Thr Pro Val Pro
            35                  40                  45 cgc ttc ctg gac cgg gtg ccg ttc cgc cgc tcg ccc agc ctg ttc cag     192
Arg Phe Leu Asp Arg Val Pro Phe Arg Arg Ser Pro Ser Leu Phe Gln
        50                  55                  60 ctg cac tac tcc gac cgg ttc ttc gcc tgc tgc gcc tgg ctg ggg gcc     240
Leu His Tyr Ser Asp Arg Phe Phe Ala Cys Cys Ala Trp Leu Gly Ala
65                  70                  75                  80 gcg ctg tcg gcc gcg ctg ctg gtg ggg gcg gcg gac cgg gcg ccg ctg     288
Ala Leu Ser Ala Ala Leu Leu Val Gly Ala Ala Asp Arg Ala Pro Leu
                85                  90                  95 gcg gtc gcg atg gtg gcg tgg ctg gtg ctg tgg ctg ctg tat ctg tcg     336
Ala Val Ala Met Val Ala Trp Leu Val Leu Trp Leu Leu Tyr Leu Ser
            100                 105                 110 atc gtc aac gtg ggg cag gtg tgg tac ggc ttc ggc tgg gag acc ctg     384
Ile Val Asn Val Gly Gln Val Trp Tyr Gly Phe Gly Trp Glu Thr Leu
        115                 120                 125 ctg ctg gag tcg ggg ttc ctc gcc gtg ttc ctg ggc aat gag cac acc     432
Leu Leu Glu Ser Gly Phe Leu Ala Val Phe Leu Gly Asn Glu His Thr
    130                 135                 140 gcg cca ccc gtg ctc atc ctg tgg ctg acg cgc tgg ctg ctg ttc cgg     480
Ala Pro Pro Val Leu Ile Leu Trp Leu Thr Arg Trp Leu Leu Phe Arg
145                 150                 155                 160 gtg gag ttc ggc gcc ggg ctg atc aag atc cgt ggg gac cgc tgc tgg     528
Val Glu Phe Gly Ala Gly Leu Ile Lys Ile Arg Gly Asp Arg Cys Trp
                165                 170                 175 cgg gac ctg acc tgt ctg tac tac cac cat gag acc cag ccg atg ccg     576
Arg Asp Leu Thr Cys Leu Tyr Tyr His His Glu Thr Gln Pro Met Pro
            180                 185                 190 ggg ccg ctg agc tgg tac ttc cac cat ctg ccg aag ccg ctg cac cgg     624
Gly Pro Leu Ser Trp Tyr Phe His His Leu Pro Lys Pro Leu His Arg
        195                 200                 205 gtg gag gcg gcg gcc aac cat gtg gcg cag ctg atc gtg ccc gtg gtg     672
Val Glu Ala Ala Ala Asn His Val Ala Gln Leu Ile Val Pro Val Val
    210                 215                 220 ctg ttc act ccg cag ccg gtc gcc ggc gtg gcc gcg ggg atc gtc gtg     720
Leu Phe Thr Pro Gln Pro Val Ala Gly Val Ala Ala Gly Ile Val Val
225                 230                 235                 240 gtc acc cag ttg tgg ctg gtg acc tcg ggc aac ttc tcc tgg ctc aac     768
Val Thr Gln Leu Trp Leu Val Thr Ser Gly Asn Phe Ser Trp Leu Asn
                245                 250                 255 tgg ctg acc atc ctg ctg gcg ctc ccg gcg gtc gac ggg cgc cgg gcc     816
Trp Leu Thr Ile Leu Leu Ala Leu Pro Ala Val Asp Gly Arg Arg Ala
            260                 265                 270 gcg gag gtg ctg ggg ctg ccc ggg ccg ccg gac ctc gcc gct ccc ccg     864
Ala Glu Val Leu Gly Leu Pro Gly Pro Pro Asp Leu Ala Ala Pro Pro
        275                 280                 285 gtc tgg tac gag gcg gtg gtg ctg gcc gcc acc gtc ctg gtg ctg gtg     912
Val Trp Tyr Glu Ala Val Val Leu Ala Ala Thr Val Leu Val Leu Val
    290                 295                 300 ctc agc tac tgg ccg gcc cgc aat ctg ctg tcg ggc cgt cag ctg atg     960
Leu Ser Tyr Trp Pro Ala Arg Asn Leu Leu Ser Gly Arg Gln Leu Met
305                 310                 315                 320
```

```
aac ttc tcc ttc aat ccg ctg cac ctg gcc aac acc tac ggg gcg ttc      1008
Asn Phe Ser Phe Asn Pro Leu His Leu Ala Asn Thr Tyr Gly Ala Phe
                325                 330                 335 ggc agc gtc aac cgc agc cgg cag gag gtg gtg atc cag ggc acc gac      1056
Gly Ser Val Asn Arg Ser Arg Gln Glu Val Val Ile Gln Gly Thr Asp
                340                 345                 350 gag gcg gtc ctc acc ccg gac acg gtc tgg cgg gac tat gag ttc cgg      1104
Glu Ala Val Leu Thr Pro Asp Thr Val Trp Arg Asp Tyr Glu Phe Arg
                355                 360                 365 ggc aag ccg ggc gat gtg cgc cgg ttg ccg cgc cag tac gcc ccg tac      1152
Gly Lys Pro Gly Asp Val Arg Arg Leu Pro Arg Gln Tyr Ala Pro Tyr
    370                 375                 380 cat ctg cgg ctg gac tgg atg atg tgg ttc gcg ggg ctc tca ccg ggc      1200
His Leu Arg Leu Asp Trp Met Met Trp Phe Ala Gly Leu Ser Pro Gly
385                 390                 395                 400 tac gcc ggg tcc tgg ttc acc ccg ctg atc ggc aag ctg ctg gtc aac      1248
Tyr Ala Gly Ser Trp Phe Thr Pro Leu Ile Gly Lys Leu Leu Val Asn
                405                 410                 415 gac cgg gcg acg gtg aag ctg ctg cgg acc aac ccc ttc ccg ggg acg      1296
Asp Arg Ala Thr Val Lys Leu Leu Arg Thr Asn Pro Phe Pro Gly Thr
                420                 425                 430 ccg ccc acc cat ctg cgg gcg cgg ctg tat ctc tac cgc ttc acc acc      1344
Pro Pro Thr His Leu Arg Ala Arg Leu Tyr Leu Tyr Arg Phe Thr Thr
                435                 440                 445 cgg gcg gag cgg cgg gcc acc ggg gcc tgg tgg cac cgc acc ctg ctg      1392
Arg Ala Glu Arg Arg Ala Thr Gly Ala Trp Trp His Arg Thr Leu Leu
    450                 455                 460 agc gag ttc ctg ccg ccg gtc agg ctg gag gat cac ggc tcg tca cgg      1440
Ser Glu Phe Leu Pro Pro Val Arg Leu Glu Asp His Gly Ser Ser Arg
465                 470                 475                 480 gcg tga                                                              1446
Ala

<210> SEQ ID NO 2
<211> LENGTH: 481
<212> TYPE: PRT
<213> ORGANISM: Streptomyces sp. NRRL 30748

<400> SEQUENCE: 2

Met Glu Trp Phe Thr Ser Ser Asp Tyr Trp Leu Ser Arg Leu Val Phe
1               5                   10                  15

Gln Arg Gly Leu Ala Ala Val Tyr Leu Ile Ala Phe Leu Val Ala Ala
            20                  25                  30

Arg Gln Gly Arg Ala Leu Leu Gly Glu Arg Gly Leu Thr Pro Val Pro
        35                  40                  45

Arg Phe Leu Asp Arg Val Pro Phe Arg Arg Ser Pro Ser Leu Phe Gln
    50                  55                  60

Leu His Tyr Ser Asp Arg Phe Phe Ala Cys Cys Ala Trp Leu Gly Ala
65                  70                  75                  80

Ala Leu Ser Ala Ala Leu Leu Val Gly Ala Ala Asp Arg Ala Pro Leu
                85                  90                  95

Ala Val Ala Met Val Ala Trp Leu Val Leu Trp Leu Tyr Leu Ser
            100                 105                 110

Ile Val Asn Val Gly Gln Val Trp Tyr Gly Phe Gly Trp Glu Thr Leu
        115                 120                 125

Leu Leu Glu Ser Gly Phe Leu Ala Val Phe Leu Gly Asn Glu His Thr
    130                 135                 140
```

```
Ala Pro Pro Val Leu Ile Leu Trp Leu Thr Arg Trp Leu Leu Phe Arg
145                 150                 155                 160

Val Glu Phe Gly Ala Gly Leu Ile Lys Ile Arg Gly Asp Arg Cys Trp
                165                 170                 175

Arg Asp Leu Thr Cys Leu Tyr Tyr His His Glu Thr Gln Pro Met Pro
            180                 185                 190

Gly Pro Leu Ser Trp Tyr Phe His His Leu Pro Lys Pro Leu His Arg
        195                 200                 205

Val Glu Ala Ala Ala Asn His Val Ala Gln Leu Ile Val Pro Val Val
    210                 215                 220

Leu Phe Thr Pro Gln Pro Val Ala Gly Val Ala Gly Ile Val Val
225                 230                 235                 240

Val Thr Gln Leu Trp Leu Val Thr Ser Gly Asn Phe Ser Trp Leu Asn
                245                 250                 255

Trp Leu Thr Ile Leu Leu Ala Leu Pro Ala Val Asp Gly Arg Arg Ala
            260                 265                 270

Ala Glu Val Leu Gly Leu Pro Gly Pro Pro Asp Leu Ala Ala Pro Pro
        275                 280                 285

Val Trp Tyr Glu Ala Val Val Leu Ala Ala Thr Val Leu Val Leu Val
    290                 295                 300

Leu Ser Tyr Trp Pro Ala Arg Asn Leu Leu Ser Gly Arg Gln Leu Met
305                 310                 315                 320

Asn Phe Ser Phe Asn Pro Leu His Leu Ala Asn Thr Tyr Gly Ala Phe
                325                 330                 335

Gly Ser Val Asn Arg Ser Arg Gln Glu Val Val Ile Gln Gly Thr Asp
            340                 345                 350

Glu Ala Val Leu Thr Pro Asp Thr Val Trp Arg Asp Tyr Glu Phe Arg
        355                 360                 365

Gly Lys Pro Gly Asp Val Arg Arg Leu Pro Arg Gln Tyr Ala Pro Tyr
    370                 375                 380

His Leu Arg Leu Asp Trp Met Met Trp Phe Ala Gly Leu Ser Pro Gly
385                 390                 395                 400

Tyr Ala Gly Ser Trp Phe Thr Pro Leu Ile Gly Lys Leu Leu Val Asn
                405                 410                 415

Asp Arg Ala Thr Val Lys Leu Leu Arg Thr Asn Pro Phe Pro Gly Thr
            420                 425                 430

Pro Pro Thr His Leu Arg Ala Arg Leu Tyr Leu Tyr Arg Phe Thr Thr
        435                 440                 445

Arg Ala Glu Arg Arg Ala Thr Gly Ala Trp Trp His Arg Thr Leu Leu
    450                 455                 460

Ser Glu Phe Leu Pro Pro Val Arg Leu Glu Asp His Gly Ser Ser Arg
465                 470                 475                 480

Ala

<210> SEQ ID NO 3
<211> LENGTH: 1041
<212> TYPE: DNA
<213> ORGANISM: Streptomyces sp. NRRL 30748
<220> FEATURE:
<221> NAME/KEY: CDS
<222> LOCATION: (1)..(1041)

<400> SEQUENCE: 3 atg acc gag cag ccg gtc cgg aca tcc ggc ggg cgg ccc atc ggg atc      48
Met Thr Glu Gln Pro Val Arg Thr Ser Gly Gly Arg Pro Ile Gly Ile
1               5                   10                  15
```

```
ctc ggc acc ggc tcg tat ctg ccc gcc gag acc gtg tcc aac gag ctg       96
Leu Gly Thr Gly Ser Tyr Leu Pro Ala Glu Thr Val Ser Asn Glu Leu
         20                  25                  30 gtg gcc gag cgc gcg ggg gtg acc ccg gac tgg atc tcg gcg aag acc      144
Val Ala Glu Arg Ala Gly Val Thr Pro Asp Trp Ile Ser Ala Lys Thr
    35                  40                  45 ggg atc cac cgc cgc cgt tac gcc gcc gac cac gag gcc acc tcc gat      192
Gly Ile His Arg Arg Arg Tyr Ala Ala Asp His Glu Ala Thr Ser Asp
50                  55                  60 ctg gcc gtg gag gcc gcc cgc gcc gcc ctc gcg gac gcc ggg atc ggc      240
Leu Ala Val Glu Ala Ala Arg Ala Ala Leu Ala Asp Ala Gly Ile Gly
65                  70                  75                  80 gcc gat cag ctc ggc tgg atc gtg gtg gcc acc tcg acc ccc gat cac      288
Ala Asp Gln Leu Gly Trp Ile Val Val Ala Thr Ser Thr Pro Asp His
                85                  90                  95 ccc cag ccc gcc acc gcc tgt ctg gtg cag cac cgg atc ggc gcg acc      336
Pro Gln Pro Ala Thr Ala Cys Leu Val Gln His Arg Ile Gly Ala Thr
            100                 105                 110 ggc gcc gcc gcc ttc gac ctc aac gcg gtc tgc agc ggc ttt gtc ttc      384
Gly Ala Ala Ala Phe Asp Leu Asn Ala Val Cys Ser Gly Phe Val Phe
        115                 120                 125 gcc ctg gtg acg gcg gcc ggg ctg ctg tcc gcc ggg tcc ggc gcc ccc      432
Ala Leu Val Thr Ala Ala Gly Leu Leu Ser Ala Gly Ser Gly Ala Pro
130                 135                 140 gcc ccg tac gcc ttg gtg atc ggc gcc gat gtc tac tcc cgc atc atc      480
Ala Pro Tyr Ala Leu Val Ile Gly Ala Asp Val Tyr Ser Arg Ile Ile
145                 150                 155                 160 gac cgc acc gac cgg cgg acc gcc gtg ctc ttc ggc gac ggg gcc ggg      528
Asp Arg Thr Asp Arg Arg Thr Ala Val Leu Phe Gly Asp Gly Ala Gly
                165                 170                 175 gcg gtg gtg ctc gga ccc gtg cgt ccc ggc tac ggc ctc agc gga tcg      576
Ala Val Val Leu Gly Pro Val Arg Pro Gly Tyr Gly Leu Ser Gly Ser
            180                 185                 190 ctg ctc acc agc gac ggc gcg ctc cat gag ctg atc gag gtg acg gcg      624
Leu Leu Thr Ser Asp Gly Ala Leu His Glu Leu Ile Glu Val Thr Ala
        195                 200                 205 ggc ggc agc cgt gtc ccg gcg tcg gag aag acc ctc gcc gac ggg ggc      672
Gly Gly Ser Arg Val Pro Ala Ser Glu Lys Thr Leu Ala Asp Gly Gly
210                 215                 220 cac ttc ttc cgg atg cgg ggc cgc gcg gtc agc gaa tac gtc ctg gcc      720
His Phe Phe Arg Met Arg Gly Arg Ala Val Ser Glu Tyr Val Leu Ala
225                 230                 235                 240 gag ctg ccg cgc gcg ata ggg cgc ctg ctg gcc gcg cac cgc acg gac      768
Glu Leu Pro Arg Ala Ile Gly Arg Leu Leu Ala Ala His Arg Thr Asp
                245                 250                 255 ccc gcg agc gtg gac cac ttc atc ccc cat cag gcc aat ggt gtg ctg      816
Pro Ala Ser Val Asp His Phe Ile Pro His Gln Ala Asn Gly Val Leu
            260                 265                 270 ctg gcc aag gcg ctt ccg gac ctc gga ctg ccg cgg gcg cgc act cat      864
Leu Ala Lys Ala Leu Pro Asp Leu Gly Leu Pro Arg Ala Arg Thr His
        275                 280                 285 ctg acg gtg gcc gag cac ggc aac acc agc gcc gcc tcc atc ccg ctg      912
Leu Thr Val Ala Glu His Gly Asn Thr Ser Ala Ala Ser Ile Pro Leu
    290                 295                 300 gcg ctc gac gac gcc cgg cgg cag ggc gtg ttc ggc gac ggg gag ttg      960
Ala Leu Asp Asp Ala Arg Arg Gln Gly Val Phe Gly Asp Gly Glu Leu
305                 310                 315                 320 ctg ctg ctg gcc ggt ttc ggc ggc ggg atg tcg ctc ggc gcc gcg ctg     1008
Leu Leu Leu Ala Gly Phe Gly Gly Gly Met Ser Leu Gly Ala Ala Leu
```

```
                      325                 330                 335
ctc ata tgg cag gac ggc cac cgc ggt ccg tga                             1041
Leu Ile Trp Gln Asp Gly His Arg Gly Pro
            340                 345

<210> SEQ ID NO 4
<211> LENGTH: 346
<212> TYPE: PRT
<213> ORGANISM: Streptomyces sp. NRRL 30748

<400> SEQUENCE: 4

Met Thr Glu Gln Pro Val Arg Thr Ser Gly Gly Arg Pro Ile Gly Ile
1               5                   10                  15

Leu Gly Thr Gly Ser Tyr Leu Pro Ala Glu Thr Val Ser Asn Glu Leu
            20                  25                  30

Val Ala Glu Arg Ala Gly Val Thr Pro Asp Trp Ile Ser Ala Lys Thr
        35                  40                  45

Gly Ile His Arg Arg Tyr Ala Ala Asp His Glu Ala Thr Ser Asp
    50                  55                  60

Leu Ala Val Glu Ala Ala Arg Ala Ala Leu Ala Asp Ala Gly Ile Gly
65                  70                  75                  80

Ala Asp Gln Leu Gly Trp Ile Val Val Ala Thr Ser Thr Pro Asp His
                85                  90                  95

Pro Gln Pro Ala Thr Ala Cys Leu Val Gln His Arg Ile Gly Ala Thr
            100                 105                 110

Gly Ala Ala Ala Phe Asp Leu Asn Ala Val Cys Ser Gly Phe Val Phe
        115                 120                 125

Ala Leu Val Thr Ala Ala Gly Leu Leu Ser Ala Gly Ser Gly Ala Pro
    130                 135                 140

Ala Pro Tyr Ala Leu Val Ile Gly Ala Asp Val Tyr Ser Arg Ile Ile
145                 150                 155                 160

Asp Arg Thr Asp Arg Arg Thr Ala Val Leu Phe Gly Asp Gly Ala Gly
                165                 170                 175

Ala Val Val Leu Gly Pro Val Arg Pro Gly Tyr Gly Leu Ser Gly Ser
            180                 185                 190

Leu Leu Thr Ser Asp Gly Ala Leu His Glu Leu Ile Glu Val Thr Ala
        195                 200                 205

Gly Gly Ser Arg Val Pro Ala Ser Glu Lys Thr Leu Ala Asp Gly Gly
    210                 215                 220

His Phe Phe Arg Met Arg Gly Arg Ala Val Ser Glu Tyr Val Leu Ala
225                 230                 235                 240

Glu Leu Pro Arg Ala Ile Gly Arg Leu Leu Ala Ala His Arg Thr Asp
                245                 250                 255

Pro Ala Ser Val Asp His Phe Ile Pro His Gln Ala Asn Gly Val Leu
            260                 265                 270

Leu Ala Lys Ala Leu Pro Asp Leu Gly Leu Pro Arg Ala Arg Thr His
        275                 280                 285

Leu Thr Val Ala Glu His Gly Asn Thr Ser Ala Ala Ser Ile Pro Leu
    290                 295                 300

Ala Leu Asp Asp Ala Arg Arg Gln Gly Val Phe Gly Asp Gly Glu Leu
305                 310                 315                 320

Leu Leu Leu Ala Gly Phe Gly Gly Gly Met Ser Leu Gly Ala Ala Leu
                325                 330                 335

Leu Ile Trp Gln Asp Gly His Arg Gly Pro
            340                 345
```

<210> SEQ ID NO 5
<211> LENGTH: 1719
<212> TYPE: DNA
<213> ORGANISM: Streptomyces sp. NRRL 30748
<220> FEATURE:
<221> NAME/KEY: CDS
<222> LOCATION: (1)..(1719)

<400> SEQUENCE: 5

| | | | | | | | | | | | | | | | | |
|---|---|---|---|---|---|---|---|---|---|---|---|---|---|---|---|---|
| atg | gca | cag | cgc | ttc | ccc | acc | gtc | gcg | gtg | ttc | ggg | ctc | ggc | acc | acc | 48 |
| Met | Ala | Gln | Arg | Phe | Pro | Thr | Val | Ala | Val | Phe | Gly | Leu | Gly | Thr | Thr | |
| 1 | | | | 5 | | | | | 10 | | | | | 15 | | |
| ggc | cgc | cac | ctc | gtg | gac | gcg | ctg | gtc | cgc | ggt | ggc | cgg | cgg | gtg | atc | 96 |
| Gly | Arg | His | Leu | Val | Asp | Ala | Leu | Val | Arg | Gly | Gly | Arg | Arg | Val | Ile | |
| | | | 20 | | | | | 25 | | | | | 30 | | | |
| gcc | gtg | gag | cgg | gac | gaa | ccg | gcc | ctg | cga | cgt | ggc | cgg | gcg | gag | gtg | 144 |
| Ala | Val | Glu | Arg | Asp | Glu | Pro | Ala | Leu | Arg | Arg | Gly | Arg | Ala | Glu | Val | |
| | | 35 | | | | | 40 | | | | | 45 | | | | |
| acc | gcg | ccc | gat | tcc | gca | gtc | gaa | ttc | acc | acc | gac | ccg | gcg | gcc | gcc | 192 |
| Thr | Ala | Pro | Asp | Ser | Ala | Val | Glu | Phe | Thr | Thr | Asp | Pro | Ala | Ala | Ala | |
| 50 | | | | | 55 | | | | | 60 | | | | | | |
| gcc | cgg | gcc | gat | ctg | gtg | gtc | gag | gcg | gtc | ccc | gaa | cgg | ctg | gag | acc | 240 |
| Ala | Arg | Ala | Asp | Leu | Val | Val | Glu | Ala | Val | Pro | Glu | Arg | Leu | Glu | Thr | |
| 65 | | | | | 70 | | | | | 75 | | | | | 80 | |
| aag | ctc | ggg | ctg | ctc | gcc | cgc | gcc | cac | gcc | gac | tgc | ccg | ccg | gag | acg | 288 |
| Lys | Leu | Gly | Leu | Leu | Ala | Arg | Ala | His | Ala | Asp | Cys | Pro | Pro | Glu | Thr | |
| | | | | 85 | | | | | 90 | | | | | 95 | | |
| gtg | ttc | gcc | acc | acg | acc | acc | ggc | ctc | ccg | gtg | acc | gag | atc | gcc | gtc | 336 |
| Val | Phe | Ala | Thr | Thr | Thr | Thr | Gly | Leu | Pro | Val | Thr | Glu | Ile | Ala | Val | |
| | | | 100 | | | | | 105 | | | | | 110 | | | |
| ggc | tcc | ggg | cgg | acc | gac | cgc | acg | gtg | ggg | ctg | cac | ctc | ttc | ccg | ctg | 384 |
| Gly | Ser | Gly | Arg | Thr | Asp | Arg | Thr | Val | Gly | Leu | His | Leu | Phe | Pro | Leu | |
| | | 115 | | | | | 120 | | | | | 125 | | | | |
| ggc | ccc | gac | cgc | gag | cag | ccg | gcg | gtg | gag | gtg | gtg | ggc | acc | ccg | ctc | 432 |
| Gly | Pro | Asp | Arg | Glu | Gln | Pro | Ala | Val | Glu | Val | Val | Gly | Thr | Pro | Leu | |
| | 130 | | | | | 135 | | | | | 140 | | | | | |
| acc | gcg | gac | gcg | gtc | ctg | gcc | gac | gtc | cgg | gaa | ctc | ata | cgc | gac | ctg | 480 |
| Thr | Ala | Asp | Ala | Val | Leu | Ala | Asp | Val | Arg | Glu | Leu | Ile | Arg | Asp | Leu | |
| 145 | | | | | 150 | | | | | 155 | | | | | 160 | |
| ggc | cgg | atc | ccg | gtg | cgg | gtg | gcc | gac | cgg | ccg | ggc | ttc | gtc | ggg | ggc | 528 |
| Gly | Arg | Ile | Pro | Val | Arg | Val | Ala | Asp | Arg | Pro | Gly | Phe | Val | Gly | Gly | |
| | | | | 165 | | | | | 170 | | | | | 175 | | |
| gcg | ctc | acc | atg | gcg | tac | ctc | aac | aac | gcg | gtg | gcc | atg | tac | gag | cgg | 576 |
| Ala | Leu | Thr | Met | Ala | Tyr | Leu | Asn | Asn | Ala | Val | Ala | Met | Tyr | Glu | Arg | |
| | | | 180 | | | | | 185 | | | | | 190 | | | |
| cgc | tac | gcc | tcg | cgc | gac | agc | atc | gac | acc | gcc | atg | acc | ctc | ggc | tgc | 624 |
| Arg | Tyr | Ala | Ser | Arg | Asp | Ser | Ile | Asp | Thr | Ala | Met | Thr | Leu | Gly | Cys | |
| | | | 195 | | | | | 200 | | | | | 205 | | | |
| gga | ctg | ccg | atg | ggg | ccg | ctg | gcc | cag | ctg | gac | gcc | atg | ggt | ctg | gac | 672 |
| Gly | Leu | Pro | Met | Gly | Pro | Leu | Ala | Gln | Leu | Asp | Ala | Met | Gly | Leu | Asp | |
| | 210 | | | | | 215 | | | | | 220 | | | | | |
| acc | gcg | cgg | gac | tcc | ctg | gag | gcg | ctg | tac | gag | cgc | acc | ggc | gat | ccg | 720 |
| Thr | Ala | Arg | Asp | Ser | Leu | Glu | Ala | Leu | Tyr | Glu | Arg | Thr | Gly | Asp | Pro | |
| 225 | | | | | 230 | | | | | 235 | | | | | 240 | |
| cgg | tac | gcg | ccc | gcg | ccc | acc | ctg | gcc | cat | atg | gtg | acc | gcc | ggt | ctg | 768 |
| Arg | Tyr | Ala | Pro | Ala | Pro | Thr | Leu | Ala | His | Met | Val | Thr | Ala | Gly | Leu | |
| | | | | 245 | | | | | 250 | | | | | 255 | | |
| ctc | ggg | gtg | aag | gcg | ggc | cgc | ggc | ttc | tac | gag | tac | ggg | gcg | ggc | ggc | 816 |
| Leu | Gly | Val | Lys | Ala | Gly | Arg | Gly | Phe | Tyr | Glu | Tyr | Gly | Ala | Gly | Gly | |
| | | | 260 | | | | | 265 | | | | | 270 | | | |

```
gcg gcg ccg ggc ggg gcg acg gac ggc ctg ggc gag ccc gta ccg gcc      864
Ala Ala Pro Gly Gly Ala Thr Asp Gly Leu Gly Glu Pro Val Pro Ala
            275                 280                 285 cgc gcg gtg cgg cgg atc ggg gtg gtg ggc tcg ggc acg atg gcc gtc      912
Arg Ala Val Arg Arg Ile Gly Val Val Gly Ser Gly Thr Met Ala Val
        290                 295                 300 ggc atc gcg gag gtg tgc gcg cgc tcc ggc tat ccg acg gtg ctg gtg      960
Gly Ile Ala Glu Val Cys Ala Arg Ser Gly Tyr Pro Thr Val Leu Val
305                 310                 315                 320 gcc cgg agc gag atg cgc gcg aag gag gcc acg gcc gcc gtg gag cgc     1008
Ala Arg Ser Glu Met Arg Ala Lys Glu Ala Thr Ala Ala Val Glu Arg
                325                 330                 335 tcg ctg gag cgc gga gtg cgg cgc ggc aag ctg gcg ccc gag ctg ctc     1056
Ser Leu Glu Arg Gly Val Arg Arg Gly Lys Leu Ala Pro Glu Leu Leu
            340                 345                 350 acc gag gcg atg ggc cgg ctg acc gcg ggc tgt gaa ctc cag gcc ctc     1104
Thr Glu Ala Met Gly Arg Leu Thr Ala Gly Cys Glu Leu Gln Ala Leu
        355                 360                 365 ggc gcc tgc gat ctg gtg gtc gag gcc gtg gcg gag gac atc gac gtc     1152
Gly Ala Cys Asp Leu Val Val Glu Ala Val Ala Glu Asp Ile Asp Val
370                 375                 380 aag cgg gcc gtc ttc gcc gat ctg gac cgg gtg tgc gca ccg ggt gcg     1200
Lys Arg Ala Val Phe Ala Asp Leu Asp Arg Val Cys Ala Pro Gly Ala
                385                 390                 395                 400 gtg ctc gcc acc tcc acc tcc agc ctg ccc gtg atc gag tgc gcg atg     1248
Val Leu Ala Thr Ser Thr Ser Ser Leu Pro Val Ile Glu Cys Ala Met
            405                 410                 415 gcg acg cgg cgg ccc gag gac gtc atc ggg atg cac ttc ttc aac ccc     1296
Ala Thr Arg Arg Pro Glu Asp Val Ile Gly Met His Phe Phe Asn Pro
        420                 425                 430 gcc ccg gtg atg cgg ctg gtc gag gtg gtg cac acc gtg ctg acc tcc     1344
Ala Pro Val Met Arg Leu Val Glu Val Val His Thr Val Leu Thr Ser
435                 440                 445 aag gag gcg ctc ggc acg gcc cac gcg gtg gcc gcg gcg ctc ggc aag     1392
Lys Glu Ala Leu Gly Thr Ala His Ala Val Ala Ala Ala Leu Gly Lys
                450                 455                 460 cgc gcg gtg gac tgc ccc gac cgg gcc ggt ttc atc gtc aac gcc ctg     1440
Arg Ala Val Asp Cys Pro Asp Arg Ala Gly Phe Ile Val Asn Ala Leu
465                 470                 475                 480 ctc ttc ccc tat ctg aac agc gcg gtg gcg atg ctc gag gag ggc tgg     1488
Leu Phe Pro Tyr Leu Asn Ser Ala Val Ala Met Leu Glu Glu Gly Trp
            485                 490                 495 gcc acc gcc gat gac atc gat acg gtg atg gcg gcc ggt cag ggc tat     1536
Ala Thr Ala Asp Asp Ile Asp Thr Val Met Ala Ala Gly Gln Gly Tyr
        500                 505                 510 ccg atg ggc ccg ctg cgg ctg ctg gat gtg atc ggt ctg gat gtc tcg     1584
Pro Met Gly Pro Leu Arg Leu Leu Asp Val Ile Gly Leu Asp Val Ser
            515                 520                 525 ctc gcc atc cag cgc act ctg tac ggc acc ttc cgg gat ccg gcc ctg     1632
Leu Ala Ile Gln Arg Thr Leu Tyr Gly Thr Phe Arg Asp Pro Ala Leu
        530                 535                 540 acc ccg gcg cgc cat ctc cgg cgg ctg gtc gag gcg ggc cac ctg ggc     1680
Thr Pro Ala Arg His Leu Arg Arg Leu Val Glu Ala Gly His Leu Gly
545                 550                 555                 560 cgc aag ggc ggg agg ggg ctg cac ctc cac gag cga tag                 1719
Arg Lys Gly Gly Arg Gly Leu His Leu His Glu Arg
                565                 570
```

<210> SEQ ID NO 6

<211> LENGTH: 572
<212> TYPE: PRT
<213> ORGANISM: Streptomyces sp. NRRL 30748

<400> SEQUENCE: 6

```
Met Ala Gln Arg Phe Pro Thr Val Ala Val Phe Gly Leu Gly Thr Thr
 1               5                  10                  15

Gly Arg His Leu Val Asp Ala Leu Val Arg Gly Gly Arg Arg Val Ile
            20                  25                  30

Ala Val Glu Arg Asp Glu Pro Ala Leu Arg Arg Gly Arg Ala Glu Val
        35                  40                  45

Thr Ala Pro Asp Ser Ala Val Glu Phe Thr Thr Asp Pro Ala Ala Ala
    50                  55                  60

Ala Arg Ala Asp Leu Val Val Glu Ala Val Pro Glu Arg Leu Glu Thr
65                  70                  75                  80

Lys Leu Gly Leu Leu Ala Arg Ala His Ala Asp Cys Pro Pro Glu Thr
                85                  90                  95

Val Phe Ala Thr Thr Thr Thr Gly Leu Pro Val Thr Glu Ile Ala Val
            100                 105                 110

Gly Ser Gly Arg Thr Asp Arg Thr Val Gly Leu His Leu Phe Pro Leu
        115                 120                 125

Gly Pro Asp Arg Glu Gln Pro Ala Val Glu Val Gly Thr Pro Leu
    130                 135                 140

Thr Ala Asp Ala Val Leu Ala Asp Val Arg Glu Leu Ile Arg Asp Leu
145                 150                 155                 160

Gly Arg Ile Pro Val Arg Val Ala Asp Arg Pro Gly Phe Val Gly Gly
                165                 170                 175

Ala Leu Thr Met Ala Tyr Leu Asn Asn Ala Val Ala Met Tyr Glu Arg
            180                 185                 190

Arg Tyr Ala Ser Arg Asp Ser Ile Asp Thr Ala Met Thr Leu Gly Cys
        195                 200                 205

Gly Leu Pro Met Gly Pro Leu Ala Gln Leu Asp Ala Met Gly Leu Asp
    210                 215                 220

Thr Ala Arg Asp Ser Leu Glu Ala Leu Tyr Glu Arg Thr Gly Asp Pro
225                 230                 235                 240

Arg Tyr Ala Pro Ala Pro Thr Leu Ala His Met Val Thr Ala Gly Leu
                245                 250                 255

Leu Gly Val Lys Ala Gly Arg Gly Phe Tyr Glu Tyr Gly Ala Gly Gly
            260                 265                 270

Ala Ala Pro Gly Gly Ala Thr Asp Gly Leu Gly Glu Pro Val Pro Ala
        275                 280                 285

Arg Ala Val Arg Arg Ile Gly Val Val Gly Ser Gly Thr Met Ala Val
    290                 295                 300

Gly Ile Ala Glu Val Cys Ala Arg Ser Gly Tyr Pro Thr Val Leu Val
305                 310                 315                 320

Ala Arg Ser Glu Met Arg Ala Lys Glu Ala Thr Ala Ala Val Glu Arg
                325                 330                 335

Ser Leu Glu Arg Gly Val Arg Arg Gly Lys Leu Ala Pro Glu Leu Leu
            340                 345                 350

Thr Glu Ala Met Gly Arg Leu Thr Ala Gly Cys Glu Leu Gln Ala Leu
        355                 360                 365

Gly Ala Cys Asp Leu Val Val Glu Ala Val Ala Glu Asp Ile Asp Val
    370                 375                 380

Lys Arg Ala Val Phe Ala Asp Leu Asp Arg Val Cys Ala Pro Gly Ala
```

-continued

```
              385                 390                 395                 400
Val Leu Ala Thr Ser Thr Ser Ser Leu Pro Val Ile Glu Cys Ala Met
                405                 410                 415

Ala Thr Arg Arg Pro Glu Asp Val Ile Gly Met His Phe Phe Asn Pro
            420                 425                 430

Ala Pro Val Met Arg Leu Val Glu Val Val His Thr Val Leu Thr Ser
        435                 440                 445

Lys Glu Ala Leu Gly Thr Ala His Ala Val Ala Ala Leu Gly Lys
    450                 455                 460

Arg Ala Val Asp Cys Pro Asp Arg Ala Gly Phe Ile Val Asn Ala Leu
465                 470                 475                 480

Leu Phe Pro Tyr Leu Asn Ser Ala Val Ala Met Leu Glu Glu Gly Trp
                485                 490                 495

Ala Thr Ala Asp Asp Ile Asp Thr Val Met Ala Ala Gly Gln Gly Tyr
            500                 505                 510

Pro Met Gly Pro Leu Arg Leu Leu Asp Val Ile Gly Leu Asp Val Ser
        515                 520                 525

Leu Ala Ile Gln Arg Thr Leu Tyr Gly Thr Phe Arg Asp Pro Ala Leu
    530                 535                 540

Thr Pro Ala Arg His Leu Arg Arg Leu Val Glu Ala Gly His Leu Gly
545                 550                 555                 560

Arg Lys Gly Gly Arg Gly Leu His Leu His Glu Arg
                565                 570

<210> SEQ ID NO 7
<211> LENGTH: 2874
<212> TYPE: DNA
<213> ORGANISM: Streptomyces sp. NRRL 30748
<220> FEATURE:
<221> NAME/KEY: CDS
<222> LOCATION: (1)..(2874)

<400> SEQUENCE: 7 gtg ttt tca tcg gcc aga gcc aga caa ttc gac gcg caa ttc gag aga      48
Val Phe Ser Ser Ala Arg Ala Arg Gln Phe Asp Ala Gln Phe Glu Arg
1               5                   10                  15 ctt cgg cgg gca ttt tcc aga tgc ctg tcc gga gag gcg ggc atc gtg      96
Leu Arg Arg Ala Phe Ser Arg Cys Leu Ser Gly Glu Ala Gly Ile Val
            20                  25                  30 ctc gtc gag ggt gcg gtc ggt tgt ggc aag acc cat acg ctg gaa gcc     144
Leu Val Glu Gly Ala Val Gly Cys Gly Lys Thr His Thr Leu Glu Ala
        35                  40                  45 gtc acg gcc cat gcg gcg aag gcc gga gcc ctt gtc ctc aag gca tac     192
Val Thr Ala His Ala Ala Lys Ala Gly Ala Leu Val Leu Lys Ala Tyr
    50                  55                  60 gga acc tcg gcc gac cgg gcc ccg ctc ggc aca ctg cgc cag ctc ctg     240
Gly Thr Ser Ala Asp Arg Ala Pro Leu Gly Thr Leu Arg Gln Leu Leu
65                  70                  75                  80 gac tcg ccc cgg ctg ccc agg gcg acc gcc gac cag ctg cgc cgg gca     288
Asp Ser Pro Arg Leu Pro Arg Ala Thr Ala Asp Gln Leu Arg Arg Ala
                85                  90                  95 ctc gac cac ggc gcc ctc gac gcc gca ccg ccc cgg gaa acc cct ggt     336
Leu Asp His Gly Ala Leu Asp Ala Ala Pro Pro Arg Glu Thr Pro Gly
            100                 105                 110 ggc gac ccc gtc ggc gcg aac ccc acc cat gtc cag gga gcc cgg gag     384
Gly Asp Pro Val Gly Ala Asn Pro Thr His Val Gln Gly Ala Arg Glu
        115                 120                 125 ttc cgt gcc gca ctc cat gaa ctc gcc tcc cgt gaa ccg gtg gtg atc     432
```

```
               Phe Arg Ala Ala Leu His Glu Leu Ala Ser Arg Glu Pro Val Val Ile
                   130                 135                 140 tgc gtc gac gaa ctc cag ctc gtc gac gcg gcg tca ctt cag tac ctg         480
Cys Val Asp Glu Leu Gln Leu Val Asp Ala Ala Ser Leu Gln Tyr Leu
145                 150                 155                 160 ctg tac ctg gcg acc cgt tcg cgc tcc gcc aaa ctc ctc atg gtg ttc         528
Leu Tyr Leu Ala Thr Arg Ser Arg Ser Ala Lys Leu Leu Met Val Phe
                    165                 170                 175 gca cag gcg acg gac agc gaa cga caa gac gcg gtc ttc aat acc gaa         576
Ala Gln Ala Thr Asp Ser Glu Arg Gln Asp Ala Val Phe Asn Thr Glu
                180                 185                 190 ctg ctg cgc cag ccc aat ttc cag cgg ctg cgg ctg gaa cgg ctg tcc         624
Leu Leu Arg Gln Pro Asn Phe Gln Arg Leu Arg Leu Glu Arg Leu Ser
            195                 200                 205 tgg gat gag acg gca cat ctg ctc acc act cgt ctg gga ctt ccg gat         672
Trp Asp Glu Thr Ala His Leu Leu Thr Thr Arg Leu Gly Leu Pro Asp
210                 215                 220 tcc acc gat gtg gcc tac acc tgg tat gag gtg agc ggc ggt aat ccg         720
Ser Thr Asp Val Ala Tyr Thr Trp Tyr Glu Val Ser Gly Gly Asn Pro
225                 230                 235                 240 ttg ttg cta cgc gcg gtg ata gac gat tac cgc acc gcg ggg gcg ccc         768
Leu Leu Leu Arg Ala Val Ile Asp Asp Tyr Arg Thr Ala Gly Ala Pro
                    245                 250                 255 cca cgg cgc agc cgc gca gtg gag ccc gtg gtg ggc gac atg ttt gtg         816
Pro Arg Arg Ser Arg Ala Val Glu Pro Val Val Gly Asp Met Phe Val
                260                 265                 270 cag gcc gtg ctc acc tgc gtc tac cgc agc ggg cgc acc gtc tcc cgg         864
Gln Ala Val Leu Thr Cys Val Tyr Arg Ser Gly Arg Thr Val Ser Arg
            275                 280                 285 ctg gcc gag gga atc gcg gtg ctc ggt gcg tcc gcc tcc ctc gaa ctc         912
Leu Ala Glu Gly Ile Ala Val Leu Gly Ala Ser Ala Ser Leu Glu Leu
290                 295                 300 ctc ggc cgg ctg ctg cgc atc ggc ccc gcc gga acc cgc cgc gga gtc         960
Leu Gly Arg Leu Leu Arg Ile Gly Pro Ala Gly Thr Arg Arg Gly Val
305                 310                 315                 320 gcc gcg ctg gac gcg gcg ggg ctc gtc gac ggt ctg gcc ttc cgc cac        1008
Ala Ala Leu Asp Ala Ala Gly Leu Val Asp Gly Leu Ala Phe Arg His
                    325                 330                 335 ccg tat gtc gag gcc gcg gtg ctg gag gac atg gac ccc gag gtc cgg        1056
Pro Tyr Val Glu Ala Ala Val Leu Glu Asp Met Asp Pro Glu Val Arg
                340                 345                 350 ctg gac atg aac cgc cgc gcc gcc gtc ctg ctg cac cag ggc ggc ggg        1104
Leu Asp Met Asn Arg Arg Ala Ala Val Leu Leu His Gln Gly Gly Gly
            355                 360                 365 gcg acc ctc gcc gtg gcc cgc cat ctg ctc gcg gcc cag gcc gcg gac        1152
Ala Thr Leu Ala Val Ala Arg His Leu Leu Ala Ala Gln Ala Ala Asp
370                 375                 380 gag ccc tgg ggg gtg ccg ctg ctg cgg gac gcc gcg cag cag gcg ctc        1200
Glu Pro Trp Gly Val Pro Leu Leu Arg Asp Ala Ala Gln Gln Ala Leu
385                 390                 395                 400 gcc gag gac gac gcc aag ctg gcg gtg gcc tgt ctg gag ctg gcg tac        1248
Ala Glu Asp Asp Ala Lys Leu Ala Val Ala Cys Leu Glu Leu Ala Tyr
                    405                 410                 415 gcg gcc tgc gcg gac gag gag ctg cgc gcc ggc atc agg atc ggc acc        1296
Ala Ala Cys Ala Asp Glu Glu Leu Arg Ala Gly Ile Arg Ile Gly Thr
                420                 425                 430 gcc ggg atc atg tgg cgg ctc aac ccc tcg gcg tcc gag cgg atg ctg        1344
Ala Gly Ile Met Trp Arg Leu Asn Pro Ser Ala Ser Glu Arg Met Leu
            435                 440                 445
```

```
gag gag ccg ctg gcc gcg ctg tgc gcc gac cgg ctg ccc gcc tcc cat      1392
Glu Glu Pro Leu Ala Ala Leu Cys Ala Asp Arg Leu Pro Ala Ser His
    450                 455                 460 atc ggg cgg ctg atc gag ctg ttg ctc gcc cac ggc cgg atc gag gag      1440
Ile Gly Arg Leu Ile Glu Leu Leu Leu Ala His Gly Arg Ile Glu Glu
465                 470                 475                 480 gcg cgc ggc gcg atc ggc cgg ctc aac gcc gtg atg agc aac gcg ggg      1488
Ala Arg Gly Ala Ile Gly Arg Leu Asn Ala Val Met Ser Asn Ala Gly
                485                 490                 495 ccc act tcg atg tcc cag ttc cgg ctg acc gcc cgc tgg gcc cag gag      1536
Pro Thr Ser Met Ser Gln Phe Arg Leu Thr Ala Arg Trp Ala Gln Glu
            500                 505                 510 tcc ggt gcg tcg gac cgg gcc ccc ggg gcc acg gcg cgc cag ggc gag      1584
Ser Gly Ala Ser Asp Arg Ala Pro Gly Ala Thr Ala Arg Gln Gly Glu
        515                 520                 525 gac ggc ggc gcc ctc cgt gcg cag ctc aga tcc cgc aga ccc ttc gcg      1632
Asp Gly Gly Ala Leu Arg Ala Gln Leu Arg Ser Arg Arg Pro Phe Ala
    530                 535                 540 ctg tcg acg atc acg gcg gcg ttc agc ggc ttc ttc ggc cgc ggg ggg      1680
Leu Ser Thr Ile Thr Ala Ala Phe Ser Gly Phe Phe Gly Arg Gly Gly
545                 550                 555                 560 acc gag gag tcg ccg gtg gcc gcg gcg gag aag gtc ctc gat gtc tcg      1728
Thr Glu Glu Ser Pro Val Ala Ala Ala Glu Lys Val Leu Asp Val Ser
                565                 570                 575 ccg ctc acc gac gcc acc ttc gag ccc atc gtc aac tcg gtg aac gcg      1776
Pro Leu Thr Asp Ala Thr Phe Glu Pro Ile Val Asn Ser Val Asn Ala
            580                 585                 590 ctg gtg tac gcg ggc cgc ccg gac aag gcg gcg ccg tgg tgc gac gcg      1824
Leu Val Tyr Ala Gly Arg Pro Asp Lys Ala Ala Pro Trp Cys Asp Ala
        595                 600                 605 ctg atg gag gag gcc gag cgg cgc cgg gcg ccg ggc tgg cgg gcc atc      1872
Leu Met Glu Glu Ala Glu Arg Arg Arg Ala Pro Gly Trp Arg Ala Ile
    610                 615                 620 ttc gcc tcg atc cgc gcc gaa atc gcc ctg cgg cag ggc aat ctc gtg      1920
Phe Ala Ser Ile Arg Ala Glu Ile Ala Leu Arg Gln Gly Asn Leu Val
625                 630                 635                 640 gag tcg gcg gcc tat gcg acc atc gcc ctg gag atc gtt ccc ggc cgc      1968
Glu Ser Ala Ala Tyr Ala Thr Ile Ala Leu Glu Ile Val Pro Gly Arg
                645                 650                 655 gac gga agc gtc ttc atc ggc ggc ccc ctg gcc agc cag atc ctg gcg      2016
Asp Gly Ser Val Phe Ile Gly Gly Pro Leu Ala Ser Gln Ile Leu Ala
            660                 665                 670 tac acg gag atg ggc aag cac gac gcg gcg gcg cgg cat ctg agc cgc      2064
Tyr Thr Glu Met Gly Lys His Asp Ala Ala Ala Arg His Leu Ser Arg
        675                 680                 685 ccg gtc ccc gag gcg ctg ttc aag agc atc tac gga ctg ggc tac acc      2112
Pro Val Pro Glu Ala Leu Phe Lys Ser Ile Tyr Gly Leu Gly Tyr Thr
    690                 695                 700 cgc gcc cgc ggc cgc tac tac ctg gcc acc aac cgc atc aac gcg gcg      2160
Arg Ala Arg Gly Arg Tyr Tyr Leu Ala Thr Asn Arg Ile Asn Ala Ala
705                 710                 715                 720 ctc ggc gaa ttc ctc atg gcc ggc cgg ctc gcc cag ctg tgg gag ctc      2208
Leu Gly Glu Phe Leu Met Ala Gly Arg Leu Ala Gln Leu Trp Glu Leu
                725                 730                 735 gac cag ccg gcg ctg ctg ccc tgg cgc tcg gac gcc gcc gag gca tgg      2256
Asp Gln Pro Ala Leu Leu Pro Trp Arg Ser Asp Ala Ala Glu Ala Trp
            740                 745                 750 ctg gag ctc ggc gac cgg gag aag gcc gcc aac ctg gtc tcc gag cag      2304
Leu Glu Leu Gly Asp Arg Glu Lys Ala Ala Asn Leu Val Ser Glu Gln
        755                 760                 765
```

-continued

```
ctg gcc agg aac ggc gcc ggg gac tcc cgg gtc cgt ggc gtc tcc ctg      2352
Leu Ala Arg Asn Gly Ala Gly Asp Ser Arg Val Arg Gly Val Ser Leu
    770                 775                 780 cgg tta ctg gcc gcg gcg ggc gac atc gag aac cgg tcc cgg ctg ctc      2400
Arg Leu Leu Ala Ala Ala Gly Asp Ile Glu Asn Arg Ser Arg Leu Leu
785                 790                 795                 800 ggc cag gcc gtc gag gag ctg cag tgc tcc ggc gac cgc ctg gag ctg      2448
Gly Gln Ala Val Glu Glu Leu Gln Cys Ser Gly Asp Arg Leu Glu Leu
                805                 810                 815 gcc cgg gcg ctg gac gat ctg gga cgt acg ctg cgc gga tcc ggg gag      2496
Ala Arg Ala Leu Asp Asp Leu Gly Arg Thr Leu Arg Gly Ser Gly Glu
            820                 825                 830 ctg ggg cgg gcc gac gcc atc atg ggc cgg gcc tgg cgg atg gcc aag      2544
Leu Gly Arg Ala Asp Ala Ile Met Gly Arg Ala Trp Arg Met Ala Lys
        835                 840                 845 gag tgc ggc gcc gag gag ctg tgc gcc cgc atc cgt ctc gac tcg ggt      2592
Glu Cys Gly Ala Glu Glu Leu Cys Ala Arg Ile Arg Leu Asp Ser Gly
    850                 855                 860 ctg gag gcc cgc gat cca cgg ccg gtg gtg cga ccg gtg tcc gca ccg      2640
Leu Glu Ala Arg Asp Pro Arg Pro Val Val Arg Pro Val Ser Ala Pro
865                 870                 875                 880 ctc ggc ccg aag ccg gcg gtg ccg ccg tcc ctg ggc acc aag ctc agc      2688
Leu Gly Pro Lys Pro Ala Val Pro Pro Ser Leu Gly Thr Lys Leu Ser
                885                 890                 895 gaa tcc gag gcc cgg gtg gcc gcc ctg gcg gtg gac ggt tat acg aac      2736
Glu Ser Glu Ala Arg Val Ala Ala Leu Ala Val Asp Gly Tyr Thr Asn
            900                 905                 910 cgg gaa ata gcc gcc agc ctg ttc atc acc atc agc acg gtg gaa cag      2784
Arg Glu Ile Ala Ala Ser Leu Phe Ile Thr Ile Ser Thr Val Glu Gln
        915                 920                 925 cat ttg acg cgg gtg tac cgc aag ctg aat atc agg agc cgg cag cag      2832
His Leu Thr Arg Val Tyr Arg Lys Leu Asn Ile Arg Ser Arg Gln Gln
    930                 935                 940 ctg ccg acc gcg ctc cgg gcc cag gtg gac gaa atc gcc tga              2874
Leu Pro Thr Ala Leu Arg Ala Gln Val Asp Glu Ile Ala
945                 950                 955

<210> SEQ ID NO 8
<211> LENGTH: 957
<212> TYPE: PRT
<213> ORGANISM: Streptomyces sp. NRRL 30748

<400> SEQUENCE: 8

Val Phe Ser Ser Ala Arg Ala Arg Gln Phe Asp Ala Gln Phe Glu Arg
1               5                   10                  15

Leu Arg Arg Ala Phe Ser Arg Cys Leu Ser Gly Glu Ala Gly Ile Val
            20                  25                  30

Leu Val Glu Gly Ala Val Gly Cys Gly Lys Thr His Thr Leu Glu Ala
        35                  40                  45

Val Thr Ala His Ala Ala Lys Ala Gly Ala Leu Val Leu Lys Ala Tyr
    50                  55                  60

Gly Thr Ser Ala Asp Arg Ala Pro Leu Gly Thr Leu Arg Gln Leu Leu
65                  70                  75                  80

Asp Ser Pro Arg Leu Pro Arg Ala Thr Ala Asp Gln Leu Arg Arg Ala
                85                  90                  95

Leu Asp His Gly Ala Leu Asp Ala Ala Pro Pro Arg Glu Thr Pro Gly
            100                 105                 110

Gly Asp Pro Val Gly Ala Asn Pro Thr His Val Gln Gly Ala Arg Glu
```

-continued

```
            115                 120                 125
Phe Arg Ala Ala Leu His Glu Leu Ala Ser Arg Glu Pro Val Val Ile
        130                 135                 140
Cys Val Asp Glu Leu Gln Leu Val Asp Ala Ala Ser Leu Gln Tyr Leu
145                 150                 155                 160
Leu Tyr Leu Ala Thr Arg Ser Arg Ser Ala Lys Leu Leu Met Val Phe
                165                 170                 175
Ala Gln Ala Thr Asp Ser Glu Arg Gln Asp Ala Val Phe Asn Thr Glu
            180                 185                 190
Leu Leu Arg Gln Pro Asn Phe Gln Arg Leu Arg Leu Glu Arg Leu Ser
                195                 200                 205
Trp Asp Glu Thr Ala His Leu Leu Thr Thr Arg Leu Gly Leu Pro Asp
        210                 215                 220
Ser Thr Asp Val Ala Tyr Thr Trp Tyr Glu Val Ser Gly Gly Asn Pro
225                 230                 235                 240
Leu Leu Leu Arg Ala Val Ile Asp Asp Tyr Arg Thr Ala Gly Ala Pro
                245                 250                 255
Pro Arg Arg Ser Arg Ala Val Glu Pro Val Val Gly Asp Met Phe Val
            260                 265                 270
Gln Ala Val Leu Thr Cys Val Tyr Arg Ser Gly Arg Thr Val Ser Arg
            275                 280                 285
Leu Ala Glu Gly Ile Ala Val Leu Gly Ala Ser Ala Ser Leu Glu Leu
        290                 295                 300
Leu Gly Arg Leu Leu Arg Ile Gly Pro Ala Gly Thr Arg Arg Gly Val
305                 310                 315                 320
Ala Ala Leu Asp Ala Ala Gly Leu Val Asp Gly Leu Ala Phe Arg His
                325                 330                 335
Pro Tyr Val Glu Ala Ala Val Leu Glu Asp Met Asp Pro Glu Val Arg
            340                 345                 350
Leu Asp Met Asn Arg Arg Ala Ala Val Leu Leu His Gln Gly Gly Gly
            355                 360                 365
Ala Thr Leu Ala Val Ala Arg His Leu Leu Ala Ala Gln Ala Ala Asp
        370                 375                 380
Glu Pro Trp Gly Val Pro Leu Leu Arg Asp Ala Ala Gln Gln Ala Leu
385                 390                 395                 400
Ala Glu Asp Asp Ala Lys Leu Ala Val Ala Cys Leu Glu Leu Ala Tyr
                405                 410                 415
Ala Ala Cys Ala Asp Glu Glu Leu Arg Ala Gly Ile Arg Ile Gly Thr
            420                 425                 430
Ala Gly Ile Met Trp Arg Leu Asn Pro Ser Ala Ser Glu Arg Met Leu
            435                 440                 445
Glu Glu Pro Leu Ala Ala Leu Cys Ala Asp Arg Leu Pro Ala Ser His
450                 455                 460
Ile Gly Arg Leu Ile Glu Leu Leu Ala His Gly Arg Ile Glu Glu
465                 470                 475                 480
Ala Arg Gly Ala Ile Gly Arg Leu Asn Ala Val Met Ser Asn Ala Gly
                485                 490                 495
Pro Thr Ser Met Ser Gln Phe Arg Leu Thr Ala Arg Trp Ala Gln Glu
            500                 505                 510
Ser Gly Ala Ser Asp Arg Ala Pro Gly Ala Thr Ala Arg Gln Gly Glu
        515                 520                 525
Asp Gly Gly Ala Leu Arg Ala Gln Leu Arg Ser Arg Arg Pro Phe Ala
        530                 535                 540
```

-continued

```
Leu Ser Thr Ile Thr Ala Ala Phe Ser Gly Phe Gly Arg Gly Gly
545                 550                 555                 560

Thr Glu Glu Ser Pro Val Ala Ala Glu Lys Val Leu Asp Val Ser
                565                 570                 575

Pro Leu Thr Asp Ala Thr Phe Glu Pro Ile Val Asn Ser Val Asn Ala
                580                 585                 590

Leu Val Tyr Ala Gly Arg Pro Asp Lys Ala Ala Pro Trp Cys Asp Ala
                595                 600                 605

Leu Met Glu Glu Ala Glu Arg Arg Ala Pro Gly Trp Arg Ala Ile
            610                 615                 620

Phe Ala Ser Ile Arg Ala Glu Ile Ala Leu Arg Gln Gly Asn Leu Val
625                 630                 635                 640

Glu Ser Ala Ala Tyr Ala Thr Ile Ala Leu Glu Ile Val Pro Gly Arg
                645                 650                 655

Asp Gly Ser Val Phe Ile Gly Gly Pro Leu Ala Ser Gln Ile Leu Ala
                660                 665                 670

Tyr Thr Glu Met Gly Lys His Asp Ala Ala Arg His Leu Ser Arg
            675                 680                 685

Pro Val Pro Glu Ala Leu Phe Lys Ser Ile Tyr Gly Leu Gly Tyr Thr
                690                 695                 700

Arg Ala Arg Gly Arg Tyr Tyr Leu Ala Thr Asn Arg Ile Asn Ala Ala
705                 710                 715                 720

Leu Gly Glu Phe Leu Met Ala Gly Arg Leu Ala Gln Leu Trp Glu Leu
                725                 730                 735

Asp Gln Pro Ala Leu Leu Pro Trp Arg Ser Asp Ala Ala Glu Ala Trp
                740                 745                 750

Leu Glu Leu Gly Asp Arg Glu Lys Ala Ala Asn Leu Val Ser Glu Gln
            755                 760                 765

Leu Ala Arg Asn Gly Ala Gly Asp Ser Arg Val Arg Gly Val Ser Leu
770                 775                 780

Arg Leu Leu Ala Ala Gly Asp Ile Glu Asn Arg Ser Arg Leu Leu
785                 790                 795                 800

Gly Gln Ala Val Glu Glu Leu Gln Cys Ser Gly Asp Arg Leu Glu Leu
                805                 810                 815

Ala Arg Ala Leu Asp Asp Leu Gly Arg Thr Leu Arg Gly Ser Gly Glu
                820                 825                 830

Leu Gly Arg Ala Asp Ala Ile Met Gly Arg Ala Trp Arg Met Ala Lys
            835                 840                 845

Glu Cys Gly Ala Glu Glu Leu Cys Ala Arg Ile Arg Leu Asp Ser Gly
850                 855                 860

Leu Glu Ala Arg Asp Pro Arg Pro Val Val Arg Pro Val Ser Ala Pro
865                 870                 875                 880

Leu Gly Pro Lys Pro Ala Val Pro Pro Ser Leu Gly Thr Lys Leu Ser
                885                 890                 895

Glu Ser Glu Ala Arg Val Ala Ala Leu Ala Val Asp Gly Tyr Thr Asn
            900                 905                 910

Arg Glu Ile Ala Ala Ser Leu Phe Ile Thr Ile Ser Thr Val Glu Gln
            915                 920                 925

His Leu Thr Arg Val Tyr Arg Lys Leu Asn Ile Arg Ser Arg Gln Gln
            930                 935                 940

Leu Pro Thr Ala Leu Arg Ala Gln Val Asp Glu Ile Ala
945                 950                 955
```

```
<210> SEQ ID NO 9
<211> LENGTH: 867
<212> TYPE: DNA
<213> ORGANISM: Streptomyces sp. NRRL 30748
<220> FEATURE:
<221> NAME/KEY: CDS
<222> LOCATION: (1)..(867)

<400> SEQUENCE: 9 atg aag ggc ata gtc ctc gcc gga gga agc ggt acc cga ctg cat cct      48
Met Lys Gly Ile Val Leu Ala Gly Gly Ser Gly Thr Arg Leu His Pro
 1               5                  10                  15 ttg aca cat gcg gtg tcg aag cag atc ctt ccc gtc tac aac aaa ccg      96
Leu Thr His Ala Val Ser Lys Gln Ile Leu Pro Val Tyr Asn Lys Pro
                20                  25                  30 atg atc tat tac ccg ctg tcg gtg ctc atg ctc ggc ggc gtc agg gaa     144
Met Ile Tyr Tyr Pro Leu Ser Val Leu Met Leu Gly Gly Val Arg Glu
            35                  40                  45 atc cag atc atc tcg acc ccg ctc cat gtg gag ctg ttc cgc gcg ctt     192
Ile Gln Ile Ile Ser Thr Pro Leu His Val Glu Leu Phe Arg Ala Leu
        50                  55                  60 ctc ggc gac ggc ggc cga ctg ggt ctt tcg atc gag tac gcc gag cag     240
Leu Gly Asp Gly Gly Arg Leu Gly Leu Ser Ile Glu Tyr Ala Glu Gln
65                  70                  75                  80 ccc gag gcc aat gga atc gcc gag gca ttc atc atc gga gcc gag ttc     288
Pro Glu Ala Asn Gly Ile Ala Glu Ala Phe Ile Ile Gly Ala Glu Phe
                85                  90                  95 atc ggc gat gac cag gtg gcg ctg gtc ctc ggc gac aat atc ttc cac     336
Ile Gly Asp Asp Gln Val Ala Leu Val Leu Gly Asp Asn Ile Phe His
            100                 105                 110 ggg ccc gga ttc tcg aag atg ctg cac cat gag gca aac cat gtc gac     384
Gly Pro Gly Phe Ser Lys Met Leu His His Glu Ala Asn His Val Asp
        115                 120                 125 ggc tgt gtg ctc ttc ggc tac gga gtc aag gac ccc gag cgc tac ggt     432
Gly Cys Val Leu Phe Gly Tyr Gly Val Lys Asp Pro Glu Arg Tyr Gly
    130                 135                 140 gtc ggg gaa atg gat gag cag ggc cgg ctg atc tcc ttg gag gag aag     480
Val Gly Glu Met Asp Glu Gln Gly Arg Leu Ile Ser Leu Glu Glu Lys
145                 150                 155                 160 ccg acc gcc ccc aaa tcc aat ctg gcg atc acc ggt ctg tat ctc tac     528
Pro Thr Ala Pro Lys Ser Asn Leu Ala Ile Thr Gly Leu Tyr Leu Tyr
                165                 170                 175 gac aac gac gtc gtg gac atc gcc aag aac gta cgg ccc tcc gcg cgc     576
Asp Asn Asp Val Val Asp Ile Ala Lys Asn Val Arg Pro Ser Ala Arg
            180                 185                 190 ggc gaa ctg gag atc acc gac gtc aac cgc gtc tat ctg gaa cgc gga     624
Gly Glu Leu Glu Ile Thr Asp Val Asn Arg Val Tyr Leu Glu Arg Gly
        195                 200                 205 aaa gcc aga ctg gtg ggg ctc ggc cgc gga ttc gcc tgg ctg gac act     672
Lys Ala Arg Leu Val Gly Leu Gly Arg Gly Phe Ala Trp Leu Asp Thr
    210                 215                 220 gga acc cat gac tca ctg ctc cag gcg ggc cag tat gtg cag ctt ctg     720
Gly Thr His Asp Ser Leu Leu Gln Ala Gly Gln Tyr Val Gln Leu Leu
225                 230                 235                 240 gag cag cgc cag gga gtg cgg atc gcc tgt ctc gag gag ata gcc ttc     768
Glu Gln Arg Gln Gly Val Arg Ile Ala Cys Leu Glu Glu Ile Ala Phe
                245                 250                 255 cgc atg ggg ttc atc gac gcc gcc gcc tgt tat gag ctc ggt gcg gag     816
Arg Met Gly Phe Ile Asp Ala Ala Ala Cys Tyr Glu Leu Gly Ala Glu
            260                 265                 270
```

```
ctc agc aag acg gac tac gga caa tat ctg atg gat atc gcg ggc caa         864
Leu Ser Lys Thr Asp Tyr Gly Gln Tyr Leu Met Asp Ile Ala Gly Gln
        275                 280                 285 taa                                                                      867
```

<210> SEQ ID NO 10
<211> LENGTH: 288
<212> TYPE: PRT
<213> ORGANISM: Streptomyces sp. NRRL 30748

<400> SEQUENCE: 10

```
Met Lys Gly Ile Val Leu Ala Gly Gly Ser Gly Thr Arg Leu His Pro
1               5                   10                  15

Leu Thr His Ala Val Ser Lys Gln Ile Leu Pro Val Tyr Asn Lys Pro
            20                  25                  30

Met Ile Tyr Tyr Pro Leu Ser Val Leu Met Leu Gly Gly Val Arg Glu
        35                  40                  45

Ile Gln Ile Ile Ser Thr Pro Leu His Val Glu Leu Phe Arg Ala Leu
    50                  55                  60

Leu Gly Asp Gly Gly Arg Leu Gly Leu Ser Ile Glu Tyr Ala Glu Gln
65                  70                  75                  80

Pro Glu Ala Asn Gly Ile Ala Glu Ala Phe Ile Ile Gly Ala Glu Phe
                85                  90                  95

Ile Gly Asp Asp Gln Val Ala Leu Val Leu Gly Asp Asn Ile Phe His
            100                 105                 110

Gly Pro Gly Phe Ser Lys Met Leu His His Glu Ala Asn His Val Asp
        115                 120                 125

Gly Cys Val Leu Phe Gly Tyr Gly Val Lys Asp Pro Glu Arg Tyr Gly
    130                 135                 140

Val Gly Glu Met Asp Glu Gln Gly Arg Leu Ile Ser Leu Glu Glu Lys
145                 150                 155                 160

Pro Thr Ala Pro Lys Ser Asn Leu Ala Ile Thr Gly Leu Tyr Leu Tyr
                165                 170                 175

Asp Asn Asp Val Val Asp Ile Ala Lys Asn Val Arg Pro Ser Ala Arg
            180                 185                 190

Gly Glu Leu Glu Ile Thr Asp Val Asn Arg Val Tyr Leu Glu Arg Gly
        195                 200                 205

Lys Ala Arg Leu Val Gly Leu Gly Arg Gly Phe Ala Trp Leu Asp Thr
    210                 215                 220

Gly Thr His Asp Ser Leu Leu Gln Ala Gly Gln Tyr Val Gln Leu Leu
225                 230                 235                 240

Glu Gln Arg Gln Gly Val Arg Ile Ala Cys Leu Glu Glu Ile Ala Phe
                245                 250                 255

Arg Met Gly Phe Ile Asp Ala Ala Cys Tyr Glu Leu Gly Ala Glu
            260                 265                 270

Leu Ser Lys Thr Asp Tyr Gly Gln Tyr Leu Met Asp Ile Ala Gly Gln
        275                 280                 285
```

<210> SEQ ID NO 11
<211> LENGTH: 975
<212> TYPE: DNA
<213> ORGANISM: Streptomyces sp. NRRL 30748
<220> FEATURE:
<221> NAME/KEY: CDS
<222> LOCATION: (1)..(975)

<400> SEQUENCE: 11

```
gtg cgc ata gtt gtg acc ggc ggc gcg ggc ttc atc ggc tcc cac ttc     48
Val Arg Ile Val Val Thr Gly Gly Ala Gly Phe Ile Gly Ser His Phe
1               5                   10                  15 gtc cgg cag acc ctg aca ggg gcg tac gcg gcc tgg gcg gac gcc cag     96
Val Arg Gln Thr Leu Thr Gly Ala Tyr Ala Ala Trp Ala Asp Ala Gln
                20                  25                  30 gtc gtg gtg gtc gac aag ctc acc tac gcg ggc aac gag gcc aac ctg    144
Val Val Val Val Asp Lys Leu Thr Tyr Ala Gly Asn Glu Ala Asn Leu
            35                  40                  45 gcc gag gtc gcg gac agc ccc cgg ctg cgc ttc gtg cgc ggt gac atc    192
Ala Glu Val Ala Asp Ser Pro Arg Leu Arg Phe Val Arg Gly Asp Ile
50                  55                  60 tgc gac ggc gag ctc gtc ggc gaa ctg ctg cgg gac acc gat ctg gtg    240
Cys Asp Gly Glu Leu Val Gly Glu Leu Leu Arg Asp Thr Asp Leu Val
65                  70                  75                  80 gtc cac ttc gcc gcg gaa tca cat gtc gac cgc tcg ata tcc ggc gcc    288
Val His Phe Ala Ala Glu Ser His Val Asp Arg Ser Ile Ser Gly Ala
                85                  90                  95 gag gaa ttc gtg cgc acc aat gtc ctg ggc acc cac acc ctc ctc aac    336
Glu Glu Phe Val Arg Thr Asn Val Leu Gly Thr His Thr Leu Leu Asn
            100                 105                 110 gcg gcc gcg aac gcg gag gtc gga aag ttc gtc cac atc tcc acg gac    384
Ala Ala Ala Asn Ala Glu Val Gly Lys Phe Val His Ile Ser Thr Asp
        115                 120                 125 gag gtc tac ggc tcc atc gaa aac ggc tcc tgg agc gag gag gaa ccc    432
Glu Val Tyr Gly Ser Ile Glu Asn Gly Ser Trp Ser Glu Glu Glu Pro
    130                 135                 140 ctc gaa ccc aac tcg ccg tat tcc gcc tcc aag gcg tcc tcc gat ctg    480
Leu Glu Pro Asn Ser Pro Tyr Ser Ala Ser Lys Ala Ser Ser Asp Leu
145                 150                 155                 160 ctg gcc cgg gcc ttc cac cgc acc cac gga ctg ccc gtc tgt gtg acc    528
Leu Ala Arg Ala Phe His Arg Thr His Gly Leu Pro Val Cys Val Thr
                165                 170                 175 cgc tgc tcc aac aac tac ggc ccg tac caa cac ccc gag aag gtc ata    576
Arg Cys Ser Asn Asn Tyr Gly Pro Tyr Gln His Pro Glu Lys Val Ile
            180                 185                 190 ccg ctc ttc gtc acc aac ctc atg gac ggc aaa ccg gtg ccg ctc tac    624
Pro Leu Phe Val Thr Asn Leu Met Asp Gly Lys Pro Val Pro Leu Tyr
        195                 200                 205 ggc gac ggc gga aat gtc cgg gac tgg ctg cat gtg gac gac cac tgc    672
Gly Asp Gly Gly Asn Val Arg Asp Trp Leu His Val Asp Asp His Cys
    210                 215                 220 cgc ggt atc gcc ctg gtc gcc gag aac ggc cgc ccg gga gag gtc tac    720
Arg Gly Ile Ala Leu Val Ala Glu Asn Gly Arg Pro Gly Glu Val Tyr
225                 230                 235                 240 aac atc ggc ggc ggc acc gaa ctg acc aat ctg gaa ctc acg gaa cgg    768
Asn Ile Gly Gly Gly Thr Glu Leu Thr Asn Leu Glu Leu Thr Glu Arg
                245                 250                 255 ctg ctc gaa ctg ctc ggc gcc gac cgg tcc ctg atc gag cgg gtg ccc    816
Leu Leu Glu Leu Leu Gly Ala Asp Arg Ser Leu Ile Glu Arg Val Pro
            260                 265                 270 gac cgc aag ggc cat gac cgc cgt tac tcg gtg gac atc aca aaa atc    864
Asp Arg Lys Gly His Asp Arg Arg Tyr Ser Val Asp Ile Thr Lys Ile
        275                 280                 285 tcc act gaa ctc ggc tac cgc ccc cag atg tcg ttc gag aac ggc ctc    912
Ser Thr Glu Leu Gly Tyr Arg Pro Gln Met Ser Phe Glu Asn Gly Leu
    290                 295                 300 gcg gaa acc gcc aag tgg tac atg aca cac cgc ggt tgg tgg gaa ccg    960
Ala Glu Thr Ala Lys Trp Tyr Met Thr His Arg Gly Trp Trp Glu Pro
305                 310                 315                 320
```

```
ctc aag aag atg tga                                                   975
Leu Lys Lys Met <210> SEQ ID NO 12
<211> LENGTH: 324
<212> TYPE: PRT
<213> ORGANISM: Streptomyces sp. NRRL 30748

<400> SEQUENCE: 12

Val Arg Ile Val Val Thr Gly Gly Ala Gly Phe Ile Gly Ser His Phe
1               5                   10                  15

Val Arg Gln Thr Leu Thr Gly Ala Tyr Ala Ala Trp Ala Asp Ala Gln
            20                  25                  30

Val Val Val Val Asp Lys Leu Thr Tyr Ala Gly Asn Glu Ala Asn Leu
        35                  40                  45

Ala Glu Val Ala Asp Ser Pro Arg Leu Arg Phe Val Arg Gly Asp Ile
    50                  55                  60

Cys Asp Gly Glu Leu Val Gly Glu Leu Leu Arg Asp Thr Asp Leu Val
65                  70                  75                  80

Val His Phe Ala Ala Glu Ser His Val Asp Arg Ser Ile Ser Gly Ala
                85                  90                  95

Glu Glu Phe Val Arg Thr Asn Val Leu Gly Thr His Thr Leu Leu Asn
            100                 105                 110

Ala Ala Ala Asn Ala Glu Val Gly Lys Phe Val His Ile Ser Thr Asp
        115                 120                 125

Glu Val Tyr Gly Ser Ile Glu Asn Gly Ser Trp Ser Glu Glu Glu Pro
    130                 135                 140

Leu Glu Pro Asn Ser Pro Tyr Ser Ala Ser Lys Ala Ser Ser Asp Leu
145                 150                 155                 160

Leu Ala Arg Ala Phe His Arg Thr His Gly Leu Pro Val Cys Val Thr
                165                 170                 175

Arg Cys Ser Asn Asn Tyr Gly Pro Tyr Gln His Pro Glu Lys Val Ile
            180                 185                 190

Pro Leu Phe Val Thr Asn Leu Met Asp Gly Lys Pro Val Pro Leu Tyr
        195                 200                 205

Gly Asp Gly Gly Asn Val Arg Asp Trp Leu His Val Asp Asp His Cys
    210                 215                 220

Arg Gly Ile Ala Leu Val Ala Glu Asn Gly Arg Pro Gly Glu Val Tyr
225                 230                 235                 240

Asn Ile Gly Gly Gly Thr Glu Leu Thr Asn Leu Glu Leu Thr Glu Arg
                245                 250                 255

Leu Leu Glu Leu Leu Gly Ala Asp Arg Ser Leu Ile Glu Arg Val Pro
            260                 265                 270

Asp Arg Lys Gly His Asp Arg Arg Tyr Ser Val Asp Ile Thr Lys Ile
        275                 280                 285

Ser Thr Glu Leu Gly Tyr Arg Pro Gln Met Ser Phe Glu Asn Gly Leu
    290                 295                 300

Ala Glu Thr Ala Lys Trp Tyr Met Thr His Arg Gly Trp Trp Glu Pro
305                 310                 315                 320

Leu Lys Lys Met

<210> SEQ ID NO 13
<211> LENGTH: 13095
<212> TYPE: DNA
<213> ORGANISM: Streptomyces sp. NRRL 30748
```

```
<220> FEATURE:
<221> NAME/KEY: CDS
<222> LOCATION: (1)..(13095)

<400> SEQUENCE: 13 gtg cgt gac ggg cac atc gcg gtc gtc ggt atg gca tgt cgc gtg ccg      48
Val Arg Asp Gly His Ile Ala Val Val Gly Met Ala Cys Arg Val Pro
1               5                   10                  15 ggc gca tcg acc ccg gat gag ttc cgg cag ttg ctg cgc aat gga gag      96
Gly Ala Ser Thr Pro Asp Glu Phe Arg Gln Leu Leu Arg Asn Gly Glu
            20                  25                  30 agt gcc atc acg gag atc ccg gcg gac cgg tat gcc gat gag ctc cgg     144
Ser Ala Ile Thr Glu Ile Pro Ala Asp Arg Tyr Ala Asp Glu Leu Arg
        35                  40                  45 gac gcg ggt att cga ttc ggc ggg ttc gtc gaa agg gca gcc gag ttc     192
Asp Ala Gly Ile Arg Phe Gly Gly Phe Val Glu Arg Ala Ala Glu Phe
    50                  55                  60 gat ccg gag ttc ttc ggg att tca ccc cga gag gca cgg gcg atg gac     240
Asp Pro Glu Phe Phe Gly Ile Ser Pro Arg Glu Ala Arg Ala Met Asp
65                  70                  75                  80 ccc cag cag cgg ctc gcg ctg gaa ctg tgc tgg gag gcc ctg gaa aac     288
Pro Gln Gln Arg Leu Ala Leu Glu Leu Cys Trp Glu Ala Leu Glu Asn
                85                  90                  95 gcc gga ctc gtc ccg gcg aga ctc gag ggc agc cgc acc ggc gtc ttc     336
Ala Gly Leu Val Pro Ala Arg Leu Glu Gly Ser Arg Thr Gly Val Phe
            100                 105                 110 atc ggc gcc atc gcc gac gac tac gcg gcc ctg gtc cac cgg ggc gaa     384
Ile Gly Ala Ile Ala Asp Asp Tyr Ala Ala Leu Val His Arg Gly Glu
        115                 120                 125 ccc gcc gcc atc acc cag cac acc ctc acc ggg ctg aac cgc ggc atc     432
Pro Ala Ala Ile Thr Gln His Thr Leu Thr Gly Leu Asn Arg Gly Ile
    130                 135                 140 atc gcc aac cgg gtc tcc tac gcc ctc ggg ctg cgc ggc ccg agc gtc     480
Ile Ala Asn Arg Val Ser Tyr Ala Leu Gly Leu Arg Gly Pro Ser Val
145                 150                 155                 160 gcc gtg gac acc ggg cag tcg tcc tcc ctg gcc gcc gtg cac ctg gcc     528
Ala Val Asp Thr Gly Gln Ser Ser Ser Leu Ala Ala Val His Leu Ala
                165                 170                 175 tgc gag agc ctg cgg cgc ggc gag acc gag acc gcc gtc gcg ggc ggc     576
Cys Glu Ser Leu Arg Arg Gly Glu Thr Glu Thr Ala Val Ala Gly Gly
            180                 185                 190 gtc cag ctc aac ctc gcc ccc gac ggc ttc atc gcc gcc tcc cgg ttc     624
Val Gln Leu Asn Leu Ala Pro Asp Gly Phe Ile Ala Ala Ser Arg Phe
        195                 200                 205 ggc gcg ctc tcc ccg gac ggc cgc tcc ttc acc ttc gac gcc cgg gcc     672
Gly Ala Leu Ser Pro Asp Gly Arg Ser Phe Thr Phe Asp Ala Arg Ala
    210                 215                 220 aat ggc tat gtg cgc ggc gag ggc ggc ctc gtc gtg ctc aag cgg         720
Asn Gly Tyr Val Arg Gly Glu Gly Gly Leu Val Val Leu Lys Arg
225                 230                 235                 240 ctg ccg gac gcg ctg cgc gac ggc gac ccg gtg ctg tgt gtg atc cgc     768
Leu Pro Asp Ala Leu Arg Asp Gly Asp Pro Val Leu Cys Val Ile Arg
                245                 250                 255 ggt tcc gac gcc aac aac gac ggc ggc ggc gac agc ctc acc acc ccc     816
Gly Ser Asp Ala Asn Asn Asp Gly Gly Gly Asp Ser Leu Thr Thr Pro
            260                 265                 270 gcg gcc cac ggg cag gag gcc atg ctc cgc gcc gcc tac gag cgc gcc     864
Ala Ala His Gly Gln Glu Ala Met Leu Arg Ala Ala Tyr Glu Arg Ala
        275                 280                 285 ggg gtc gac ccc gcc cgg gtc cag tac gtc gaa ctg cac ggc acc ggc     912
Gly Val Asp Pro Ala Arg Val Gln Tyr Val Glu Leu His Gly Thr Gly
```

```
                Gly Val Asp Pro Ala Arg Val Gln Tyr Val Glu Leu His Gly Thr Gly
                    290                 295                 300 acc aag gtc ggc gac ccg gtc gag gcc gtg gcg ctg ggc gcg gtc ctc        960
Thr Lys Val Gly Asp Pro Val Glu Ala Val Ala Leu Gly Ala Val Leu
305                 310                 315                 320 ggc gcg ggc cgg gcg gac ggc gcg ccg ctg cgg gtc ggc tcc gcc aag       1008
Gly Ala Gly Arg Ala Asp Gly Ala Pro Leu Arg Val Gly Ser Ala Lys
                325                 330                 335 acg aac gtg ggc cac ctc gaa ggc gcg gcc ggg atc acc ggt ctc atc       1056
Thr Asn Val Gly His Leu Glu Gly Ala Ala Gly Ile Thr Gly Leu Ile
            340                 345                 350 aag acg gtg ctc tcg ctc gcc cac cgg gag ctg ttc ccg agc ctc aac       1104
Lys Thr Val Leu Ser Leu Ala His Arg Glu Leu Phe Pro Ser Leu Asn
        355                 360                 365 cac cag acg ccg aac ccc gcg atc ccc ctg gac acc ctg ggc ctg acg       1152
His Gln Thr Pro Asn Pro Ala Ile Pro Leu Asp Thr Leu Gly Leu Thr
    370                 375                 380 gtc cag acc gcc ctc gac gac tgg gcc ccg cag gcg gac acc cca cgg       1200
Val Gln Thr Ala Leu Asp Asp Trp Ala Pro Gln Ala Asp Thr Pro Arg
385                 390                 395                 400 ctc gcg ggc gtc agc tcg ttc ggc atg ggc ggc acc aat gtg cac atg       1248
Leu Ala Gly Val Ser Ser Phe Gly Met Gly Gly Thr Asn Val His Met
                405                 410                 415 gtg ctg gag gag gca ccc gcc gac gac ccg gcc gcg gaa cgg ccg acg       1296
Val Leu Glu Glu Ala Pro Ala Asp Asp Pro Ala Ala Glu Arg Pro Thr
                420                 425                 430 gcc ctc gac acg gtg ccg tgg gtg ctc tcg gcc cgt acc gag ggc gcg       1344
Ala Leu Asp Thr Val Pro Trp Val Leu Ser Ala Arg Thr Glu Gly Ala
            435                 440                 445 ttg cgg gcc cag gcg gag cgg ctg cgg tcg tat gtg ggg gcg cgg ccg       1392
Leu Arg Ala Gln Ala Glu Arg Leu Arg Ser Tyr Val Gly Ala Arg Pro
        450                 455                 460 gag ttg gat ccg gtg gat gtg ggt tac tcg ctg gcg ttg acc cgg tcc       1440
Glu Leu Asp Pro Val Asp Val Gly Tyr Ser Leu Ala Leu Thr Arg Ser
465                 470                 475                 480 gct ttc ggt cac cgc gcg gcg gtc gtc ggc cgc aac tgt ggg gag ctg       1488
Ala Phe Gly His Arg Ala Ala Val Val Gly Arg Asn Cys Gly Glu Leu
                485                 490                 495 ttg agc ggt ctt gag cag ctc gcc gcg ggt gtg gtc ccg ggc gcg gtg       1536
Leu Ser Gly Leu Glu Gln Leu Ala Ala Gly Val Val Pro Gly Ala Val
                500                 505                 510 gct gac gag gag ggc agg acg gcg ttt ctg ttc act ggt cag ggt gct       1584
Ala Asp Glu Glu Gly Arg Thr Ala Phe Leu Phe Thr Gly Gln Gly Ala
            515                 520                 525 caa cgg ctg ggt atg ggg cgg ggg ttg tat tcg gcg ttt ccg gtg ttc       1632
Gln Arg Leu Gly Met Gly Arg Gly Leu Tyr Ser Ala Phe Pro Val Phe
        530                 535                 540 gcg gtg tcg ttc gac gag gtg tgc gcg gag ctg gac cgt cat ctg gat       1680
Ala Val Ser Phe Asp Glu Val Cys Ala Glu Leu Asp Arg His Leu Asp
545                 550                 555                 560 ggt tcg gtg ggg gag gtg gtg ttc ggc gag gat gcc gag gcg ttg gat       1728
Gly Ser Val Gly Glu Val Val Phe Gly Glu Asp Ala Glu Ala Leu Asp
                565                 570                 575 cgg acg gtg ttc act cag gcc ggg ctg ttc gct ttg gag gtg ggg ctg       1776
Arg Thr Val Phe Thr Gln Ala Gly Leu Phe Ala Leu Glu Val Gly Leu
            580                 585                 590 ttc cgg ctg gtg gag tcg tgg ggt ctg gcg ccg gat ttc ctg gtg ggg       1824
Phe Arg Leu Val Glu Ser Trp Gly Leu Ala Pro Asp Phe Leu Val Gly
        595                 600                 605
```

```
cat tcg gtg ggg gag ttg gcg gcc gcc cat gtg gcg ggg gtg ttt tcg      1872
His Ser Val Gly Glu Leu Ala Ala Ala His Val Ala Gly Val Phe Ser
    610                 615                 620 ctg gag gac gcc tgt gcg ctg gtg gcg gcg cgt ggt cgg ctg atg cag      1920
Leu Glu Asp Ala Cys Ala Leu Val Ala Ala Arg Gly Arg Leu Met Gln
625                 630                 635                 640 gcg ctg ccc ggc ggt ggt gcg atg gtg tcg ctg aag gct ccg gag gcc      1968
Ala Leu Pro Gly Gly Gly Ala Met Val Ser Leu Lys Ala Pro Glu Ala
                645                 650                 655 gag gtg ctg ccg cat ctg gcc ggt tac gag gac cgg gtg agc gtt gcg      2016
Glu Val Leu Pro His Leu Ala Gly Tyr Glu Asp Arg Val Ser Val Ala
            660                 665                 670 gcg gtc aat ggc ccg tcg gcg acc gtg atc tcc ggt gag gag tcg gcg      2064
Ala Val Asn Gly Pro Ser Ala Thr Val Ile Ser Gly Glu Glu Ser Ala
        675                 680                 685 gtg ctc gcg gtg gcg gag gcg gtg ggg gtc aag agc aag cgg ctg agc      2112
Val Leu Ala Val Ala Glu Ala Val Gly Val Lys Ser Lys Arg Leu Ser
    690                 695                 700 gtc tcg cat gcc ttt cac tcg ccg ctg atg gag ggg atg ctg gct gcg      2160
Val Ser His Ala Phe His Ser Pro Leu Met Glu Gly Met Leu Ala Ala
705                 710                 715                 720 ttc gcc gag gtg gcg gcc ggg atc gcc tac gcc acg cca ggc atc gcg      2208
Phe Ala Glu Val Ala Ala Gly Ile Ala Tyr Ala Thr Pro Gly Ile Ala
                725                 730                 735 atc gtc tcg aac gtg acg ggc gag ttg gcg ggg gag gag gtg tgc tcg      2256
Ile Val Ser Asn Val Thr Gly Glu Leu Ala Gly Glu Glu Val Cys Ser
            740                 745                 750 ccg gag tac tgg gtg cgc cat gtg cgt cag gcg gtg cgc ttc ggg gat      2304
Pro Glu Tyr Trp Val Arg His Val Arg Gln Ala Val Arg Phe Gly Asp
        755                 760                 765 ggc ata cgg ttc ctc gag acc cag ggc gtc acc cgc ttt gtg gag ctc      2352
Gly Ile Arg Phe Leu Glu Thr Gln Gly Val Thr Arg Phe Val Glu Leu
    770                 775                 780 gga ccc gcg ggt gtg ctc tcc gcc atg ggc cag gaa tgc gtc tcc ggc      2400
Gly Pro Ala Gly Val Leu Ser Ala Met Gly Gln Glu Cys Val Ser Gly
785                 790                 795                 800 ccg gcc gcg ttc gta cct ctg ttg cgc aag gac cgc gag gag acc gag      2448
Pro Ala Ala Phe Val Pro Leu Leu Arg Lys Asp Arg Glu Glu Thr Glu
                805                 810                 815 gcg ctg ctc tcc ggt gtc gcc cag gtg cac gct cac ggt ggc gag gtg      2496
Ala Leu Leu Ser Gly Val Ala Gln Val His Ala His Gly Gly Glu Val
            820                 825                 830 gac tgg gag gcg gtg ttc gcc ggg cgc ggt gcg cat cgg gtg gag ctg      2544
Asp Trp Glu Ala Val Phe Ala Gly Arg Gly Ala His Arg Val Glu Leu
        835                 840                 845 ccc aca tac gcc ttc cag cgg cag cgc tac tgg ctg gac acc gac ctc      2592
Pro Thr Tyr Ala Phe Gln Arg Gln Arg Tyr Trp Leu Asp Thr Asp Leu
    850                 855                 860 ccc ggc acc gag gac gcc gcc acc gat gaa ccc ctc tcc tgg cgc gag      2640
Pro Gly Thr Glu Asp Ala Ala Thr Asp Glu Pro Leu Ser Trp Arg Glu
865                 870                 875                 880 gag ttc gcg gcc ctg acc gac tcc gcc gag cgc gag cgc gtg gcg ctg      2688
Glu Phe Ala Ala Leu Thr Asp Ser Ala Glu Arg Glu Arg Val Ala Leu
                885                 890                 895 gag ctg gtc cgt acg cac acc gcc tgg gtc ctg ggc tct ccg gga ccc      2736
Glu Leu Val Arg Thr His Thr Ala Trp Val Leu Gly Ser Pro Gly Pro
            900                 905                 910 gac gcc gtc gac ccc gag aag atc ttc aag gac ctc ggc ttc gac tcg      2784
Asp Ala Val Asp Pro Glu Lys Ile Phe Lys Asp Leu Gly Phe Asp Ser
        915                 920                 925
```

```
ctg atg tcc gtc gag ctg tgc aac ctc ctc agc acc gcc acc gga acg    2832
Leu Met Ser Val Glu Leu Cys Asn Leu Leu Ser Thr Ala Thr Gly Thr
    930                 935                 940 cgg ctc gcc ggg acc gtc ctc ttc gac cac ccc acc ccg ctg gcc ctc    2880
Arg Leu Ala Gly Thr Val Leu Phe Asp His Pro Thr Pro Leu Ala Leu
945                 950                 955                 960 tcc cac cac ctc cgg gag gtg gtg gtg ggc act cgg ccg gtc gtg gcc    2928
Ser His His Leu Arg Glu Val Val Val Gly Thr Arg Pro Val Val Ala
                965                 970                 975 ccg cgc ccg gcc gcc acc cgg acc gtc acc acg ggc gac gac gac ccg    2976
Pro Arg Pro Ala Ala Thr Arg Thr Val Thr Thr Gly Asp Asp Asp Pro
            980                 985                 990 atc gcc atc gtg gcg atg agc tgc cgc ctc ccc gga ggg gtg cgc acc    3024
Ile Ala Ile Val Ala Met Ser Cys Arg Leu Pro Gly Gly Val Arg Thr
        995                 1000                1005 ccc gag cag ctg tgg gag ctg gtc agc gag ggc cgg gac gcc atc        3069
Pro Glu Gln Leu Trp Glu Leu Val Ser Glu Gly Arg Asp Ala Ile
    1010                1015                1020 gcc ggc ttc ccc gcc aac cgg ggc tgg gac ctc gag ggg ctc tac        3114
Ala Gly Phe Pro Ala Asn Arg Gly Trp Asp Leu Glu Gly Leu Tyr
    1025                1030                1035 gac ccg gac ccg gcc cgc cac ggc acc agc tat gtg cgc gag ggc        3159
Asp Pro Asp Pro Ala Arg His Gly Thr Ser Tyr Val Arg Glu Gly
    1040                1045                1050 gga ttc ctc tac gag gcg gac cag ttc gac ccg gcc ttc ttc ggc        3204
Gly Phe Leu Tyr Glu Ala Asp Gln Phe Asp Pro Ala Phe Phe Gly
    1055                1060                1065 atc agc ccc cgc gag gcc cag gcg atg gac ccc cag cag cgg ctg        3249
Ile Ser Pro Arg Glu Ala Gln Ala Met Asp Pro Gln Gln Arg Leu
    1070                1075                1080 ctg atg gag acc gcg tgg gag gcg ttc gag cgc gcc ggg atc gac        3294
Leu Met Glu Thr Ala Trp Glu Ala Phe Glu Arg Ala Gly Ile Asp
    1085                1090                1095 ccc acc acg ctc aag ggc agt gac gcg ggt gtc ttc gtc ggc gcc        3339
Pro Thr Thr Leu Lys Gly Ser Asp Ala Gly Val Phe Val Gly Ala
    1100                1105                1110 atg ccg cag gac tac ggg ccc cgg atg gac gag gcg tcg gaa ggg        3384
Met Pro Gln Asp Tyr Gly Pro Arg Met Asp Glu Ala Ser Glu Gly
    1115                1120                1125 ttc gag ggc tat ctg ctg acc ggt ggc acc acc agt gtc gcc tcc        3429
Phe Glu Gly Tyr Leu Leu Thr Gly Gly Thr Thr Ser Val Ala Ser
    1130                1135                1140 ggc cgg atc gcc tac acc tgg ggg ctc gag ggc ccg gcg gtc acc        3474
Gly Arg Ile Ala Tyr Thr Trp Gly Leu Glu Gly Pro Ala Val Thr
    1145                1150                1155 gtc gac acg gcc tgc tcg tcc tcg ctg gtg gcc ctg cac atg gcc        3519
Val Asp Thr Ala Cys Ser Ser Ser Leu Val Ala Leu His Met Ala
    1160                1165                1170 gta cgg tcg ctg cgc cag ggc gag tgc tcg ctg gcg ctg gcc ggc        3564
Val Arg Ser Leu Arg Gln Gly Glu Cys Ser Leu Ala Leu Ala Gly
    1175                1180                1185 ggc gcc acc gtg atg tcc agc ccc ggg atc ttc gtg gag ctg agc        3609
Gly Ala Thr Val Met Ser Ser Pro Gly Ile Phe Val Glu Leu Ser
    1190                1195                1200 cgc cag aag gcg ctg tcg ccg gac ggc cgc tgc aag gcg ttc tcg        3654
Arg Gln Lys Ala Leu Ser Pro Asp Gly Arg Cys Lys Ala Phe Ser
    1205                1210                1215 tcc gac gcc gac ggc acc ggc tgg ggc gag ggc gtg ggc atg gtg        3699
Ser Asp Ala Asp Gly Thr Gly Trp Gly Glu Gly Val Gly Met Val
```

-continued

| | | | | | | | | | | | | |
|---|---|---|---|---|---|---|---|---|---|---|---|---|
| | | | | 1220 | | | | 1225 | | | 1230 | |
| ctg | ctg | gag | cgg | ctg | tcg | gac | gcg | cgg | cgc | aac | ggc | cac cag gtg | 3744 |
| Leu | Leu | Glu | Arg | Leu | Ser | Asp | Ala | Arg | Arg | Asn | Gly | His Gln Val |
| 1235 | | | | | 1240 | | | | | 1245 | | |
| ctg | gcg | ctg | gtc | cgt | ggt | tcc | gcc | acc | aac | cag | gac | ggc gcg agc | 3789 |
| Leu | Ala | Leu | Val | Arg | Gly | Ser | Ala | Thr | Asn | Gln | Asp | Gly Ala Ser |
| 1250 | | | | | 1255 | | | | | 1260 | | |
| aac | gga | ctc | acc | gcc | ccg | agc | ggc | ccg | gcc | cag | cag | cgg gtc atc | 3834 |
| Asn | Gly | Leu | Thr | Ala | Pro | Ser | Gly | Pro | Ala | Gln | Gln | Arg Val Ile |
| 1265 | | | | | 1270 | | | | | 1275 | | |
| cgg | cag | gcg | ctg | gcc | gac | gcg | ggg | ctg | agc | acg | gcc | gat gtg gac | 3879 |
| Arg | Gln | Ala | Leu | Ala | Asp | Ala | Gly | Leu | Ser | Thr | Ala | Asp Val Asp |
| 1280 | | | | | 1285 | | | | | 1290 | | |
| gcg | gtc | gag | gca | cac | ggc | acc | ggc | acc | tcg | ctc | ggc | gac ccc atc | 3924 |
| Ala | Val | Glu | Ala | His | Gly | Thr | Gly | Thr | Ser | Leu | Gly | Asp Pro Ile |
| 1295 | | | | | 1300 | | | | | 1305 | | |
| gag | gcg | ggc | gcg | ctg | ctg | gcc | acc | tac | ggc | cag | gac | cgc gcc ggg | 3969 |
| Glu | Ala | Gly | Ala | Leu | Leu | Ala | Thr | Tyr | Gly | Gln | Asp | Arg Ala Gly |
| 1310 | | | | | 1315 | | | | | 1320 | | |
| gac | cgg | ccg | ctg | tgg | ctg | ggc | tcg | ctg | aag | tcc | aac | gtc ggc cac | 4014 |
| Asp | Arg | Pro | Leu | Trp | Leu | Gly | Ser | Leu | Lys | Ser | Asn | Val Gly His |
| 1325 | | | | | 1330 | | | | | 1335 | | |
| ccc | cag | gcg | gcg | gcg | ggc | gtg | gcc | ggt | gtc | atc | aag | atg gtg ctg | 4059 |
| Pro | Gln | Ala | Ala | Ala | Gly | Val | Ala | Gly | Val | Ile | Lys | Met Val Leu |
| 1340 | | | | | 1345 | | | | | 1350 | | |
| gcg | ctg | cgc | cac | ggc | gtg | ctg | ccc | cag | acc | ctg | cac | gta cac gag | 4104 |
| Ala | Leu | Arg | His | Gly | Val | Leu | Pro | Gln | Thr | Leu | His | Val His Glu |
| 1355 | | | | | 1360 | | | | | 1365 | | |
| ccc | tcg | ccg | cat | gtc | gac | tgg | tcg | tcc | ggg | gcc | gtg | gag ctg ctg | 4149 |
| Pro | Ser | Pro | His | Val | Asp | Trp | Ser | Ser | Gly | Ala | Val | Glu Leu Leu |
| 1370 | | | | | 1375 | | | | | 1380 | | |
| acc | gag | tcc | cgg | ccg | tgg | ccg | gag | ccc | gag | agc | gag | cgg ccg cgc | 4194 |
| Thr | Glu | Ser | Arg | Pro | Trp | Pro | Glu | Pro | Glu | Ser | Glu | Arg Pro Arg |
| 1385 | | | | | 1390 | | | | | 1395 | | |
| cgc | gcg | ggc | gtg | tcg | tcc | ttc | ggc | atc | agc | ggt | acc | aac gca cac | 4239 |
| Arg | Ala | Gly | Val | Ser | Ser | Phe | Gly | Ile | Ser | Gly | Thr | Asn Ala His |
| 1400 | | | | | 1405 | | | | | 1410 | | |
| gcc | atc | ctg | gag | cag | gcc | ccg | gcc | gaa | ccg | gcc | gcc | ggc cac gac | 4284 |
| Ala | Ile | Leu | Glu | Gln | Ala | Pro | Ala | Glu | Pro | Ala | Ala | Gly His Asp |
| 1415 | | | | | 1420 | | | | | 1425 | | |
| gcg | ccg | cgc | ccg | gcg | gcc | ccg | gag | ctg | ccc | gtg | ctg | ccc tgg gtg | 4329 |
| Ala | Pro | Arg | Pro | Ala | Ala | Pro | Glu | Leu | Pro | Val | Leu | Pro Trp Val |
| 1430 | | | | | 1435 | | | | | 1440 | | |
| ctg | tcc | ggg | cgc | acc | gaa | cag | gcc | ctg | cgc | acc | cgg | gcc gag cag | 4374 |
| Leu | Ser | Gly | Arg | Thr | Glu | Gln | Ala | Leu | Arg | Thr | Arg | Ala Glu Gln |
| 1445 | | | | | 1450 | | | | | 1455 | | |
| ttg | cgg | aac | cag | ctg | gcc | gac | cac | ccc | ggc | acc | gac | ctc gcc gcg | 4419 |
| Leu | Arg | Asn | Gln | Leu | Ala | Asp | His | Pro | Gly | Thr | Asp | Leu Ala Ala |
| 1460 | | | | | 1465 | | | | | 1470 | | |
| ctc | ggc | cac | gcc | ctc | gcc | acc | acc | cgc | acg | gcc | ttc | ggc cac cgg | 4464 |
| Leu | Gly | His | Ala | Leu | Ala | Thr | Thr | Arg | Thr | Ala | Phe | Gly His Arg |
| 1475 | | | | | 1480 | | | | | 1485 | | |
| gcg | gtg | gtc | ctc | ggc | cgg | gac | ccg | gag | cgg | ctc | ctg | gac ggc ctc | 4509 |
| Ala | Val | Val | Leu | Gly | Arg | Asp | Pro | Glu | Arg | Leu | Leu | Asp Gly Leu |
| 1490 | | | | | 1495 | | | | | 1500 | | |
| ggc | gcg | ctc | gcg | cag | ggc | acc | ccg | gcg | ccc | cac | gtg | gtc cag ggc | 4554 |
| Gly | Ala | Leu | Ala | Gln | Gly | Thr | Pro | Ala | Pro | His | Val | Val Gln Gly |
| 1505 | | | | | 1510 | | | | | 1515 | | |
| acg | gcg | ggc | ggc | cgg | cgg | aag | acc | gtg | ttc | gtc | ttc | ccc gga cag | 4599 |

```
       Thr Ala Gly Gly Arg Arg Lys Thr Val Phe Val Phe Pro Gly Gln
           1520                1525                1530 ggc tcg cag tgg atc ggg atg gca ctt ccg ctg tgg gac gcc tcg          4644
Gly Ser Gln Trp Ile Gly Met Ala Leu Pro Leu Trp Asp Ala Ser
1535                1540                1545 ccc gtc ttc gcg gag cgg ctg gag gag tgc gcc gac gcc ctg gag          4689
Pro Val Phe Ala Glu Arg Leu Glu Glu Cys Ala Asp Ala Leu Glu
1550                1555                1560 ccg ttc ctg gac tgg tcg ttg cgc gat gtg ctg cgc ggc gag ccg          4734
Pro Phe Leu Asp Trp Ser Leu Arg Asp Val Leu Arg Gly Glu Pro
1565                1570                1575 ggc gcc ccg tcg ctg tcc cgt atc gac gtg gtg cag ccc gcg ctg          4779
Gly Ala Pro Ser Leu Ser Arg Ile Asp Val Val Gln Pro Ala Leu
1580                1585                1590 ttc gcg gtg atg gtg tcg ctg gcg gcg ctg tgg cgc agt cac ggc          4824
Phe Ala Val Met Val Ser Leu Ala Ala Leu Trp Arg Ser His Gly
1595                1600                1605 gtc gaa ccg gcc gcg gtc ggc cat tcg cag ggc gag atc gcc              4869
Val Glu Pro Ala Ala Val Gly His Ser Gln Gly Glu Ile Ala
1610                1615                1620 gcc gcg tac gtg gcc gga ggg ctt tcg ctc cag gac gcc gcc aag          4914
Ala Ala Tyr Val Ala Gly Gly Leu Ser Leu Gln Asp Ala Ala Lys
1625                1630                1635 gtg gtg gcc cgg cgc agc cag gca tgg gcc gag ctg agc ggc aag          4959
Val Val Ala Arg Arg Ser Gln Ala Trp Ala Glu Leu Ser Gly Lys
1640                1645                1650 ggc ggc atg ctc tcg gtg ctc gcg tcg gcc ggg acg gtc gcg gag          5004
Gly Gly Met Leu Ser Val Leu Ala Ser Ala Gly Thr Val Ala Glu
1655                1660                1665 cgg ctg cgg ccg tgg agc gaa cgg ctc ggc atc gcc gcc gtc aac          5049
Arg Leu Arg Pro Trp Ser Glu Arg Leu Gly Ile Ala Ala Val Asn
1670                1675                1680 agc ccc gcc acc gtg acc gtc tcc ggc gac ccg gag gcc ctg gac          5094
Ser Pro Ala Thr Val Thr Val Ser Gly Asp Pro Glu Ala Leu Asp
1685                1690                1695 gcc ttc atg gcc gag ctc gcc gcc gac ggg gtg aag tcc cgc cgg          5139
Ala Phe Met Ala Glu Leu Ala Ala Asp Gly Val Lys Ser Arg Arg
1700                1705                1710 gtg ccg ggc gtg gac acc gcc gga cac tcc ccg cag gtc gac ggg          5184
Val Pro Gly Val Asp Thr Ala Gly His Ser Pro Gln Val Asp Gly
1715                1720                1725 ttg cgc gag cgg ctg ctg cgc gag gtg gcg ggg gta cgg ccg cgc          5229
Leu Arg Glu Arg Leu Leu Arg Glu Val Ala Gly Val Arg Pro Arg
1730                1735                1740 ccc tcg cgg atc gcg tac tac tcc acg gtg acc ggc ggg ccg ctg          5274
Pro Ser Arg Ile Ala Tyr Tyr Ser Thr Val Thr Gly Gly Pro Leu
1745                1750                1755 gac acc acc gag ctg gac acc gac tac tgg tac cgg aac atg cgc          5319
Asp Thr Thr Glu Leu Asp Thr Asp Tyr Trp Tyr Arg Asn Met Arg
1760                1765                1770 gag ccg gtg gac ttc gag cgg gcc acc cgg gcg ctg ctg gcc gac          5364
Glu Pro Val Asp Phe Glu Arg Ala Thr Arg Ala Leu Leu Ala Asp
1775                1780                1785 ggc cac acg gcg ttc atc gaa tgc gcc ccg cac ccc atg ctc gcc          5409
Gly His Thr Ala Phe Ile Glu Cys Ala Pro His Pro Met Leu Ala
1790                1795                1800 atg tcg ctc cag cag acc atc gag gac gcg ggc gga aac gcc gcc          5454
Met Ser Leu Gln Gln Thr Ile Glu Asp Ala Gly Gly Asn Ala Ala
1805                1810                1815
```

-continued

| | | |
|---|---|---|
| gtc gtc ggc acg ctg cgc cgg gac gag ggc ggc ccg gag cgc ttc<br>Val Val Gly Thr Leu Arg Arg Asp Glu Gly Gly Pro Glu Arg Phe<br>1820                          1825                     1830 | 5499 |
| gcg ggc tcg ttc gcc gag gcg tac gtc cag ggt gtc gaa ccg tcg<br>Ala Gly Ser Phe Ala Glu Ala Tyr Val Gln Gly Val Glu Pro Ser<br>1835                          1840                     1845 | 5544 |
| tgg gac acc gtg ttc ggg ggc gcg ccg ggg cgc ggt gag cgt gcc<br>Trp Asp Thr Val Phe Gly Gly Ala Pro Gly Arg Gly Glu Arg Ala<br>1850                          1855                     1860 | 5589 |
| ctg gag ctg ccg acg tat ccg ttc cag cgg cag cgg tac tgg ctg<br>Leu Glu Leu Pro Thr Tyr Pro Phe Gln Arg Gln Arg Tyr Trp Leu<br>1865                          1870                     1875 | 5634 |
| gac aag ccg gtc gcg gcg agc gat gtg gcg gcg gcc gga ctc gac<br>Asp Lys Pro Val Ala Ala Ser Asp Val Ala Ala Ala Gly Leu Asp<br>1880                          1885                     1890 | 5679 |
| gcg gcc ggg cat ccg ctg ctc ggc gcg gcg gtc ccg ctg gcc ggg<br>Ala Ala Gly His Pro Leu Leu Gly Ala Ala Val Pro Leu Ala Gly<br>1895                          1900                     1905 | 5724 |
| gcg gac gac cac ctg ttc acc ggc cgg atc tcc gca cag gac cac<br>Ala Asp Asp His Leu Phe Thr Gly Arg Ile Ser Ala Gln Asp His<br>1910                          1915                     1920 | 5769 |
| ccc tgg ctc acc gag cgc acc gga ctc gac gcg gcc gtg ctg ccc<br>Pro Trp Leu Thr Glu Arg Thr Gly Leu Asp Ala Ala Val Leu Pro<br>1925                          1930                     1935 | 5814 |
| ggc agc gcc ctc gcc gaa ctg gcg atc cgc gcg ggc gac cag gtc<br>Gly Ser Ala Leu Ala Glu Leu Ala Ile Arg Ala Gly Asp Gln Val<br>1940                          1945                     1950 | 5859 |
| ggc tgc gac cgg atc ggg gaa ctg tcc ctg gac gcg ccg ctg gta<br>Gly Cys Asp Arg Ile Gly Glu Leu Ser Leu Asp Ala Pro Leu Val<br>1955                          1960                     1965 | 5904 |
| ctg ccc gag aag ggt gcc gcg gtg atc cag gtg cgt atc ggc gcc<br>Leu Pro Glu Lys Gly Ala Ala Val Ile Gln Val Arg Ile Gly Ala<br>1970                          1975                     1980 | 5949 |
| ccg gac gac gag ggc tcg cgc gcc ctc agc gtc cac gcg cgc gcc<br>Pro Asp Asp Glu Gly Ser Arg Ala Leu Ser Val His Ala Arg Ala<br>1985                          1990                     1995 | 5994 |
| gag ggc gcc gac gcc gac gag ccg tgg acg cgg tac gcc acg gcg<br>Glu Gly Ala Asp Ala Asp Glu Pro Trp Thr Arg Tyr Ala Thr Ala<br>2000                          2005                     2010 | 6039 |
| gtc ctg ggc atg ggt gct ccg gcc gcc gac gtc ggc ctc gtc gcg<br>Val Leu Gly Met Gly Ala Pro Ala Ala Asp Val Gly Leu Val Ala<br>2015                          2020                     2025 | 6084 |
| tgg ccc ccg gcc gac gcc gtc ccg gcg gag gtg gcg gga ggc gcc<br>Trp Pro Pro Ala Asp Ala Val Pro Ala Glu Val Ala Gly Gly Ala<br>2030                          2035                     2040 | 6129 |
| gtc gcg gcc tgg cgg ctc ggt gag gac ctc tac gtc gag gtc ggg<br>Val Ala Ala Trp Arg Leu Gly Glu Asp Leu Tyr Val Glu Val Gly<br>2045                          2050                     2055 | 6174 |
| ctg acc gag gcc gag gag gcc gac gcc ggg cgc tac gga ctg cac<br>Leu Thr Glu Ala Glu Glu Ala Asp Ala Gly Arg Tyr Gly Leu His<br>2060                          2065                     2070 | 6219 |
| ccg gcg ctg ctg gag tcg gcg ctc gac gcg gtg gag acc ccg ggc<br>Pro Ala Leu Leu Glu Ser Ala Leu Asp Ala Val Glu Thr Pro Gly<br>2075                          2080                     2085 | 6264 |
| gac ggt ggc ggg tcg tgg ctg gcc gcc gta tgg agt ggt gtc gcc<br>Asp Gly Gly Gly Ser Trp Leu Ala Ala Val Trp Ser Gly Val Ala<br>2090                          2095                     2100 | 6309 |
| ctg cac gcc acg ggc gcc acg gcg ctg cgg gtg cgg ctg acg ccg<br>Leu His Ala Thr Gly Ala Thr Ala Leu Arg Val Arg Leu Thr Pro<br>2105                          2110                     2115 | 6354 |

```
acg ggt ccc gat gcg tac gcg gtc gtc gcg gcc gac ctg agc ggt      6399
Thr Gly Pro Asp Ala Tyr Ala Val Val Ala Ala Asp Leu Ser Gly
    2120            2125                2130 gcc ccg gtg gcc tcg gtg gac cgg ctc gtg ctg cgc gcg gtg gac      6444
Ala Pro Val Ala Ser Val Asp Arg Leu Val Leu Arg Ala Val Asp
    2135            2140                2145 acg ccc gaa ccg atc ggc ggc cgc tcc gcc ctc cac ccg tcg ctg      6489
Thr Pro Glu Pro Ile Gly Gly Arg Ser Ala Leu His Pro Ser Leu
    2150            2155                2160 ttc cgg ctg gag tgg ccc gcg gtg tcc gcc gcg gac acc acc gcg      6534
Phe Arg Leu Glu Trp Pro Ala Val Ser Ala Ala Asp Thr Thr Ala
    2165            2170                2175 acc gcg cct ccg gcg acc tgg gcg gtg ctc ggc gac gac ccg ctc      6579
Thr Ala Pro Pro Ala Thr Trp Ala Val Leu Gly Asp Asp Pro Leu
    2180            2185                2190 ggg ctc tcc gcg gcc gtg gac gcg gtg ccg tac gac gag acg gcg      6624
Gly Leu Ser Ala Ala Val Asp Ala Val Pro Tyr Asp Glu Thr Ala
    2195            2200                2205 gat gcg ccg gac gcg gtc ctg gtg ccg tgc gtc gcg gga gtc gac      6669
Asp Ala Pro Asp Ala Val Leu Val Pro Cys Val Ala Gly Val Asp
    2210            2215                2220 ggc gat gtg gcg gag gcg gcc cac gcg gcc acc cac cga gcg ctt      6714
Gly Asp Val Ala Glu Ala Ala His Ala Ala Thr His Arg Ala Leu
    2225            2230                2235 gcg ctg atc cag cgc tgg acc tcc gat gac cgc ctc gcc tcc tcc      6759
Ala Leu Ile Gln Arg Trp Thr Ser Asp Asp Arg Leu Ala Ser Ser
    2240            2245                2250 cgg ctg gtg ttc ctc acc cgc ggc gcg gtc gcg ggt gcc ccc ggt      6804
Arg Leu Val Phe Leu Thr Arg Gly Ala Val Ala Gly Ala Pro Gly
    2255            2260                2265 gaa gag gtc ccg gac gtg gcc cac ggc gcc gta tgg ggc ctg gtg      6849
Glu Glu Val Pro Asp Val Ala His Gly Ala Val Trp Gly Leu Val
    2270            2275                2280 cgc tcg gcc cag tcg gaa cac ccc ggc cgc ttc gtc ctc gtc gac      6894
Arg Ser Ala Gln Ser Glu His Pro Gly Arg Phe Val Leu Val Asp
    2285            2290                2295 ctc gac gcc gag ccg gag tcg gtg acc gct ctc ccg gcc gcg gtg      6939
Leu Asp Ala Glu Pro Glu Ser Val Thr Ala Leu Pro Ala Ala Val
    2300            2305                2310 gct tct ggc gaa cct cag tgc gcg gta cgc gag gga ctg gtg agg      6984
Ala Ser Gly Glu Pro Gln Cys Ala Val Arg Glu Gly Leu Val Arg
    2315            2320                2325 gtg ccc cgg ctg ggg cgg gtg gcg agg ggg acg ggg gcc gcc gag      7029
Val Pro Arg Leu Gly Arg Val Ala Arg Gly Thr Gly Ala Ala Glu
    2330            2335                2340 gcc acc gcg ccc cgg gcc acc ggg ctc gcc gac ggc cac cga ccg      7074
Ala Thr Ala Pro Arg Ala Thr Gly Leu Ala Asp Gly His Arg Pro
    2345            2350                2355 ctg gac ccc gaa ggc acc gtt ctc atc acc ggc gcc acc ggg acc      7119
Leu Asp Pro Glu Gly Thr Val Leu Ile Thr Gly Ala Thr Gly Thr
    2360            2365                2370 ctc ggc ggg ctc gtc gcc cgc cat ctg gtg gcc gag cat ggc gta      7164
Leu Gly Gly Leu Val Ala Arg His Leu Val Ala Glu His Gly Val
    2375            2380                2385 cgg cat ctg ctg ctg gtc agt cgg cgt ggg ccc gcg gcc gac ggt      7209
Arg His Leu Leu Leu Val Ser Arg Arg Gly Pro Ala Ala Asp Gly
    2390            2395                2400 atg ggc gaa ctc cgc tcc gag ctg gcc gag ttg gga gcc acc gtc      7254
Met Gly Glu Leu Arg Ser Glu Leu Ala Glu Leu Gly Ala Thr Val
```

-continued

```
                  2405                2410                2415
acc gtc gcc gcc tgc gat gcc gcc gac cgg gag gcg ctc gcc ggg      7299
Thr Val Ala Ala Cys Asp Ala Ala Asp Arg Glu Ala Leu Ala Gly
    2420                2425                2430 ctt ctc ggc gcg ata ccc gcc gcg cat ccg ctg acc gcc gtg atc      7344
Leu Leu Gly Ala Ile Pro Ala Ala His Pro Leu Thr Ala Val Ile
    2435                2440                2445 cac gcg gcg ggt gtg ctc gac gac ggc gtc gtg gac gcg ctg aac      7389
His Ala Ala Gly Val Leu Asp Asp Gly Val Val Asp Ala Leu Asn
    2450                2455                2460 ccc gag cgg ctc gac cgc gtg ctg cgg ccc aag gtc gac gcc gcg      7434
Pro Glu Arg Leu Asp Arg Val Leu Arg Pro Lys Val Asp Ala Ala
    2465                2470                2475 tgg aat ctg cac gag ctg acc gcg ggg cac gac ctg tcc gcg ttc      7479
Trp Asn Leu His Glu Leu Thr Ala Gly His Asp Leu Ser Ala Phe
    2480                2485                2490 gtg ctc tac tcc tcc gtc gtc gcc acc atc ggc aac gcc gga cag      7524
Val Leu Tyr Ser Ser Val Val Ala Thr Ile Gly Asn Ala Gly Gln
    2495                2500                2505 gcc aac tac gcc gcc gcc aac gcc ttc ctg gac tcg ctc gcc cag      7569
Ala Asn Tyr Ala Ala Ala Asn Ala Phe Leu Asp Ser Leu Ala Gln
    2510                2515                2520 cac cgc agg gcc cgt ggc ctg gcc gcc cag tcc ctc gcc tgg ggc      7614
His Arg Arg Ala Arg Gly Leu Ala Ala Gln Ser Leu Ala Trp Gly
    2525                2530                2535 ctg tgg gag cag cgc agc ggc atg agc ggg cat ctg gac gac gcc      7659
Leu Trp Glu Gln Arg Ser Gly Met Ser Gly His Leu Asp Asp Ala
    2540                2545                2550 gat gtg cgg cgc atg gcg cgc tcc ggc atc cgt ccg ctg ccc agc      7704
Asp Val Arg Arg Met Ala Arg Ser Gly Ile Arg Pro Leu Pro Ser
    2555                2560                2565 gcg gag ggc atg gaa ctc ttc gac gcc gcg cgg gag gcg ggc gat      7749
Ala Glu Gly Met Glu Leu Phe Asp Ala Ala Arg Glu Ala Gly Asp
    2570                2575                2580 gcc acg ctc gta ccc gtc cgg ctc gac ctc gcc gat ctg cgc aag      7794
Ala Thr Leu Val Pro Val Arg Leu Asp Leu Ala Asp Leu Arg Lys
    2585                2590                2595 cgc gcc gcg agc acc gcc gcc acc ccc ggc cag gac gcc gta ccg      7839
Arg Ala Ala Ser Thr Ala Ala Thr Pro Gly Gln Asp Ala Val Pro
    2600                2605                2610 gcc cat ctg cgc ggc ctg gtc cgg aca ccg gtc cgc cgc gtc gta      7884
Ala His Leu Arg Gly Leu Val Arg Thr Pro Val Arg Arg Val Val
    2615                2620                2625 cgg gcc ggt ggc gga ggc ggg gcc gcg gag agc gac gag agc tcg      7929
Arg Ala Gly Gly Gly Gly Ala Ala Glu Ser Asp Glu Ser Ser
    2630                2635                2640 ttc ggg cgg cgg ctg gcc gcc ctg ccg acg gcc gac cgg gac ccg      7974
Phe Gly Arg Arg Leu Ala Ala Leu Pro Thr Ala Asp Arg Asp Pro
    2645                2650                2655 ttc ctg ctg gac ctg gtg cgg gaa cac gcg gcg ggc gtg ctg ggg      8019
Phe Leu Leu Asp Leu Val Arg Glu His Ala Ala Gly Val Leu Gly
    2660                2665                2670 ctc gcc gcc ccg gac gac atc gag gcc acc cgc gcc ttc cgc gag      8064
Leu Ala Ala Pro Asp Asp Ile Glu Ala Thr Arg Ala Phe Arg Glu
    2675                2680                2685 gtc ggt ttc gac tcc ctg acc gcc gtg gag ttg cgc aac cgg ctg      8109
Val Gly Phe Asp Ser Leu Thr Ala Val Glu Leu Arg Asn Arg Leu
    2690                2695                2700 ggc gcc gcc acc ggg ctg cgg ctg ccg acc act ctc ctc ttc gac      8154
```

```
Gly Ala  Ala Thr Gly Leu Arg  Leu Pro Thr Thr Leu  Leu Phe Asp
        2705              2710             2715 tac ccg acc ccc gcc gtg ctg  gtg gac cac ttg cgg  cgc gag gca           8199
Tyr Pro Thr Pro Ala Val Leu  Val Asp His Leu Arg  Arg Glu Ala
        2720              2725             2730 ctg ggc gag cag gcg gaa gtg  gcg gcc gtg gtg gcc  gcc gtc cgc           8244
Leu Gly Glu Gln Ala Glu Val  Ala Ala Val Val Ala  Ala Val Arg
        2735              2740             2745 ccc gcc gac gac gat ccg atc  gcc atc gtg gcc atg  agc tgc cgg           8289
Pro Ala Asp Asp Asp Pro Ile  Ala Ile Val Ala Met  Ser Cys Arg
        2750              2755             2760 ctg ccc ggc ggg gtc cgc ggc  ccc gag gat ctg tgg  gag ctg gtg           8334
Leu Pro Gly Gly Val Arg Gly  Pro Glu Asp Leu Trp  Glu Leu Val
        2765              2770             2775 gcg gac ggt cgc gat gtg atc  tcg acc ttc ccg acc  gac cgc ggc           8379
Ala Asp Gly Arg Asp Val Ile  Ser Thr Phe Pro Thr  Asp Arg Gly
        2780              2785             2790 tgg aac gtc gag gag ctc tac  gac ccc aac ccc gat  acg ccg ggc           8424
Trp Asn Val Glu Glu Leu Tyr  Asp Pro Asn Pro Asp  Thr Pro Gly
        2795              2800             2805 agg agt tac gcc aag gaa ggc  ggt ttc ctc tac gac  gcc tac gac           8469
Arg Ser Tyr Ala Lys Glu Gly  Gly Phe Leu Tyr Asp  Ala Tyr Asp
        2810              2815             2820 ttc gac ccc gag ttc ttc ggg  atc tcg ccg cgc gag  gcg ctg gcc           8514
Phe Asp Pro Glu Phe Phe Gly  Ile Ser Pro Arg Glu  Ala Leu Ala
        2825              2830             2835 atg gac ccg cag cag cgg ctg  ctg ctg gag acc tcc  tgg gag gcg           8559
Met Asp Pro Gln Gln Arg Leu  Leu Leu Glu Thr Ser  Trp Glu Ala
        2840              2845             2850 ctg gag cgc gcc ggg atc gac  ccg cac tcc acg aag  ggc agc acg           8604
Leu Glu Arg Ala Gly Ile Asp  Pro His Ser Thr Lys  Gly Ser Thr
        2855              2860             2865 gcg ggc gtg ttc atc ggc tcc  acc ggc cag gac tac  gcc tcg cgg           8649
Ala Gly Val Phe Ile Gly Ser  Thr Gly Gln Asp Tyr  Ala Ser Arg
        2870              2875             2880 ctg ggc gag atc ccc gag gac  atg gag ggg tat ctg  ctg acc ggc           8694
Leu Gly Glu Ile Pro Glu Asp  Met Glu Gly Tyr Leu  Leu Thr Gly
        2885              2890             2895 aag gcc gcc agc gtg gtc tcc  ggc cgc atc gcc tac  tcc ctc ggc           8739
Lys Ala Ala Ser Val Val Ser  Gly Arg Ile Ala Tyr  Ser Leu Gly
        2900              2905             2910 tgg gag ggc ccg gcg ctc acc  atc gac acc gcg tgc  tcc tcc tcc           8784
Trp Glu Gly Pro Ala Leu Thr  Ile Asp Thr Ala Cys  Ser Ser Ser
        2915              2920             2925 ctg gtc gcc atc cac cag gcg  gcg cag gcg ctg cgc  cag ggc gag           8829
Leu Val Ala Ile His Gln Ala  Ala Gln Ala Leu Arg  Gln Gly Glu
        2930              2935             2940 tgc tcg atg gcg ctg gcg ggt  ggc acg acg atg atg  tcg acg ccg           8874
Cys Ser Met Ala Leu Ala Gly  Gly Thr Thr Met Met  Ser Thr Pro
        2945              2950             2955 agt ctg ttc atc gag ttc agc  agg cag cgc ggg ctc  gcc cct gac           8919
Ser Leu Phe Ile Glu Phe Ser  Arg Gln Arg Gly Leu  Ala Pro Asp
        2960              2965             2970 ggc cgg tcg aag gcg ttc tcc  tcg gac acc gac ggc  acc agc tgg           8964
Gly Arg Ser Lys Ala Phe Ser  Ser Asp Thr Asp Gly  Thr Ser Trp
        2975              2980             2985 ggc gag ggc gtc agc atg gtg  ctc ctg gag cgg ctg  tcc gac gcg           9009
Gly Glu Gly Val Ser Met Val  Leu Leu Glu Arg Leu  Ser Asp Ala
        2990              2995             3000
```

```
cgg gcg aac ggc cat gag gtg ctg gcg ctg gtg tgt ggc tcg gcc         9054
Arg Ala Asn Gly His Glu Val Leu Ala Leu Val Cys Gly Ser Ala
    3005            3010                3015 gtc aac cag gac ggc gcc agc aac ggc ctc acc gcc ccc aac ggc         9099
Val Asn Gln Asp Gly Ala Ser Asn Gly Leu Thr Ala Pro Asn Gly
    3020            3025                3030 ccc tcc cag cag cgg gtg atc cgg cag gcg ctg gcg aac gcc ggg         9144
Pro Ser Gln Gln Arg Val Ile Arg Gln Ala Leu Ala Asn Ala Gly
    3035            3040                3045 ctg tcg gcc gcc gag gtg gac gcc gtc gag gcg cac ggc acc ggc         9189
Leu Ser Ala Ala Glu Val Asp Ala Val Glu Ala His Gly Thr Gly
    3050            3055                3060 acc acg ctc ggt gac ccg atc gag gcc cag gcc atc ctc gcc acc         9234
Thr Thr Leu Gly Asp Pro Ile Glu Ala Gln Ala Ile Leu Ala Thr
    3065            3070                3075 tac ggc cag ggc cgg gag gca gaa cgg ccg ctg cgg ctg ggc gcg         9279
Tyr Gly Gln Gly Arg Glu Ala Glu Arg Pro Leu Arg Leu Gly Ala
    3080            3085                3090 ttg aag tcc aac atc ggc cac acc cag ggc gcg gcc ggc ggc gcg         9324
Leu Lys Ser Asn Ile Gly His Thr Gln Gly Ala Ala Gly Gly Ala
    3095            3100                3105 gga gtc atc aag atg gtc atg gcg atg cgc cac ggc ctg ctg ccc         9369
Gly Val Ile Lys Met Val Met Ala Met Arg His Gly Leu Leu Pro
    3110            3115                3120 agg acg ctc cac gtc aag gag ccc acc ccg cat gtg gac tgg acg         9414
Arg Thr Leu His Val Lys Glu Pro Thr Pro His Val Asp Trp Thr
    3125            3130                3135 gcc ggg gcc gtc gag ctg ctg acc gag gcc agg gag tgg ccc gcg         9459
Ala Gly Ala Val Glu Leu Leu Thr Glu Ala Arg Glu Trp Pro Ala
    3140            3145                3150 ggc gag cgg gtg cgg cgc gcc ggg gtg tcc gcc ttc ggc atc agc         9504
Gly Glu Arg Val Arg Arg Ala Gly Val Ser Ala Phe Gly Ile Ser
    3155            3160                3165 ggc acc aac gcc cac ctc atc ctg gag gaa ccg ccc gcc gcc ccg         9549
Gly Thr Asn Ala His Leu Ile Leu Glu Glu Pro Pro Ala Ala Pro
    3170            3175                3180 gcc acc gaa ccg gcc acc gaa cct gat ccg gag tcg gag ccg acg         9594
Ala Thr Glu Pro Ala Thr Glu Pro Asp Pro Glu Ser Glu Pro Thr
    3185            3190                3195 gtg cgc acc gat gtg gtg ccg tgg atg gtg tcc ggg cgt acc gag         9639
Val Arg Thr Asp Val Val Pro Trp Met Val Ser Gly Arg Thr Glu
    3200            3205                3210 ggc gcg ttg cgg gcc cag gcg gag cgg ctg cgg tcg tat gtg ggg         9684
Gly Ala Leu Arg Ala Gln Ala Glu Arg Leu Arg Ser Tyr Val Gly
    3215            3220                3225 gcg cgg ccg gag ttg gat ccg gtg gat gtg ggt tac tcg ctg gcg         9729
Ala Arg Pro Glu Leu Asp Pro Val Asp Val Gly Tyr Ser Leu Ala
    3230            3235                3240 ctg acc cgg tcc gcc ttc ggt cac cgc gcg gcg gtc gtc ggc cgc         9774
Leu Thr Arg Ser Ala Phe Gly His Arg Ala Ala Val Val Gly Arg
    3245            3250                3255 gac cgt ggg gag ctg ttg agc ggt ctt gag cag ctc gcc gcg ggt         9819
Asp Arg Gly Glu Leu Leu Ser Gly Leu Glu Gln Leu Ala Ala Gly
    3260            3265                3270 gtg gtc ccg ggc gcg gtg gct gac gac gag ggc agg acg gcg ttt         9864
Val Val Pro Gly Ala Val Ala Asp Asp Glu Gly Arg Thr Ala Phe
    3275            3280                3285 ctg ttc act ggt cag ggt gct caa cgg ctg ggt atg ggg cgg ggg         9909
Leu Phe Thr Gly Gln Gly Ala Gln Arg Leu Gly Met Gly Arg Gly
    3290            3295                3300
```

-continued

| | | | | | | | | | | | | | | |
|---|---|---|---|---|---|---|---|---|---|---|---|---|---|---|
| ttg | tat | tcg | gcg | ttt | ccg | gtg | ttc | gcg | gtg | gcg | ttc | gat | gag | gtg | 9954 |
| Leu | Tyr | Ser | Ala | Phe | Pro | Val | Phe | Ala | Val | Ala | Phe | Asp | Glu | Val | |
| | 3305 | | | | 3310 | | | | 3315 | | | | | | |

| tgc | gcg | gag | ctg | gac | cgt | cat | ctg | gat | ggt | tcg | gtg | ggg | gag | gtg | 9999 |
| Cys | Ala | Glu | Leu | Asp | Arg | His | Leu | Asp | Gly | Ser | Val | Gly | Glu | Val | |
| | 3320 | | | | 3325 | | | | 3330 | | | | | | |

| gtg | ttc | ggc | gag | gat | gcc | gag | gcg | ttg | gat | cgg | acg | gtg | ttc | act | 10044 |
| Val | Phe | Gly | Glu | Asp | Ala | Glu | Ala | Leu | Asp | Arg | Thr | Val | Phe | Thr | |
| | 3335 | | | | 3340 | | | | 3345 | | | | | | |

| cag | gcc | ggg | ctg | ttc | gct | ttg | gag | gtg | ggg | ctg | ttc | cgg | ctg | gtg | 10089 |
| Gln | Ala | Gly | Leu | Phe | Ala | Leu | Glu | Val | Gly | Leu | Phe | Arg | Leu | Val | |
| | 3350 | | | | 3355 | | | | 3360 | | | | | | |

| gag | tcg | tgg | ggt | ctg | gtg | ccg | gat | ttt | ctg | gtg | ggg | cat | tcg | gtg | 10134 |
| Glu | Ser | Trp | Gly | Leu | Val | Pro | Asp | Phe | Leu | Val | Gly | His | Ser | Val | |
| | 3365 | | | | 3370 | | | | 3375 | | | | | | |

| ggg | gag | ttg | gcg | gcc | gcc | cat | gtg | gcg | ggg | gtg | ttt | tcg | ctg | gag | 10179 |
| Gly | Glu | Leu | Ala | Ala | Ala | His | Val | Ala | Gly | Val | Phe | Ser | Leu | Glu | |
| | 3380 | | | | 3385 | | | | 3390 | | | | | | |

| gac | gcc | tgt | gcg | ctg | gtg | gcg | gcg | cgt | ggt | cgg | ctg | atg | cag | gcg | 10224 |
| Asp | Ala | Cys | Ala | Leu | Val | Ala | Ala | Arg | Gly | Arg | Leu | Met | Gln | Ala | |
| | 3395 | | | | 3400 | | | | 3405 | | | | | | |

| ctg | ccc | ggc | ggt | ggt | gcg | atg | gtg | tcg | ctg | aag | gct | ccg | gag | gcc | 10269 |
| Leu | Pro | Gly | Gly | Gly | Ala | Met | Val | Ser | Leu | Lys | Ala | Pro | Glu | Ala | |
| | 3410 | | | | 3415 | | | | 3420 | | | | | | |

| gag | gtg | ctg | ccg | cat | ctg | gcc | ggt | tac | gag | gac | cgg | gtg | agc | gtt | 10314 |
| Glu | Val | Leu | Pro | His | Leu | Ala | Gly | Tyr | Glu | Asp | Arg | Val | Ser | Val | |
| | 3425 | | | | 3430 | | | | 3435 | | | | | | |

| gcg | gcg | gtc | aat | ggc | ccg | gtg | gcg | acc | gtg | atc | tcc | ggt | gag | gag | 10359 |
| Ala | Ala | Val | Asn | Gly | Pro | Val | Ala | Thr | Val | Ile | Ser | Gly | Glu | Glu | |
| | 3440 | | | | 3445 | | | | 3450 | | | | | | |

| tcg | gcg | gtg | ctc | gcg | gtg | gcg | gag | gcg | gtg | ggg | gtg | agg | agt | aag | 10404 |
| Ser | Ala | Val | Leu | Ala | Val | Ala | Glu | Ala | Val | Gly | Val | Arg | Ser | Lys | |
| | 3455 | | | | 3460 | | | | 3465 | | | | | | |

| cgg | ctg | agc | gtc | tcg | cat | gcc | ttt | cac | tcg | ccg | ctg | atg | gag | ggg | 10449 |
| Arg | Leu | Ser | Val | Ser | His | Ala | Phe | His | Ser | Pro | Leu | Met | Glu | Gly | |
| | 3470 | | | | 3475 | | | | 3480 | | | | | | |

| atg | ctg | gcc | gag | ttc | gcc | gag | gtg | gcg | ggc | cgg | atc | ggc | tac | tcc | 10494 |
| Met | Leu | Ala | Glu | Phe | Ala | Glu | Val | Ala | Gly | Arg | Ile | Gly | Tyr | Ser | |
| | 3485 | | | | 3490 | | | | 3495 | | | | | | |

| gca | ccg | cgc | atg | gcg | atc | gtc | tcg | aac | ctc | acg | ggc | gag | ttg | gcg | 10539 |
| Ala | Pro | Arg | Met | Ala | Ile | Val | Ser | Asn | Leu | Thr | Gly | Glu | Leu | Ala | |
| | 3500 | | | | 3505 | | | | 3510 | | | | | | |

| ggg | gat | gag | gtg | tgc | tcg | ccg | gag | tac | tgg | gtg | cgc | cat | gtg | cgt | 10584 |
| Gly | Asp | Glu | Val | Cys | Ser | Pro | Glu | Tyr | Trp | Val | Arg | His | Val | Arg | |
| | 3515 | | | | 3520 | | | | 3525 | | | | | | |

| cag | gcg | gtg | cgc | ttc | ggg | gat | ggc | ata | cgg | ttc | ctc | gag | acc | cag | 10629 |
| Gln | Ala | Val | Arg | Phe | Gly | Asp | Gly | Ile | Arg | Phe | Leu | Glu | Thr | Gln | |
| | 3530 | | | | 3535 | | | | 3540 | | | | | | |

| ggc | gtc | acc | cgc | ttt | gtg | gag | ctc | gga | ccc | gcg | ggt | gtg | ctc | tcc | 10674 |
| Gly | Val | Thr | Arg | Phe | Val | Glu | Leu | Gly | Pro | Ala | Gly | Val | Leu | Ser | |
| | 3545 | | | | 3550 | | | | 3555 | | | | | | |

| gcc | atg | ggc | cgc | gag | tgc | gtc | tct | ggt | ccg | gcc | gcg | ttc | gta | cct | 10719 |
| Ala | Met | Gly | Arg | Glu | Cys | Val | Ser | Gly | Pro | Ala | Ala | Phe | Val | Pro | |
| | 3560 | | | | 3565 | | | | 3570 | | | | | | |

| ctg | ttg | cgc | aag | gac | cgc | gag | gag | acc | gag | gcg | ctg | ctc | tcc | ggt | 10764 |
| Leu | Leu | Arg | Lys | Asp | Arg | Glu | Glu | Thr | Glu | Ala | Leu | Leu | Ser | Gly | |
| | 3575 | | | | 3580 | | | | 3585 | | | | | | |

| gtc | gcc | cag | gtg | cac | gct | cac | ggt | ggc | gag | gtg | gac | tgg | gag | gcg | 10809 |
| Val | Ala | Gln | Val | His | Ala | His | Gly | Gly | Glu | Val | Asp | Trp | Glu | Ala | |

-continued

```
          3590                3595                3600
gtg ttc gcc ggg cgc ggt gcg cag cgg gtg gag ctg ccc aca tac       10854
Val Phe Ala Gly Arg Gly Ala Gln Arg Val Glu Leu Pro Thr Tyr
         3605                3610                3615 gcc ttc cag cgg cag cgc tac tgg ttc gac ccc gcc acg ccg gga       10899
Ala Phe Gln Arg Gln Arg Tyr Trp Phe Asp Pro Ala Thr Pro Gly
         3620                3625                3630 acg ccg acc gcc gcc acc acg gac acg tcc tcc gtg gag gcc cgt       10944
Thr Pro Thr Ala Ala Thr Thr Asp Thr Ser Ser Val Glu Ala Arg
         3635                3640                3645 ttc tgg gag gcg gtc gag cgc gag gac ctg gag gcg ctg acc acc       10989
Phe Trp Glu Ala Val Glu Arg Glu Asp Leu Glu Ala Leu Thr Thr
         3650                3655                3660 acc ctg gag atc gac cag cag gcg cgg ctc ggc gac ctg ctg ccc       11034
Thr Leu Glu Ile Asp Gln Gln Ala Arg Leu Gly Asp Leu Leu Pro
         3665                3670                3675 gcg ctc tcc tcc tgg cgc cgg ggc cag agc gac cgc gcc acc gtg       11079
Ala Leu Ser Ser Trp Arg Arg Gly Gln Ser Asp Arg Ala Thr Val
         3680                3685                3690 gac tcc tgg cgc tac cgg atc acc tgg tcc ccg acg gcc gtc gaa       11124
Asp Ser Trp Arg Tyr Arg Ile Thr Trp Ser Pro Thr Ala Val Glu
         3695                3700                3705 gag cgt acg gcg ctg ctg tcc ggc atc tgg tgg gtg gcc gta ccg       11169
Glu Arg Thr Ala Leu Leu Ser Gly Ile Trp Trp Val Ala Val Pro
         3710                3715                3720 gag ggc cgg gcg gac ggc gcg ggg atc gcc gcc gtg gcg gcc gcc       11214
Glu Gly Arg Ala Asp Gly Ala Gly Ile Ala Ala Val Ala Ala Ala
         3725                3730                3735 ctc gac cgg cgg ggg gcg cgc gtc gtg ccc ctc acc gtg gcc acg       11259
Leu Asp Arg Arg Gly Ala Arg Val Val Pro Leu Thr Val Ala Thr
         3740                3745                3750 acc ggc cgt gac gcg ctc gcc gcg cgg ctg cgc cac gag gcg gat       11304
Thr Gly Arg Asp Ala Leu Ala Ala Arg Leu Arg His Glu Ala Asp
         3755                3760                3765 acc ggt ggc aca ccg gcc ggt gtg ctc tcg ctg ctc gcc ctc gac       11349
Thr Gly Gly Thr Pro Ala Gly Val Leu Ser Leu Leu Ala Leu Asp
         3770                3775                3780 gac ggt cca cac ccc gaa cac ggt gcg ctc agc acc ggt ctg gcc       11394
Asp Gly Pro His Pro Glu His Gly Ala Leu Ser Thr Gly Leu Ala
         3785                3790                3795 ctc aac gtc ggg ctg atc cag gcg ctg ggc gac gcg ggg atc gcc       11439
Leu Asn Val Gly Leu Ile Gln Ala Leu Gly Asp Ala Gly Ile Ala
         3800                3805                3810 gcc ccg ctg tgg ctc gcc acc acc ggc gcc gtc tcg gtg agc gga       11484
Ala Pro Leu Trp Leu Ala Thr Thr Gly Ala Val Ser Val Ser Gly
         3815                3820                3825 tcc gat ccg ctc ggc agc ccc gca cag gcc gcc acc tgg ggc ctc       11529
Ser Asp Pro Leu Gly Ser Pro Ala Gln Ala Ala Thr Trp Gly Leu
         3830                3835                3840 ggc cgg gtc gtg gcc ctg gag cac ccg cag cgg tgg ggc ggt ctg       11574
Gly Arg Val Val Ala Leu Glu His Pro Gln Arg Trp Gly Gly Leu
         3845                3850                3855 atc gac ctc ccc ggg gac ctc gac gaa cgg acg gcg gac cgg ctg       11619
Ile Asp Leu Pro Gly Asp Leu Asp Glu Arg Thr Ala Asp Arg Leu
         3860                3865                3870 tgc gcc gcg ctc tcc ggc atc gcc ggc ggc agc ggc ccg gag gac       11664
Cys Ala Ala Leu Ser Gly Ile Ala Gly Gly Ser Gly Pro Glu Asp
         3875                3880                3885 caa ctc gcc ctc cgt gac gcc ggg gtg ttc gtc cga cgg ctg gtc       11709
```

```
                Gln Leu Ala Leu Arg Asp Ala Gly Val Phe Val Arg Arg Leu Val
                    3890            3895                3900 cgg gcg ccg ctg cgc aca ccg ggc cgg gag agc tgg aag ccg cat            11754
Arg Ala Pro Leu Arg Thr Pro Gly Arg Glu Ser Trp Lys Pro His
    3905            3910                3915 ggc acc gtg ctg atc acc ggg ggc acc ggt ggg ctc ggc gcc cag            11799
Gly Thr Val Leu Ile Thr Gly Gly Thr Gly Gly Leu Gly Ala Gln
    3920            3925                3930 gtc gcc cgc tgg ctg gcc cgc tcc ggt gcc gaa cac ctc gtg ctc            11844
Val Ala Arg Trp Leu Ala Arg Ser Gly Ala Glu His Leu Val Leu
    3935            3940                3945 acc agc cgc cgt ggc atc gcg gcg ccc ggc gcc gcc gga ctg cgc            11889
Thr Ser Arg Arg Gly Ile Ala Ala Pro Gly Ala Ala Gly Leu Arg
    3950            3955                3960 gac gag ctg atc gcg ctg ggc gag ggc ggt gtc cgg gtg acg gtg            11934
Asp Glu Leu Ile Ala Leu Gly Glu Gly Gly Val Arg Val Thr Val
    3965            3970                3975 gcg gcg tgc gac gtc cgc gac cgt gac gag gtg gcg gcg ctg ctg            11979
Ala Ala Cys Asp Val Arg Asp Arg Asp Glu Val Ala Ala Leu Leu
    3980            3985                3990 cgc cgg atc acc acc ggg ggc gac ccg gtg cac gcc gtc ttc cac            12024
Arg Arg Ile Thr Thr Gly Gly Asp Pro Val His Ala Val Phe His
    3995            4000                4005 gcc gcg ggc gtc gtg gag ttc tcc cag ctc gcc gac agt acg gtg            12069
Ala Ala Gly Val Val Glu Phe Ser Gln Leu Ala Asp Ser Thr Val
    4010            4015                4020 gcc gac ttc gcg gag atg gcc gac ggc aag gtg ctg ggc gcc gcc            12114
Ala Asp Phe Ala Glu Met Ala Asp Gly Lys Val Leu Gly Ala Ala
    4025            4030                4035 cat ctg gac gcg ttg ctg gac cag gac cac ctc gag gcg ttc gtg            12159
His Leu Asp Ala Leu Leu Asp Gln Asp His Leu Glu Ala Phe Val
    4040            4045                4050 ctc ttc tcg tcc atc gcc gcc acc tgg ggg agc ggc ggg cag agc            12204
Leu Phe Ser Ser Ile Ala Ala Thr Trp Gly Ser Gly Gly Gln Ser
    4055            4060                4065 gcc tac gcg gcc gcc aac gcc cac ctg gac gcc ctc gcc gag cac            12249
Ala Tyr Ala Ala Ala Asn Ala His Leu Asp Ala Leu Ala Glu His
    4070            4075                4080 cgc gag gca cgc ggc ctc ccc gcc acc tcg gtg gcc tgg ggt ccg            12294
Arg Glu Ala Arg Gly Leu Pro Ala Thr Ser Val Ala Trp Gly Pro
    4085            4090                4095 tgg gcc gac cac ggc atg atc gag cac ggc gag gtg gcg gag cac            12339
Trp Ala Asp His Gly Met Ile Glu His Gly Glu Val Ala Glu His
    4100            4105                4110 ctc agc cgc cgt gga ctc ccc gcg atg gca ccg gag ttg gcc gtg            12384
Leu Ser Arg Arg Gly Leu Pro Ala Met Ala Pro Glu Leu Ala Val
    4115            4120                4125 gcc gcg ctg agc gag gcg ctg cac acc ggc gag acc tcg ctc gtc            12429
Ala Ala Leu Ser Glu Ala Leu His Thr Gly Glu Thr Ser Leu Val
    4130            4135                4140 ctc gcc gat gtg cgc tgg gac cgc ttc gtc ccc ggc ttc acc gcg            12474
Leu Ala Asp Val Arg Trp Asp Arg Phe Val Pro Gly Phe Thr Ala
    4145            4150                4155 gcg cgc ccc cgg ccg ctg atc ggc gag ctg ccg gag gtg cgc gat            12519
Ala Arg Pro Arg Pro Leu Ile Gly Glu Leu Pro Glu Val Arg Asp
    4160            4165                4170 gcc ctc gcc acc acc gcg gcc ccc gac acc acc ggt ccg gac gac            12564
Ala Leu Ala Thr Thr Ala Ala Pro Asp Thr Thr Gly Pro Asp Asp
    4175            4180                4185
```

-continued

```
gtg gcg gac acc ttc ctg gcg ggc ctc gcg ggc ctg tcg ggc gag      12609
Val Ala Asp Thr Phe Leu Ala Gly Leu Ala Gly Leu Ser Gly Glu
    4190                4195                4200 gac ctg gac cgg gcc ctg cgg gac ctg gtg cac gcc cag gcg gcg      12654
Asp Leu Asp Arg Ala Leu Arg Asp Leu Val His Ala Gln Ala Ala
4205                4210                4215 gcc gta ctc ggc cac tcc tcg tcc gac gcg gtc gcc ggc ggc cgc      12699
Ala Val Leu Gly His Ser Ser Ser Asp Ala Val Ala Gly Gly Arg
        4220                4225                4230 ccg ttc aag gag ctg ggc ttc gac tcg ctc acc gcc gtc gaa ctg      12744
Pro Phe Lys Glu Leu Gly Phe Asp Ser Leu Thr Ala Val Glu Leu
            4235                4240                4245 cgc aac cgg ctg gcc gcg gtc acc gga ctc gac ctg ccc gcc acc      12789
Arg Asn Arg Leu Ala Ala Val Thr Gly Leu Asp Leu Pro Ala Thr
                4250                4255                4260 ctc gtc ttc gac tat ccg gcg ccc gcg cca ctg gcc gag tac ctg      12834
Leu Val Phe Asp Tyr Pro Ala Pro Ala Pro Leu Ala Glu Tyr Leu
4265                4270                4275 cgc ggc gag ctg ccg tcg gcc cgc ccg gcg gac gcg cgc acc ctc      12879
Arg Gly Glu Leu Pro Ser Ala Arg Pro Ala Asp Ala Arg Thr Leu
    4280                4285                4290 ttc gac gac ctg gac cgg tgg gag tcc gcg ctg ccg gag ctg atg      12924
Phe Asp Asp Leu Asp Arg Trp Glu Ser Ala Leu Pro Glu Leu Met
        4295                4300                4305 gcc gag gac ggg gtg cgg gag cgg ctg acg ggg cgg ctg aac gac      12969
Ala Glu Asp Gly Val Arg Glu Arg Leu Thr Gly Arg Leu Asn Asp
            4310                4315                4320 ctc atg gcg aag ttg ggc ggc acg ccc ggg gaa cac acc ggc ggg      13014
Leu Met Ala Lys Leu Gly Gly Thr Pro Gly Glu His Thr Gly Gly
                4325                4330                4335 ccg tcc ccc gac acc ggc ctc ctc tcc gct acc gcc gac gag gtc      13059
Pro Ser Pro Asp Thr Gly Leu Leu Ser Ala Thr Ala Asp Glu Val
4340                4345                4350 ttc gac ttc atc gac aac gaa ttc ggg gct tcc tga                  13095
Phe Asp Phe Ile Asp Asn Glu Phe Gly Ala Ser
    4355                4360
```

<210> SEQ ID NO 14
<211> LENGTH: 4364
<212> TYPE: PRT
<213> ORGANISM: Streptomyces sp. NRRL 30748

<400> SEQUENCE: 14

```
Val Arg Asp Gly His Ile Ala Val Val Gly Met Ala Cys Arg Val Pro
1               5                   10                  15

Gly Ala Ser Thr Pro Asp Glu Phe Arg Gln Leu Leu Arg Asn Gly Glu
            20                  25                  30

Ser Ala Ile Thr Glu Ile Pro Ala Asp Arg Tyr Ala Asp Glu Leu Arg
        35                  40                  45

Asp Ala Gly Ile Arg Phe Gly Phe Val Glu Ala Ala Glu Phe
    50                  55                  60

Asp Pro Glu Phe Phe Gly Ile Ser Pro Arg Glu Ala Arg Ala Met Asp
65                  70                  75                  80

Pro Gln Gln Arg Leu Ala Leu Glu Leu Cys Trp Glu Ala Leu Glu Asn
                85                  90                  95

Ala Gly Leu Val Pro Ala Arg Leu Glu Gly Ser Arg Thr Gly Val Phe
            100                 105                 110

Ile Gly Ala Ile Ala Asp Asp Tyr Ala Ala Leu Val His Arg Gly Glu
        115                 120                 125
```

```
Pro Ala Ala Ile Thr Gln His Thr Leu Thr Gly Leu Asn Arg Gly Ile
        130                 135                 140

Ile Ala Asn Arg Val Ser Tyr Ala Leu Gly Leu Arg Gly Pro Ser Val
145                 150                 155                 160

Ala Val Asp Thr Gly Gln Ser Ser Leu Ala Ala Val His Leu Ala
                165                 170                 175

Cys Glu Ser Leu Arg Arg Gly Glu Thr Glu Thr Ala Val Ala Gly Gly
                180                 185                 190

Val Gln Leu Asn Leu Ala Pro Asp Gly Phe Ile Ala Ala Ser Arg Phe
        195                 200                 205

Gly Ala Leu Ser Pro Asp Gly Arg Ser Phe Thr Phe Asp Ala Arg Ala
        210                 215                 220

Asn Gly Tyr Val Arg Gly Glu Gly Gly Leu Val Leu Lys Arg
225                 230                 235                 240

Leu Pro Asp Ala Leu Arg Asp Gly Asp Pro Val Leu Cys Val Ile Arg
                245                 250                 255

Gly Ser Asp Ala Asn Asn Asp Gly Gly Asp Ser Leu Thr Thr Pro
                260                 265                 270

Ala Ala His Gly Gln Glu Ala Met Leu Arg Ala Ala Tyr Glu Arg Ala
        275                 280                 285

Gly Val Asp Pro Ala Arg Val Gln Tyr Val Glu Leu His Gly Thr Gly
        290                 295                 300

Thr Lys Val Gly Asp Pro Val Glu Ala Val Ala Leu Gly Ala Val Leu
305                 310                 315                 320

Gly Ala Gly Arg Ala Asp Gly Ala Pro Leu Arg Val Gly Ser Ala Lys
                325                 330                 335

Thr Asn Val Gly His Leu Glu Gly Ala Ala Gly Ile Thr Gly Leu Ile
                340                 345                 350

Lys Thr Val Leu Ser Leu Ala His Arg Glu Leu Phe Pro Ser Leu Asn
        355                 360                 365

His Gln Thr Pro Asn Pro Ala Ile Pro Leu Asp Thr Leu Gly Leu Thr
        370                 375                 380

Val Gln Thr Ala Leu Asp Asp Trp Ala Pro Gln Ala Asp Thr Pro Arg
385                 390                 395                 400

Leu Ala Gly Val Ser Ser Phe Gly Met Gly Gly Thr Asn Val His Met
                405                 410                 415

Val Leu Glu Glu Ala Pro Ala Asp Asp Pro Ala Ala Glu Arg Pro Thr
                420                 425                 430

Ala Leu Asp Thr Val Pro Trp Val Leu Ser Ala Arg Thr Glu Gly Ala
        435                 440                 445

Leu Arg Ala Gln Ala Glu Arg Leu Arg Ser Tyr Val Gly Ala Arg Pro
        450                 455                 460

Glu Leu Asp Pro Val Asp Val Gly Tyr Ser Leu Ala Leu Thr Arg Ser
465                 470                 475                 480

Ala Phe Gly His Arg Ala Ala Val Val Gly Arg Asn Cys Gly Glu Leu
                485                 490                 495

Leu Ser Gly Leu Glu Gln Leu Ala Ala Gly Val Val Pro Gly Ala Val
                500                 505                 510

Ala Asp Glu Glu Gly Arg Thr Ala Phe Leu Phe Thr Gly Gln Gly Ala
        515                 520                 525

Gln Arg Leu Gly Met Gly Arg Gly Leu Tyr Ser Ala Phe Pro Val Phe
        530                 535                 540
```

-continued

```
Ala Val Ser Phe Asp Glu Val Cys Ala Glu Leu Asp Arg His Leu Asp
545                 550                 555                 560

Gly Ser Val Gly Glu Val Val Phe Gly Glu Asp Ala Glu Ala Leu Asp
                565                 570                 575

Arg Thr Val Phe Thr Gln Ala Gly Leu Phe Ala Leu Glu Val Gly Leu
            580                 585                 590

Phe Arg Leu Val Glu Ser Trp Gly Leu Ala Pro Asp Phe Leu Val Gly
        595                 600                 605

His Ser Val Gly Glu Leu Ala Ala His Val Ala Gly Val Phe Ser
    610                 615                 620

Leu Glu Asp Ala Cys Ala Leu Val Ala Ala Arg Gly Arg Leu Met Gln
625                 630                 635                 640

Ala Leu Pro Gly Gly Gly Ala Met Val Ser Leu Lys Ala Pro Glu Ala
                645                 650                 655

Glu Val Leu Pro His Leu Ala Gly Tyr Glu Asp Arg Val Ser Val Ala
                660                 665                 670

Ala Val Asn Gly Pro Ser Ala Thr Val Ile Ser Gly Glu Glu Ser Ala
            675                 680                 685

Val Leu Ala Val Ala Glu Ala Val Gly Val Lys Ser Lys Arg Leu Ser
        690                 695                 700

Val Ser His Ala Phe His Ser Pro Leu Met Glu Gly Met Leu Ala Ala
705                 710                 715                 720

Phe Ala Glu Val Ala Ala Gly Ile Ala Tyr Ala Thr Pro Gly Ile Ala
                725                 730                 735

Ile Val Ser Asn Val Thr Gly Glu Leu Ala Gly Glu Glu Val Cys Ser
                740                 745                 750

Pro Glu Tyr Trp Val Arg His Val Arg Gln Ala Val Arg Phe Gly Asp
            755                 760                 765

Gly Ile Arg Phe Leu Glu Thr Gln Gly Val Thr Arg Phe Val Glu Leu
        770                 775                 780

Gly Pro Ala Gly Val Leu Ser Ala Met Gly Gln Glu Cys Val Ser Gly
785                 790                 795                 800

Pro Ala Ala Phe Val Pro Leu Leu Arg Lys Asp Arg Glu Glu Thr Glu
                805                 810                 815

Ala Leu Leu Ser Gly Val Ala Gln Val His Ala His Gly Gly Glu Val
            820                 825                 830

Asp Trp Glu Ala Val Phe Ala Gly Arg Gly Ala His Arg Val Glu Leu
        835                 840                 845

Pro Thr Tyr Ala Phe Gln Arg Gln Arg Tyr Trp Leu Asp Thr Asp Leu
850                 855                 860

Pro Gly Thr Glu Asp Ala Ala Thr Asp Glu Pro Leu Ser Trp Arg Glu
865                 870                 875                 880

Glu Phe Ala Ala Leu Thr Asp Ser Ala Glu Arg Glu Arg Val Ala Leu
                885                 890                 895

Glu Leu Val Arg Thr His Thr Ala Trp Val Leu Gly Ser Pro Gly Pro
            900                 905                 910

Asp Ala Val Asp Pro Glu Lys Ile Phe Lys Asp Leu Gly Phe Asp Ser
        915                 920                 925

Leu Met Ser Val Glu Leu Cys Asn Leu Leu Ser Thr Ala Thr Gly Thr
930                 935                 940

Arg Leu Ala Gly Thr Val Leu Phe Asp His Pro Thr Pro Leu Ala Leu
945                 950                 955                 960

Ser His His Leu Arg Glu Val Val Val Gly Thr Arg Pro Val Val Ala
```

-continued

```
                965                 970                 975
Pro Arg Pro Ala Ala Thr Arg Thr Val Thr Thr Gly Asp Asp Pro
            980                 985                 990
Ile Ala Ile Val Ala Met Ser Cys Arg Leu Pro Gly Gly Val Arg Thr
        995                 1000                1005
Pro Glu Gln Leu Trp Glu Leu Val Ser Glu Gly Arg Asp Ala Ile
    1010                1015                1020
Ala Gly Phe Pro Ala Asn Arg Gly Trp Asp Leu Glu Gly Leu Tyr
    1025                1030                1035
Asp Pro Asp Pro Ala Arg His Gly Thr Ser Tyr Val Arg Glu Gly
    1040                1045                1050
Gly Phe Leu Tyr Glu Ala Asp Gln Phe Asp Pro Ala Phe Phe Gly
    1055                1060                1065
Ile Ser Pro Arg Glu Ala Gln Ala Met Asp Pro Gln Gln Arg Leu
    1070                1075                1080
Leu Met Glu Thr Ala Trp Glu Ala Phe Glu Arg Ala Gly Ile Asp
    1085                1090                1095
Pro Thr Thr Leu Lys Gly Ser Asp Ala Gly Val Phe Val Gly Ala
    1100                1105                1110
Met Pro Gln Asp Tyr Gly Pro Arg Met Asp Glu Ala Ser Glu Gly
    1115                1120                1125
Phe Glu Gly Tyr Leu Leu Thr Gly Gly Thr Thr Ser Val Ala Ser
    1130                1135                1140
Gly Arg Ile Ala Tyr Thr Trp Gly Leu Glu Gly Pro Ala Val Thr
    1145                1150                1155
Val Asp Thr Ala Cys Ser Ser Ser Leu Val Ala Leu His Met Ala
    1160                1165                1170
Val Arg Ser Leu Arg Gln Gly Glu Cys Ser Leu Ala Leu Ala Gly
    1175                1180                1185
Gly Ala Thr Val Met Ser Ser Pro Gly Ile Phe Val Glu Leu Ser
    1190                1195                1200
Arg Gln Lys Ala Leu Ser Pro Asp Gly Arg Cys Lys Ala Phe Ser
    1205                1210                1215
Ser Asp Ala Asp Gly Thr Gly Trp Gly Glu Gly Val Gly Met Val
    1220                1225                1230
Leu Leu Glu Arg Leu Ser Asp Ala Arg Arg Asn Gly His Gln Val
    1235                1240                1245
Leu Ala Leu Val Arg Gly Ser Ala Thr Asn Gln Asp Gly Ala Ser
    1250                1255                1260
Asn Gly Leu Thr Ala Pro Ser Gly Pro Ala Gln Gln Arg Val Ile
    1265                1270                1275
Arg Gln Ala Leu Ala Asp Ala Gly Leu Ser Thr Ala Asp Val Asp
    1280                1285                1290
Ala Val Glu Ala His Gly Thr Gly Thr Ser Leu Gly Asp Pro Ile
    1295                1300                1305
Glu Ala Gly Ala Leu Leu Ala Thr Tyr Gly Gln Asp Arg Ala Gly
    1310                1315                1320
Asp Arg Pro Leu Trp Leu Gly Ser Leu Lys Ser Asn Val Gly His
    1325                1330                1335
Pro Gln Ala Ala Ala Gly Val Ala Gly Val Ile Lys Met Val Leu
    1340                1345                1350
Ala Leu Arg His Gly Val Leu Pro Gln Thr Leu His Val His Glu
    1355                1360                1365
```

```
Pro Ser Pro His Val Asp Trp Ser Ser Gly Ala Val Glu Leu Leu
    1370            1375                1380

Thr Glu Ser Arg Pro Trp Pro Glu Pro Glu Ser Glu Arg Pro Arg
    1385            1390                1395

Arg Ala Gly Val Ser Ser Phe Gly Ile Ser Gly Thr Asn Ala His
    1400            1405                1410

Ala Ile Leu Glu Gln Ala Pro Ala Glu Pro Ala Ala Gly His Asp
    1415            1420                1425

Ala Pro Arg Pro Ala Ala Pro Glu Leu Pro Val Leu Pro Trp Val
    1430            1435                1440

Leu Ser Gly Arg Thr Glu Gln Ala Leu Arg Thr Arg Ala Glu Gln
    1445            1450                1455

Leu Arg Asn Gln Leu Ala Asp His Pro Gly Thr Asp Leu Ala Ala
    1460            1465                1470

Leu Gly His Ala Leu Ala Thr Thr Arg Thr Ala Phe Gly His Arg
    1475            1480                1485

Ala Val Val Leu Gly Arg Asp Pro Glu Arg Leu Leu Asp Gly Leu
    1490            1495                1500

Gly Ala Leu Ala Gln Gly Thr Pro Ala Pro His Val Val Gln Gly
    1505            1510                1515

Thr Ala Gly Gly Arg Arg Lys Thr Val Phe Val Phe Pro Gly Gln
    1520            1525                1530

Gly Ser Gln Trp Ile Gly Met Ala Leu Pro Leu Trp Asp Ala Ser
    1535            1540                1545

Pro Val Phe Ala Glu Arg Leu Glu Glu Cys Ala Asp Ala Leu Glu
    1550            1555                1560

Pro Phe Leu Asp Trp Ser Leu Arg Asp Val Leu Arg Gly Glu Pro
    1565            1570                1575

Gly Ala Pro Ser Leu Ser Arg Ile Asp Val Val Gln Pro Ala Leu
    1580            1585                1590

Phe Ala Val Met Val Ser Leu Ala Ala Leu Trp Arg Ser His Gly
    1595            1600                1605

Val Glu Pro Ala Ala Val Val Gly His Ser Gln Gly Glu Ile Ala
    1610            1615                1620

Ala Ala Tyr Val Ala Gly Gly Leu Ser Leu Gln Asp Ala Ala Lys
    1625            1630                1635

Val Val Ala Arg Arg Ser Gln Ala Trp Ala Glu Leu Ser Gly Lys
    1640            1645                1650

Gly Gly Met Leu Ser Val Leu Ala Ser Ala Gly Thr Val Ala Glu
    1655            1660                1665

Arg Leu Arg Pro Trp Ser Glu Arg Leu Gly Ile Ala Ala Val Asn
    1670            1675                1680

Ser Pro Ala Thr Val Thr Val Ser Gly Asp Pro Glu Ala Leu Asp
    1685            1690                1695

Ala Phe Met Ala Glu Leu Ala Ala Asp Gly Val Lys Ser Arg Arg
    1700            1705                1710

Val Pro Gly Val Asp Thr Ala Gly His Ser Pro Gln Val Asp Gly
    1715            1720                1725

Leu Arg Glu Arg Leu Leu Arg Glu Val Ala Gly Val Arg Pro Arg
    1730            1735                1740

Pro Ser Arg Ile Ala Tyr Tyr Ser Thr Val Thr Gly Gly Pro Leu
    1745            1750                1755
```

-continued

| | | | | | | | | | | | | |
|---|---|---|---|---|---|---|---|---|---|---|---|---|
|Asp|Thr|Thr|Glu|Leu|Asp|Thr|Asp|Tyr|Trp|Tyr|Arg|Asn|Met|Arg|
| |1760| | | |1765| | | |1770| | | | | |
|Glu|Pro|Val|Asp|Phe|Glu|Arg|Ala|Thr|Arg|Ala|Leu|Leu|Ala|Asp|
| |1775| | | |1780| | | |1785| | | | | |
|Gly|His|Thr|Ala|Phe|Ile|Glu|Cys|Ala|Pro|His|Pro|Met|Leu|Ala|
| |1790| | | |1795| | | |1800| | | | | |
|Met|Ser|Leu|Gln|Gln|Thr|Ile|Glu|Asp|Ala|Gly|Gly|Asn|Ala|Ala|
| |1805| | | |1810| | | |1815| | | | | |
|Val|Val|Gly|Thr|Leu|Arg|Arg|Asp|Glu|Gly|Gly|Pro|Glu|Arg|Phe|
| |1820| | | |1825| | | |1830| | | | | |
|Ala|Gly|Ser|Phe|Ala|Glu|Ala|Tyr|Val|Gln|Gly|Val|Glu|Pro|Ser|
| |1835| | | |1840| | | |1845| | | | | |
|Trp|Asp|Thr|Val|Phe|Gly|Gly|Ala|Pro|Gly|Arg|Gly|Glu|Arg|Ala|
| |1850| | | |1855| | | |1860| | | | | |
|Leu|Glu|Leu|Pro|Thr|Tyr|Pro|Phe|Gln|Arg|Gln|Arg|Tyr|Trp|Leu|
| |1865| | | |1870| | | |1875| | | | | |
|Asp|Lys|Pro|Val|Ala|Ala|Ser|Asp|Val|Ala|Ala|Ala|Gly|Leu|Asp|
| |1880| | | |1885| | | |1890| | | | | |
|Ala|Ala|Gly|His|Pro|Leu|Leu|Gly|Ala|Ala|Val|Pro|Leu|Ala|Gly|
| |1895| | | |1900| | | |1905| | | | | |
|Ala|Asp|Asp|His|Leu|Phe|Thr|Gly|Arg|Ile|Ser|Ala|Gln|Asp|His|
| |1910| | | |1915| | | |1920| | | | | |
|Pro|Trp|Leu|Thr|Glu|Arg|Thr|Gly|Leu|Asp|Ala|Ala|Val|Leu|Pro|
| |1925| | | |1930| | | |1935| | | | | |
|Gly|Ser|Ala|Leu|Ala|Glu|Leu|Ala|Ile|Arg|Ala|Gly|Asp|Gln|Val|
| |1940| | | |1945| | | |1950| | | | | |
|Gly|Cys|Asp|Arg|Ile|Gly|Glu|Leu|Ser|Leu|Asp|Ala|Pro|Leu|Val|
| |1955| | | |1960| | | |1965| | | | | |
|Leu|Pro|Glu|Lys|Gly|Ala|Ala|Val|Ile|Gln|Val|Arg|Ile|Gly|Ala|
| |1970| | | |1975| | | |1980| | | | | |
|Pro|Asp|Asp|Glu|Gly|Ser|Arg|Ala|Leu|Ser|Val|His|Ala|Arg|Ala|
| |1985| | | |1990| | | |1995| | | | | |
|Glu|Gly|Ala|Asp|Ala|Asp|Glu|Pro|Trp|Thr|Arg|Tyr|Ala|Thr|Ala|
| |2000| | | |2005| | | |2010| | | | | |
|Val|Leu|Gly|Met|Gly|Ala|Pro|Ala|Ala|Asp|Val|Gly|Leu|Val|Ala|
| |2015| | | |2020| | | |2025| | | | | |
|Trp|Pro|Pro|Ala|Asp|Ala|Val|Pro|Ala|Glu|Val|Ala|Gly|Gly|Ala|
| |2030| | | |2035| | | |2040| | | | | |
|Val|Ala|Ala|Trp|Arg|Leu|Gly|Glu|Asp|Leu|Tyr|Val|Glu|Val|Gly|
| |2045| | | |2050| | | |2055| | | | | |
|Leu|Thr|Glu|Ala|Glu|Glu|Ala|Asp|Ala|Gly|Arg|Tyr|Gly|Leu|His|
| |2060| | | |2065| | | |2070| | | | | |
|Pro|Ala|Leu|Leu|Glu|Ser|Ala|Leu|Asp|Ala|Val|Glu|Thr|Pro|Gly|
| |2075| | | |2080| | | |2085| | | | | |
|Asp|Gly|Gly|Gly|Ser|Trp|Leu|Ala|Ala|Val|Trp|Ser|Gly|Val|Ala|
| |2090| | | |2095| | | |2100| | | | | |
|Leu|His|Ala|Thr|Gly|Ala|Thr|Ala|Leu|Arg|Val|Arg|Leu|Thr|Pro|
| |2105| | | |2110| | | |2115| | | | | |
|Thr|Gly|Pro|Asp|Ala|Tyr|Ala|Val|Val|Ala|Ala|Asp|Leu|Ser|Gly|
| |2120| | | |2125| | | |2130| | | | | |
|Ala|Pro|Val|Ala|Ser|Val|Asp|Arg|Leu|Val|Leu|Arg|Ala|Val|Asp|
| |2135| | | |2140| | | |2145| | | | | |
|Thr|Pro|Glu|Pro|Ile|Gly|Gly|Arg|Ser|Ala|Leu|His|Pro|Ser|Leu|

-continued

```
            2150                2155                2160

Phe Arg Leu Glu Trp Pro Ala Val Ser Ala Ala Asp Thr Thr Ala
    2165                2170                2175

Thr Ala Pro Pro Ala Thr Trp Ala Val Leu Gly Asp Asp Pro Leu
    2180                2185                2190

Gly Leu Ser Ala Ala Val Asp Ala Val Pro Tyr Asp Glu Thr Ala
    2195                2200                2205

Asp Ala Pro Asp Ala Val Leu Val Pro Cys Val Ala Gly Val Asp
    2210                2215                2220

Gly Asp Val Ala Glu Ala Ala His Ala Ala Thr His Arg Ala Leu
    2225                2230                2235

Ala Leu Ile Gln Arg Trp Thr Ser Asp Asp Arg Leu Ala Ser Ser
    2240                2245                2250

Arg Leu Val Phe Leu Thr Arg Gly Ala Val Ala Gly Ala Pro Gly
    2255                2260                2265

Glu Glu Val Pro Asp Val Ala His Gly Ala Val Trp Gly Leu Val
    2270                2275                2280

Arg Ser Ala Gln Ser Glu His Pro Gly Arg Phe Val Leu Val Asp
    2285                2290                2295

Leu Asp Ala Glu Pro Glu Ser Val Thr Ala Leu Pro Ala Ala Val
    2300                2305                2310

Ala Ser Gly Glu Pro Gln Cys Ala Val Arg Glu Gly Leu Val Arg
    2315                2320                2325

Val Pro Arg Leu Gly Arg Val Ala Arg Gly Thr Gly Ala Ala Glu
    2330                2335                2340

Ala Thr Ala Pro Arg Ala Thr Gly Leu Ala Asp Gly His Arg Pro
    2345                2350                2355

Leu Asp Pro Glu Gly Thr Val Leu Ile Thr Gly Ala Thr Gly Thr
    2360                2365                2370

Leu Gly Gly Leu Val Ala Arg His Leu Val Ala Glu His Gly Val
    2375                2380                2385

Arg His Leu Leu Leu Val Ser Arg Arg Gly Pro Ala Ala Asp Gly
    2390                2395                2400

Met Gly Glu Leu Arg Ser Glu Leu Ala Glu Leu Gly Ala Thr Val
    2405                2410                2415

Thr Val Ala Ala Cys Asp Ala Ala Asp Arg Glu Ala Leu Ala Gly
    2420                2425                2430

Leu Leu Gly Ala Ile Pro Ala Ala His Pro Leu Thr Ala Val Ile
    2435                2440                2445

His Ala Ala Gly Val Leu Asp Asp Gly Val Val Asp Ala Leu Asn
    2450                2455                2460

Pro Glu Arg Leu Asp Arg Val Leu Arg Pro Lys Val Asp Ala Ala
    2465                2470                2475

Trp Asn Leu His Glu Leu Thr Ala Gly His Asp Leu Ser Ala Phe
    2480                2485                2490

Val Leu Tyr Ser Ser Val Val Ala Thr Ile Gly Asn Ala Gly Gln
    2495                2500                2505

Ala Asn Tyr Ala Ala Ala Asn Ala Phe Leu Asp Ser Leu Ala Gln
    2510                2515                2520

His Arg Arg Ala Arg Gly Leu Ala Ala Gln Ser Leu Ala Trp Gly
    2525                2530                2535

Leu Trp Glu Gln Arg Ser Gly Met Ser Gly His Leu Asp Asp Ala
    2540                2545                2550
```

-continued

```
Asp Val Arg Arg Met Ala Arg Ser Gly Ile Arg Pro Leu Pro Ser
    2555                2560                2565

Ala Glu Gly Met Glu Leu Phe Asp Ala Ala Arg Glu Ala Gly Asp
    2570                2575                2580

Ala Thr Leu Val Pro Val Arg Leu Asp Leu Ala Asp Leu Arg Lys
    2585                2590                2595

Arg Ala Ala Ser Thr Ala Ala Thr Pro Gly Gln Asp Ala Val Pro
    2600                2605                2610

Ala His Leu Arg Gly Leu Val Arg Thr Pro Val Arg Arg Val Val
    2615                2620                2625

Arg Ala Gly Gly Gly Gly Ala Ala Glu Ser Asp Glu Ser Ser
    2630                2635                2640

Phe Gly Arg Arg Leu Ala Ala Leu Pro Thr Ala Asp Arg Asp Pro
    2645                2650                2655

Phe Leu Leu Asp Leu Val Arg Glu His Ala Ala Gly Val Leu Gly
    2660                2665                2670

Leu Ala Ala Pro Asp Asp Ile Glu Ala Thr Arg Ala Phe Arg Glu
    2675                2680                2685

Val Gly Phe Asp Ser Leu Thr Ala Val Glu Leu Arg Asn Arg Leu
    2690                2695                2700

Gly Ala Ala Thr Gly Leu Arg Leu Pro Thr Thr Leu Leu Phe Asp
    2705                2710                2715

Tyr Pro Thr Pro Ala Val Leu Val Asp His Leu Arg Arg Glu Ala
    2720                2725                2730

Leu Gly Glu Gln Ala Glu Val Ala Ala Val Ala Ala Val Arg
    2735                2740                2745

Pro Ala Asp Asp Asp Pro Ile Ala Ile Val Ala Met Ser Cys Arg
    2750                2755                2760

Leu Pro Gly Gly Val Arg Gly Pro Glu Asp Leu Trp Glu Leu Val
    2765                2770                2775

Ala Asp Gly Arg Asp Val Ile Ser Thr Phe Pro Thr Asp Arg Gly
    2780                2785                2790

Trp Asn Val Glu Glu Leu Tyr Asp Pro Asn Pro Asp Thr Pro Gly
    2795                2800                2805

Arg Ser Tyr Ala Lys Glu Gly Gly Phe Leu Tyr Asp Ala Tyr Asp
    2810                2815                2820

Phe Asp Pro Glu Phe Phe Gly Ile Ser Pro Arg Glu Ala Leu Ala
    2825                2830                2835

Met Asp Pro Gln Gln Arg Leu Leu Leu Glu Thr Ser Trp Glu Ala
    2840                2845                2850

Leu Glu Arg Ala Gly Ile Asp Pro His Ser Thr Lys Gly Ser Thr
    2855                2860                2865

Ala Gly Val Phe Ile Gly Ser Thr Gly Gln Asp Tyr Ala Ser Arg
    2870                2875                2880

Leu Gly Glu Ile Pro Glu Asp Met Glu Gly Tyr Leu Leu Thr Gly
    2885                2890                2895

Lys Ala Ala Ser Val Val Ser Gly Arg Ile Ala Tyr Ser Leu Gly
    2900                2905                2910

Trp Glu Gly Pro Ala Leu Thr Ile Asp Thr Ala Cys Ser Ser Ser
    2915                2920                2925

Leu Val Ala Ile His Gln Ala Ala Gln Ala Leu Arg Gln Gly Glu
    2930                2935                2940
```

-continued

```
Cys Ser Met Ala Leu Ala Gly Gly Thr Thr Met Met Ser Thr Pro
    2945                2950                2955

Ser Leu Phe Ile Glu Phe Ser Arg Gln Arg Gly Leu Ala Pro Asp
    2960                2965                2970

Gly Arg Ser Lys Ala Phe Ser Ser Asp Thr Asp Gly Thr Ser Trp
    2975                2980                2985

Gly Glu Gly Val Ser Met Val Leu Leu Glu Arg Leu Ser Asp Ala
    2990                2995                3000

Arg Ala Asn Gly His Glu Val Leu Ala Leu Val Cys Gly Ser Ala
    3005                3010                3015

Val Asn Gln Asp Gly Ala Ser Asn Gly Leu Thr Ala Pro Asn Gly
    3020                3025                3030

Pro Ser Gln Gln Arg Val Ile Arg Gln Ala Leu Ala Asn Ala Gly
    3035                3040                3045

Leu Ser Ala Ala Glu Val Asp Ala Val Glu Ala His Gly Thr Gly
    3050                3055                3060

Thr Thr Leu Gly Asp Pro Ile Glu Ala Gln Ala Ile Leu Ala Thr
    3065                3070                3075

Tyr Gly Gln Gly Arg Glu Ala Glu Arg Pro Leu Arg Leu Gly Ala
    3080                3085                3090

Leu Lys Ser Asn Ile Gly His Thr Gln Gly Ala Ala Gly Gly Ala
    3095                3100                3105

Gly Val Ile Lys Met Val Met Ala Met Arg His Gly Leu Leu Pro
    3110                3115                3120

Arg Thr Leu His Val Lys Glu Pro Thr Pro His Val Asp Trp Thr
    3125                3130                3135

Ala Gly Ala Val Glu Leu Leu Thr Glu Ala Arg Glu Trp Pro Ala
    3140                3145                3150

Gly Glu Arg Val Arg Arg Ala Gly Val Ser Ala Phe Gly Ile Ser
    3155                3160                3165

Gly Thr Asn Ala His Leu Ile Leu Glu Glu Pro Ala Ala Pro
    3170                3175                3180

Ala Thr Glu Pro Ala Thr Glu Pro Asp Pro Glu Ser Glu Pro Thr
    3185                3190                3195

Val Arg Thr Asp Val Val Pro Trp Met Val Ser Gly Arg Thr Glu
    3200                3205                3210

Gly Ala Leu Arg Ala Gln Ala Glu Arg Leu Arg Ser Tyr Val Gly
    3215                3220                3225

Ala Arg Pro Glu Leu Asp Pro Val Asp Val Gly Tyr Ser Leu Ala
    3230                3235                3240

Leu Thr Arg Ser Ala Phe Gly His Arg Ala Ala Val Val Gly Arg
    3245                3250                3255

Asp Arg Gly Glu Leu Leu Ser Gly Leu Glu Gln Leu Ala Ala Gly
    3260                3265                3270

Val Val Pro Gly Ala Val Ala Asp Asp Glu Gly Arg Thr Ala Phe
    3275                3280                3285

Leu Phe Thr Gly Gln Gly Ala Gln Arg Leu Gly Met Gly Arg Gly
    3290                3295                3300

Leu Tyr Ser Ala Phe Pro Val Phe Ala Val Ala Phe Asp Glu Val
    3305                3310                3315

Cys Ala Glu Leu Asp Arg His Leu Asp Gly Ser Val Gly Glu Val
    3320                3325                3330

Val Phe Gly Glu Asp Ala Glu Ala Leu Asp Arg Thr Val Phe Thr
```

```
                3335                3340                3345
Gln Ala Gly Leu Phe Ala Leu Glu Val Gly Leu Phe Arg Leu Val
    3350                3355                3360
Glu Ser Trp Gly Leu Val Pro Asp Phe Leu Val Gly His Ser Val
    3365                3370                3375
Gly Glu Leu Ala Ala Ala His Val Ala Gly Val Phe Ser Leu Glu
    3380                3385                3390
Asp Ala Cys Ala Leu Val Ala Ala Arg Gly Arg Leu Met Gln Ala
    3395                3400                3405
Leu Pro Gly Gly Gly Ala Met Val Ser Leu Lys Ala Pro Glu Ala
    3410                3415                3420
Glu Val Leu Pro His Leu Ala Gly Tyr Glu Asp Arg Val Ser Val
    3425                3430                3435
Ala Ala Val Asn Gly Pro Val Ala Thr Val Ile Ser Gly Glu Glu
    3440                3445                3450
Ser Ala Val Leu Ala Val Ala Glu Ala Val Gly Val Arg Ser Lys
    3455                3460                3465
Arg Leu Ser Val Ser His Ala Phe His Ser Pro Leu Met Glu Gly
    3470                3475                3480
Met Leu Ala Glu Phe Ala Glu Val Ala Gly Arg Ile Gly Tyr Ser
    3485                3490                3495
Ala Pro Arg Met Ala Ile Val Ser Asn Leu Thr Gly Glu Leu Ala
    3500                3505                3510
Gly Asp Glu Val Cys Ser Pro Glu Tyr Trp Val Arg His Val Arg
    3515                3520                3525
Gln Ala Val Arg Phe Gly Asp Gly Ile Arg Phe Leu Glu Thr Gln
    3530                3535                3540
Gly Val Thr Arg Phe Val Glu Leu Gly Pro Ala Gly Val Leu Ser
    3545                3550                3555
Ala Met Gly Arg Glu Cys Val Ser Gly Pro Ala Ala Phe Val Pro
    3560                3565                3570
Leu Leu Arg Lys Asp Arg Glu Glu Thr Glu Ala Leu Leu Ser Gly
    3575                3580                3585
Val Ala Gln Val His Ala His Gly Gly Glu Val Asp Trp Glu Ala
    3590                3595                3600
Val Phe Ala Gly Arg Gly Ala Gln Arg Val Glu Leu Pro Thr Tyr
    3605                3610                3615
Ala Phe Gln Arg Gln Arg Tyr Trp Phe Asp Pro Ala Thr Pro Gly
    3620                3625                3630
Thr Pro Thr Ala Ala Thr Thr Asp Thr Ser Ser Val Glu Ala Arg
    3635                3640                3645
Phe Trp Glu Ala Val Glu Arg Glu Asp Leu Glu Ala Leu Thr Thr
    3650                3655                3660
Thr Leu Glu Ile Asp Gln Gln Ala Arg Leu Gly Asp Leu Leu Pro
    3665                3670                3675
Ala Leu Ser Ser Trp Arg Arg Gly Gln Ser Arg Ala Thr Val
    3680                3685                3690
Asp Ser Trp Arg Tyr Arg Ile Thr Trp Ser Pro Thr Ala Val Glu
    3695                3700                3705
Glu Arg Thr Ala Leu Leu Ser Gly Ile Trp Trp Val Ala Val Pro
    3710                3715                3720
Glu Gly Arg Ala Asp Gly Ala Gly Ile Ala Ala Val Ala Ala Ala
    3725                3730                3735
```

-continued

```
Leu Asp Arg Arg Gly Ala Arg Val Val Pro Leu Thr Val Ala Thr
    3740            3745                3750
Thr Gly Arg Asp Ala Leu Ala Ala Arg Leu Arg His Glu Ala Asp
    3755            3760                3765
Thr Gly Gly Thr Pro Ala Gly Val Leu Ser Leu Leu Ala Leu Asp
    3770            3775                3780
Asp Gly Pro His Pro Glu His Gly Ala Leu Ser Thr Gly Leu Ala
    3785            3790                3795
Leu Asn Val Gly Leu Ile Gln Ala Leu Gly Asp Ala Gly Ile Ala
    3800            3805                3810
Ala Pro Leu Trp Leu Ala Thr Thr Gly Ala Val Ser Val Ser Gly
    3815            3820                3825
Ser Asp Pro Leu Gly Ser Pro Ala Gln Ala Ala Thr Trp Gly Leu
    3830            3835                3840
Gly Arg Val Val Ala Leu Glu His Pro Gln Arg Trp Gly Gly Leu
    3845            3850                3855
Ile Asp Leu Pro Gly Asp Leu Asp Glu Arg Thr Ala Asp Arg Leu
    3860            3865                3870
Cys Ala Ala Leu Ser Gly Ile Ala Gly Gly Ser Gly Pro Glu Asp
    3875            3880                3885
Gln Leu Ala Leu Arg Asp Ala Gly Val Phe Val Arg Arg Leu Val
    3890            3895                3900
Arg Ala Pro Leu Arg Thr Pro Gly Arg Glu Ser Trp Lys Pro His
    3905            3910                3915
Gly Thr Val Leu Ile Thr Gly Gly Thr Gly Leu Gly Ala Gln
    3920            3925                3930
Val Ala Arg Trp Leu Ala Arg Ser Gly Ala Glu His Leu Val Leu
    3935            3940                3945
Thr Ser Arg Arg Gly Ile Ala Ala Pro Gly Ala Ala Gly Leu Arg
    3950            3955                3960
Asp Glu Leu Ile Ala Leu Gly Glu Gly Gly Val Arg Val Thr Val
    3965            3970                3975
Ala Ala Cys Asp Val Arg Asp Arg Asp Glu Val Ala Ala Leu Leu
    3980            3985                3990
Arg Arg Ile Thr Thr Gly Gly Asp Pro Val His Ala Val Phe His
    3995            4000                4005
Ala Ala Gly Val Val Glu Phe Ser Gln Leu Ala Asp Ser Thr Val
    4010            4015                4020
Ala Asp Phe Ala Glu Met Ala Asp Gly Lys Val Leu Gly Ala Ala
    4025            4030                4035
His Leu Asp Ala Leu Leu Asp Gln Asp His Leu Glu Ala Phe Val
    4040            4045                4050
Leu Phe Ser Ser Ile Ala Ala Thr Trp Gly Ser Gly Gly Gln Ser
    4055            4060                4065
Ala Tyr Ala Ala Ala Asn Ala His Leu Asp Ala Leu Ala Glu His
    4070            4075                4080
Arg Glu Ala Arg Gly Leu Pro Ala Thr Ser Val Ala Trp Gly Pro
    4085            4090                4095
Trp Ala Asp His Gly Met Ile Glu His Gly Glu Val Ala Glu His
    4100            4105                4110
Leu Ser Arg Arg Gly Leu Pro Ala Met Ala Pro Glu Leu Ala Val
    4115            4120                4125
```

```
Ala Ala Leu Ser Glu Ala Leu His Thr Gly Glu Thr Ser Leu Val
    4130                4135                4140

Leu Ala Asp Val Arg Trp Asp Arg Phe Val Pro Gly Phe Thr Ala
    4145                4150                4155

Ala Arg Pro Arg Pro Leu Ile Gly Glu Leu Pro Glu Val Arg Asp
    4160                4165                4170

Ala Leu Ala Thr Thr Ala Ala Pro Asp Thr Thr Gly Pro Asp Asp
    4175                4180                4185

Val Ala Asp Thr Phe Leu Ala Gly Leu Ala Gly Leu Ser Gly Glu
    4190                4195                4200

Asp Leu Asp Arg Ala Leu Arg Asp Leu Val His Ala Gln Ala Ala
    4205                4210                4215

Ala Val Leu Gly His Ser Ser Ser Asp Ala Val Ala Gly Gly Arg
    4220                4225                4230

Pro Phe Lys Glu Leu Gly Phe Asp Ser Leu Thr Ala Val Glu Leu
    4235                4240                4245

Arg Asn Arg Leu Ala Ala Val Thr Gly Leu Asp Leu Pro Ala Thr
    4250                4255                4260

Leu Val Phe Asp Tyr Pro Ala Pro Ala Pro Leu Ala Glu Tyr Leu
    4265                4270                4275

Arg Gly Glu Leu Pro Ser Ala Arg Pro Ala Asp Ala Arg Thr Leu
    4280                4285                4290

Phe Asp Asp Leu Asp Arg Trp Glu Ser Ala Leu Pro Glu Leu Met
    4295                4300                4305

Ala Glu Asp Gly Val Arg Glu Arg Leu Thr Gly Arg Leu Asn Asp
    4310                4315                4320

Leu Met Ala Lys Leu Gly Gly Thr Pro Gly Glu His Thr Gly Gly
    4325                4330                4335

Pro Ser Pro Asp Thr Gly Leu Leu Ser Ala Thr Ala Asp Glu Val
    4340                4345                4350

Phe Asp Phe Ile Asp Asn Glu Phe Gly Ala Ser
    4355                4360
```

<210> SEQ ID NO 15
<211> LENGTH: 4872
<212> TYPE: DNA
<213> ORGANISM: Streptomyces sp. NRRL 30748
<220> FEATURE:
<221> NAME/KEY: CDS
<222> LOCATION: (1)..(4872)

<400> SEQUENCE: 15

```
atg gcg aac gag aac gaa gag aaa ctc ctc acc tac ctc aag cgg gtc       48
Met Ala Asn Glu Asn Glu Glu Lys Leu Leu Thr Tyr Leu Lys Arg Val
1               5                   10                  15 tcc tcc gac ctc aag cag gcg cgt gac cgg ctg gag cgg atc gag gcc       96
Ser Ser Asp Leu Lys Gln Ala Arg Asp Arg Leu Glu Arg Ile Glu Ala
                20                  25                  30 gac gag cgg gag ccg atc gcc atc gtc tcg atg ggc tgc cgg ttc ccc      144
Asp Glu Arg Glu Pro Ile Ala Ile Val Ser Met Gly Cys Arg Phe Pro
            35                  40                  45 ggc ggt gtc cgc tcg ccg gag gac ctg tgg cgg ctg gtg gcc gag ggc      192
Gly Gly Val Arg Ser Pro Glu Asp Leu Trp Arg Leu Val Ala Glu Gly
        50                  55                  60 cgg gac gcg atc tcg gag ttc ccc gcc aac cgc ggc tgg gac gtc gag      240
Arg Asp Ala Ile Ser Glu Phe Pro Ala Asn Arg Gly Trp Asp Val Glu
65                  70                  75                  80
```

-continued

| | | |
|---|---|---|
| gga ctc tac gac ccc gac ccg ggc cgg tcc ggc acc tgc aac acc cgc<br>Gly Leu Tyr Asp Pro Asp Pro Gly Arg Ser Gly Thr Cys Asn Thr Arg<br>               85                          90                         95 | | 288 |
| gag ggc ggc ttc gtc cac gac gcc gac cag ttc gac ccg gcc ttc ttc<br>Glu Gly Gly Phe Val His Asp Ala Asp Gln Phe Asp Pro Ala Phe Phe<br>              100                       105                      110 | | 336 |
| ggc atc tcc ccg cgc gag gcg ctg gcc atg gac cca cag cag cgg ctg<br>Gly Ile Ser Pro Arg Glu Ala Leu Ala Met Asp Pro Gln Gln Arg Leu<br>              115                       120                      125 | | 384 |
| ctg ctg gag gtg tcc tgg gag gcg atc gag cgc gcg ggc atc gac ccg<br>Leu Leu Glu Val Ser Trp Glu Ala Ile Glu Arg Ala Gly Ile Asp Pro<br>130                       135                      140 | | 432 |
| ctc tcg ctg aag ggc acc agg gcc ggg gtc tat gtg ggg ctc gcc tcg<br>Leu Ser Leu Lys Gly Thr Arg Ala Gly Val Tyr Val Gly Leu Ala Ser<br>145                       150                      155                      160 | | 480 |
| ttc cag tac ggc ggg gac ccg cag tac gcc ccg cag agc gtc gag ggc<br>Phe Gln Tyr Gly Gly Asp Pro Gln Tyr Ala Pro Gln Ser Val Glu Gly<br>                165                       170                      175 | | 528 |
| cat ctg ctg atc ggt aat gtc tcc agc gtg gcc tcc ggc cgg atc tcc<br>His Leu Leu Ile Gly Asn Val Ser Ser Val Ala Ser Gly Arg Ile Ser<br>              180                       185                      190 | | 576 |
| tac acc ctc ggc ctc gag gga ccg gcc atc acc ctg gac acc gcg tgc<br>Tyr Thr Leu Gly Leu Glu Gly Pro Ala Ile Thr Leu Asp Thr Ala Cys<br>                195                       200                      205 | | 624 |
| tcg tcc tcg ctg gtg acc atg cat ctg gcg gcc cag gcg ctg cgt cgc<br>Ser Ser Ser Leu Val Thr Met His Leu Ala Ala Gln Ala Leu Arg Arg<br>            210                       215                      220 | | 672 |
| ggc gaa tgc tcg ctg gcg ctg gcc gga ggg gtg gcg gtc atg gcc acc<br>Gly Glu Cys Ser Leu Ala Leu Ala Gly Gly Val Ala Val Met Ala Thr<br>225                       230                      235                      240 | | 720 |
| ccg ggt gtc ttc gtc gag ttc agc cat cag cgc gga ctg gcc gcc aac<br>Pro Gly Val Phe Val Glu Phe Ser His Gln Arg Gly Leu Ala Ala Asn<br>                245                       250                      255 | | 768 |
| ggc cgc tgc aag tcc ttc gcc gcg ggc gcc gac ggc acc ggc tgg ggc<br>Gly Arg Cys Lys Ser Phe Ala Ala Gly Ala Asp Gly Thr Gly Trp Gly<br>              260                       265                      270 | | 816 |
| gag ggg gcg ggc atg gtg ctg ctg gag cgg ctg tcc gac gcc cgc cgc<br>Glu Gly Ala Gly Met Val Leu Leu Glu Arg Leu Ser Asp Ala Arg Arg<br>             275                       280                      285 | | 864 |
| aac ggc cac ccc gtc ctc gcc gtg ctg cgc tcc agc gcc atg aac cag<br>Asn Gly His Pro Val Leu Ala Val Leu Arg Ser Ser Ala Met Asn Gln<br>            290                       295                      300 | | 912 |
| gac ggc gcc agc aac ggc ctc gcc gcg ccc aac ggc ccg gcc cag cgc<br>Asp Gly Ala Ser Asn Gly Leu Ala Ala Pro Asn Gly Pro Ala Gln Arg<br>305                       310                      315                      320 | | 960 |
| cgg gtc atc gag gcg gcg ctg act gcc gcc ggg ctc acg gtg gac gac<br>Arg Val Ile Glu Ala Ala Leu Thr Ala Ala Gly Leu Thr Val Asp Asp<br>                325                       330                      335 | | 1008 |
| gtc gac gcc gtc gag gcc cat ggc acg ggc acg gcg ctc ggc gat ccg<br>Val Asp Ala Val Glu Ala His Gly Thr Gly Thr Ala Leu Gly Asp Pro<br>                340                       345                      350 | | 1056 |
| atc gag gcg ggc gcg ctc ctc gcc acg tac ggc aag ggc cgc acc tcc<br>Ile Glu Ala Gly Ala Leu Leu Ala Thr Tyr Gly Lys Gly Arg Thr Ser<br>                355                       360                      365 | | 1104 |
| ggc cat ccg ctg tgg ctc ggc tcg ctc aag tcc aac atc ggc cac acc<br>Gly His Pro Leu Trp Leu Gly Ser Leu Lys Ser Asn Ile Gly His Thr<br>            370                       375                      380 | | 1152 |
| cag gcg gcg gcc ggg gtc ggc ggg gtc atc aag acg gtg atg gcc ctg<br>Gln Ala Ala Ala Gly Val Gly Gly Val Ile Lys Thr Val Met Ala Leu<br>385                       390                      395                      400 | | 1200 |

```
                                                              -continued cgc cac ggg acg ctg ccg agg aca ctc cat gtc gag cgg gcg tcc ccg    1248
Arg His Gly Thr Leu Pro Arg Thr Leu His Val Glu Arg Ala Ser Pro
             405                 410                 415 ggc gtc aac tgg tcc tcc ggc gcg gtc gag ttg ctg acc gag gcc cgg    1296
Gly Val Asn Trp Ser Ser Gly Ala Val Glu Leu Leu Thr Glu Ala Arg
             420                 425                 430 gag tgg ccc gag cgt ggc cgt ccg cgc cgc gcc ggg gtg tcc gcg ttc    1344
Glu Trp Pro Glu Arg Gly Arg Pro Arg Arg Ala Gly Val Ser Ala Phe
             435                 440                 445 ggg gtg agc ggc acc aac gcc cat gtc atc ctc gaa cag gcc ccg gcc    1392
Gly Val Ser Gly Thr Asn Ala His Val Ile Leu Glu Gln Ala Pro Ala
450                  455                 460 gag ggg gag gac gac gaa gaa ggc gcc ccc gcc ctg gac ggg acc gcg    1440
Glu Gly Glu Asp Asp Glu Glu Gly Ala Pro Ala Leu Asp Gly Thr Ala
465                  470                 475                 480 ctc ggt ggc tcc gcc gtc ccc tgg gcg ctc tcc ggc agg agc gaa gcg    1488
Leu Gly Gly Ser Ala Val Pro Trp Ala Leu Ser Gly Arg Ser Glu Ala
                 485                 490                 495 gcc ctg cgg gcg cag gcg gag cgg ctg ctg gcg cat ctg aac gag cgc    1536
Ala Leu Arg Ala Gln Ala Glu Arg Leu Leu Ala His Leu Asn Glu Arg
             500                 505                 510 ccc gag gtg tcc ccg gcc gat gtc ggc cac tca ctc gcc acc gga cgg    1584
Pro Glu Val Ser Pro Ala Asp Val Gly His Ser Leu Ala Thr Gly Arg
             515                 520                 525 tcg gcc ttc gaa tac cgc gcc gcg gtg gtg ggc gcg gac cgg ccc caa    1632
Ser Ala Phe Glu Tyr Arg Ala Ala Val Val Gly Ala Asp Arg Pro Gln
             530                 535                 540 ctg ctg ggc caa ctt gag gcg ttg gcc tcc ggt ggg gtc tcc gca ggt    1680
Leu Leu Gly Gln Leu Glu Ala Leu Ala Ser Gly Gly Val Ser Ala Gly
545                  550                 555                 560 gtg gtg cgt ggc gag gga gtc acg gcg gcc gat gcc cgt ccg gtg ttc    1728
Val Val Arg Gly Glu Gly Val Thr Ala Ala Asp Ala Arg Pro Val Phe
                 565                 570                 575 gtg ttt ccg ggg cag ggg tcg cag tgg gtg ggg atg gcg gtg gag ttg    1776
Val Phe Pro Gly Gln Gly Ser Gln Trp Val Gly Met Ala Val Glu Leu
             580                 585                 590 ctg gat tcg tcg ccg gtg ttc gcg ggt cgg ttg gcg gag tgt gag gtg    1824
Leu Asp Ser Ser Pro Val Phe Ala Gly Arg Leu Ala Glu Cys Glu Val
             595                 600                 605 gcg ctg tcg ggg ttt gtg gac tgg tcg ttg agt ggt gtg ttg cgg ggt    1872
Ala Leu Ser Gly Phe Val Asp Trp Ser Leu Ser Gly Val Leu Arg Gly
             610                 615                 620 gag ggg ccg ggg ttg ggg cgg gtg gat gtg gtg cag ccg gcg ttg tgg    1920
Glu Gly Pro Gly Leu Gly Arg Val Asp Val Val Gln Pro Ala Leu Trp
625                  630                 635                 640 gcg gtg atg gtg tcg ttg gcg gag gtg tgg cgt gcg tgt ggg gtg acg    1968
Ala Val Met Val Ser Leu Ala Glu Val Trp Arg Ala Cys Gly Val Thr
                 645                 650                 655 cct gcc gct gtg gtg ggg cat tcg cag ggg gag atc gcg gcg gcg gtg    2016
Pro Ala Ala Val Val Gly His Ser Gln Gly Glu Ile Ala Ala Ala Val
             660                 665                 670 gtg gcg ggt gcg ctg tcg ttg gag gac ggg gca cgg gtc gtc gcg ctg    2064
Val Ala Gly Ala Leu Ser Leu Glu Asp Gly Ala Arg Val Val Ala Leu
             675                 680                 685 cgg tcg cag gcc atc gga cgc ggg ctg gcc gga cac ggc ggc atg atg    2112
Arg Ser Gln Ala Ile Gly Arg Gly Leu Ala Gly His Gly Gly Met Met
690                  695                 700 tcc gtg tcg ctc ccg gtc gag gag gtg cgg gag cgg atc gcc gcc tgg    2160
Ser Val Ser Leu Pro Val Glu Glu Val Arg Glu Arg Ile Ala Ala Trp
```

```
                705                 710                 715                 720
gag ggg cgt atc tcc gtg gcg gcc gtc aac ggc ccc ggc gcg gtg gtc       2208
Glu Gly Arg Ile Ser Val Ala Ala Val Asn Gly Pro Gly Ala Val Val
                    725                 730                 735 gtc tcc ggc gaa ccg gag gcg ctg cgt gaa ctc cag gcg gag tgc gag       2256
Val Ser Gly Glu Pro Glu Ala Leu Arg Glu Leu Gln Ala Glu Cys Glu
                740                 745                 750 gcc gag gac gta cgg gcg aag ctg atc ccg gtg gac tac gcc tcg cac       2304
Ala Glu Asp Val Arg Ala Lys Leu Ile Pro Val Asp Tyr Ala Ser His
            755                 760                 765 tcg gcg cag gtg gag aag atc cac gac gag ctg ctg cgg atc ctc gcc       2352
Ser Ala Gln Val Glu Lys Ile His Asp Glu Leu Leu Arg Ile Leu Ala
        770                 775                 780 ccc atc cgg ccg cgc acc tcg cgg atc gtc ttc cac tcg acc gtc acc       2400
Pro Ile Arg Pro Arg Thr Ser Arg Ile Val Phe His Ser Thr Val Thr
785                 790                 795                 800 ggt gaa ccc ctg gac acc gct ggg ctc gac gcc gcc tac tgg gcg cgc       2448
Gly Glu Pro Leu Asp Thr Ala Gly Leu Asp Ala Ala Tyr Trp Ala Arg
                805                 810                 815 aac ctt cgg gag agc gta cag ctc gaa gcg gcc acc cgg gcg ctg ctc       2496
Asn Leu Arg Glu Ser Val Gln Leu Glu Ala Ala Thr Arg Ala Leu Leu
                820                 825                 830 acc agc ggc cac cgg ctg ttc gtg gag gtg agc ccg cac ccc gtg ctg       2544
Thr Ser Gly His Arg Leu Phe Val Glu Val Ser Pro His Pro Val Leu
            835                 840                 845 gcc gcg gcc atc gag gcc acc gtc gag gcc gcc gag ggc tcg gcc gcc       2592
Ala Ala Ala Ile Glu Ala Thr Val Glu Ala Ala Glu Gly Ser Ala Ala
        850                 855                 860 gtc atc ggc acc ctg cgc cgc gag gag ggc ggc ccc gag cgg atg ctg       2640
Val Ile Gly Thr Leu Arg Arg Glu Glu Gly Gly Pro Glu Arg Met Leu
865                 870                 875                 880 ctc tcg ctc gcc cag ggc tac gtc cat ggc gcg gag gtg gac tgg cgg       2688
Leu Ser Leu Ala Gln Gly Tyr Val His Gly Ala Glu Val Asp Trp Arg
                885                 890                 895 ggg ctg ttc gcc ggg cgg gga gcg agg cgc gtc gac ctt ccc acg tac       2736
Gly Leu Phe Ala Gly Arg Gly Ala Arg Arg Val Asp Leu Pro Thr Tyr
                900                 905                 910 gcg ttc cag cgc gcc cgc tac tgg gtc gag ccc cgg acc ggg ccc gcc       2784
Ala Phe Gln Arg Ala Arg Tyr Trp Val Glu Pro Arg Thr Gly Pro Ala
            915                 920                 925 gag gcg gcc acc ggc ccg gcg gag gcg gag ttc tgg acc gcg gtc gag       2832
Glu Ala Ala Thr Gly Pro Ala Glu Ala Glu Phe Trp Thr Ala Val Glu
        930                 935                 940 aag gcc gac ctg gac acg ctg acg gcg aca ctg ggc gcg gac gcc gac       2880
Lys Ala Asp Leu Asp Thr Leu Thr Ala Thr Leu Gly Ala Asp Ala Asp
945                 950                 955                 960 gcg ccg ctc agc gag gtg ctt ccg ctg ctc tcg tcg tgg cgg tcc cgg       2928
Ala Pro Leu Ser Glu Val Leu Pro Leu Leu Ser Ser Trp Arg Ser Arg
                965                 970                 975 ctg agc gac cag gcg gag ctc gac gcc tgg cgc tac cgc atc ggc tgg       2976
Leu Ser Asp Gln Ala Glu Leu Asp Ala Trp Arg Tyr Arg Ile Gly Trp
                980                 985                 990 caa ccg ctc gac ggc cgg cgg acc  ccc acg ctc ccg ggc  cgc ctg ctg     3024
Gln Pro Leu Asp Gly Arg Arg Thr  Pro Thr Leu Pro Gly  Arg Leu Leu
            995                 1000                1005 gtg gcg  gtg ccc acc gag gcc  cgc gcc act gat acc  gag gcc atc        3069
Val Ala  Val Pro Thr Glu Ala  Arg Ala Thr Asp Thr  Glu Ala Ile
         1010                1015                1020 acc gcc  ggg ctc gcc gcg ctc  ggc gtc gag gtc gtc  ccc gtg cgc        3114
```

```
Thr Ala Gly Leu Ala Ala Leu Gly Val Glu Val Val Pro Val Arg
    1025              1030                1035 atc ggc ccg gac gac acc gac cgc gcc cgg ctc gcc acc cgt atc         3159
Ile Gly Pro Asp Asp Thr Asp Arg Ala Arg Leu Ala Thr Arg Ile
    1040              1045                1050 acc gag gcc ctc ggg gac acc ggg gcg ccc ggc ggc gtg gtg tcc         3204
Thr Glu Ala Leu Gly Asp Thr Gly Ala Pro Gly Gly Val Val Ser
    1055              1060                1065 ctc ctc gct ctc gac gaa gca ccg cac ccg gaa cac ccc gag gtg         3249
Leu Leu Ala Leu Asp Glu Ala Pro His Pro Glu His Pro Glu Val
    1070              1075                1080 ccc acc ggg ttc gcc acc acc ctc gac ctg gtg cgg gcg ctg ggc         3294
Pro Thr Gly Phe Ala Thr Thr Leu Asp Leu Val Arg Ala Leu Gly
    1085              1090                1095 gag gcg ggc gtc gac gcg ccg ctg tgg tgt gtc acc cgt ggc gcc         3339
Glu Ala Gly Val Asp Ala Pro Leu Trp Cys Val Thr Arg Gly Ala
    1100              1105                1110 gtg tcc gcc agt ggc gcc gac cgt ctc gga gcc ccc gcg cag gcc         3384
Val Ser Ala Ser Gly Ala Asp Arg Leu Gly Ala Pro Ala Gln Ala
    1115              1120                1125 ctc gtc tgg ggc ctg ggc ggt gcg gtc gcc ctg gag cat ccg cag         3429
Leu Val Trp Gly Leu Gly Gly Ala Val Ala Leu Glu His Pro Gln
    1130              1135                1140 cgc tgg ggc ggg ctg gtc gat ctg ccc ggg acg ctc gac gag ggc         3474
Arg Trp Gly Gly Leu Val Asp Leu Pro Gly Thr Leu Asp Glu Gly
    1145              1150                1155 gcc ctc cgg gcg ctc gcc cgc gcc ctg acc ggc cag gac ggc gaa         3519
Ala Leu Arg Ala Leu Ala Arg Ala Leu Thr Gly Gln Asp Gly Glu
    1160              1165                1170 aac cag ctg gcc atc cgc gcc tcg ggc acc ctc gcc cgg cgg ctc         3564
Asn Gln Leu Ala Ile Arg Ala Ser Gly Thr Leu Ala Arg Arg Leu
    1175              1180                1185 cgg cgg gcc ggg gcc ggc cgc tcc ggt gag cgc tgg cag ccc cgc         3609
Arg Arg Ala Gly Ala Gly Arg Ser Gly Glu Arg Trp Gln Pro Arg
    1190              1195                1200 ggc acc gtc ctg atc acc ggc ggc acc ggt ggc gtc ggc gcc cag         3654
Gly Thr Val Leu Ile Thr Gly Gly Thr Gly Gly Val Gly Ala Gln
    1205              1210                1215 atc gcc cgt gga ctg gtc gac gag ggc gcc gag cac gtg gtg ctc         3699
Ile Ala Arg Gly Leu Val Asp Glu Gly Ala Glu His Val Val Leu
    1220              1225                1230 atc agc cgc cgt ggc ccc cag gcc ccc ggc gcg gcc gag ctg gag         3744
Ile Ser Arg Arg Gly Pro Gln Ala Pro Gly Ala Ala Glu Leu Glu
    1235              1240                1245 gcc gaa ctg acc gag cgc ggc gcc cgg gtg acc gtc gcc gca tgc         3789
Ala Glu Leu Thr Glu Arg Gly Ala Arg Val Thr Val Ala Ala Cys
    1250              1255                1260 gat gtg gcc gac cgc gag gcg ctg gca cac ctg ctg aac cag gtc         3834
Asp Val Ala Asp Arg Glu Ala Leu Ala His Leu Leu Asn Gln Val
    1265              1270                1275 acc cac gac ggc gcg gac cac ccg ctc acc gcc gtg gtg cac gcc         3879
Thr His Asp Gly Ala Asp His Pro Leu Thr Ala Val Val His Ala
    1280              1285                1290 gcg ggc gcg ctg gac gac gcc acc gtg gac gcg ctc acc ccc gag         3924
Ala Gly Ala Leu Asp Asp Ala Thr Val Asp Ala Leu Thr Pro Glu
    1295              1300                1305 cgg atc gag gcc gta ctg cgc ccc aag gtg gcg ggc gcg cgc cat         3969
Arg Ile Glu Ala Val Leu Arg Pro Lys Val Ala Gly Ala Arg His
    1310              1315                1320
```

```
ctg cac gag ctc acc cgg gac ctg gac ctg gac ctc gac gcg ttc    4014
Leu His Glu Leu Thr Arg Asp Leu Asp Leu Asp Leu Asp Ala Phe
1325            1330                1335 gtc ctg atc tcc tcg atc gcc ggc acc gtg ggc gcc gcc ggc cag    4059
Val Leu Ile Ser Ser Ile Ala Gly Thr Val Gly Ala Ala Gly Gln
    1340            1345                1350 ggc aac tac gcg gcg gcc agc gcg tat ctc gac gcg ctc gcc cag    4104
Gly Asn Tyr Ala Ala Ala Ser Ala Tyr Leu Asp Ala Leu Ala Gln
    1355            1360                1365 ctg cgc cgc gcg gac ggt ctg ccc gcc acc tcg gtg gcc tgg agt    4149
Leu Arg Arg Ala Asp Gly Leu Pro Ala Thr Ser Val Ala Trp Ser
1370            1375                1380 gcc tgg gcg ggc ggc gga atg atc gac ggc gag gtg gcg gac cag    4194
Ala Trp Ala Gly Gly Gly Met Ile Asp Gly Glu Val Ala Asp Gln
1385            1390                1395 ctg cga cgc cgt ggc gcg ccg ccc atc gac ggc gta cgg gcg ctg    4239
Leu Arg Arg Arg Gly Ala Pro Pro Ile Asp Gly Val Arg Ala Leu
1400            1405                1410 gaa ctg ctg cgg cag acg gtc gcg cag agc gat ggc ttc ctc gtc    4284
Glu Leu Leu Arg Gln Thr Val Ala Gln Ser Asp Gly Phe Leu Val
1415            1420                1425 gcg gcc gac atc gat tgg ggc cgt ttc gcc ccc gcc ctg tcc gcc    4329
Ala Ala Asp Ile Asp Trp Gly Arg Phe Ala Pro Ala Leu Ser Ala
1430            1435                1440 acc cgc ccg ttg ccg ctg ctc gcc gac ctc ccc gag gcg ggc ggc    4374
Thr Arg Pro Leu Pro Leu Leu Ala Asp Leu Pro Glu Ala Gly Gly
    1445            1450                1455 acc ttg cag gat ccg gcc gga gcg gag cgg gag gag gcc ggt ggc    4419
Thr Leu Gln Asp Pro Ala Gly Ala Glu Arg Glu Glu Ala Gly Gly
    1460            1465                1470 gcc gcc gcg ctg cgc acg cgg ctc gcg gag ctc agc ccg gcc gac    4464
Ala Ala Ala Leu Arg Thr Arg Leu Ala Glu Leu Ser Pro Ala Asp
1475            1480                1485 cgc cac acc gcc ctc gtg gag ctg gtg agc gag cag gcg gcc gcg    4509
Arg His Thr Ala Leu Val Glu Leu Val Ser Glu Gln Ala Ala Ala
1490            1495                1500 gcc ctc ggc tac gcc gac gcg ggc gcg ttc gag acc gga cgg gcc    4554
Ala Leu Gly Tyr Ala Asp Ala Gly Ala Phe Glu Thr Gly Arg Ala
1505            1510                1515 ttc aag gag ctg ggc ttc gac tcg ctg acc gcc gtc gat ctg cgc    4599
Phe Lys Glu Leu Gly Phe Asp Ser Leu Thr Ala Val Asp Leu Arg
1520            1525                1530 aac cgg ctg aac gcc gcc acc gga ctc cgg ctg ccg gtc acc ctc    4644
Asn Arg Leu Asn Ala Ala Thr Gly Leu Arg Leu Pro Val Thr Leu
1535            1540                1545 gtc ttc gac tac ccg acc gcc gac gac ctc gcc gtg ctg ctg cgg    4689
Val Phe Asp Tyr Pro Thr Ala Asp Asp Leu Ala Val Leu Leu Arg
1550            1555                1560 gag gaa ctc ctg cca tcg ggc ggg gag ccc gtg gac acc gtg gcg    4734
Glu Glu Leu Leu Pro Ser Gly Gly Glu Pro Val Asp Thr Val Ala
1565            1570                1575 ctc gcc gag ctc gac cgc gtc cag tcc acc ctc gcc gcc ctg gag    4779
Leu Ala Glu Leu Asp Arg Val Gln Ser Thr Leu Ala Ala Leu Glu
1580            1585                1590 ctg gac gac atc gaa tcg gcc acc gac gac gag atg ttc gag ctg    4824
Leu Asp Asp Ile Glu Ser Ala Thr Asp Asp Glu Met Phe Glu Leu
1595            1600                1605 ctc gac ggg atg ttc gag ctg ctg ggc cgg gat ctg acg gcc cca    4869
Leu Asp Gly Met Phe Glu Leu Leu Gly Arg Asp Leu Thr Ala Pro
1610            1615                1620
``` tga                                                                        4872

<210> SEQ ID NO 16
<211> LENGTH: 1623
<212> TYPE: PRT
<213> ORGANISM: Streptomyces sp. NRRL 30748

<400> SEQUENCE: 16

Met Ala Asn Glu Asn Glu Glu Lys Leu Leu Thr Tyr Leu Lys Arg Val
1               5                   10                  15

Ser Ser Asp Leu Lys Gln Ala Arg Asp Arg Leu Glu Arg Ile Glu Ala
            20                  25                  30

Asp Glu Arg Glu Pro Ile Ala Ile Val Ser Met Gly Cys Arg Phe Pro
        35                  40                  45

Gly Gly Val Arg Ser Pro Glu Asp Leu Trp Arg Leu Ala Glu Gly
    50                  55                  60

Arg Asp Ala Ile Ser Glu Phe Pro Ala Asn Arg Gly Trp Asp Val Glu
65                  70                  75                  80

Gly Leu Tyr Asp Pro Asp Pro Gly Arg Ser Gly Thr Cys Asn Thr Arg
                85                  90                  95

Glu Gly Gly Phe Val His Asp Ala Asp Gln Phe Asp Pro Ala Phe Phe
            100                 105                 110

Gly Ile Ser Pro Arg Glu Ala Leu Ala Met Asp Pro Gln Gln Arg Leu
        115                 120                 125

Leu Leu Glu Val Ser Trp Glu Ala Ile Glu Arg Ala Gly Ile Asp Pro
    130                 135                 140

Leu Ser Leu Lys Gly Thr Arg Ala Gly Val Tyr Val Gly Leu Ala Ser
145                 150                 155                 160

Phe Gln Tyr Gly Gly Asp Pro Gln Tyr Ala Pro Gln Ser Val Glu Gly
                165                 170                 175

His Leu Leu Ile Gly Asn Val Ser Val Ala Ser Gly Arg Ile Ser
            180                 185                 190

Tyr Thr Leu Gly Leu Glu Gly Pro Ala Ile Thr Leu Asp Thr Ala Cys
        195                 200                 205

Ser Ser Ser Leu Val Thr Met His Leu Ala Ala Gln Ala Leu Arg Arg
    210                 215                 220

Gly Glu Cys Ser Leu Ala Leu Ala Gly Gly Val Ala Val Met Ala Thr
225                 230                 235                 240

Pro Gly Val Phe Val Glu Phe Ser His Gln Arg Gly Leu Ala Ala Asn
                245                 250                 255

Gly Arg Cys Lys Ser Phe Ala Gly Ala Asp Gly Thr Gly Trp Gly
            260                 265                 270

Glu Gly Ala Gly Met Val Leu Leu Glu Arg Leu Ser Asp Ala Arg Arg
        275                 280                 285

Asn Gly His Pro Val Leu Ala Val Leu Arg Ser Ser Ala Met Asn Gln
    290                 295                 300

Asp Gly Ala Ser Asn Gly Leu Ala Pro Asn Gly Pro Ala Gln Arg
305                 310                 315                 320

Arg Val Ile Glu Ala Ala Leu Thr Ala Gly Leu Thr Val Asp Asp
                325                 330                 335

Val Asp Ala Val Glu Ala His Gly Thr Gly Thr Ala Leu Gly Asp Pro
            340                 345                 350

Ile Glu Ala Gly Ala Leu Leu Ala Thr Tyr Gly Lys Gly Arg Thr Ser
        355                 360                 365

-continued

```
Gly His Pro Leu Trp Leu Gly Ser Leu Lys Ser Asn Ile Gly His Thr
        370                 375                 380

Gln Ala Ala Ala Gly Val Gly Val Ile Lys Thr Val Met Ala Leu
385                 390                 395                 400

Arg His Gly Thr Leu Pro Arg Thr Leu His Val Glu Arg Ala Ser Pro
                    405                 410                 415

Gly Val Asn Trp Ser Ser Gly Ala Val Glu Leu Leu Thr Glu Ala Arg
                420                 425                 430

Glu Trp Pro Glu Arg Gly Arg Pro Arg Arg Ala Gly Val Ser Ala Phe
            435                 440                 445

Gly Val Ser Gly Thr Asn Ala His Val Ile Leu Glu Gln Ala Pro Ala
        450                 455                 460

Glu Gly Glu Asp Asp Glu Gly Ala Pro Ala Leu Asp Gly Thr Ala
465                 470                 475                 480

Leu Gly Gly Ser Ala Val Pro Trp Ala Leu Ser Gly Arg Ser Glu Ala
                    485                 490                 495

Ala Leu Arg Ala Gln Ala Glu Arg Leu Leu Ala His Leu Asn Glu Arg
                500                 505                 510

Pro Glu Val Ser Pro Ala Asp Val Gly His Ser Leu Ala Thr Gly Arg
            515                 520                 525

Ser Ala Phe Glu Tyr Arg Ala Ala Val Val Gly Ala Asp Arg Pro Gln
        530                 535                 540

Leu Leu Gly Gln Leu Glu Ala Leu Ala Ser Gly Gly Val Ser Ala Gly
545                 550                 555                 560

Val Val Arg Gly Glu Gly Val Thr Ala Ala Asp Ala Arg Pro Val Phe
                    565                 570                 575

Val Phe Pro Gly Gln Gly Ser Gln Trp Val Gly Met Ala Val Glu Leu
                580                 585                 590

Leu Asp Ser Ser Pro Val Phe Ala Gly Arg Leu Ala Glu Cys Glu Val
            595                 600                 605

Ala Leu Ser Gly Phe Val Asp Trp Ser Leu Ser Gly Val Leu Arg Gly
        610                 615                 620

Glu Gly Pro Gly Leu Gly Arg Val Asp Val Val Gln Pro Ala Leu Trp
625                 630                 635                 640

Ala Val Met Val Ser Leu Ala Glu Val Trp Arg Ala Cys Gly Val Thr
                    645                 650                 655

Pro Ala Ala Val Val Gly His Ser Gln Gly Glu Ile Ala Ala Ala Val
                660                 665                 670

Val Ala Gly Ala Leu Ser Leu Glu Asp Gly Ala Arg Val Val Ala Leu
            675                 680                 685

Arg Ser Gln Ala Ile Gly Arg Gly Leu Ala Gly His Gly Gly Met Met
        690                 695                 700

Ser Val Ser Leu Pro Val Glu Glu Val Arg Glu Arg Ile Ala Ala Trp
705                 710                 715                 720

Glu Gly Arg Ile Ser Val Ala Ala Val Asn Gly Pro Gly Ala Val Val
                    725                 730                 735

Val Ser Gly Glu Pro Glu Ala Leu Arg Glu Leu Gln Ala Glu Cys Glu
                740                 745                 750

Ala Glu Asp Val Arg Ala Lys Leu Ile Pro Val Asp Tyr Ala Ser His
            755                 760                 765

Ser Ala Gln Val Glu Lys Ile His Asp Glu Leu Leu Arg Ile Leu Ala
        770                 775                 780
```

```
Pro Ile Arg Pro Arg Thr Ser Arg Ile Val Phe His Ser Thr Val Thr
785                 790                 795                 800

Gly Glu Pro Leu Asp Thr Ala Gly Leu Asp Ala Ala Tyr Trp Ala Arg
                805                 810                 815

Asn Leu Arg Glu Ser Val Gln Leu Glu Ala Ala Thr Arg Ala Leu Leu
            820                 825                 830

Thr Ser Gly His Arg Leu Phe Val Glu Val Ser Pro His Pro Val Leu
        835                 840                 845

Ala Ala Ala Ile Glu Ala Thr Val Glu Ala Ala Glu Gly Ser Ala Ala
    850                 855                 860

Val Ile Gly Thr Leu Arg Arg Glu Glu Gly Pro Glu Arg Met Leu
865             870                 875                 880

Leu Ser Leu Ala Gln Gly Tyr Val His Gly Ala Glu Val Asp Trp Arg
                885                 890                 895

Gly Leu Phe Ala Gly Arg Gly Ala Arg Arg Val Asp Leu Pro Thr Tyr
            900                 905                 910

Ala Phe Gln Arg Ala Arg Tyr Trp Val Glu Pro Arg Thr Gly Pro Ala
        915                 920                 925

Glu Ala Ala Thr Gly Pro Ala Glu Ala Glu Phe Trp Thr Ala Val Glu
    930                 935                 940

Lys Ala Asp Leu Asp Thr Leu Thr Ala Thr Leu Gly Ala Asp Ala Asp
945                 950                 955                 960

Ala Pro Leu Ser Glu Val Leu Pro Leu Ser Ser Trp Arg Ser Arg
                965                 970                 975

Leu Ser Asp Gln Ala Glu Leu Asp Ala Trp Arg Tyr Arg Ile Gly Trp
            980                 985                 990

Gln Pro Leu Asp Gly Arg Arg Thr Pro Thr Leu Pro Gly Arg Leu Leu
        995                 1000                1005

Val Ala Val Pro Thr Glu Ala Arg Ala Thr Asp Thr Glu Ala Ile
    1010                1015                1020

Thr Ala Gly Leu Ala Ala Leu Gly Val Glu Val Val Pro Val Arg
    1025                1030                1035

Ile Gly Pro Asp Asp Thr Asp Arg Ala Arg Leu Ala Thr Arg Ile
    1040                1045                1050

Thr Glu Ala Leu Gly Asp Thr Gly Ala Pro Gly Gly Val Val Ser
    1055                1060                1065

Leu Leu Ala Leu Asp Glu Ala Pro His Pro Glu His Pro Glu Val
    1070                1075                1080

Pro Thr Gly Phe Ala Thr Thr Leu Asp Leu Val Arg Ala Leu Gly
    1085                1090                1095

Glu Ala Gly Val Asp Ala Pro Leu Trp Cys Val Thr Arg Gly Ala
    1100                1105                1110

Val Ser Ala Ser Gly Ala Asp Arg Leu Gly Ala Pro Ala Gln Ala
    1115                1120                1125

Leu Val Trp Gly Leu Gly Gly Ala Val Ala Leu Glu His Pro Gln
    1130                1135                1140

Arg Trp Gly Gly Leu Val Asp Leu Pro Gly Thr Leu Asp Glu Gly
    1145                1150                1155

Ala Leu Arg Ala Leu Ala Arg Ala Leu Thr Gly Gln Asp Gly Glu
    1160                1165                1170

Asn Gln Leu Ala Ile Arg Ala Ser Gly Thr Leu Ala Arg Arg Leu
    1175                1180                1185

Arg Arg Ala Gly Ala Gly Arg Ser Gly Glu Arg Trp Gln Pro Arg
```

-continued

```
            1190                1195                1200
Gly Thr Val Leu Ile Thr Gly Thr Gly Val Gly Ala Gln
        1205                1210                1215
Ile Ala Arg Gly Leu Val Asp Glu Gly Ala Glu His Val Val Leu
        1220                1225                1230
Ile Ser Arg Arg Gly Pro Gln Ala Pro Gly Ala Ala Glu Leu Glu
        1235                1240                1245
Ala Glu Leu Thr Glu Arg Gly Ala Arg Val Thr Val Ala Ala Cys
        1250                1255                1260
Asp Val Ala Asp Arg Glu Ala Leu Ala His Leu Leu Asn Gln Val
        1265                1270                1275
Thr His Asp Gly Ala Asp His Pro Leu Thr Ala Val Val His Ala
        1280                1285                1290
Ala Gly Ala Leu Asp Asp Ala Thr Val Asp Ala Leu Thr Pro Glu
        1295                1300                1305
Arg Ile Glu Ala Val Leu Arg Pro Lys Val Ala Gly Ala Arg His
        1310                1315                1320
Leu His Glu Leu Thr Arg Asp Leu Asp Leu Asp Leu Asp Ala Phe
        1325                1330                1335
Val Leu Ile Ser Ser Ile Ala Gly Thr Val Gly Ala Ala Gly Gln
        1340                1345                1350
Gly Asn Tyr Ala Ala Ala Ser Ala Tyr Leu Asp Ala Leu Ala Gln
        1355                1360                1365
Leu Arg Arg Ala Asp Gly Leu Pro Ala Thr Ser Val Ala Trp Ser
        1370                1375                1380
Ala Trp Ala Gly Gly Gly Met Ile Asp Gly Glu Val Ala Asp Gln
        1385                1390                1395
Leu Arg Arg Arg Gly Ala Pro Pro Ile Asp Gly Val Arg Ala Leu
        1400                1405                1410
Glu Leu Leu Arg Gln Thr Val Ala Gln Ser Asp Gly Phe Leu Val
        1415                1420                1425
Ala Ala Asp Ile Asp Trp Gly Arg Phe Ala Pro Ala Leu Ser Ala
        1430                1435                1440
Thr Arg Pro Leu Pro Leu Leu Ala Asp Leu Pro Glu Ala Gly Gly
        1445                1450                1455
Thr Leu Gln Asp Pro Ala Gly Ala Glu Arg Glu Ala Gly Gly
        1460                1465                1470
Ala Ala Ala Leu Arg Thr Arg Leu Ala Glu Leu Ser Pro Ala Asp
        1475                1480                1485
Arg His Thr Ala Leu Val Glu Leu Val Ser Glu Gln Ala Ala Ala
        1490                1495                1500
Ala Leu Gly Tyr Ala Asp Ala Gly Ala Phe Glu Thr Gly Arg Ala
        1505                1510                1515
Phe Lys Glu Leu Gly Phe Asp Ser Leu Thr Ala Val Asp Leu Arg
        1520                1525                1530
Asn Arg Leu Asn Ala Ala Thr Gly Leu Arg Leu Pro Val Thr Leu
        1535                1540                1545
Val Phe Asp Tyr Pro Thr Ala Asp Asp Leu Ala Val Leu Leu Arg
        1550                1555                1560
Glu Glu Leu Leu Pro Ser Gly Gly Glu Pro Val Asp Thr Val Ala
        1565                1570                1575
Leu Ala Glu Leu Asp Arg Val Gln Ser Thr Leu Ala Ala Leu Glu
        1580                1585                1590
```

```
Leu Asp  Asp Ile Glu Ser Ala  Thr Asp Asp Glu Met  Phe Glu Leu
    1595             1600                 1605

Leu Asp  Gly Met Phe Glu Leu  Leu Gly Arg Asp Leu  Thr Ala Pro
    1610             1615                 1620

<210> SEQ ID NO 17
<211> LENGTH: 4929
<212> TYPE: DNA
<213> ORGANISM: Streptomyces sp. NRRL 30748
<220> FEATURE:
<221> NAME/KEY: CDS
<222> LOCATION: (1)..(4929)

<400> SEQUENCE: 17 atg gac aac gag aag aag ctg cgc gac tac ctc aag cgg gcc acc ggc        48
Met Asp Asn Glu Lys Lys Leu Arg Asp Tyr Leu Lys Arg Ala Thr Gly
 1               5                  10                  15 cac ctc cgc gcc gca cac cgc cgg atc cag gag ttg cag gcc ccc gag        96
His Leu Arg Ala Ala His Arg Arg Ile Gln Glu Leu Gln Ala Pro Glu
             20                  25                  30 ccc atc gcc atc gtg gcg atg aac tgc cgc tac gcg ggc gac atc cgg       144
Pro Ile Ala Ile Val Ala Met Asn Cys Arg Tyr Ala Gly Asp Ile Arg
         35                  40                  45 tcc ccc gag gac ctg tgg cag gcc gtg gcc gaa ggc cgg gac ggc atg       192
Ser Pro Glu Asp Leu Trp Gln Ala Val Ala Glu Gly Arg Asp Gly Met
     50                  55                  60 ggc gac ttc ccg gcc gac cgg ggc tgg gac ctg ccg aac ctc ttc gac       240
Gly Asp Phe Pro Ala Asp Arg Gly Trp Asp Leu Pro Asn Leu Phe Asp
 65                  70                  75                  80 ccg gac ccg gac cgc gag ggc cgc acc tac gcc cgc cag ggc gga ttc       288
Pro Asp Pro Asp Arg Glu Gly Arg Thr Tyr Ala Arg Gln Gly Gly Phe
                 85                  90                  95 ctc cag gac gtg gac cag ttc gac ccg gcg ttc ttc ggc atc tcg ccg       336
Leu Gln Asp Val Asp Gln Phe Asp Pro Ala Phe Phe Gly Ile Ser Pro
            100                 105                 110 cgc gag gcc ctc acc atg gac ccg cag cag cgg ctg ctg ctg gaa gtg       384
Arg Glu Ala Leu Thr Met Asp Pro Gln Gln Arg Leu Leu Leu Glu Val
        115                 120                 125 gtg tgg gag acc ttc gaa cgg gcc gga atc gat ccg ggc acc ctg cgc       432
Val Trp Glu Thr Phe Glu Arg Ala Gly Ile Asp Pro Gly Thr Leu Arg
    130                 135                 140 ggc agc gac acc ggc atc ttc atg ggc gcc acc gac ttc gac tac gcc       480
Gly Ser Asp Thr Gly Ile Phe Met Gly Ala Thr Asp Phe Asp Tyr Ala
145                 150                 155                 160 cgt gat ctg acc gag ctc ccc gag ggg ctc gag ggc cag atg tcc atg       528
Arg Asp Leu Thr Glu Leu Pro Glu Gly Leu Glu Gly Gln Met Ser Met
                165                 170                 175 ggg gcc tcg ggc gcc atc ctc tcc ggc cgg gtc gcc tac acc ctg ggg       576
Gly Ala Ser Gly Ala Ile Leu Ser Gly Arg Val Ala Tyr Thr Leu Gly
            180                 185                 190 ctg gag ggc ccg gcc gtc acg gtc gac acc atg tgc tcg tcc tcg ctg       624
Leu Glu Gly Pro Ala Val Thr Val Asp Thr Met Cys Ser Ser Ser Leu
        195                 200                 205 gtg gca ctg cac atg gcg tgc cag gcg ctg cgc cag ggc gac tgc tcg       672
Val Ala Leu His Met Ala Cys Gln Ala Leu Arg Gln Gly Asp Cys Ser
    210                 215                 220 atg gcg ctc acc ggc ggc acc acc gtg atg tcc acg ccg agc ggt ttc       720
Met Ala Leu Thr Gly Gly Thr Thr Val Met Ser Thr Pro Ser Gly Phe
225                 230                 235                 240 atc gag ttc agc cgc cag cgt gcg ctg tcc acc tcc tcc cgc tgc cag       768
```

-continued

```
                Ile Glu Phe Ser Arg Gln Arg Ala Leu Ser Thr Ser Arg Cys Gln
                                245                 250                 255 gcg ttc tcc tcg acg gcc gac ggc acc gcc tgg ggc gag ggc gtc ggg        816
Ala Phe Ser Ser Thr Ala Asp Gly Thr Ala Trp Gly Glu Gly Val Gly
            260                 265                 270 gtg ctg ctg ctg gaa cgg ctc tcg gac gcc cgc cgc aac ggc cac acc        864
Val Leu Leu Leu Glu Arg Leu Ser Asp Ala Arg Arg Asn Gly His Thr
            275                 280                 285 gtg ctc gcg gtg gtc cgc ggc agc gcc atc aac cag gac ggc gcc agc        912
Val Leu Ala Val Val Arg Gly Ser Ala Ile Asn Gln Asp Gly Ala Ser
            290                 295                 300 aac ggc ctc acc gcg ccc aac ggc cgg gcc cag cag cgg gtg atc cgc        960
Asn Gly Leu Thr Ala Pro Asn Gly Arg Ala Gln Gln Arg Val Ile Arg
305                 310                 315                 320 cag gcg ctg gcc aac gcc acc ctg tcc ggg acc gat gtg gac gtg gtc       1008
Gln Ala Leu Ala Asn Ala Thr Leu Ser Gly Thr Asp Val Asp Val Val
                325                 330                 335 gag gca cac ggc acg gga acg tcg ctg ggc gac ccc atc gag gcg aac       1056
Glu Ala His Gly Thr Gly Thr Ser Leu Gly Asp Pro Ile Glu Ala Asn
                340                 345                 350 gcc ctg ctg gcc acg tac ggc agg aac cgc ccg gcc gac cgg ccg ctc       1104
Ala Leu Leu Ala Thr Tyr Gly Arg Asn Arg Pro Ala Asp Arg Pro Leu
            355                 360                 365 tgg ctc ggc tcg ctg aag tcc aac atc ggc cac acg gcc gcc gcc gcg       1152
Trp Leu Gly Ser Leu Lys Ser Asn Ile Gly His Thr Ala Ala Ala Ala
            370                 375                 380 ggg gtc ggc ggt gtg atc aag atg gtg cag gcg atc cgc cac ggg gtg       1200
Gly Val Gly Gly Val Ile Lys Met Val Gln Ala Ile Arg His Gly Val
385                 390                 395                 400 ctg ccc agc acc ctg cac atc cag gag ccg tcg ccc aac gtg gac tgg       1248
Leu Pro Ser Thr Leu His Ile Gln Glu Pro Ser Pro Asn Val Asp Trp
                405                 410                 415 acc tcg ggc gcc gtc gaa ctg ctc acc gag gcc cgg ccg tgg ccg gag       1296
Thr Ser Gly Ala Val Glu Leu Leu Thr Glu Ala Arg Pro Trp Pro Glu
                420                 425                 430 acc ggg cgg gtc cgc cgc gcc ggg gtg tcc gcc ttc ggc gcc agc ggc       1344
Thr Gly Arg Val Arg Arg Ala Gly Val Ser Ala Phe Gly Ala Ser Gly
            435                 440                 445 acc aat gcc cac gcc atc atc gag cag gcc ccc gag gcc acc gga ccg       1392
Thr Asn Ala His Ala Ile Ile Glu Gln Ala Pro Glu Ala Thr Gly Pro
            450                 455                 460 gcg gac act tca acc gag ggc gtg gca ccc gtg ggt ggc gcg gcg gtg       1440
Ala Asp Thr Ser Thr Glu Gly Val Ala Pro Val Gly Gly Ala Ala Val
465                 470                 475                 480 ccg tgg gtg ctg tcg gcc aag acc gag tcg ggt ctg cgc ggg cag gcg       1488
Pro Trp Val Leu Ser Ala Lys Thr Glu Ser Gly Leu Arg Gly Gln Ala
                485                 490                 495 gag cgg ttg ctg gca cgc ctc gcg gag ggt ccg gag ccg tcc ccg gcg       1536
Glu Arg Leu Leu Ala Arg Leu Ala Glu Gly Pro Glu Pro Ser Pro Ala
            500                 505                 510 gac gtg ggc ttc tcg ctg gcc acc acc cgc gcc cgc ttc gac cac cgc       1584
Asp Val Gly Phe Ser Leu Ala Thr Thr Arg Ala Arg Phe Asp His Arg
            515                 520                 525 gcg gtg gtg gta ggt ggc ggc gtc gag gac ttc cgc gcc ggg ctg acg       1632
Ala Val Val Val Gly Gly Gly Val Glu Asp Phe Arg Ala Gly Leu Thr
            530                 535                 540 gcg ctc acc cgg gcc gag ccc ggt ggc ctg gtg gcc cag ggc gtg gcg       1680
Ala Leu Thr Arg Ala Glu Pro Gly Gly Leu Val Ala Gln Gly Val Ala
545                 550                 555                 560
```

```
ggc cac gcc ggg aag ccg gtg ttc gtg ttt ccg ggg cag ggg tcg cag    1728
Gly His Ala Gly Lys Pro Val Phe Val Phe Pro Gly Gln Gly Ser Gln
                565                 570                 575 tgg gtg ggg atg gcg gtg gag ttg ctg gat tcg tcg ccg gtg ttc gcg    1776
Trp Val Gly Met Ala Val Glu Leu Leu Asp Ser Ser Pro Val Phe Ala
            580                 585                 590 ggt cgg ttg gcg gag tgt gag gtg gcg ctg tcg ggg ttc gtg gac tgg    1824
Gly Arg Leu Ala Glu Cys Glu Val Ala Leu Ser Gly Phe Val Asp Trp
        595                 600                 605 tcg ttg agt ggt gtg ttg cgg ggt gag ggt ccg ggg ttg gag cgg gtg    1872
Ser Leu Ser Gly Val Leu Arg Gly Glu Gly Pro Gly Leu Glu Arg Val
    610                 615                 620 gat gtg gtg cag ccg gcg ttg tgg gcg gtg atg gtg tcg ttg gcg gag    1920
Asp Val Val Gln Pro Ala Leu Trp Ala Val Met Val Ser Leu Ala Glu
625                 630                 635                 640 gtg tgg cgt gcg tgt ggg gtg acg cct gcc gct gtg gtg ggg cat tcg    1968
Val Trp Arg Ala Cys Gly Val Thr Pro Ala Ala Val Val Gly His Ser
                645                 650                 655 cag ggg gag atc gcg gcg gcg gtg gtg gcg ggt gcg ctg tcg ttg gag    2016
Gln Gly Glu Ile Ala Ala Ala Val Val Ala Gly Ala Leu Ser Leu Glu
            660                 665                 670 gac ggg gcg cgg gtg gtg gcg ctg cgc tcg cag gcc atc gga cgt ggg    2064
Asp Gly Ala Arg Val Val Ala Leu Arg Ser Gln Ala Ile Gly Arg Gly
        675                 680                 685 ctg gcg ggg cgt ggg ggg atg atg tcc gtc gcc gag ggc gcc gat cgg    2112
Leu Ala Gly Arg Gly Gly Met Met Ser Val Ala Glu Gly Ala Asp Arg
    690                 695                 700 gtg cgg gag cgc atc acc gcc tgg ggc ggt cgt ata tcg gtg gcg gcg    2160
Val Arg Glu Arg Ile Thr Ala Trp Gly Gly Arg Ile Ser Val Ala Ala
705                 710                 715                 720 gtc aac ggt ccg ggc tcg atc gtg gtg tcc ggt gac ccg gag gcg ctg    2208
Val Asn Gly Pro Gly Ser Ile Val Val Ser Gly Asp Pro Glu Ala Leu
                725                 730                 735 cgt gaa ctc cag gcg gag tgc gag gcc gag gac gta cgg gcg aag ctg    2256
Arg Glu Leu Gln Ala Glu Cys Glu Ala Glu Asp Val Arg Ala Lys Leu
            740                 745                 750 atc ccg gtg gac tac gcg tcc cac tcg gcc cat gtg gaa gcg ctc cgc    2304
Ile Pro Val Asp Tyr Ala Ser His Ser Ala His Val Glu Ala Leu Arg
        755                 760                 765 gag gag ttg ctc gac ctg ctc gcc ccg atc cgc ccg cgc acc tcg gac    2352
Glu Glu Leu Leu Asp Leu Leu Ala Pro Ile Arg Pro Arg Thr Ser Asp
    770                 775                 780 atc acc ttc cac tcc acc gtc acg ggc acc ccc ctg gac acc gcg gat    2400
Ile Thr Phe His Ser Thr Val Thr Gly Thr Pro Leu Asp Thr Ala Asp
785                 790                 795                 800 ctg gac gcc ggg tac tgg tac acc aat ctg cgg gag acg gtc gag ctg    2448
Leu Asp Ala Gly Tyr Trp Tyr Thr Asn Leu Arg Glu Thr Val Glu Leu
                805                 810                 815 gag tcg gcg gtg cgg gcc ctg tcg gcc gcc ggg ttc ggc acg ttc ctg    2496
Glu Ser Ala Val Arg Ala Leu Ser Ala Ala Gly Phe Gly Thr Phe Leu
            820                 825                 830 gag atg tcg ccg cat ccg gtg ctg acg atg ccg ctc cag gcg acc gcc    2544
Glu Met Ser Pro His Pro Val Leu Thr Met Pro Leu Gln Ala Thr Ala
        835                 840                 845 gag gac gcc gtg gtc gtg ggc tcg ctg cgg cgt gac gag ggc ggt ccg    2592
Glu Asp Ala Val Val Val Gly Ser Leu Arg Arg Asp Glu Gly Gly Pro
    850                 855                 860 gag cgg ttc ctg gcc tcg ctg ggc gag gcg ttc gtc cgg ggc gtg gcc    2640
Glu Arg Phe Leu Ala Ser Leu Gly Glu Ala Phe Val Arg Gly Val Ala
865                 870                 875                 880
```

| | | |
|---|---|---|
| gtc gac tgg gcc gcg gtg ttc gcc ggg ctg ggc gcg tcc gtg gtg gaa | 2688 | |
| Val Asp Trp Ala Ala Val Phe Ala Gly Leu Gly Ala Ser Val Val Glu | | |
| 885 890 895 | | |
| ctg ccc acg tac gcc ttc cag cgg cag cgc tac tgg ctg gag cgg ccc | 2736 | |
| Leu Pro Thr Tyr Ala Phe Gln Arg Gln Arg Tyr Trp Leu Glu Arg Pro | | |
| 900 905 910 | | |
| gcg gcg cag gcg gcc gcc acc ggg ggc gac ccg gtg gac gcc gag ttc | 2784 | |
| Ala Ala Gln Ala Ala Ala Thr Gly Gly Asp Pro Val Asp Ala Glu Phe | | |
| 915 920 925 | | |
| tgg gac gcc gtc gag cgc gag gac ctg gcc gcg ctg acc gcc gcg ctg | 2832 | |
| Trp Asp Ala Val Glu Arg Glu Asp Leu Ala Ala Leu Thr Ala Ala Leu | | |
| 930 935 940 | | |
| gag gtg gac gcc gac gag ggg cgg tcg tcg ctg cgg acc gtg ctc ccg | 2880 | |
| Glu Val Asp Ala Asp Glu Gly Arg Ser Ser Leu Arg Thr Val Leu Pro | | |
| 945 950 955 960 | | |
| gcg ctg tcc tcc tgg cgg cgc ggc cgc cgc gag cgg tcc gta ctc gac | 2928 | |
| Ala Leu Ser Ser Trp Arg Arg Gly Arg Arg Glu Arg Ser Val Leu Asp | | |
| 965 970 975 | | |
| tcc tgg cgc tac cac gtc acc tgg aac cgg gtg ccg gac ccg gcc tct | 2976 | |
| Ser Trp Arg Tyr His Val Thr Trp Asn Arg Val Pro Asp Pro Ala Ser | | |
| 980 985 990 | | |
| gcg gcc ctg acc ggc acc tgg ctg ctc gcg gtc ccg gcc gga agc ctc | 3024 | |
| Ala Ala Leu Thr Gly Thr Trp Leu Leu Ala Val Pro Ala Gly Ser Leu | | |
| 995 1000 1005 | | |
| gtc gga cac ccc gcc gga cac ctc ggc acc gag ctc gtc gac gcc | 3069 | |
| Val Gly His Pro Ala Gly His Leu Gly Thr Glu Leu Val Asp Ala | | |
| 1010 1015 1020 | | |
| gta cgc ggc ggc ctg gag acc cac ggc gcc acg gtc gtc acc gtc | 3114 | |
| Val Arg Gly Gly Leu Glu Thr His Gly Ala Thr Val Val Thr Val | | |
| 1025 1030 1035 | | |
| gag gtg gcc gag gcc gac cgc gcc gcg gtc gcc gcg cgg ctc gcc | 3159 | |
| Glu Val Ala Glu Ala Asp Arg Ala Ala Val Ala Ala Arg Leu Ala | | |
| 1040 1045 1050 | | |
| gag gcc acc gcc cgg gcc acc ccg gcc ggg gtg ctc tca ctg ctc | 3204 | |
| Glu Ala Thr Ala Arg Ala Thr Pro Ala Gly Val Leu Ser Leu Leu | | |
| 1055 1060 1065 | | |
| ggg ctc ccc gac gca ccg cac ccc gca cac gcg ggc gtg ccc atg | 3249 | |
| Gly Leu Pro Asp Ala Pro His Pro Ala His Ala Gly Val Pro Met | | |
| 1070 1075 1080 | | |
| gga ctc gcg ctc acc ctc gcc ctc gtc cag gcc ctc ggc gac acg | 3294 | |
| Gly Leu Ala Leu Thr Leu Ala Leu Val Gln Ala Leu Gly Asp Thr | | |
| 1085 1090 1095 | | |
| ggg gtg gac gcc ccg ctg tgg ctg gcc acc cgt ggc ggc gtg tcc | 3339 | |
| Gly Val Asp Ala Pro Leu Trp Leu Ala Thr Arg Gly Gly Val Ser | | |
| 1100 1105 1110 | | |
| gtc ggc ggc acc gac gcc ctc ggc agc ccc gcc cag gcg gcc gta | 3384 | |
| Val Gly Gly Thr Asp Ala Leu Gly Ser Pro Ala Gln Ala Ala Val | | |
| 1115 1120 1125 | | |
| tgg ggc ctt ggc cgg gtc gcc gct ctc gaa cac ccc cag cgc tgg | 3429 | |
| Trp Gly Leu Gly Arg Val Ala Ala Leu Glu His Pro Gln Arg Trp | | |
| 1130 1135 1140 | | |
| ggc ggc atg gtc gac ctg ccg gac acc gtc gac ggc cgg gtg acc | 3474 | |
| Gly Gly Met Val Asp Leu Pro Asp Thr Val Asp Gly Arg Val Thr | | |
| 1145 1150 1155 | | |
| acc cgg ctg tgc ggc gcg ctc gcg ggc cgc ctc gat gac gag gac | 3519 | |
| Thr Arg Leu Cys Gly Ala Leu Ala Gly Arg Leu Asp Asp Glu Asp | | |
| 1160 1165 1170 | | |
| cag ctg gcc ctg cgg tcc tcc ggg gtg ttc gtc cgg cgg ctg gta | 3564 | |
| Gln Leu Ala Leu Arg Ser Ser Gly Val Phe Val Arg Arg Leu Val | | |

```
                1175                1180                1185 cgg gcc gcg gag cac cgg ggg agc ggc ccc gtg tgg agc ccc gag      3609
Arg Ala Ala Glu His Arg Gly Ser Gly Pro Val Trp Ser Pro Glu
1190                1195                1200 ggc acc gtg ctg ctc acc ggc ggc acc ggt ggc gtc ggc gcc cag      3654
Gly Thr Val Leu Leu Thr Gly Gly Thr Gly Gly Val Gly Ala Gln
1205                1210                1215 atc gcc cgc cgg ctg gcc cag gcc ggt gcc gaa cac ctg gtg ctc      3699
Ile Ala Arg Arg Leu Ala Gln Ala Gly Ala Glu His Leu Val Leu
1220                1225                1230 acc agc cgc cgg ggc ccc gac gcc ccc ggc gcg gac aag ctc aag      3744
Thr Ser Arg Arg Gly Pro Asp Ala Pro Gly Ala Asp Lys Leu Lys
1235                1240                1245 gcc gaa ctg acc gag ctc ggc gcc aag gtc acc gtg gcc gcg tgc      3789
Ala Glu Leu Thr Glu Leu Gly Ala Lys Val Thr Val Ala Ala Cys
1250                1255                1260 gat gtg gcc gac cgc gcc gcg ctg gag gcg ctc gta cgg aag gtg      3834
Asp Val Ala Asp Arg Ala Ala Leu Glu Ala Leu Val Arg Lys Val
1265                1270                1275 gag gcc gag ggc ccg ccg atc cgt tcc gta ctg cac atc gcc ggt      3879
Glu Ala Glu Gly Pro Pro Ile Arg Ser Val Leu His Ile Ala Gly
1280                1285                1290 gcc ggt gtg ctc gtc ccg ctc gcc gac acc gat ctg gcg gag ttc      3924
Ala Gly Val Leu Val Pro Leu Ala Asp Thr Asp Leu Ala Glu Phe
1295                1300                1305 gcg gac acg gcg gag gcc aag gtc gcg ggc gcg gcg aac ctg gac      3969
Ala Asp Thr Ala Glu Ala Lys Val Ala Gly Ala Ala Asn Leu Asp
1310                1315                1320 gcg ctc ttc gac cgg gac acg ctc gac tcc ttc gtg ctc ttc tcc      4014
Ala Leu Phe Asp Arg Asp Thr Leu Asp Ser Phe Val Leu Phe Ser
1325                1330                1335 tcc atc tcg gcc gtc tgg ggc agt ggc gaa cac ggc gcg tac gcc      4059
Ser Ile Ser Ala Val Trp Gly Ser Gly Glu His Gly Ala Tyr Ala
1340                1345                1350 gcc gcc aac gcc tat ctc gac ggg ctg gcc gag cac cgc cgg gcc      4104
Ala Ala Asn Ala Tyr Leu Asp Gly Leu Ala Glu His Arg Arg Ala
1355                1360                1365 cgc ggg ctc acc gcc acc tcg gtg gtg tgg ggc atc tgg agc ccc      4149
Arg Gly Leu Thr Ala Thr Ser Val Val Trp Gly Ile Trp Ser Pro
1370                1375                1380 gag gag ggc ggg atg gcc gcc aac ctc gcc gag gag caa ctg cgc      4194
Glu Glu Gly Gly Met Ala Ala Asn Leu Ala Glu Glu Gln Leu Arg
1385                1390                1395 ggc cgg ggc atc ccg ttc atg tcc ccc cgg ctc gcc atc gac gcg      4239
Gly Arg Gly Ile Pro Phe Met Ser Pro Arg Leu Ala Ile Asp Ala
1400                1405                1410 ttc tgg cag gtg atg gag cgg gac gag acc gtg gtc gtg gtc gcc      4284
Phe Trp Gln Val Met Glu Arg Asp Glu Thr Val Val Val Val Ala
1415                1420                1425 gac gtg gac tgg gag cgg ttc gtc ccc gtc ttc acc tcg gcc cgg      4329
Asp Val Asp Trp Glu Arg Phe Val Pro Val Phe Thr Ser Ala Arg
1430                1435                1440 acc agc ccg ctc atc ggc cag gtg ccc gac gtg gcg cgg atc ctc      4374
Thr Ser Pro Leu Ile Gly Gln Val Pro Asp Val Ala Arg Ile Leu
1445                1450                1455 gcg gcc gac gcc gac acc cgg acg gac acg acc cgc gag tcc tcc      4419
Ala Ala Asp Ala Asp Thr Arg Thr Asp Thr Thr Arg Glu Ser Ser
1460                1465                1470 tcg ctg cgc gac cgg ctg gcc gag ttg gcc ccg gcg gac cgg cag      4464
```

-continued

```
Ser Leu Arg Asp Arg Leu Ala Glu Leu Ala Pro Ala Asp Arg Gln
    1475                1480                1485 gcg gca gtg ctg tcg ctg gtg cgc tcg cag atc gcc acc gtc ctc    4509
Ala Ala Val Leu Ser Leu Val Arg Ser Gln Ile Ala Thr Val Leu
    1490                1495                1500 ggc tac tcc ggc ccc gag gcc gtc gac gcc acg cgc gcc ttc cgc    4554
Gly Tyr Ser Gly Pro Glu Ala Val Asp Ala Thr Arg Ala Phe Arg
    1505                1510                1515 gag ctg ggc ttc gac tcc ctg agc gcc gtc gac ctg cgc aac cgc    4599
Glu Leu Gly Phe Asp Ser Leu Ser Ala Val Asp Leu Arg Asn Arg
    1520                1525                1530 ctg ggc acc gcc acc ggg ctc cgc ttc ccc gtc acc gtc gtc ttc    4644
Leu Gly Thr Ala Thr Gly Leu Arg Phe Pro Val Thr Val Val Phe
    1535                1540                1545 gac tac ccg agc gcg gag gag ctc gcc gga cac atc ggc gcc gaa    4689
Asp Tyr Pro Ser Ala Glu Glu Leu Ala Gly His Ile Gly Ala Glu
    1550                1555                1560 ctc ttc ccc gac gac acc gcc gcc acc gcc ctc gac ccc gaa gag    4734
Leu Phe Pro Asp Asp Thr Ala Ala Thr Ala Leu Asp Pro Glu Glu
    1565                1570                1575 gcc gac gtc cgc agg gcg ttg acc tcc atc ccg ctg ctc cgg ctc    4779
Ala Asp Val Arg Arg Ala Leu Thr Ser Ile Pro Leu Leu Arg Leu
    1580                1585                1590 cgc gaa tcc gga ctg ctg gac gag ctg ctg cgg ctg gcc ggt tcc    4824
Arg Glu Ser Gly Leu Leu Asp Glu Leu Leu Arg Leu Ala Gly Ser
    1595                1600                1605 cac gac ccc gcc acc gca ccg gcg gac gag gag ccc gcc gag tcc    4869
His Asp Pro Ala Thr Ala Pro Ala Asp Glu Glu Pro Ala Glu Ser
    1610                1615                1620 atc gac gac ctg gac gtg gat gac ctc gtg cgc atg gcc tac gac    4914
Ile Asp Asp Leu Asp Val Asp Asp Leu Val Arg Met Ala Tyr Asp
    1625                1630                1635 aag aac gac ctc tga                                            4929
Lys Asn Asp Leu
    1640

<210> SEQ ID NO 18
<211> LENGTH: 1642
<212> TYPE: PRT
<213> ORGANISM: Streptomyces sp. NRRL 30748

<400> SEQUENCE: 18

Met Asp Asn Glu Lys Lys Leu Arg Asp Tyr Leu Lys Arg Ala Thr Gly
1               5                   10                  15

His Leu Arg Ala Ala His Arg Arg Ile Gln Glu Leu Gln Ala Pro Glu
                20                  25                  30

Pro Ile Ala Ile Val Ala Met Asn Cys Arg Tyr Ala Gly Asp Ile Arg
            35                  40                  45

Ser Pro Glu Asp Leu Trp Gln Ala Val Ala Glu Gly Arg Asp Gly Met
        50                  55                  60

Gly Asp Phe Pro Ala Asp Arg Gly Trp Asp Leu Pro Asn Leu Phe Asp
65                  70                  75                  80

Pro Asp Pro Asp Arg Glu Gly Arg Thr Tyr Ala Arg Gln Gly Gly Phe
                85                  90                  95

Leu Gln Asp Val Asp Gln Phe Asp Pro Ala Phe Phe Gly Ile Ser Pro
            100                 105                 110

Arg Glu Ala Leu Thr Met Asp Pro Gln Gln Arg Leu Leu Leu Glu Val
        115                 120                 125
```

```
Val Trp Glu Thr Phe Glu Arg Ala Gly Ile Asp Pro Gly Thr Leu Arg
    130                 135                 140

Gly Ser Asp Thr Gly Ile Phe Met Gly Ala Thr Asp Phe Asp Tyr Ala
145                 150                 155                 160

Arg Asp Leu Thr Glu Leu Pro Glu Gly Leu Glu Gly Gln Met Ser Met
                165                 170                 175

Gly Ala Ser Gly Ala Ile Leu Ser Gly Arg Val Ala Tyr Thr Leu Gly
            180                 185                 190

Leu Glu Gly Pro Ala Val Thr Val Asp Thr Met Cys Ser Ser Ser Leu
        195                 200                 205

Val Ala Leu His Met Ala Cys Gln Ala Leu Arg Gln Gly Asp Cys Ser
    210                 215                 220

Met Ala Leu Thr Gly Gly Thr Thr Val Met Ser Thr Pro Ser Gly Phe
225                 230                 235                 240

Ile Glu Phe Ser Arg Gln Arg Ala Leu Ser Thr Ser Ser Arg Cys Gln
                245                 250                 255

Ala Phe Ser Ser Thr Ala Asp Gly Thr Ala Trp Gly Glu Gly Val Gly
            260                 265                 270

Val Leu Leu Leu Glu Arg Leu Ser Asp Ala Arg Arg Asn Gly His Thr
        275                 280                 285

Val Leu Ala Val Val Arg Gly Ser Ala Ile Asn Gln Asp Gly Ala Ser
    290                 295                 300

Asn Gly Leu Thr Ala Pro Asn Gly Arg Ala Gln Gln Arg Val Ile Arg
305                 310                 315                 320

Gln Ala Leu Ala Asn Ala Thr Leu Ser Gly Thr Asp Val Asp Val Val
                325                 330                 335

Glu Ala His Gly Thr Gly Thr Ser Leu Gly Asp Pro Ile Glu Ala Asn
            340                 345                 350

Ala Leu Leu Ala Thr Tyr Gly Arg Asn Arg Pro Ala Asp Arg Pro Leu
        355                 360                 365

Trp Leu Gly Ser Leu Lys Ser Asn Ile Gly His Thr Ala Ala Ala Ala
    370                 375                 380

Gly Val Gly Gly Val Ile Lys Met Val Gln Ala Ile Arg His Gly Val
385                 390                 395                 400

Leu Pro Ser Thr Leu His Ile Gln Glu Pro Ser Pro Asn Val Asp Trp
                405                 410                 415

Thr Ser Gly Ala Val Glu Leu Leu Thr Glu Ala Arg Pro Trp Pro Glu
            420                 425                 430

Thr Gly Arg Val Arg Arg Ala Gly Val Ser Ala Phe Gly Ala Ser Gly
        435                 440                 445

Thr Asn Ala His Ala Ile Ile Glu Gln Ala Pro Glu Ala Thr Gly Pro
    450                 455                 460

Ala Asp Thr Ser Thr Glu Gly Val Ala Pro Val Gly Ala Ala Val
465                 470                 475                 480

Pro Trp Val Leu Ser Ala Lys Thr Glu Ser Gly Leu Arg Gly Gln Ala
                485                 490                 495

Glu Arg Leu Leu Ala Arg Leu Ala Glu Gly Pro Glu Pro Ser Pro Ala
            500                 505                 510

Asp Val Gly Phe Ser Leu Ala Thr Thr Arg Ala Arg Phe Asp His Arg
        515                 520                 525

Ala Val Val Val Gly Gly Val Glu Asp Phe Arg Ala Gly Leu Thr
530                 535                 540

Ala Leu Thr Arg Ala Glu Pro Gly Gly Leu Val Ala Gln Gly Val Ala
```

```
                545                 550                 555                 560
Gly His Ala Gly Lys Pro Val Phe Val Phe Pro Gly Gln Gly Ser Gln
                565                 570                 575
Trp Val Gly Met Ala Val Glu Leu Leu Asp Ser Ser Pro Val Phe Ala
                580                 585                 590
Gly Arg Leu Ala Glu Cys Glu Val Ala Leu Ser Gly Phe Val Asp Trp
                595                 600                 605
Ser Leu Ser Gly Val Leu Arg Gly Glu Gly Pro Gly Leu Glu Arg Val
                610                 615                 620
Asp Val Val Gln Pro Ala Leu Trp Ala Val Met Val Ser Leu Ala Glu
625                 630                 635                 640
Val Trp Arg Ala Cys Gly Val Thr Pro Ala Ala Val Val Gly His Ser
                645                 650                 655
Gln Gly Glu Ile Ala Ala Ala Val Val Ala Gly Ala Leu Ser Leu Glu
                660                 665                 670
Asp Gly Ala Arg Val Val Ala Leu Arg Ser Gln Ala Ile Gly Arg Gly
                675                 680                 685
Leu Ala Gly Arg Gly Gly Met Met Ser Val Ala Glu Gly Ala Asp Arg
                690                 695                 700
Val Arg Glu Arg Ile Thr Ala Trp Gly Gly Arg Ile Ser Val Ala Ala
705                 710                 715                 720
Val Asn Gly Pro Gly Ser Ile Val Val Ser Gly Asp Pro Glu Ala Leu
                725                 730                 735
Arg Glu Leu Gln Ala Glu Cys Glu Ala Glu Asp Val Arg Ala Lys Leu
                740                 745                 750
Ile Pro Val Asp Tyr Ala Ser His Ser Ala His Val Glu Ala Leu Arg
                755                 760                 765
Glu Glu Leu Leu Asp Leu Leu Ala Pro Ile Arg Pro Arg Thr Ser Asp
                770                 775                 780
Ile Thr Phe His Ser Thr Val Thr Gly Thr Pro Leu Asp Thr Ala Asp
785                 790                 795                 800
Leu Asp Ala Gly Tyr Trp Tyr Thr Asn Leu Arg Glu Thr Val Glu Leu
                805                 810                 815
Glu Ser Ala Val Arg Ala Leu Ser Ala Ala Gly Phe Gly Thr Phe Leu
                820                 825                 830
Glu Met Ser Pro His Pro Val Leu Thr Met Pro Leu Gln Ala Thr Ala
                835                 840                 845
Glu Asp Ala Val Val Val Gly Ser Leu Arg Arg Asp Glu Gly Gly Pro
                850                 855                 860
Glu Arg Phe Leu Ala Ser Leu Gly Glu Ala Phe Val Arg Gly Val Ala
865                 870                 875                 880
Val Asp Trp Ala Ala Val Phe Ala Gly Leu Gly Ala Ser Val Val Glu
                885                 890                 895
Leu Pro Thr Tyr Ala Phe Gln Arg Gln Arg Tyr Trp Leu Glu Arg Pro
                900                 905                 910
Ala Ala Gln Ala Ala Ala Thr Gly Gly Asp Pro Val Asp Ala Glu Phe
                915                 920                 925
Trp Asp Ala Val Glu Arg Glu Asp Leu Ala Ala Leu Thr Ala Ala Leu
                930                 935                 940
Glu Val Asp Ala Asp Glu Gly Arg Ser Ser Leu Arg Thr Val Leu Pro
945                 950                 955                 960
Ala Leu Ser Ser Trp Arg Arg Gly Arg Arg Glu Arg Ser Val Leu Asp
                965                 970                 975
```

-continued

```
Ser Trp Arg Tyr His Val Thr Trp Asn Arg Val Pro Asp Pro Ala Ser
            980                 985                 990

Ala Ala Leu Thr Gly Thr Trp Leu Leu Ala Val Pro Ala Gly Ser Leu
            995                1000                1005

Val Gly His Pro Ala Gly His Leu Gly Thr Glu Leu Val Asp Ala
    1010                1015                1020

Val Arg Gly Gly Leu Glu Thr His Gly Ala Thr Val Val Thr Val
    1025                1030                1035

Glu Val Ala Glu Ala Asp Arg Ala Ala Val Ala Ala Arg Leu Ala
    1040                1045                1050

Glu Ala Thr Ala Arg Ala Thr Pro Ala Gly Val Leu Ser Leu Leu
    1055                1060                1065

Gly Leu Pro Asp Ala Pro His Pro Ala His Ala Gly Val Pro Met
    1070                1075                1080

Gly Leu Ala Leu Thr Leu Ala Leu Val Gln Ala Leu Gly Asp Thr
    1085                1090                1095

Gly Val Asp Ala Pro Leu Trp Leu Ala Thr Arg Gly Gly Val Ser
    1100                1105                1110

Val Gly Gly Thr Asp Ala Leu Gly Ser Pro Ala Gln Ala Ala Val
    1115                1120                1125

Trp Gly Leu Gly Arg Val Ala Ala Leu Glu His Pro Gln Arg Trp
    1130                1135                1140

Gly Gly Met Val Asp Leu Pro Asp Thr Val Asp Gly Arg Val Thr
    1145                1150                1155

Thr Arg Leu Cys Gly Ala Leu Ala Gly Arg Leu Asp Asp Glu Asp
    1160                1165                1170

Gln Leu Ala Leu Arg Ser Ser Gly Val Phe Val Arg Arg Leu Val
    1175                1180                1185

Arg Ala Ala Glu His Arg Gly Ser Gly Pro Val Trp Ser Pro Glu
    1190                1195                1200

Gly Thr Val Leu Leu Thr Gly Gly Thr Gly Gly Val Gly Ala Gln
    1205                1210                1215

Ile Ala Arg Arg Leu Ala Gln Ala Gly Ala Glu His Leu Val Leu
    1220                1225                1230

Thr Ser Arg Arg Gly Pro Asp Ala Pro Gly Ala Asp Lys Leu Lys
    1235                1240                1245

Ala Glu Leu Thr Glu Leu Gly Ala Lys Val Thr Val Ala Ala Cys
    1250                1255                1260

Asp Val Ala Asp Arg Ala Ala Leu Glu Ala Leu Val Arg Lys Val
    1265                1270                1275

Glu Ala Glu Gly Pro Pro Ile Arg Ser Val Leu His Ile Ala Gly
    1280                1285                1290

Ala Gly Val Leu Val Pro Leu Ala Asp Thr Asp Leu Ala Glu Phe
    1295                1300                1305

Ala Asp Thr Ala Glu Ala Lys Val Ala Gly Ala Ala Asn Leu Asp
    1310                1315                1320

Ala Leu Phe Asp Arg Asp Thr Leu Asp Ser Phe Val Leu Phe Ser
    1325                1330                1335

Ser Ile Ser Ala Val Trp Gly Ser Gly Glu His Gly Ala Tyr Ala
    1340                1345                1350

Ala Ala Asn Ala Tyr Leu Asp Gly Leu Ala Glu His Arg Arg Ala
    1355                1360                1365
```

| Arg | Gly | Leu | Thr | Ala | Thr | Ser | Val | Val | Trp | Gly | Ile | Trp | Ser | Pro |
| | 1370 | | | | 1375 | | | | | 1380 | | | | |

| Glu | Glu | Gly | Gly | Met | Ala | Ala | Asn | Leu | Ala | Glu | Glu | Gln | Leu | Arg |
| 1385 | | | | | 1390 | | | | | 1395 | | | | |

| Gly | Arg | Gly | Ile | Pro | Phe | Met | Ser | Pro | Arg | Leu | Ala | Ile | Asp | Ala |
| | 1400 | | | | | 1405 | | | | | 1410 | | | |

| Phe | Trp | Gln | Val | Met | Glu | Arg | Asp | Glu | Thr | Val | Val | Val | Ala |
| 1415 | | | | | 1420 | | | | | 1425 | | | | |

| Asp | Val | Asp | Trp | Glu | Arg | Phe | Val | Pro | Val | Phe | Thr | Ser | Ala | Arg |
| | 1430 | | | | 1435 | | | | | 1440 | | | | |

| Thr | Ser | Pro | Leu | Ile | Gly | Gln | Val | Pro | Asp | Val | Ala | Arg | Ile | Leu |
| | 1445 | | | | | 1450 | | | | | 1455 | | | |

| Ala | Ala | Asp | Ala | Asp | Thr | Arg | Thr | Asp | Thr | Thr | Arg | Glu | Ser | Ser |
| 1460 | | | | | 1465 | | | | | 1470 | | | | |

| Ser | Leu | Arg | Asp | Arg | Leu | Ala | Glu | Leu | Ala | Pro | Ala | Asp | Arg | Gln |
| 1475 | | | | | 1480 | | | | | 1485 | | | | |

| Ala | Ala | Val | Leu | Ser | Leu | Val | Arg | Ser | Gln | Ile | Ala | Thr | Val | Leu |
| | 1490 | | | | | 1495 | | | | | 1500 | | | |

| Gly | Tyr | Ser | Gly | Pro | Glu | Ala | Val | Asp | Ala | Thr | Arg | Ala | Phe | Arg |
| 1505 | | | | | 1510 | | | | | 1515 | | | | |

| Glu | Leu | Gly | Phe | Asp | Ser | Leu | Ser | Ala | Val | Asp | Leu | Arg | Asn | Arg |
| | 1520 | | | | | 1525 | | | | | 1530 | | | |

| Leu | Gly | Thr | Ala | Thr | Gly | Leu | Arg | Phe | Pro | Val | Thr | Val | Val | Phe |
| 1535 | | | | | 1540 | | | | | 1545 | | | | |

| Asp | Tyr | Pro | Ser | Ala | Glu | Glu | Leu | Ala | Gly | His | Ile | Gly | Ala | Glu |
| | 1550 | | | | | 1555 | | | | | 1560 | | | |

| Leu | Phe | Pro | Asp | Asp | Thr | Ala | Ala | Thr | Ala | Leu | Asp | Pro | Glu | Glu |
| 1565 | | | | | 1570 | | | | | 1575 | | | | |

| Ala | Asp | Val | Arg | Arg | Ala | Leu | Thr | Ser | Ile | Pro | Leu | Leu | Arg | Leu |
| | 1580 | | | | | 1585 | | | | | 1590 | | | |

| Arg | Glu | Ser | Gly | Leu | Leu | Asp | Glu | Leu | Leu | Arg | Leu | Ala | Gly | Ser |
| 1595 | | | | | 1600 | | | | | 1605 | | | | |

| His | Asp | Pro | Ala | Thr | Ala | Pro | Ala | Asp | Glu | Glu | Pro | Ala | Glu | Ser |
| | 1610 | | | | | 1615 | | | | | 1620 | | | |

| Ile | Asp | Asp | Leu | Asp | Val | Asp | Leu | Val | Arg | Met | Ala | Tyr | Asp |
| 1625 | | | | | 1630 | | | | | 1635 | | | | |

| Lys | Asn | Asp | Leu |
| 1640 | | | |

<210> SEQ ID NO 19
<211> LENGTH: 10158
<212> TYPE: DNA
<213> ORGANISM: Streptomyces sp. NRRL 30748
<220> FEATURE:
<221> NAME/KEY: CDS
<222> LOCATION: (1)..(10158)

<400> SEQUENCE: 19

| atg | gca | aac | cca | acc | gac | aag | atc | gtt | ggc | gcg | ctg | cgg | gag | tct | ctg | 48 |
| Met | Ala | Asn | Pro | Thr | Asp | Lys | Ile | Val | Gly | Ala | Leu | Arg | Glu | Ser | Leu | |
| 1 | | | | 5 | | | | | 10 | | | | | 15 | | |

| aag | gag | acc | gaa | cgg | ctg | cgc | cgg | gtc | aat | cag | caa | ctc | acc | gcc | gcc | 96 |
| Lys | Glu | Thr | Glu | Arg | Leu | Arg | Arg | Val | Asn | Gln | Gln | Leu | Thr | Ala | Ala | |
| | | | 20 | | | | | 25 | | | | | 30 | | | |

| tcc | cgg | gaa | ccc | atc | gcc | atc | gtg | gcg | atg | agc | tgc | cgc | tac | ccc | ggc | 144 |
| Ser | Arg | Glu | Pro | Ile | Ala | Ile | Val | Ala | Met | Ser | Cys | Arg | Tyr | Pro | Gly | |
| | | | 35 | | | | | 40 | | | | | 45 | | | |

-continued

```
gat gtg cgc ggc ccc gag gac ctg tgg gag ctg gtc acc ggc ggg cgc    192
Asp Val Arg Gly Pro Glu Asp Leu Trp Glu Leu Val Thr Gly Gly Arg
 50                  55                  60 gac gcc atc tcc ggg ttc ccc ggc aac cgc ggc tgg gac ctg gag aac    240
Asp Ala Ile Ser Gly Phe Pro Gly Asn Arg Gly Trp Asp Leu Glu Asn
 65                  70                  75                  80 ctc tac gac ccg gac ccc gac cgg cag ggc acc gtc tac gcc acc gag    288
Leu Tyr Asp Pro Asp Pro Asp Arg Gln Gly Thr Val Tyr Ala Thr Glu
                 85                  90                  95 ggc gga ttc ctc cac gac gcc gac cag ttc gac ccc gcc ttc ttc ggc    336
Gly Gly Phe Leu His Asp Ala Asp Gln Phe Asp Pro Ala Phe Phe Gly
            100                 105                 110 atc tcg ccc cgc gag gcc acc gtg atg gac ccg cag cag cgg ctg ctg    384
Ile Ser Pro Arg Glu Ala Thr Val Met Asp Pro Gln Gln Arg Leu Leu
        115                 120                 125 ctg gag acc tcc tgg gag gcg ttc gag cgc gcc gga atc gat ccg gcg    432
Leu Glu Thr Ser Trp Glu Ala Phe Glu Arg Ala Gly Ile Asp Pro Ala
130                 135                 140 gcg ctg cgc ggc agc aag acc ggc atc ttc gtg ggc gcc gcc tac cag    480
Ala Leu Arg Gly Ser Lys Thr Gly Ile Phe Val Gly Ala Ala Tyr Gln
145                 150                 155                 160 ggc tac atc ccc gac tgg ccc cat atg ccc gag ggt ctc gag ggc cac    528
Gly Tyr Ile Pro Asp Trp Pro His Met Pro Glu Gly Leu Glu Gly His
                165                 170                 175 ctg gtc acg ggc atc tcc gcg agc atc atg tcc ggc cgc gtc gcc tac    576
Leu Val Thr Gly Ile Ser Ala Ser Ile Met Ser Gly Arg Val Ala Tyr
            180                 185                 190 acc ctg ggc ctg gag ggc ccg gcc gtc acc atc gac acc gcc tgc tcg    624
Thr Leu Gly Leu Glu Gly Pro Ala Val Thr Ile Asp Thr Ala Cys Ser
        195                 200                 205 tcc tcg ctg gtc gcc ctc cac ctg gcc tgc cag tcg ctg cgc cag ggc    672
Ser Ser Leu Val Ala Leu His Leu Ala Cys Gln Ser Leu Arg Gln Gly
210                 215                 220 gac tgc tcg ctc gcc ctc gcg ggc ggc gcc gcc gtg atg ggc gcc ccg    720
Asp Cys Ser Leu Ala Leu Ala Gly Gly Ala Ala Val Met Gly Ala Pro
225                 230                 235                 240 atg ggg ctc atc ggc ttc gcc cgg cag cgc gga ctg gcg cag gac ggc    768
Met Gly Leu Ile Gly Phe Ala Arg Gln Arg Gly Leu Ala Gln Asp Gly
                245                 250                 255 cgc tgc aag gcg ttc gcc gag ggg gcc gac ggc atg ggc ctc ggc gag    816
Arg Cys Lys Ala Phe Ala Glu Gly Ala Asp Gly Met Gly Leu Gly Glu
            260                 265                 270 ggc gtc ggc atg ctg ctg ctg gaa cgc ctc tcg gac gcg cgg cgc aac    864
Gly Val Gly Met Leu Leu Leu Glu Arg Leu Ser Asp Ala Arg Arg Asn
        275                 280                 285 ggc cac gag gtg ctg gcc gtg gtg cgc ggc tcg gcc gtc aac cag gac    912
Gly His Glu Val Leu Ala Val Val Arg Gly Ser Ala Val Asn Gln Asp
290                 295                 300 ggc gcc agc aac ggc ctc acc gcc ccc aac ggc cgc tcc cag cag cgg    960
Gly Ala Ser Asn Gly Leu Thr Ala Pro Asn Gly Arg Ser Gln Gln Arg
305                 310                 315                 320 gtg atc cgc cag gcg ctc gcc aac gcc gcg ctc acg gcg gag cag atc    1008
Val Ile Arg Gln Ala Leu Ala Asn Ala Ala Leu Thr Ala Glu Gln Ile
                325                 330                 335 gac gcg gtc gag gcc cac ggc acc ggc acc ccg ctg ggc gac ccg atc    1056
Asp Ala Val Glu Ala His Gly Thr Gly Thr Pro Leu Gly Asp Pro Ile
            340                 345                 350 gag gcg ggc gcg ctg ctc gcc acg tac ggg aag gac cgc gcg gcg gac    1104
Glu Ala Gly Ala Leu Leu Ala Thr Tyr Gly Lys Asp Arg Ala Ala Asp
```

```
                      355                 360                 365
cga ccc gtg ctg atc ggc tcg ctg aag tcc aac atc ggc cat ccg cag       1152
Arg Pro Val Leu Ile Gly Ser Leu Lys Ser Asn Ile Gly His Pro Gln
        370                 375                 380 gcc gcc ggc ggt gtc ggc ggt gtc atc aag atg gtg cag gcc atg cgc       1200
Ala Ala Gly Gly Val Gly Gly Val Ile Lys Met Val Gln Ala Met Arg
385                 390                 395                 400 cac ggc ctg ctg ccc agg aca ctc cac gcc gag gag cgc tcc tcg cgg       1248
His Gly Leu Leu Pro Arg Thr Leu His Ala Glu Glu Arg Ser Ser Arg
                405                 410                 415 atc gac tgg tcg gcg ggg gcg gtg gaa ctg ctg acc gag gcc agg gag       1296
Ile Asp Trp Ser Ala Gly Ala Val Glu Leu Leu Thr Glu Ala Arg Glu
            420                 425                 430 tgg ccg cgc ggc gag gaa ccc cgc cgg gcc gcc gtc tcg gcc ttc ggg       1344
Trp Pro Arg Gly Glu Glu Pro Arg Arg Ala Ala Val Ser Ala Phe Gly
                435                 440                 445 gcc agt ggc acc aat gtg cac acc atc ctc gag gat gcg ccc gag gag       1392
Ala Ser Gly Thr Asn Val His Thr Ile Leu Glu Asp Ala Pro Glu Glu
        450                 455                 460 gag ctt tcg gag acc gcg gcc gag ggg gac gcc ccg gtg ggc ggg gga       1440
Glu Leu Ser Glu Thr Ala Ala Glu Gly Asp Ala Pro Val Gly Gly Gly
465                 470                 475                 480 gtg gtg ccg tgg gtg ctg tcg gcg aag agc gcg gcg ggt ctg cgg gcg       1488
Val Val Pro Trp Val Leu Ser Ala Lys Ser Ala Ala Gly Leu Arg Ala
                485                 490                 495 cag gcc gag cgg ctg ctg acg cat gtc acc gcg cgc ccc ggg ctg tcc       1536
Gln Ala Glu Arg Leu Leu Thr His Val Thr Ala Arg Pro Gly Leu Ser
            500                 505                 510 ccg gcc gat gtc ggc cac tcg ctc gcc acc acc cgt ggc cgc ttc gac       1584
Pro Ala Asp Val Gly His Ser Leu Ala Thr Thr Arg Gly Arg Phe Asp
                515                 520                 525 cac cgc gcg ctc gtc ctg ggc ggc ggc cgc gac gag ctg atc gac gca       1632
His Arg Ala Leu Val Leu Gly Gly Gly Arg Asp Glu Leu Ile Asp Ala
        530                 535                 540 ctg ggc gca ctg gcg tcg ggc ggc gag tcc ccg cgt gtg gtg cgt ggc       1680
Leu Gly Ala Leu Ala Ser Gly Gly Glu Ser Pro Arg Val Val Arg Gly
545                 550                 555                 560 gag gga gtc acg gcg gcc gat gcc cgt ccg gtg ttc gtg ttt ccg ggg       1728
Glu Gly Val Thr Ala Ala Asp Ala Arg Pro Val Phe Val Phe Pro Gly
                565                 570                 575 cag ggg tcg cag tgg gtg ggg atg gcg gtg gag ttg ctg gat tcg tcg       1776
Gln Gly Ser Gln Trp Val Gly Met Ala Val Glu Leu Leu Asp Ser Ser
            580                 585                 590 ccg gtg ttc gcg ggt cgg ttg gcg gag tgt gag gtg gcg ctg tcg ggg       1824
Pro Val Phe Ala Gly Arg Leu Ala Glu Cys Glu Val Ala Leu Ser Gly
                595                 600                 605 ttt gtg gag tgg tcg ttg agt ggt gtg ttg cgg ggt gag ggt ccg ggg       1872
Phe Val Glu Trp Ser Leu Ser Gly Val Leu Arg Gly Glu Gly Pro Gly
        610                 615                 620 ttg gag cgg gtg gat gtg gtg cag ccg gcg ttg tgg gcg gtg atg gtg       1920
Leu Glu Arg Val Asp Val Val Gln Pro Ala Leu Trp Ala Val Met Val
625                 630                 635                 640 tcg ttg gcg gag gtg tgg cgt gcg tgt ggg gtg acg cct gcc gct gtg       1968
Ser Leu Ala Glu Val Trp Arg Ala Cys Gly Val Thr Pro Ala Ala Val
                645                 650                 655 gtg ggg cat tcg cag ggg gag atc gcg gcg gcg gtg gtg gcg ggt gcg       2016
Val Gly His Ser Gln Gly Glu Ile Ala Ala Ala Val Val Ala Gly Ala
            660                 665                 670 ctg tcg ttg gag gac ggg gcg cgg gtg gtg gcg ctg cgg tcg cag gcc       2064
```

```
                Leu Ser Leu Glu Asp Gly Ala Arg Val Val Ala Leu Arg Ser Gln Ala
                            675                 680                 685 atc gga cgc ggg ctg gcg ggg cgt ggg ggg atg atg tcc gtc gcc gag                2112
Ile Gly Arg Gly Leu Ala Gly Arg Gly Gly Met Met Ser Val Ala Glu
            690                 695                 700 ggc gcc gat tgg gtg cgg gag cgc atc acc gcc tgg ggt ggt cgt ata                2160
Gly Ala Asp Trp Val Arg Glu Arg Ile Thr Ala Trp Gly Gly Arg Ile
705                 710                 715                 720 tcg gtg gcg gcg gtc aac ggt ccg ggc tcg atc gtg gtg tcc ggt gac                2208
Ser Val Ala Ala Val Asn Gly Pro Gly Ser Ile Val Val Ser Gly Asp
                725                 730                 735 ccg gag gcg ctg cgt gaa ctc cag gcg gag tgc gag gcc gag gac gta                2256
Pro Glu Ala Leu Arg Glu Leu Gln Ala Glu Cys Glu Ala Glu Asp Val
            740                 745                 750 cgg gcg aag ctg atc ccg gtg gac tac gcg tcc cac tcg gcc cat gtc                2304
Arg Ala Lys Leu Ile Pro Val Asp Tyr Ala Ser His Ser Ala His Val
        755                 760                 765 gag gag ttg cgc gat gaa ctc ctc gac gtc ctg gcc ccg atc gcc ccg                2352
Glu Glu Leu Arg Asp Glu Leu Leu Asp Val Leu Ala Pro Ile Ala Pro
    770                 775                 780 cgc cgc gcc gag gtg ccg ttc tgc tcg acg gtc acc ggc gac acc atc                2400
Arg Arg Ala Glu Val Pro Phe Cys Ser Thr Val Thr Gly Asp Thr Ile
785                 790                 795                 800 gac acc acc gga ctc gac gcc ggg tac tgg tac acc aat ctg cgg gag                2448
Asp Thr Thr Gly Leu Asp Ala Gly Tyr Trp Tyr Thr Asn Leu Arg Glu
                805                 810                 815 acg gtc gag ctg gag tcg gcg gtg cgg gcc ctg tcg gcc gcc ggg ttc                2496
Thr Val Glu Leu Glu Ser Ala Val Arg Ala Leu Ser Ala Ala Gly Phe
            820                 825                 830 ggc acg ttc ctg gag atg tcg ccg cat ccg gta ctg acc atg ccg ctc                2544
Gly Thr Phe Leu Glu Met Ser Pro His Pro Val Leu Thr Met Pro Leu
        835                 840                 845 cag gcg acc gcc gag gac gcc gtg gtc gtg ggc tcg ctg cgg cgt gac                2592
Gln Ala Thr Ala Glu Asp Ala Val Val Val Gly Ser Leu Arg Arg Asp
    850                 855                 860 gag ggc ggt ccg gag cgg ttc ctg gcc tcg ctg ggc gag gcg ttc gtc                2640
Glu Gly Gly Pro Glu Arg Phe Leu Ala Ser Leu Gly Glu Ala Phe Val
865                 870                 875                 880 cgg ggc gtg gcc gtc gac tgg gcg gcg gtg tgc gcc ggg tcc acg gtc                2688
Arg Gly Val Ala Val Asp Trp Ala Ala Val Cys Ala Gly Ser Thr Val
                885                 890                 895 gtg gaa ctg ccg acg tac gcc ttc cag cgg cag cgc tac tgg ctc gaa                2736
Val Glu Leu Pro Thr Tyr Ala Phe Gln Arg Gln Arg Tyr Trp Leu Glu
            900                 905                 910 ggc tcc tcc gca ccc gcc gaa ggc gcg gcg gtg gac gcg gac ttc tgg                2784
Gly Ser Ser Ala Pro Ala Glu Gly Ala Ala Val Asp Ala Asp Phe Trp
        915                 920                 925 gac gcc gtg gag cgc gag gac ctg acc gcg ctg gcc gcg gcg ctg gag                2832
Asp Ala Val Glu Arg Glu Asp Leu Thr Ala Leu Ala Ala Ala Leu Glu
    930                 935                 940 gtg gac gcc gag gag tcg tcc ctg gcc atg gtg gtt ccg gcg ctg gcc                2880
Val Asp Ala Glu Glu Ser Ser Leu Ala Met Val Val Pro Ala Leu Ala
945                 950                 955                 960 gca tgg cgc cgg gcg cgc cgt gag cgg tcc gtg ctc gac tcc tgg cgc                2928
Ala Trp Arg Arg Ala Arg Arg Glu Arg Ser Val Leu Asp Ser Trp Arg
                965                 970                 975 tac cag gtc acc tgg aag ccc ctg ggc gac gcc ctc acc tcc gcc cac                2976
Tyr Gln Val Thr Trp Lys Pro Leu Gly Asp Ala Leu Thr Ser Ala His
            980                 985                 990
```

```
gac cgg tcg tcg gcc ggt gcg acc tgg ctg atc gcc gcg ccc gcc gga    3024
Asp Arg Ser Ser Ala Gly Ala Thr Trp Leu Ile Ala Ala Pro Ala Gly
        995                 1000                1005 gcg ccg gag ggc ccg cgt gtc gcg gag gcg ctg cgg gaa cgc ggc        3069
Ala Pro Glu Gly Pro Arg Val Ala Glu Ala Leu Arg Glu Arg Gly
    1010                1015                1020 gcc cgg gtg cgg ctg gtg gag ctg acc gaa gcg gac gcc gta cgc        3114
Ala Arg Val Arg Leu Val Glu Leu Thr Glu Ala Asp Ala Val Arg
    1025                1030                1035 gag gcg ctc gcc cgc ggg ctc ggc gag gcc acg gcc gat acg cca        3159
Glu Ala Leu Ala Arg Gly Leu Gly Glu Ala Thr Ala Asp Thr Pro
    1040                1045                1050 ccg acc gct gtg ctc tcg ctc ctc gcg ctc gcc gag gac ccg tac        3204
Pro Thr Ala Val Leu Ser Leu Leu Ala Leu Ala Glu Asp Pro Tyr
    1055                1060                1065 cgc gcg ggc acg gcg cag ccg ctc ggc ctt gcc ctc aac ctc gcc        3249
Arg Ala Gly Thr Ala Gln Pro Leu Gly Leu Ala Leu Asn Leu Ala
    1070                1075                1080 ctc ctc cag gcg ctc ttc gac acc ggg gcc gat gtc ccg gtg tgg        3294
Leu Leu Gln Ala Leu Phe Asp Thr Gly Ala Asp Val Pro Val Trp
    1085                1090                1095 tac gcc acg cgc ggc gcg gtg tcc gtg ggc cgc gcg gac gcg ctg        3339
Tyr Ala Thr Arg Gly Ala Val Ser Val Gly Arg Ala Asp Ala Leu
    1100                1105                1110 gac cat ccg ctg cag gcg ctc agc tgg ggc ctg ggc cgg atc gcg        3384
Asp His Pro Leu Gln Ala Leu Ser Trp Gly Leu Gly Arg Ile Ala
    1115                1120                1125 gcg gtg gag tac ccg cgg tgc cgg ggc ggt ctg gtg gat ctg ccc        3429
Ala Val Glu Tyr Pro Arg Cys Arg Gly Gly Leu Val Asp Leu Pro
    1130                1135                1140 ggc act ctc gac gac cgt gcc gtc gcg cgg ctg tgc ggt gtg ctc        3474
Gly Thr Leu Asp Asp Arg Ala Val Ala Arg Leu Cys Gly Val Leu
    1145                1150                1155 gcg ggc cgg ctg acc gac gag gac cag gtc gcg gtg cgc gcc tcc        3519
Ala Gly Arg Leu Thr Asp Glu Asp Gln Val Ala Val Arg Ala Ser
    1160                1165                1170 ggg gtc cac ggg cgc agg ctg gtc agg gcc tcg gcg gca ccg gcc        3564
Gly Val His Gly Arg Arg Leu Val Arg Ala Ser Ala Ala Pro Ala
    1175                1180                1185 gac gcc acc gcg ccg tgg cgg ccg cgc ggc acc gtg ctg gtc acc        3609
Asp Ala Thr Ala Pro Trp Arg Pro Arg Gly Thr Val Leu Val Thr
    1190                1195                1200 gga ggc acc ggc ggc ctg ggc gcc cat gtg gcg cgc tgg ctg gcc        3654
Gly Gly Thr Gly Gly Leu Gly Ala His Val Ala Arg Trp Leu Ala
    1205                1210                1215 cgg ggc ggc gcc gaa cac ctg gtg ctc tcc agc cgc cgg ggc ccc        3699
Arg Gly Gly Ala Glu His Leu Val Leu Ser Ser Arg Arg Gly Pro
    1220                1225                1230 gac gcc ccc gga gcg gcc gaa ctc gcc gac ggg ata agg gag tcg        3744
Asp Ala Pro Gly Ala Ala Glu Leu Ala Asp Gly Ile Arg Glu Ser
    1235                1240                1245 ggg gtc cgg gtg acc gtg gcc gcg tgc gac gcc gcc gac cgc gac        3789
Gly Val Arg Val Thr Val Ala Ala Cys Asp Ala Ala Asp Arg Asp
    1250                1255                1260 gcg ctg gcc gac ctc ctc gcc acg ctg gac gcc gac gag gca ccg        3834
Ala Leu Ala Asp Leu Leu Ala Thr Leu Asp Ala Asp Glu Ala Pro
    1265                1270                1275 ctc gac gcg gtc gtc cac acc gcg ggc gtc ctg gac gac ggg gtg        3879
Leu Asp Ala Val Val His Thr Ala Gly Val Leu Asp Asp Gly Val
    1280                1285                1290
```

```
ctc gac acc ctc acc ccc gag cgc gcc gac ggg gtg ctg cgc ccg      3924
Leu Asp Thr Leu Thr Pro Glu Arg Ala Asp Gly Val Leu Arg Pro
1295                1300                1305 aag gtg gac gcg gcg ctc cat ctg cac gag ctc acc cgg gac cgc      3969
Lys Val Asp Ala Ala Leu His Leu His Glu Leu Thr Arg Asp Arg
1310                1315                1320 gag ctg tcc gcc ttc gtg ctc ttc tcc tcc ttc gcg ggc acg ctc      4014
Glu Leu Ser Ala Phe Val Leu Phe Ser Ser Phe Ala Gly Thr Leu
1325                1330                1335 ggc ggt ccc ggc cag ggc agc tac gcg gcc gcc aac gcc ttc ctc      4059
Gly Gly Pro Gly Gln Gly Ser Tyr Ala Ala Ala Asn Ala Phe Leu
1340                1345                1350 gac gcg ctc gca cac gcc cgc cgc gcc cag ggc ctc ccc gcc acc      4104
Asp Ala Leu Ala His Ala Arg Arg Ala Gln Gly Leu Pro Ala Thr
1355                1360                1365 tcc gtg gcc tgg ggc gcg tgg tcc ggc ggc ggg ctg gtg gac gag      4149
Ser Val Ala Trp Gly Ala Trp Ser Gly Gly Gly Leu Val Asp Glu
1370                1375                1380 gcc gtc cag gcg cgg ctg cgc gcc acc ggt atg ccc gcg atg gca      4194
Ala Val Gln Ala Arg Leu Arg Ala Thr Gly Met Pro Ala Met Ala
1385                1390                1395 ccc gac ctg gcg atc gcc gcc ctc cag cgc gcc ctg gac gtg gcc      4239
Pro Asp Leu Ala Ile Ala Ala Leu Gln Arg Ala Leu Asp Val Ala
1400                1405                1410 gac acc cat gtg gcc gtg gcc gat gtc gag tgg gac cgg ctc atc      4284
Asp Thr His Val Ala Val Ala Asp Val Glu Trp Asp Arg Leu Ile
1415                1420                1425 gcc gcc acg ccc tcc ctg gac ggg gcc gcc gtg ctc ggc gaa ctc      4329
Ala Ala Thr Pro Ser Leu Asp Gly Ala Ala Val Leu Gly Glu Leu
1430                1435                1440 ccc gac gcg cga cgg gcg gag gtg gcg gcc gcg acc acg ggc gag      4374
Pro Asp Ala Arg Arg Ala Glu Val Ala Ala Ala Thr Thr Gly Glu
1445                1450                1455 gag gac acc ccg ctg agc cag cgg ctg gcc ggg ctg tcg ccg cag      4419
Glu Asp Thr Pro Leu Ser Gln Arg Leu Ala Gly Leu Ser Pro Gln
1460                1465                1470 gag gcc gag gag gcg ctg gcc gac ctc gtc agc gcc gaa gtg gcc      4464
Glu Ala Glu Glu Ala Leu Ala Asp Leu Val Ser Ala Glu Val Ala
1475                1480                1485 gcc gcg ctc ggc tac gcc gac acc gcg gcg gtc gag gcc ggg cgg      4509
Ala Ala Leu Gly Tyr Ala Asp Thr Ala Ala Val Glu Ala Gly Arg
1490                1495                1500 gcc ttc cgc gag ctg ggc ttc gac tcg ctg acc gcc gtc gat ctg      4554
Ala Phe Arg Glu Leu Gly Phe Asp Ser Leu Thr Ala Val Asp Leu
1505                1510                1515 cgc aac cgg ctg aac gcg gcc acc ggg ctg cgg ctg ccg gtc acc      4599
Arg Asn Arg Leu Asn Ala Ala Thr Gly Leu Arg Leu Pro Val Thr
1520                1525                1530 ctc gtc ttc gac tac ccg acc gtc gcc gcg ctg gcc cgc ttc ctg      4644
Leu Val Phe Asp Tyr Pro Thr Val Ala Ala Leu Ala Arg Phe Leu
1535                1540                1545 ctc gcc gag agc ggt gcc ggt gaa acc gcg gcc acc gcc ccg gcg      4689
Leu Ala Glu Ser Gly Ala Gly Glu Thr Ala Ala Thr Ala Pro Ala
1550                1555                1560 ggc ccg gtg ccc gcc gcc gtc gcg gtg gac gac gac ccg atc gcc      4734
Gly Pro Val Pro Ala Ala Val Ala Val Asp Asp Asp Pro Ile Ala
1565                1570                1575 atc gtg gcc atg agc tgc cgc ctc ccc ggc ggg gtg acc acc ccc      4779
Ile Val Ala Met Ser Cys Arg Leu Pro Gly Gly Val Thr Thr Pro
```

```
      1580                1585                1590 gag gag ctg tgg cgg ctg ttg atg gat ggc cgg gac gcc atc tcg    4824
Glu Glu Leu Trp Arg Leu Leu Met Asp Gly Arg Asp Ala Ile Ser
        1595                1600                1605 gac ttc ccc acc gac cgc ggc tgg gac atc gag ggc cac tac gac    4869
Asp Phe Pro Thr Asp Arg Gly Trp Asp Ile Glu Gly His Tyr Asp
1610                1615                1620 ccc gac ccc gac aag ccg ggc acg ttc tac gcc acc ggc ggt ggt    4914
Pro Asp Pro Asp Lys Pro Gly Thr Phe Tyr Ala Thr Gly Gly Gly
    1625                1630                1635 ttc ctc cac cag gcc gac cac ttc gac ccc gag ttc ttc ggg atc    4959
Phe Leu His Gln Ala Asp His Phe Asp Pro Glu Phe Phe Gly Ile
        1640                1645                1650 tcc ccg cgc gag gcg ctc gcc atc gac ccc cag cag cgg ctg ctg    5004
Ser Pro Arg Glu Ala Leu Ala Ile Asp Pro Gln Gln Arg Leu Leu
1655                1660                1665 ctg gag acc agc tgg gag acg ttc gag cgg gcc ggg atc gac ccg    5049
Leu Glu Thr Ser Trp Glu Thr Phe Glu Arg Ala Gly Ile Asp Pro
    1670                1675                1680 gcc tcg gtg aag ggc acc cag gcc gga gtc ttc atc ggc gcc agc    5094
Ala Ser Val Lys Gly Thr Gln Ala Gly Val Phe Ile Gly Ala Ser
        1685                1690                1695 tac aac gac tac ggc tcg cgc ttc acc cgc gca ccc gag gag ttc    5139
Tyr Asn Asp Tyr Gly Ser Arg Phe Thr Arg Ala Pro Glu Glu Phe
1700                1705                1710 gag ggc tat ctg gcc acc ggc agc gcc agc agc gtg gcg tcc ggg    5184
Glu Gly Tyr Leu Ala Thr Gly Ser Ala Ser Ser Val Ala Ser Gly
    1715                1720                1725 cgc atc tcg tac acc ttc ggc ctc gaa ggg ccc gcg gtc acc gtg    5229
Arg Ile Ser Tyr Thr Phe Gly Leu Glu Gly Pro Ala Val Thr Val
        1730                1735                1740 gac acc gcc tgc tcg tcc tcg ctg gtc gcc ctc cac cag gcg gcc    5274
Asp Thr Ala Cys Ser Ser Ser Leu Val Ala Leu His Gln Ala Ala
1745                1750                1755 cag gcg ctg cgc cag ggg gag tgc tcg ctg gcg ctc gcg ggc ggt    5319
Gln Ala Leu Arg Gln Gly Glu Cys Ser Leu Ala Leu Ala Gly Gly
    1760                1765                1770 gtc gtg gtg atg tcc acg ctg gac acc ttc atc gag ttc agc agg    5364
Val Val Val Met Ser Thr Leu Asp Thr Phe Ile Glu Phe Ser Arg
        1775                1780                1785 cag cgg gcc atg gcc ccc gac ggc cgc tgc aag gcg ttc tcg gcg    5409
Gln Arg Ala Met Ala Pro Asp Gly Arg Cys Lys Ala Phe Ser Ala
1790                1795                1800 gcc gcc gac ggc gcc gga tgg gcc gag ggc gtc ggc atg ctg ctg    5454
Ala Ala Asp Gly Ala Gly Trp Ala Glu Gly Val Gly Met Leu Leu
    1805                1810                1815 ctg gag cgg ctc tcc gac gcg cgg gcg aac ggc cat gag gtg ctg    5499
Leu Glu Arg Leu Ser Asp Ala Arg Ala Asn Gly His Glu Val Leu
        1820                1825                1830 gcg ctg gtg cgt ggc tcg gcc gtc aac cag gac ggc gcc agc aac    5544
Ala Leu Val Arg Gly Ser Ala Val Asn Gln Asp Gly Ala Ser Asn
1835                1840                1845 ggc ctc acc gcc ccc aac ggc ccc tcc cag cag cgg gtg atc cgc    5589
Gly Leu Thr Ala Pro Asn Gly Pro Ser Gln Gln Arg Val Ile Arg
    1850                1855                1860 cag gcg ctg gcc ggt gcg ggc ctg tcg gcc gcc gat gtg gac gcg    5634
Gln Ala Leu Ala Gly Ala Gly Leu Ser Ala Ala Asp Val Asp Ala
        1865                1870                1875 gtc gag acc cat ggc acc ggc acc cgg ctc ggc gac ccc atc gag    5679
```

-continued

```
Val Glu Thr His Gly Thr Gly Thr Arg Leu Gly Asp Pro Ile Glu
    1880            1885                1890 gcg cag gcc ctg atg gcc acc tac ggc cag ggg cgg gac gcc gac       5724
Ala Gln Ala Leu Met Ala Thr Tyr Gly Gln Gly Arg Asp Ala Asp
1895                1900                1905 cgg ccg ctg tgg ctg ggc gcg ctg aag tcc aac atc ggc cac acc       5769
Arg Pro Leu Trp Leu Gly Ala Leu Lys Ser Asn Ile Gly His Thr
    1910                1915                1920 cag gcc gct tcg ggc gtc gcc ggg atc atc aag acg gtg ctg gcg       5814
Gln Ala Ala Ser Gly Val Ala Gly Ile Ile Lys Thr Val Leu Ala
1925                1930                1935 ctg cga cac ggc gtg ctg ccc aag acc ctc cac gcc gat gag cgc       5859
Leu Arg His Gly Val Leu Pro Lys Thr Leu His Ala Asp Glu Arg
    1940                1945                1950 tcg ccc gac gtg gac tgg tcg gcc ggt gcg gtg gag ctg ctg acc       5904
Ser Pro Asp Val Asp Trp Ser Ala Gly Ala Val Glu Leu Leu Thr
1955                1960                1965 gag gcc cgg gag tgg ccc gag acg gga cgg ccg cgg cgc gcg ggc       5949
Glu Ala Arg Glu Trp Pro Glu Thr Gly Arg Pro Arg Arg Ala Gly
    1970                1975                1980 gtg tcc gcc ttc ggc gtc agc ggc acg aac gtc cat gtg gtg ctg       5994
Val Ser Ala Phe Gly Val Ser Gly Thr Asn Val His Val Val Leu
1985                1990                1995 gag cag ggc ccc gag cac acc gcg ccg gtg gcc gag cgg acg gtc       6039
Glu Gln Gly Pro Glu His Thr Ala Pro Val Ala Glu Arg Thr Val
    2000                2005                2010 gac tcg gac gtg gtg ccg tgg gtg ctc tcc gcg cgc ggc gag acc       6084
Asp Ser Asp Val Val Pro Trp Val Leu Ser Ala Arg Gly Glu Thr
2015                2020                2025 gcg ctg cgg gcg cag gcc ggg cgg ctg cgt gcc cgt ctg gag gag       6129
Ala Leu Arg Ala Gln Ala Gly Arg Leu Arg Ala Arg Leu Glu Glu
    2030                2035                2040 cgg ccg gag ctg cgc ccg gtg gac gtc ggc tac gcg ctg gcg acg       6174
Arg Pro Glu Leu Arg Pro Val Asp Val Gly Tyr Ala Leu Ala Thr
2045                2050                2055 ggc cgc tcg gcc ttc ggc cac cgc gcc gtg gtc gtc ggc gcg gag       6219
Gly Arg Ser Ala Phe Gly His Arg Ala Val Val Val Gly Ala Glu
    2060                2065                2070 cgg gag gaa ctg ctg cgg gga ctc gcg gaa ctg gcc tcg ggg acg       6264
Arg Glu Glu Leu Leu Arg Gly Leu Ala Glu Leu Ala Ser Gly Thr
2075                2080                2085 gcg cgg gag acg gtg gcc gac gcc ggt agg acg gcc ttc ctg ttc       6309
Ala Arg Glu Thr Val Ala Asp Ala Gly Arg Thr Ala Phe Leu Phe
    2090                2095                2100 acc ggg cag ggt gct caa cgg ctc ggc atg gga cgg gag ttg tac       6354
Thr Gly Gln Gly Ala Gln Arg Leu Gly Met Gly Arg Glu Leu Tyr
2105                2110                2115 gac gcg ttc ccg gtg ttc gcg gcg gcg ttc gac gcg gtg tgc gcc       6399
Asp Ala Phe Pro Val Phe Ala Ala Ala Phe Asp Ala Val Cys Ala
    2120                2125                2130 gag ctg gac cgc cat ctg gac ggc tcg gtg cgc gag gtg gtg ttc       6444
Glu Leu Asp Arg His Leu Asp Gly Ser Val Arg Glu Val Val Phe
2135                2140                2145 ggc ggg gac gcg gag ccg ctg aac cgg acc gtg ttc acc cag acc       6489
Gly Gly Asp Ala Glu Pro Leu Asn Arg Thr Val Phe Thr Gln Thr
    2150                2155                2160 gcg ctg ttc gcc ctc gaa gtg gcg ctg tac cgg ctg gtc gag tcc       6534
Ala Leu Phe Ala Leu Glu Val Ala Leu Tyr Arg Leu Val Glu Ser
2165                2170                2175
```

```
                                         -continued
tgg ggt ctg cgc ccg gac ttc ctg gtc ggc cac tcg gtg ggc gag      6579
Trp Gly Leu Arg Pro Asp Phe Leu Val Gly His Ser Val Gly Glu
2180            2185                2190 ctg gcg gcc gcc cat gtg gcc ggg gtg ttc tcg ctg gag gac gcg      6624
Leu Ala Ala Ala His Val Ala Gly Val Phe Ser Leu Glu Asp Ala
    2195            2200                2205 tgt gcg ctg gtg gcg gcc cgg ggc cgg ctg atg cag gcg ctg ccg      6669
Cys Ala Leu Val Ala Ala Arg Gly Arg Leu Met Gln Ala Leu Pro
2210            2215                2220 gag ggc ggt gcg atg gtg tcg ctc cag gcg gcc gag gcc gat gtg      6714
Glu Gly Gly Ala Met Val Ser Leu Gln Ala Ala Glu Ala Asp Val
    2225            2230                2235 ctg cca cat ctc gaa ggc cac gag gac cgg gtg agc gtg gcg gcg      6759
Leu Pro His Leu Glu Gly His Glu Asp Arg Val Ser Val Ala Ala
2240            2245                2250 gtc aac ggg ccg cgg gcg acc gtc atc tcc ggt gac gag gac acc      6804
Val Asn Gly Pro Arg Ala Thr Val Ile Ser Gly Asp Glu Asp Thr
    2255            2260                2265 gtc ctg cgg atc gcg gag gcg acc ggg gcc aag agc aag cgg ctc      6849
Val Leu Arg Ile Ala Glu Ala Thr Gly Ala Lys Ser Lys Arg Leu
2270            2275                2280 acc gtc tcc cac gcc ttc cac tcg ccg ctg atg gac gcc atg ctc      6894
Thr Val Ser His Ala Phe His Ser Pro Leu Met Asp Ala Met Leu
    2285            2290                2295 gcg gag ttc ggc acg gtg gcc acc ggg atc ggc tac tcc aca ccg      6939
Ala Glu Phe Gly Thr Val Ala Thr Gly Ile Gly Tyr Ser Thr Pro
2300            2305                2310 cgc atc gcg gtg gtc tcc aat gtc acc ggt gag gcg gcg ggc gag      6984
Arg Ile Ala Val Val Ser Asn Val Thr Gly Glu Ala Ala Gly Glu
    2315            2320                2325 gag ctg tgc tcg ccc gag tac tgg gtg cgc cac gtc cgc cgt gcg      7029
Glu Leu Cys Ser Pro Glu Tyr Trp Val Arg His Val Arg Arg Ala
2330            2335                2340 gtg cgc ttc ggg gac ggc atc cgc ttc ctc gcc gag cgg aat gtg      7074
Val Arg Phe Gly Asp Gly Ile Arg Phe Leu Ala Glu Arg Asn Val
    2345            2350                2355 acc cgc ttc gtc gag atc ggc cgg ccg gtg tgc tct ccg cca tgg      7119
Thr Arg Phe Val Glu Ile Gly Arg Pro Val Cys Ser Pro Pro Trp
2360            2365                2370 ggc cag gag tgc ctg gcc gag gcc ggc acc gag acc gac atc gac      7164
Gly Gln Glu Cys Leu Ala Glu Ala Gly Thr Glu Thr Asp Ile Asp
    2375            2380                2385 acc gag acc gcg ttc gtc ccg ctg ctg cgc aag gac cgc agc gag      7209
Thr Glu Thr Ala Phe Val Pro Leu Leu Arg Lys Asp Arg Ser Glu
2390            2395                2400 gcc gag tcg ctg ctg gcc ggg gtg ggc cgg gtg cac gcc cac ggt      7254
Ala Glu Ser Leu Leu Ala Gly Val Gly Arg Val His Ala His Gly
    2405            2410                2415 ggc gcg gtg gac tgg gag cag gtg ttc gcg ggc cgt ggc gcc cgc      7299
Gly Ala Val Asp Trp Glu Gln Val Phe Ala Gly Arg Gly Ala Arg
2420            2425                2430 cgg gtg gag ctg ccg acg tac gcc ttc cag cgg cag cgc tac tgg      7344
Arg Val Glu Leu Pro Thr Tyr Ala Phe Gln Arg Gln Arg Tyr Trp
    2435            2440                2445 ctg gac gcg ccc gcc acc gtg ggc gat gtg gcc tcg gcc ggt ctc      7389
Leu Asp Ala Pro Ala Thr Val Gly Asp Val Ala Ser Ala Gly Leu
2450            2455                2460 ggc gcc gcc ggg cat ccg ctg ctg ggc gcg gcc gtc gaa ctc gcc      7434
Gly Ala Ala Gly His Pro Leu Leu Gly Ala Ala Val Glu Leu Ala
    2465            2470                2475
```

```
gac agc gac ggc ctg gtg ctc acc ggg cgg ctg tcc acg cgc ggc      7479
Asp Ser Asp Gly Leu Val Leu Thr Gly Arg Leu Ser Thr Arg Gly
    2480                2485                2490 cag ccc tgg ctg gcc gac cac gcg gtc tcc ggt gtg gtc ctc ttc      7524
Gln Pro Trp Leu Ala Asp His Ala Val Ser Gly Val Val Leu Phe
2495                2500                2505 ccc ggc acc gcc ttc ctg gag ctc gcc atc cag gcc ggg gac cgg      7569
Pro Gly Thr Ala Phe Leu Glu Leu Ala Ile Gln Ala Gly Asp Arg
    2510                2515                2520 gtg ggc tgc gac cgc gtc gac gag ctg acc ctc cag gcg ccg ctc      7614
Val Gly Cys Asp Arg Val Asp Glu Leu Thr Leu Gln Ala Pro Leu
2525                2530                2535 atc ctg ccc gag cgc ggc gcc gtc acc ctg caa ctg gtg gtg gac      7659
Ile Leu Pro Glu Arg Gly Ala Val Thr Leu Gln Leu Val Val Asp
    2540                2545                2550 ccg ccc gag gag gac ggc cgt cgc gcc ctg aac gtc tac tcc cgc      7704
Pro Pro Glu Glu Asp Gly Arg Arg Ala Leu Asn Val Tyr Ser Arg
2555                2560                2565 ccc gag gac acg aac ggt gag ccg ccg tgg acc cgg cac gcc acg      7749
Pro Glu Asp Thr Asn Gly Glu Pro Pro Trp Thr Arg His Ala Thr
    2570                2575                2580 ggt gtg ctg gcg gcc ggt gcc gcc gag ggc tcg tac gac ctg ggc      7794
Gly Val Leu Ala Ala Gly Ala Ala Glu Gly Ser Tyr Asp Leu Gly
2585                2590                2595 ggg gcg tgg ccg ccg ccg ggc gcc gag ccg atc gag gtc gag gac      7839
Gly Ala Trp Pro Pro Pro Gly Ala Glu Pro Ile Glu Val Glu Asp
    2600                2605                2610 ctg tac gag cgg ttc gcg gcg ggc ggc ttc ggc tac ggc ccg tcg      7884
Leu Tyr Glu Arg Phe Ala Ala Gly Gly Phe Gly Tyr Gly Pro Ser
2615                2620                2625 ttc cag ggg ctg cgc gcg gcc tgg ctg cgc ggc gac gag gtg ttc      7929
Phe Gln Gly Leu Arg Ala Ala Trp Leu Arg Gly Asp Glu Val Phe
    2630                2635                2640 gcc gag gta cgg ctg gcg cag gag cag cag tcc gcc gcc acc gcc      7974
Ala Glu Val Arg Leu Ala Gln Glu Gln Gln Ser Ala Ala Thr Ala
2645                2650                2655 tac ggc ctg cac ccc gcc ctg ctg gac gcc gcg ctg cac acc atc      8019
Tyr Gly Leu His Pro Ala Leu Leu Asp Ala Ala Leu His Thr Ile
    2660                2665                2670 gcg ctc ggc ccg atg ctc cag gcg ggc gag ggc cgg ttg ccg ttc      8064
Ala Leu Gly Pro Met Leu Gln Ala Gly Glu Gly Arg Leu Pro Phe
2675                2680                2685 tcc tgg acc ggg gtg acg ctg cac gcc tcc ggg gcc ggt gag gta      8109
Ser Trp Thr Gly Val Thr Leu His Ala Ser Gly Ala Gly Glu Val
    2690                2695                2700 cgg gtg cgg ctc acg ccg agc ggc acc gac acg gtg gcc ctg acg      8154
Arg Val Arg Leu Thr Pro Ser Gly Thr Asp Thr Val Ala Leu Thr
2705                2710                2715 gtg gcg gac acc atc gga cgg ccg gtg gcc acc gtc gaa tcc ctg      8199
Val Ala Asp Thr Ile Gly Arg Pro Val Ala Thr Val Glu Ser Leu
    2720                2725                2730 gtg ttg cgc aag cgg ccc gaa cgg ctc ggc gac gcc gcc acc ggc      8244
Val Leu Arg Lys Arg Pro Glu Arg Leu Gly Asp Ala Ala Thr Gly
2735                2740                2745 ggc gac tcg ctc tac cgg ctc gac tgg gtg gcc gcc gac acc tcc      8289
Gly Asp Ser Leu Tyr Arg Leu Asp Trp Val Ala Ala Asp Thr Ser
    2750                2755                2760 gcg gcg acg ccc gaa caa ccc tcc ggg cac tgg gcc ctg ctc ggc      8334
Ala Ala Thr Pro Glu Gln Pro Ser Gly His Trp Ala Leu Leu Gly
2765                2770                2775
```

```
               2765                2770                2775 gac  gac  gac  ttc  aag  ctg  gtc  gga  ctc  gat  gtg  cac  aca  tac  ccg     8379
Asp  Asp  Asp  Phe  Lys  Leu  Val  Gly  Leu  Asp  Val  His  Thr  Tyr  Pro
          2780                2785                2790 aac  ctg  gag  gcg  ctg  ccc  gcc  gac  ccg  gcc  gcc  gtg  ccc  gcc  acc     8424
Asn  Leu  Glu  Ala  Leu  Pro  Ala  Asp  Pro  Ala  Ala  Val  Pro  Ala  Thr
     2795                2800                2805 gta  ctg  gtg  ccc  tgc  gca  ccg  gag  ccc  cag  ggc  gtg  gcc  gac  gcc     8469
Val  Leu  Val  Pro  Cys  Ala  Pro  Glu  Pro  Gln  Gly  Val  Ala  Asp  Ala
2810                2815                2820 gta  cgg  gcc  gcg  acc  cac  cgg  gcg  ctg  acg  ctg  ctc  cgg  gcc  tgg     8514
Val  Arg  Ala  Ala  Thr  His  Arg  Ala  Leu  Thr  Leu  Leu  Arg  Ala  Trp
2825                2830                2835 ctg  acc  gag  gac  cgg  ttc  gcc  gac  tcc  cgc  ctg  gtg  ttc  atc  acc     8559
Leu  Thr  Glu  Asp  Arg  Phe  Ala  Asp  Ser  Arg  Leu  Val  Phe  Ile  Thr
2840                2845                2850 cgg  ggc  gcg  gtg  gcc  acc  aca  ccc  ggc  gcg  gac  gta  ccc  gat  ctg     8604
Arg  Gly  Ala  Val  Ala  Thr  Thr  Pro  Gly  Ala  Asp  Val  Pro  Asp  Leu
     2855                2860                2865 gcg  cac  gcc  gcc  gta  tgg  ggc  ctg  gtg  cgc  tcc  gcg  cag  tcg  gag     8649
Ala  His  Ala  Ala  Val  Trp  Gly  Leu  Val  Arg  Ser  Ala  Gln  Ser  Glu
2870                2875                2880 aac  ccc  gac  cgg  ttc  gtg  ctc  gtc  gac  ctc  gac  gag  cag  gag  gaa     8694
Asn  Pro  Asp  Arg  Phe  Val  Leu  Val  Asp  Leu  Asp  Glu  Gln  Glu  Glu
     2885                2890                2895 tcg  gcg  ctc  gcc  ctg  ccg  acc  gcg  ctc  gcc  ctg  gac  gag  cct  caa     8739
Ser  Ala  Leu  Ala  Leu  Pro  Thr  Ala  Leu  Ala  Leu  Asp  Glu  Pro  Gln
2900                2905                2910 ctc  gct  gtg  cgc  cag  ggg  gac  atc  gtg  gtg  gcc  agg  ctc  gcc  acc     8784
Leu  Ala  Val  Arg  Gln  Gly  Asp  Ile  Val  Val  Ala  Arg  Leu  Ala  Thr
     2915                2920                2925 acc  ccc  gtc  ccc  gac  acc  gcc  ccg  ccc  gcc  tgg  gac  ccc  gag  ggc     8829
Thr  Pro  Val  Pro  Asp  Thr  Ala  Pro  Pro  Ala  Trp  Asp  Pro  Glu  Gly
2930                2935                2940 acg  gtg  ctg  gtc  acc  ggg  gcc  acc  ggc  acc  atc  ggc  ggg  gtc  atc     8874
Thr  Val  Leu  Val  Thr  Gly  Ala  Thr  Gly  Thr  Ile  Gly  Gly  Val  Ile
     2945                2950                2955 gcc  cgc  cat  ctg  gtg  gcc  gag  ggc  gga  gtg  cgg  cat  ctg  ctg  ctc     8919
Ala  Arg  His  Leu  Val  Ala  Glu  Gly  Gly  Val  Arg  His  Leu  Leu  Leu
2960                2965                2970 acg  agc  cgc  cgt  ggc  ccg  gac  gcc  gag  ggc  gcg  gcc  gaa  ctc  cac     8964
Thr  Ser  Arg  Arg  Gly  Pro  Asp  Ala  Glu  Gly  Ala  Ala  Glu  Leu  His
     2975                2980                2985 gcg  gaa  ctt  gcg  gag  ttg  ggc  gcc  cag  gtc  acc  ctc  gcc  gcc  tgc     9009
Ala  Glu  Leu  Ala  Glu  Leu  Gly  Ala  Gln  Val  Thr  Leu  Ala  Ala  Cys
2990                2995                3000 gat  gtg  gcc  gac  cgg  gag  gcg  ctg  gcc  gcg  ctg  ctg  gcc  acc  gtc     9054
Asp  Val  Ala  Asp  Arg  Glu  Ala  Leu  Ala  Ala  Leu  Leu  Ala  Thr  Val
3005                3010                3015 ccc  gcc  gca  cat  ccg  ctg  acc  gcc  gtc  gtg  cac  acg  gcg  ggc  gtc     9099
Pro  Ala  Ala  His  Pro  Leu  Thr  Ala  Val  Val  His  Thr  Ala  Gly  Val
3020                3025                3030 ctg  gac  gac  ggt  gtg  gtc  tcc  tcg  ctc  acc  ccc  gag  cgg  ctg  gac     9144
Leu  Asp  Asp  Gly  Val  Val  Ser  Ser  Leu  Thr  Pro  Glu  Arg  Leu  Asp
3035                3040                3045 acg  gtg  ctg  cgg  ccc  aag  gtc  gac  gcc  gcg  ctc  acc  ctg  cac  gag     9189
Thr  Val  Leu  Arg  Pro  Lys  Val  Asp  Ala  Ala  Leu  Thr  Leu  His  Glu
3050                3055                3060 ctg  acc  cgc  gac  ctg  gac  ctg  tcc  gcg  ctc  gtc  ctg  ttc  tcg  tcc     9234
```

```
Leu Thr Arg Asp Leu Asp Leu Ser Ala Leu Val Leu Phe Ser Ser
    3065            3070                3075 atc gcc ggc acc ttc ggc gga atg ggc cag ggc aac tac gcg gcg         9279
Ile Ala Gly Thr Phe Gly Gly Met Gly Gln Gly Asn Tyr Ala Ala
3080            3085                3090 gcc aac gcc ttc ctc gac gcc ttc gcc cag cac tgc cgc gcc cag         9324
Ala Asn Ala Phe Leu Asp Ala Phe Ala Gln His Cys Arg Ala Gln
    3095            3100                3105 ggg cgg ccc gtc cag tca cac gcg tgg ggg ctg tgg gcc cag cgc         9369
Gly Arg Pro Val Gln Ser His Ala Trp Gly Leu Trp Ala Gln Arg
3110            3115                3120 agc gag atg acc ggc aag ctg gag ggc gcc gat ctg aac cgg ctg         9414
Ser Glu Met Thr Gly Lys Leu Glu Gly Ala Asp Leu Asn Arg Leu
    3125            3130                3135 gcg cgc ggt ggc atc gtc ccg ttc tcc tcg gcg gac ggc gcc ggg         9459
Ala Arg Gly Gly Ile Val Pro Phe Ser Ser Ala Asp Gly Ala Gly
3140            3145                3150 ctc ttc gac gcc gca cgc gcc gtg gac tcc gcc gtc gtg ctg ccg         9504
Leu Phe Asp Ala Ala Arg Ala Val Asp Ser Ala Val Val Leu Pro
    3155            3160                3165 atg cgc ctg gac acc gcg ggg ctc gga gcc cgg tcc ggt gac gta         9549
Met Arg Leu Asp Thr Ala Gly Leu Gly Ala Arg Ser Gly Asp Val
3170            3175                3180 ccg gcg ctg ctg cgc ggg ctg gtg agg gcc gcg ccc gcc acc agg         9594
Pro Ala Leu Leu Arg Gly Leu Val Arg Ala Ala Pro Ala Thr Arg
    3185            3190                3195 ccc gcc cgg cgg acg gcc gcc gga gcc ggg gcc gcc ccc gcg cgg         9639
Pro Ala Arg Arg Thr Ala Ala Gly Ala Gly Ala Ala Pro Ala Arg
3200            3205                3210 ccc gag ggg ctc aag cag cat ctg acg agc ctg ccg gag gcc gag         9684
Pro Glu Gly Leu Lys Gln His Leu Thr Ser Leu Pro Glu Ala Glu
    3215            3220                3225 cgc ggc cgg ttc ctg ctg gac ctg gtc cgc acc acc gtg gcc ggg         9729
Arg Gly Arg Phe Leu Leu Asp Leu Val Arg Thr Thr Val Ala Gly
3230            3235                3240 gtg ctg ggc ttc gac tcg gtg gcg gcc gtc gag gcg gag cgc ggt         9774
Val Leu Gly Phe Asp Ser Val Ala Ala Val Glu Ala Glu Arg Gly
    3245            3250                3255 ctg ctg gac ctc ggc ttc gac tcg ctc acc gcg gtc gag ctc cgt         9819
Leu Leu Asp Leu Gly Phe Asp Ser Leu Thr Ala Val Glu Leu Arg
3260            3265                3270 aac caa ctc ggc aag gcc acc ggc cgg cgc ctg ccg gtg acc ctg         9864
Asn Gln Leu Gly Lys Ala Thr Gly Arg Arg Leu Pro Val Thr Leu
    3275            3280                3285 ctc ttc gac tac ccc acc tcc acg gcg atc gcc gcg tat ctg gaa         9909
Leu Phe Asp Tyr Pro Thr Ser Thr Ala Ile Ala Ala Tyr Leu Glu
3290            3295                3300 gcg gaa atc gcc ccg gag gca ttc acc gcc gcg tcg atg acc ttc         9954
Ala Glu Ile Ala Pro Glu Ala Phe Thr Ala Ala Ser Met Thr Phe
    3305            3310                3315 ccc gaa ctc gac gcc ctg gaa agc aac ctg gcc aag gtc gcc gtc         9999
Pro Glu Leu Asp Ala Leu Glu Ser Asn Leu Ala Lys Val Ala Val
3320            3325                3330 gac gac gag gcg cgc acc acg ctc gcc tcg cgc ctg caa gac ctg        10044
Asp Asp Glu Ala Arg Thr Thr Leu Ala Ser Arg Leu Gln Asp Leu
    3335            3340                3345 ctg gta cgg ctc ggc caa ggc ccg gag gac gcg gag gac gcg gtc        10089
Leu Val Arg Leu Gly Gln Gly Pro Glu Asp Ala Glu Asp Ala Val
3350            3355                3360
```

-continued

```
gcc  ggc  cgc  atc  gac  gcc  gcc  tcg  gac  gac  gag  atc  ttc  gac  ttc        10134
Ala  Gly  Arg  Ile  Asp  Ala  Ala  Ser  Asp  Asp  Glu  Ile  Phe  Asp  Phe
     3365            3370                    3375 atc  gag  aac  gaa  ctc  ggc  ctg  tag                                            10158
Ile  Glu  Asn  Glu  Leu  Gly  Leu
3380                 3385
```

<210> SEQ ID NO 20
<211> LENGTH: 3385
<212> TYPE: PRT
<213> ORGANISM: Streptomyces sp. NRRL 30748

<400> SEQUENCE: 20

Met Ala Asn Pro Thr Asp Lys Ile Val Gly Ala Leu Arg Glu Ser Leu
1               5                   10                  15

Lys Glu Thr Glu Arg Leu Arg Arg Val Asn Gln Gln Leu Thr Ala Ala
            20                  25                  30

Ser Arg Glu Pro Ile Ala Ile Val Ala Met Ser Cys Arg Tyr Pro Gly
        35                  40                  45

Asp Val Arg Gly Pro Glu Asp Leu Trp Glu Leu Val Thr Gly Gly Arg
    50                  55                  60

Asp Ala Ile Ser Gly Phe Pro Gly Asn Arg Gly Trp Asp Leu Glu Asn
65                  70                  75                  80

Leu Tyr Asp Pro Asp Pro Asp Arg Gln Gly Thr Val Tyr Ala Thr Glu
                85                  90                  95

Gly Gly Phe Leu His Asp Ala Asp Gln Phe Asp Pro Ala Phe Phe Gly
            100                 105                 110

Ile Ser Pro Arg Glu Ala Thr Val Met Asp Pro Gln Gln Arg Leu Leu
        115                 120                 125

Leu Glu Thr Ser Trp Glu Ala Phe Glu Arg Ala Gly Ile Asp Pro Ala
    130                 135                 140

Ala Leu Arg Gly Ser Lys Thr Gly Ile Phe Val Gly Ala Ala Tyr Gln
145                 150                 155                 160

Gly Tyr Ile Pro Asp Trp Pro His Met Pro Glu Gly Leu Glu Gly His
                165                 170                 175

Leu Val Thr Gly Ile Ser Ala Ser Ile Met Ser Gly Arg Val Ala Tyr
            180                 185                 190

Thr Leu Gly Leu Glu Gly Pro Ala Val Thr Ile Asp Thr Ala Cys Ser
        195                 200                 205

Ser Ser Leu Val Ala Leu His Leu Ala Cys Gln Ser Leu Arg Gln Gly
    210                 215                 220

Asp Cys Ser Leu Ala Leu Ala Gly Gly Ala Val Met Gly Ala Pro
225                 230                 235                 240

Met Gly Leu Ile Gly Phe Ala Arg Gln Arg Gly Leu Ala Gln Asp Gly
                245                 250                 255

Arg Cys Lys Ala Phe Ala Glu Gly Ala Asp Gly Met Gly Leu Gly Glu
            260                 265                 270

Gly Val Gly Met Leu Leu Leu Glu Arg Leu Ser Asp Ala Arg Arg Asn
        275                 280                 285

Gly His Glu Val Leu Ala Val Val Arg Gly Ser Ala Val Asn Gln Asp
    290                 295                 300

Gly Ala Ser Asn Gly Leu Thr Ala Pro Asn Gly Arg Ser Gln Gln Arg
305                 310                 315                 320

Val Ile Arg Gln Ala Leu Ala Asn Ala Ala Leu Thr Ala Glu Gln Ile
                325                 330                 335

```
Asp Ala Val Glu Ala His Gly Thr Gly Thr Pro Leu Gly Asp Pro Ile
            340                 345                 350

Glu Ala Gly Ala Leu Leu Ala Thr Tyr Gly Lys Asp Arg Ala Ala Asp
        355                 360                 365

Arg Pro Val Leu Ile Gly Ser Leu Lys Ser Asn Ile Gly His Pro Gln
    370                 375                 380

Ala Ala Gly Gly Val Gly Gly Val Ile Lys Met Val Gln Ala Met Arg
385                 390                 395                 400

His Gly Leu Leu Pro Arg Thr Leu His Ala Glu Arg Ser Ser Arg
            405                 410                 415

Ile Asp Trp Ser Ala Gly Ala Val Glu Leu Leu Thr Glu Ala Arg Glu
            420                 425                 430

Trp Pro Arg Gly Glu Pro Arg Arg Ala Ala Val Ser Ala Phe Gly
        435                 440                 445

Ala Ser Gly Thr Asn Val His Thr Ile Leu Glu Asp Ala Pro Glu Glu
    450                 455                 460

Glu Leu Ser Glu Thr Ala Ala Glu Gly Asp Ala Pro Val Gly Gly Gly
465                 470                 475                 480

Val Val Pro Trp Val Leu Ser Ala Lys Ser Ala Ala Gly Leu Arg Ala
            485                 490                 495

Gln Ala Glu Arg Leu Leu Thr His Val Thr Ala Arg Pro Gly Leu Ser
        500                 505                 510

Pro Ala Asp Val Gly His Ser Leu Ala Thr Thr Arg Gly Arg Phe Asp
    515                 520                 525

His Arg Ala Leu Val Leu Gly Gly Arg Asp Glu Leu Ile Asp Ala
            530                 535                 540

Leu Gly Ala Leu Ala Ser Gly Gly Glu Ser Pro Arg Val Val Arg Gly
545                 550                 555                 560

Glu Gly Val Thr Ala Ala Asp Ala Arg Pro Val Phe Val Phe Pro Gly
            565                 570                 575

Gln Gly Ser Gln Trp Val Gly Met Ala Val Glu Leu Leu Asp Ser Ser
        580                 585                 590

Pro Val Phe Ala Gly Arg Leu Ala Glu Cys Glu Val Ala Leu Ser Gly
    595                 600                 605

Phe Val Glu Trp Ser Leu Ser Gly Val Leu Arg Gly Glu Gly Pro Gly
            610                 615                 620

Leu Glu Arg Val Asp Val Val Gln Pro Ala Leu Trp Ala Val Met Val
625                 630                 635                 640

Ser Leu Ala Glu Val Trp Arg Ala Cys Gly Val Thr Pro Ala Ala Val
            645                 650                 655

Val Gly His Ser Gln Gly Glu Ile Ala Ala Val Val Ala Gly Ala
        660                 665                 670

Leu Ser Leu Glu Asp Gly Ala Arg Val Val Ala Leu Arg Ser Gln Ala
    675                 680                 685

Ile Gly Arg Gly Leu Ala Gly Arg Gly Met Met Ser Val Ala Glu
            690                 695                 700

Gly Ala Asp Trp Val Arg Glu Arg Ile Thr Ala Trp Gly Gly Arg Ile
705                 710                 715                 720

Ser Val Ala Ala Val Asn Gly Pro Gly Ser Ile Val Val Ser Gly Asp
            725                 730                 735

Pro Glu Ala Leu Arg Glu Leu Gln Ala Glu Cys Glu Ala Glu Asp Val
        740                 745                 750

Arg Ala Lys Leu Ile Pro Val Asp Tyr Ala Ser His Ser Ala His Val
```

-continued

```
             755                 760                 765
Glu Glu Leu Arg Asp Glu Leu Leu Asp Val Leu Ala Pro Ile Ala Pro
770                 775                 780

Arg Arg Ala Glu Val Pro Phe Cys Ser Thr Val Thr Gly Asp Thr Ile
785                 790                 795                 800

Asp Thr Thr Gly Leu Asp Ala Gly Tyr Trp Tyr Thr Asn Leu Arg Glu
                    805                 810                 815

Thr Val Glu Leu Glu Ser Ala Val Arg Ala Leu Ser Ala Ala Gly Phe
                    820                 825                 830

Gly Thr Phe Leu Glu Met Ser Pro His Pro Val Leu Thr Met Pro Leu
                    835                 840                 845

Gln Ala Thr Ala Glu Asp Ala Val Val Val Gly Ser Leu Arg Arg Asp
850                 855                 860

Glu Gly Gly Pro Glu Arg Phe Leu Ala Ser Leu Gly Glu Ala Phe Val
865                 870                 875                 880

Arg Gly Val Ala Val Asp Trp Ala Ala Val Cys Ala Gly Ser Thr Val
                    885                 890                 895

Val Glu Leu Pro Thr Tyr Ala Phe Gln Arg Gln Arg Tyr Trp Leu Glu
                    900                 905                 910

Gly Ser Ser Ala Pro Ala Glu Gly Ala Ala Val Asp Ala Asp Phe Trp
                    915                 920                 925

Asp Ala Val Glu Arg Glu Asp Leu Thr Ala Leu Ala Ala Ala Leu Glu
930                 935                 940

Val Asp Ala Glu Glu Ser Ser Leu Ala Met Val Val Pro Ala Leu Ala
945                 950                 955                 960

Ala Trp Arg Arg Ala Arg Arg Glu Arg Ser Val Leu Asp Ser Trp Arg
                    965                 970                 975

Tyr Gln Val Thr Trp Lys Pro Leu Gly Asp Ala Leu Thr Ser Ala His
                    980                 985                 990

Asp Arg Ser Ser Ala Gly Ala Thr Trp Leu Ile Ala Ala Pro Ala Gly
                    995                 1000                1005

Ala Pro Glu Gly Pro Arg Val Ala Glu Ala Leu Arg Glu Arg Gly
1010                1015                1020

Ala Arg Val Arg Leu Val Glu Leu Thr Glu Ala Asp Ala Val Arg
1025                1030                1035

Glu Ala Leu Ala Arg Gly Leu Gly Glu Ala Thr Ala Asp Thr Pro
1040                1045                1050

Pro Thr Ala Val Leu Ser Leu Leu Ala Leu Ala Glu Asp Pro Tyr
1055                1060                1065

Arg Ala Gly Thr Ala Gln Pro Leu Gly Leu Ala Leu Asn Leu Ala
1070                1075                1080

Leu Leu Gln Ala Leu Phe Asp Thr Gly Ala Asp Val Pro Val Trp
1085                1090                1095

Tyr Ala Thr Arg Gly Ala Val Ser Val Gly Arg Ala Asp Ala Leu
1100                1105                1110

Asp His Pro Leu Gln Ala Leu Ser Trp Gly Leu Gly Arg Ile Ala
1115                1120                1125

Ala Val Glu Tyr Pro Arg Cys Arg Gly Gly Leu Val Asp Leu Pro
1130                1135                1140

Gly Thr Leu Asp Asp Arg Ala Val Ala Arg Leu Cys Gly Val Leu
1145                1150                1155

Ala Gly Arg Leu Thr Asp Glu Asp Gln Val Ala Val Arg Ala Ser
1160                1165                1170
```

-continued

```
Gly Val His Gly Arg Arg Leu Val Arg Ala Ser Ala Ala Pro Ala
    1175            1180                1185

Asp Ala Thr Ala Pro Trp Arg Pro Arg Gly Thr Val Leu Val Thr
    1190            1195                1200

Gly Gly Thr Gly Gly Leu Gly Ala His Val Ala Arg Trp Leu Ala
    1205            1210                1215

Arg Gly Gly Ala Glu His Leu Val Leu Ser Ser Arg Arg Gly Pro
    1220            1225                1230

Asp Ala Pro Gly Ala Ala Glu Leu Ala Asp Gly Ile Arg Glu Ser
    1235            1240                1245

Gly Val Arg Val Thr Val Ala Ala Cys Asp Ala Ala Asp Arg Asp
    1250            1255                1260

Ala Leu Ala Asp Leu Leu Ala Thr Leu Asp Ala Asp Glu Ala Pro
    1265            1270                1275

Leu Asp Ala Val Val His Thr Ala Gly Val Leu Asp Asp Gly Val
    1280            1285                1290

Leu Asp Thr Leu Thr Pro Glu Arg Ala Asp Gly Val Leu Arg Pro
    1295            1300                1305

Lys Val Asp Ala Ala Leu His Leu His Glu Leu Thr Arg Asp Arg
    1310            1315                1320

Glu Leu Ser Ala Phe Val Leu Phe Ser Ser Phe Ala Gly Thr Leu
    1325            1330                1335

Gly Gly Pro Gly Gln Gly Ser Tyr Ala Ala Ala Asn Ala Phe Leu
    1340            1345                1350

Asp Ala Leu Ala His Ala Arg Arg Ala Gln Gly Leu Pro Ala Thr
    1355            1360                1365

Ser Val Ala Trp Gly Ala Trp Ser Gly Gly Gly Leu Val Asp Glu
    1370            1375                1380

Ala Val Gln Ala Arg Leu Arg Ala Thr Gly Met Pro Ala Met Ala
    1385            1390                1395

Pro Asp Leu Ala Ile Ala Ala Leu Gln Arg Ala Leu Asp Val Ala
    1400            1405                1410

Asp Thr His Val Ala Val Ala Asp Val Glu Trp Asp Arg Leu Ile
    1415            1420                1425

Ala Ala Thr Pro Ser Leu Asp Gly Ala Ala Val Leu Gly Glu Leu
    1430            1435                1440

Pro Asp Ala Arg Arg Ala Glu Val Ala Ala Ala Thr Thr Gly Glu
    1445            1450                1455

Glu Asp Thr Pro Leu Ser Gln Arg Leu Ala Gly Leu Ser Pro Gln
    1460            1465                1470

Glu Ala Glu Glu Ala Leu Ala Asp Leu Val Ser Ala Glu Val Ala
    1475            1480                1485

Ala Ala Leu Gly Tyr Ala Asp Thr Ala Ala Val Glu Ala Gly Arg
    1490            1495                1500

Ala Phe Arg Glu Leu Gly Phe Asp Ser Leu Thr Ala Val Asp Leu
    1505            1510                1515

Arg Asn Arg Leu Asn Ala Ala Thr Gly Leu Arg Leu Pro Val Thr
    1520            1525                1530

Leu Val Phe Asp Tyr Pro Thr Val Ala Ala Leu Ala Arg Phe Leu
    1535            1540                1545

Leu Ala Glu Ser Gly Ala Gly Glu Thr Ala Ala Thr Ala Pro Ala
    1550            1555                1560
```

```
Gly Pro Val Pro Ala Ala Val Ala Val Asp Asp Pro Ile Ala
    1565                1570            1575

Ile Val Ala Met Ser Cys Arg Leu Pro Gly Gly Val Thr Thr Pro
    1580                1585            1590

Glu Glu Leu Trp Arg Leu Leu Met Asp Gly Arg Asp Ala Ile Ser
    1595                1600            1605

Asp Phe Pro Thr Asp Arg Gly Trp Asp Ile Glu Gly His Tyr Asp
    1610                1615            1620

Pro Asp Pro Asp Lys Pro Gly Thr Phe Tyr Ala Thr Gly Gly Gly
    1625                1630            1635

Phe Leu His Gln Ala Asp His Phe Asp Pro Glu Phe Gly Ile
    1640                1645            1650

Ser Pro Arg Glu Ala Leu Ala Ile Asp Pro Gln Gln Arg Leu Leu
    1655                1660            1665

Leu Glu Thr Ser Trp Glu Thr Phe Glu Arg Ala Gly Ile Asp Pro
    1670                1675            1680

Ala Ser Val Lys Gly Thr Gln Ala Gly Val Phe Ile Gly Ala Ser
    1685                1690            1695

Tyr Asn Asp Tyr Gly Ser Arg Phe Thr Arg Ala Pro Glu Glu Phe
    1700                1705            1710

Glu Gly Tyr Leu Ala Thr Gly Ser Ala Ser Ser Val Ala Ser Gly
    1715                1720            1725

Arg Ile Ser Tyr Thr Phe Gly Leu Glu Gly Pro Ala Val Thr Val
    1730                1735            1740

Asp Thr Ala Cys Ser Ser Ser Leu Val Ala Leu His Gln Ala Ala
    1745                1750            1755

Gln Ala Leu Arg Gln Gly Glu Cys Ser Leu Ala Leu Ala Gly Gly
    1760                1765            1770

Val Val Val Met Ser Thr Leu Asp Thr Phe Ile Glu Phe Ser Arg
    1775                1780            1785

Gln Arg Ala Met Ala Pro Asp Gly Arg Cys Lys Ala Phe Ser Ala
    1790                1795            1800

Ala Ala Asp Gly Ala Gly Trp Ala Glu Gly Val Gly Met Leu Leu
    1805                1810            1815

Leu Glu Arg Leu Ser Asp Ala Arg Ala Asn Gly His Glu Val Leu
    1820                1825            1830

Ala Leu Val Arg Gly Ser Ala Val Asn Gln Asp Gly Ala Ser Asn
    1835                1840            1845

Gly Leu Thr Ala Pro Asn Gly Pro Ser Gln Gln Arg Val Ile Arg
    1850                1855            1860

Gln Ala Leu Ala Gly Ala Gly Leu Ser Ala Ala Asp Val Asp Ala
    1865                1870            1875

Val Glu Thr His Gly Thr Gly Thr Arg Leu Gly Asp Pro Ile Glu
    1880                1885            1890

Ala Gln Ala Leu Met Ala Thr Tyr Gly Gln Gly Arg Asp Ala Asp
    1895                1900            1905

Arg Pro Leu Trp Leu Gly Ala Leu Lys Ser Asn Ile Gly His Thr
    1910                1915            1920

Gln Ala Ala Ser Gly Val Ala Gly Ile Ile Lys Thr Val Leu Ala
    1925                1930            1935

Leu Arg His Gly Val Leu Pro Lys Thr Leu His Ala Asp Glu Arg
    1940                1945            1950

Ser Pro Asp Val Asp Trp Ser Ala Gly Ala Val Glu Leu Leu Thr
```

-continued

```
           1955                1960                1965

Glu Ala Arg Glu Trp Pro Thr Gly Arg Pro Arg Arg Ala Gly
        1970                1975                1980

Val Ser Ala Phe Gly Val Ser Gly Thr Asn Val His Val Val Leu
        1985                1990                1995

Glu Gln Gly Pro Glu His Thr Ala Pro Val Ala Glu Arg Thr Val
        2000                2005                2010

Asp Ser Asp Val Val Pro Trp Val Leu Ser Ala Arg Gly Glu Thr
        2015                2020                2025

Ala Leu Arg Ala Gln Ala Gly Arg Leu Arg Ala Arg Leu Glu Glu
        2030                2035                2040

Arg Pro Glu Leu Arg Pro Val Asp Val Gly Tyr Ala Leu Ala Thr
        2045                2050                2055

Gly Arg Ser Ala Phe Gly His Arg Ala Val Val Gly Ala Glu
        2060                2065                2070

Arg Glu Glu Leu Leu Arg Gly Leu Ala Glu Leu Ala Ser Gly Thr
        2075                2080                2085

Ala Arg Glu Thr Val Ala Asp Ala Gly Arg Thr Ala Phe Leu Phe
        2090                2095                2100

Thr Gly Gln Gly Ala Gln Arg Leu Gly Met Gly Arg Glu Leu Tyr
        2105                2110                2115

Asp Ala Phe Pro Val Phe Ala Ala Phe Asp Ala Val Cys Ala
        2120                2125                2130

Glu Leu Asp Arg His Leu Asp Gly Ser Val Arg Glu Val Val Phe
        2135                2140                2145

Gly Gly Asp Ala Glu Pro Leu Asn Arg Thr Val Phe Thr Gln Thr
        2150                2155                2160

Ala Leu Phe Ala Leu Glu Val Ala Leu Tyr Arg Leu Val Glu Ser
        2165                2170                2175

Trp Gly Leu Arg Pro Asp Phe Leu Val Gly His Ser Val Gly Glu
        2180                2185                2190

Leu Ala Ala Ala His Val Ala Gly Val Phe Ser Leu Glu Asp Ala
        2195                2200                2205

Cys Ala Leu Val Ala Ala Arg Gly Arg Leu Met Gln Ala Leu Pro
        2210                2215                2220

Glu Gly Gly Ala Met Val Ser Leu Gln Ala Ala Glu Ala Asp Val
        2225                2230                2235

Leu Pro His Leu Glu Gly His Glu Asp Arg Val Ser Val Ala Ala
        2240                2245                2250

Val Asn Gly Pro Arg Ala Thr Val Ile Ser Gly Asp Glu Asp Thr
        2255                2260                2265

Val Leu Arg Ile Ala Glu Ala Thr Gly Ala Lys Ser Lys Arg Leu
        2270                2275                2280

Thr Val Ser His Ala Phe His Ser Pro Leu Met Asp Ala Met Leu
        2285                2290                2295

Ala Glu Phe Gly Thr Val Ala Thr Gly Ile Gly Tyr Ser Thr Pro
        2300                2305                2310

Arg Ile Ala Val Val Ser Asn Val Thr Gly Glu Ala Ala Gly Glu
        2315                2320                2325

Glu Leu Cys Ser Pro Glu Tyr Trp Val Arg His Val Arg Arg Ala
        2330                2335                2340

Val Arg Phe Gly Asp Gly Ile Arg Phe Leu Ala Glu Arg Asn Val
        2345                2350                2355
```

-continued

```
Thr Arg Phe Val Glu Ile Gly Arg Pro Val Cys Ser Pro Pro Trp
2360                2365                2370

Gly Gln Glu Cys Leu Ala Glu Ala Gly Thr Glu Thr Asp Ile Asp
    2375                2380                2385

Thr Glu Thr Ala Phe Val Pro Leu Leu Arg Lys Asp Arg Ser Glu
2390                2395                2400

Ala Glu Ser Leu Leu Ala Gly Val Gly Arg Val His Ala His Gly
    2405                2410                2415

Gly Ala Val Asp Trp Glu Gln Val Phe Ala Gly Arg Gly Ala Arg
2420                2425                2430

Arg Val Glu Leu Pro Thr Tyr Ala Phe Gln Arg Gln Arg Tyr Trp
    2435                2440                2445

Leu Asp Ala Pro Ala Thr Val Gly Asp Val Ala Ser Ala Gly Leu
2450                2455                2460

Gly Ala Ala Gly His Pro Leu Leu Gly Ala Ala Val Glu Leu Ala
    2465                2470                2475

Asp Ser Asp Gly Leu Val Leu Thr Gly Arg Leu Ser Thr Arg Gly
2480                2485                2490

Gln Pro Trp Leu Ala Asp His Ala Val Ser Gly Val Val Leu Phe
    2495                2500                2505

Pro Gly Thr Ala Phe Leu Glu Leu Ala Ile Gln Ala Gly Asp Arg
2510                2515                2520

Val Gly Cys Asp Arg Val Asp Glu Leu Thr Leu Gln Ala Pro Leu
    2525                2530                2535

Ile Leu Pro Glu Arg Gly Ala Val Thr Leu Gln Leu Val Val Asp
2540                2545                2550

Pro Pro Glu Glu Asp Gly Arg Arg Ala Leu Asn Val Tyr Ser Arg
    2555                2560                2565

Pro Glu Asp Thr Asn Gly Glu Pro Pro Trp Thr Arg His Ala Thr
2570                2575                2580

Gly Val Leu Ala Ala Gly Ala Ala Glu Gly Ser Tyr Asp Leu Gly
    2585                2590                2595

Gly Ala Trp Pro Pro Pro Gly Ala Glu Pro Ile Glu Val Glu Asp
2600                2605                2610

Leu Tyr Glu Arg Phe Ala Ala Gly Gly Phe Gly Tyr Gly Pro Ser
    2615                2620                2625

Phe Gln Gly Leu Arg Ala Ala Trp Leu Arg Gly Asp Glu Val Phe
2630                2635                2640

Ala Glu Val Arg Leu Ala Gln Glu Gln Gln Ser Ala Ala Thr Ala
    2645                2650                2655

Tyr Gly Leu His Pro Ala Leu Leu Asp Ala Ala Leu His Thr Ile
2660                2665                2670

Ala Leu Gly Pro Met Leu Gln Ala Gly Glu Gly Arg Leu Pro Phe
    2675                2680                2685

Ser Trp Thr Gly Val Thr Leu His Ala Ser Gly Ala Gly Glu Val
2690                2695                2700

Arg Val Arg Leu Thr Pro Ser Gly Thr Asp Thr Val Ala Leu Thr
    2705                2710                2715

Val Ala Asp Thr Ile Gly Arg Pro Val Ala Thr Val Glu Ser Leu
2720                2725                2730

Val Leu Arg Lys Arg Pro Glu Arg Leu Gly Asp Ala Ala Thr Gly
    2735                2740                2745
```

-continued

```
Gly Asp Ser Leu Tyr Arg Leu Asp Trp Val Ala Ala Asp Thr Ser
2750                2755                2760

Ala Ala Thr Pro Glu Gln Pro Ser Gly His Trp Ala Leu Leu Gly
2765                2770                2775

Asp Asp Asp Phe Lys Leu Val Gly Leu Asp Val His Thr Tyr Pro
2780                2785                2790

Asn Leu Glu Ala Leu Pro Ala Asp Pro Ala Ala Val Pro Ala Thr
2795                2800                2805

Val Leu Val Pro Cys Ala Pro Glu Pro Gln Gly Val Ala Asp Ala
2810                2815                2820

Val Arg Ala Ala Thr His Arg Ala Leu Thr Leu Leu Arg Ala Trp
2825                2830                2835

Leu Thr Glu Asp Arg Phe Ala Asp Ser Arg Leu Val Phe Ile Thr
2840                2845                2850

Arg Gly Ala Val Ala Thr Thr Pro Gly Ala Asp Val Pro Asp Leu
2855                2860                2865

Ala His Ala Ala Val Trp Gly Leu Val Arg Ser Ala Gln Ser Glu
2870                2875                2880

Asn Pro Asp Arg Phe Val Leu Val Asp Leu Asp Glu Gln Glu Glu
2885                2890                2895

Ser Ala Leu Ala Leu Pro Thr Ala Leu Ala Leu Asp Glu Pro Gln
2900                2905                2910

Leu Ala Val Arg Gln Gly Asp Ile Val Val Ala Arg Leu Ala Thr
2915                2920                2925

Thr Pro Val Pro Asp Thr Ala Pro Pro Ala Trp Asp Pro Glu Gly
2930                2935                2940

Thr Val Leu Val Thr Gly Ala Thr Gly Thr Ile Gly Gly Val Ile
2945                2950                2955

Ala Arg His Leu Val Ala Glu Gly Gly Val Arg His Leu Leu Leu
2960                2965                2970

Thr Ser Arg Arg Gly Pro Asp Ala Glu Gly Ala Ala Glu Leu His
2975                2980                2985

Ala Glu Leu Ala Glu Leu Gly Ala Gln Val Thr Leu Ala Ala Cys
2990                2995                3000

Asp Val Ala Asp Arg Glu Ala Leu Ala Ala Leu Leu Ala Thr Val
3005                3010                3015

Pro Ala Ala His Pro Leu Thr Ala Val Val His Thr Ala Gly Val
3020                3025                3030

Leu Asp Asp Gly Val Val Ser Ser Leu Thr Pro Glu Arg Leu Asp
3035                3040                3045

Thr Val Leu Arg Pro Lys Val Asp Ala Ala Leu Thr Leu His Glu
3050                3055                3060

Leu Thr Arg Asp Leu Asp Leu Ser Ala Leu Val Leu Phe Ser Ser
3065                3070                3075

Ile Ala Gly Thr Phe Gly Gly Met Gly Gln Gly Asn Tyr Ala Ala
3080                3085                3090

Ala Asn Ala Phe Leu Asp Ala Phe Ala Gln His Cys Arg Ala Gln
3095                3100                3105

Gly Arg Pro Val Gln Ser His Ala Trp Gly Leu Trp Ala Gln Arg
3110                3115                3120

Ser Glu Met Thr Gly Lys Leu Glu Gly Ala Asp Leu Asn Arg Leu
3125                3130                3135

Ala Arg Gly Gly Ile Val Pro Phe Ser Ser Ala Asp Gly Ala Gly
```

```
                    3140                3145                3150

Leu Phe Asp Ala Ala Arg Ala Val Asp Ser Ala Val Val Leu Pro
    3155                3160                3165

Met Arg Leu Asp Thr Ala Gly Leu Gly Ala Arg Ser Gly Asp Val
    3170                3175                3180

Pro Ala Leu Leu Arg Gly Leu Val Arg Ala Ala Pro Ala Thr Arg
    3185                3190                3195

Pro Ala Arg Arg Thr Ala Ala Gly Ala Gly Ala Ala Pro Ala Arg
    3200                3205                3210

Pro Glu Gly Leu Lys Gln His Leu Thr Ser Leu Pro Glu Ala Glu
    3215                3220                3225

Arg Gly Arg Phe Leu Leu Asp Leu Val Arg Thr Val Ala Gly
    3230                3235                3240

Val Leu Gly Phe Asp Ser Val Ala Val Glu Ala Glu Arg Gly
    3245                3250                3255

Leu Leu Asp Leu Gly Phe Asp Ser Leu Thr Ala Val Glu Leu Arg
    3260                3265                3270

Asn Gln Leu Gly Lys Ala Thr Gly Arg Arg Leu Pro Val Thr Leu
    3275                3280                3285

Leu Phe Asp Tyr Pro Thr Ser Thr Ala Ile Ala Ala Tyr Leu Glu
    3290                3295                3300

Ala Glu Ile Ala Pro Glu Ala Phe Thr Ala Ala Ser Met Thr Phe
    3305                3310                3315

Pro Glu Leu Asp Ala Leu Glu Ser Asn Leu Ala Lys Val Ala Val
    3320                3325                3330

Asp Asp Glu Ala Arg Thr Thr Leu Ala Ser Arg Leu Gln Asp Leu
    3335                3340                3345

Leu Val Arg Leu Gly Gln Gly Pro Glu Asp Ala Glu Asp Ala Val
    3350                3355                3360

Ala Gly Arg Ile Asp Ala Ala Ser Asp Asp Glu Ile Phe Asp Phe
    3365                3370                3375

Ile Glu Asn Glu Leu Gly Leu
    3380                3385

<210> SEQ ID NO 21
<211> LENGTH: 6267
<212> TYPE: DNA
<213> ORGANISM: Streptomyces sp. NRRL 30748
<220> FEATURE:
<221> NAME/KEY: CDS
<222> LOCATION: (1)..(6267)

<400> SEQUENCE: 21 gtg agc gag gca aaa ctc cgc gac tac ctc aag cga gtg acc acg gat      48
Val Ser Glu Ala Lys Leu Arg Asp Tyr Leu Lys Arg Val Thr Thr Asp
1               5                   10                  15 ctg cac cgc act cgc cag cgc ctc cag gag gcc gag gca aag gac cac      96
Leu His Arg Thr Arg Gln Arg Leu Gln Glu Ala Glu Ala Lys Asp His
                20                  25                  30 gag ccc atc gcc atc gtc ggg atg gcc tgc cgc tac ccc ggt ggc gtg     144
Glu Pro Ile Ala Ile Val Gly Met Ala Cys Arg Tyr Pro Gly Gly Val
            35                  40                  45 gcc tcg ccg gag gac ctg tgg gag ctg gtg gcc aac ggc cgg gac gcg     192
Ala Ser Pro Glu Asp Leu Trp Glu Leu Val Ala Asn Gly Arg Asp Ala
        50                  55                  60 gtc acc gag ttc ccc gcc gac cgg ggc tgg gac ctc gag gcc ctc tac     240
Val Thr Glu Phe Pro Ala Asp Arg Gly Trp Asp Leu Glu Ala Leu Tyr
```

```
                65                  70                  75                  80
gac ccg gac ccg gac aag ccg ggg acg agc tat gcg cgc gaa ggc ggc         288
Asp Pro Asp Pro Asp Lys Pro Gly Thr Ser Tyr Ala Arg Glu Gly Gly
                85                  90                  95 ttc gtc acc gac gcc gac cac ttc gac ccc gcc ttc ttc ggc atc tcc         336
Phe Val Thr Asp Ala Asp His Phe Asp Pro Ala Phe Phe Gly Ile Ser
            100                 105                 110 ccg cgc gag gcc ctc gcc atg gac ccg cag cag cgg ctg ctg ctg gag         384
Pro Arg Glu Ala Leu Ala Met Asp Pro Gln Gln Arg Leu Leu Leu Glu
        115                 120                 125 acc gcg tgg gag gcc atg gag cgg gcc ggg gtg gac ccg gcc acg ctg         432
Thr Ala Trp Glu Ala Met Glu Arg Ala Gly Val Asp Pro Ala Thr Leu
    130                 135                 140 cgc ggc agc cgc acc ggg gtc ttc gcg ggc gtg atg tac cag gac tac         480
Arg Gly Ser Arg Thr Gly Val Phe Ala Gly Val Met Tyr Gln Asp Tyr
145                 150                 155                 160 gcg acc cgg ctg cgt cag gtg ccc gac gat gtc gag ggg tac gtc ggc         528
Ala Thr Arg Leu Arg Gln Val Pro Asp Asp Val Glu Gly Tyr Val Gly
                165                 170                 175 agc ggt ggc tcc ggc agc atc gcc tcc ggc cgt atc gcc tac acc ttc         576
Ser Gly Gly Ser Gly Ser Ile Ala Ser Gly Arg Ile Ala Tyr Thr Phe
            180                 185                 190 ggt ctc gaa ggg ccc gcg gtc acc gtg gac acc gcc tgc tcg tcc tcg         624
Gly Leu Glu Gly Pro Ala Val Thr Val Asp Thr Ala Cys Ser Ser Ser
        195                 200                 205 ctg gtg gcc ctg cac ctc gcc gca cag gcg ctg cgc cgg ggg gag tgc         672
Leu Val Ala Leu His Leu Ala Ala Gln Ala Leu Arg Arg Gly Glu Cys
    210                 215                 220 tcc ctg gcc ctg gtc ggc ggg tcg atg gtg atg tcc aca ccg gtg gcc         720
Ser Leu Ala Leu Val Gly Gly Ser Met Val Met Ser Thr Pro Val Ala
225                 230                 235                 240 ttc gtg gac ttc agc cgc cag cgc ggg ctc gcc tcc gac ggc cgc tgc         768
Phe Val Asp Phe Ser Arg Gln Arg Gly Leu Ala Ser Asp Gly Arg Cys
                245                 250                 255 aag gcg ttc gcc gcc tcc gcc gac ggc acc ggc tgg ggc gag ggc gtg         816
Lys Ala Phe Ala Ala Ser Ala Asp Gly Thr Gly Trp Gly Glu Gly Val
            260                 265                 270 ggc atg ctg ctc gtg gag cgg ctg tcg gat gcg cgg cgc aac ggc cac         864
Gly Met Leu Leu Val Glu Arg Leu Ser Asp Ala Arg Arg Asn Gly His
        275                 280                 285 cag gtg ctc gcg gtc gtc acg ggc tcc gcc acc aac cag gac ggc gcc         912
Gln Val Leu Ala Val Val Thr Gly Ser Ala Thr Asn Gln Asp Gly Ala
    290                 295                 300 agc agc ggg ctg acc gcc ccc aac ggc ccc tcc cag cag cgc gtc atc         960
Ser Ser Gly Leu Thr Ala Pro Asn Gly Pro Ser Gln Gln Arg Val Ile
305                 310                 315                 320 cgg cag gca ctg gcc gac gcc ggg ctc acc gcg gcc gat gtg gac gcg        1008
Arg Gln Ala Leu Ala Asp Ala Gly Leu Thr Ala Ala Asp Val Asp Ala
                325                 330                 335 gtc gag gcc cac ggc acc ggc acc ccg ctc ggc gac ccc atc gag gcg        1056
Val Glu Ala His Gly Thr Gly Thr Pro Leu Gly Asp Pro Ile Glu Ala
            340                 345                 350 ggc gcg ctg ctc gcc acc tac ggc cag gac cgc ccc gag gac cgg ccg        1104
Gly Ala Leu Leu Ala Thr Tyr Gly Gln Asp Arg Pro Glu Asp Arg Pro
        355                 360                 365 ctg tgg ctc ggc tcg ctg aag tcc aac atc ggc cac acc cag gcc gcc        1152
Leu Trp Leu Gly Ser Leu Lys Ser Asn Ile Gly His Thr Gln Ala Ala
    370                 375                 380 gcg ggc gtc gga ggg gtc atc aag acg gtg ctg gcg ctg cgc cac ggc        1200
```

```
Ala Gly Val Gly Gly Val Ile Lys Thr Val Leu Ala Leu Arg His Gly
385                 390                 395                 400 gtg ctg ccc aag acc ctg cac gcc gac gag ccg acg ccc aac gtg gac    1248
Val Leu Pro Lys Thr Leu His Ala Asp Glu Pro Thr Pro Asn Val Asp
                405                 410                 415 tgg gag tcg ggc gcg gta cgg ctg ctg gcc gag gcc cgg ccg tgg ccc    1296
Trp Glu Ser Gly Ala Val Arg Leu Leu Ala Glu Ala Arg Pro Trp Pro
            420                 425                 430 gag ccg gag gcc gaa cgc ccg cgc gcc gcc gtg tcc gcc ttc ggc        1344
Glu Pro Glu Ala Glu Arg Pro Arg Ala Ala Val Ser Ala Phe Gly
        435                 440                 445 ttc agc ggc acc aac gcc cat gtg atc ctg gag cag gcc ccc gcc gag    1392
Phe Ser Gly Thr Asn Ala His Val Ile Leu Glu Gln Ala Pro Ala Glu
    450                 455                 460 gag acc gcg gag gag gcc gcc gac gag aca ccc ccg gat gag act ccc    1440
Glu Thr Ala Glu Glu Ala Ala Asp Glu Thr Pro Pro Asp Glu Thr Pro
465                 470                 475                 480 gcg gac acc acg ccc gcc acc gtg tcc gac ctg gtg ccg tgg ccg ctg    1488
Ala Asp Thr Thr Pro Ala Thr Val Ser Asp Leu Val Pro Trp Pro Leu
                485                 490                 495 tcg ggg cgg acc gag gag gcc ctg cgg gcc cag gcc gcg cgg ctg cgg    1536
Ser Gly Arg Thr Glu Glu Ala Leu Arg Ala Gln Ala Ala Arg Leu Arg
            500                 505                 510 tcc tac gtg gcg ggc gcg ccc gag ccg tcc ccc gtg gac atc ggc tac    1584
Ser Tyr Val Ala Gly Ala Pro Glu Pro Ser Pro Val Asp Ile Gly Tyr
        515                 520                 525 tcg ctg gcg ctc acc cgc tcc gcc ttc gcc cac cgt gcg gtg gtc gtg    1632
Ser Leu Ala Leu Thr Arg Ser Ala Phe Ala His Arg Ala Val Val Val
    530                 535                 540 gga gcg agc cgt gcc gaa ctc ctc ggt gag ctc gac cag ttg gcc tcc    1680
Gly Ala Ser Arg Ala Glu Leu Leu Gly Glu Leu Asp Gln Leu Ala Ser
545                 550                 555                 560 ggt gtc acc tcc ggc gcg gtg gcc ggt gcg ggc aag acg gcg ttc ctg    1728
Gly Val Thr Ser Gly Ala Val Ala Gly Ala Gly Lys Thr Ala Phe Leu
                565                 570                 575 ttc acc ggg cag ggc gca cag cgg ctc ggc atg gga cgc gcc ctg cat    1776
Phe Thr Gly Gln Gly Ala Gln Arg Leu Gly Met Gly Arg Ala Leu His
            580                 585                 590 acc gcc ttc ccg gtc ttc gcc gcc gcg ttc gac gcc gtc tgc gcc gag    1824
Thr Ala Phe Pro Val Phe Ala Ala Ala Phe Asp Ala Val Cys Ala Glu
        595                 600                 605 ctc gac cgc cac ttg gac ggc cat gtc ggg cac gcg gtg cgg gac gtg    1872
Leu Asp Arg His Leu Asp Gly His Val Gly His Ala Val Arg Asp Val
    610                 615                 620 gtc ttc ggc gcg gac gcc gaa ccg ctc gac cgg acc ctc tac acc cag    1920
Val Phe Gly Ala Asp Ala Glu Pro Leu Asp Arg Thr Leu Tyr Thr Gln
625                 630                 635                 640 acc ggt ctc ttc gcc gtc gag gtg gcg ctg tac cgg ctg ctg gag tcc    1968
Thr Gly Leu Phe Ala Val Glu Val Ala Leu Tyr Arg Leu Leu Glu Ser
                645                 650                 655 tgg ggc gtg acc gcg gac ttc ctg gtc ggc cac tcg gtg ggc gag ctg    2016
Trp Gly Val Thr Ala Asp Phe Leu Val Gly His Ser Val Gly Glu Leu
            660                 665                 670 gcg gcg gcc cat gtg gcg ggc gtg ttc tcg ctg gag gac gcc tgt gcg    2064
Ala Ala Ala His Val Ala Gly Val Phe Ser Leu Glu Asp Ala Cys Ala
        675                 680                 685 ctg gtg gcg gcc cgg ggc cgg ctg atg gac gcg ctg ccc gcc gga ggc    2112
Leu Val Ala Ala Arg Gly Arg Leu Met Asp Ala Leu Pro Ala Gly Gly
    690                 695                 700
```

```
gcg atg gtg tcg ctg cag acc ggc gag gcc gag gtg ctg ccc cat ctg    2160
Ala Met Val Ser Leu Gln Thr Gly Glu Ala Glu Val Leu Pro His Leu
705                 710                 715                 720 gag ggc gag gag ggc cag gtg tcg ctg ggc gcg gtc aac ggc ccg gcg    2208
Glu Gly Glu Glu Gly Gln Val Ser Leu Gly Ala Val Asn Gly Pro Ala
                725                 730                 735 gcc acg gtg atc tcc ggc gag gag aag gcc gtc ctg cgg atc gcg gac    2256
Ala Thr Val Ile Ser Gly Glu Glu Lys Ala Val Leu Arg Ile Ala Asp
            740                 745                 750 gcg gtc ggc gtc aag agc aag cgg ctg cgg atc ggt atc gcg gcc cat    2304
Ala Val Gly Val Lys Ser Lys Arg Leu Arg Ile Gly Ile Ala Ala His
        755                 760                 765 tcg ccg ctg gtg gac ccc atg ctg gag gag ttc gcc aag gtc gcc ggt    2352
Ser Pro Leu Val Asp Pro Met Leu Glu Glu Phe Ala Lys Val Ala Gly
    770                 775                 780 gaa ctg acc tac gcc acc ccc cgg atc gcg gtg gtg tcc aat gtg acc    2400
Glu Leu Thr Tyr Ala Thr Pro Arg Ile Ala Val Val Ser Asn Val Thr
785                 790                 795                 800 gga gag gcg gtc gcc gag gag ctg tgc tcg ccg gat tac tgg gtg cgc    2448
Gly Glu Ala Val Ala Glu Glu Leu Cys Ser Pro Asp Tyr Trp Val Arg
                805                 810                 815 cat gtg cgg cag ccg gtg cgg ttc cag gac ggg gtg cgg ttc ctc gag    2496
His Val Arg Gln Pro Val Arg Phe Gln Asp Gly Val Arg Phe Leu Glu
            820                 825                 830 gac cag ggc gtg acc cgc tat gtg gag gtc ggc ccg tcc ggt gtg ctg    2544
Asp Gln Gly Val Thr Arg Tyr Val Glu Val Gly Pro Ser Gly Val Leu
        835                 840                 845 tcc gtg atg ggc cag gag tgc gtc gcc gac ccc gac gcc gcc gcg ttc    2592
Ser Val Met Gly Gln Glu Cys Val Ala Asp Pro Asp Ala Ala Ala Phe
    850                 855                 860 gtc ccg ctg ctg cgc aag gac cgt ggc gag gcc gag tcg ctg ctg gcc    2640
Val Pro Leu Leu Arg Lys Asp Arg Gly Glu Ala Glu Ser Leu Leu Ala
865                 870                 875                 880 ggg gtg ggc cgg gtg cac gcc cac ggt ggc gtg gtg gac tgg gag cag    2688
Gly Val Gly Arg Val His Ala His Gly Gly Val Val Asp Trp Glu Gln
                885                 890                 895 gtg ttc gcg ggc cgt ggc gcc cgc cgg gtg gag ctg ccc acg tac gcc    2736
Val Phe Ala Gly Arg Gly Ala Arg Arg Val Glu Leu Pro Thr Tyr Ala
            900                 905                 910 ttc cag cgg cag cgc tac tgg ctc gac ggc tcg gac cgg gcg ggc gat    2784
Phe Gln Arg Gln Arg Tyr Trp Leu Asp Gly Ser Asp Arg Ala Gly Asp
        915                 920                 925 gtg acc tcg gcg ggg ctg ggc tcg gcc ggg cat ccg ctg ctg ggc gcc    2832
Val Thr Ser Ala Gly Leu Gly Ser Ala Gly His Pro Leu Leu Gly Ala
    930                 935                 940 gct gtc gaa ctc gcc gac agc gac ggc ctg gtg ctc acc ggg cgg ctg    2880
Ala Val Glu Leu Ala Asp Ser Asp Gly Leu Val Leu Thr Gly Arg Leu
945                 950                 955                 960 tcc ctg gcc gcc cag ccc tgg ctg gcc gat cac gcc gtc tcc ggc acg    2928
Ser Leu Ala Ala Gln Pro Trp Leu Ala Asp His Ala Val Ser Gly Thr
                965                 970                 975 gtc ctc ttc ccc ggc acc gcg ttc ctc gag ctc gcg atc cag gcc ggt    2976
Val Leu Phe Pro Gly Thr Ala Phe Leu Glu Leu Ala Ile Gln Ala Gly
            980                 985                 990 gac cag gtc ggc tgc gac cag gtc gag gag ctg acc ctc cag gcg ccg    3024
Asp Gln Val Gly Cys Asp Gln Val Glu Glu Leu Thr Leu Gln Ala Pro
        995                1000                1005 ctg atc ctc ccc gcg cgt ggc gcg ctc acc ctc cgg gtg acc gtc        3069
Leu Ile Leu Pro Ala Arg Gly Ala Leu Thr Leu Arg Val Thr Val
    1010                1015                1020
```

```
ggc gaa ccc gac gag agc gga cgg cgc ccg ctg aac gtc cac tcc      3114
Gly Glu Pro Asp Glu Ser Gly Arg Arg Pro Leu Asn Val His Ser
    1025                1030                1035 cgc ccc gag ggc gcc ggg ttc ggc gag ccg tgg acc ccg cac gcc      3159
Arg Pro Glu Gly Ala Gly Phe Gly Glu Pro Trp Thr Pro His Ala
1040                1045                1050 acc ggc acg ctc acc acc gcc aca ccg gat gcc ccc gcc gag ctg      3204
Thr Gly Thr Leu Thr Thr Ala Thr Pro Asp Ala Pro Ala Glu Leu
    1055                1060                1065 acc gcg tgg cct ccg gcg gac gcc acc gaa ctc gac gtc agc gac      3249
Thr Ala Trp Pro Pro Ala Asp Ala Thr Glu Leu Asp Val Ser Asp
1070                1075                1080 atg tac gag cgg tac gcg gcg ggc ggc ttc ggc tac ggc ccg gcc      3294
Met Tyr Glu Arg Tyr Ala Ala Gly Gly Phe Gly Tyr Gly Pro Ala
    1085                1090                1095 ttc cgg ggc ctg cgc gcc gcc tgg ctg cgc ggc gac gag gtg ttc      3339
Phe Arg Gly Leu Arg Ala Ala Trp Leu Arg Gly Asp Glu Val Phe
1100                1105                1110 gcc gag gtg cgg ctg gcc cag gag cag cgg ccg gcc gcc gcc ggg      3384
Ala Glu Val Arg Leu Ala Gln Glu Gln Arg Pro Ala Ala Ala Gly
    1115                1120                1125 tac ggg atc cac ccg gcc ctg ctc gac gcc tcc ctg cac ggc atc      3429
Tyr Gly Ile His Pro Ala Leu Leu Asp Ala Ser Leu His Gly Ile
1130                1135                1140 gcg ctc ggc acc ctc ttc gcc ggg gag gac ccc gag acg gcg cag      3474
Ala Leu Gly Thr Leu Phe Ala Gly Glu Asp Pro Glu Thr Ala Gln
    1145                1150                1155 ggg cgg ttg ccg ttc tcc tgg acc ggg gtg tcg ctg cac gcc gcc      3519
Gly Arg Leu Pro Phe Ser Trp Thr Gly Val Ser Leu His Ala Ala
1160                1165                1170 ggg gcc gac gag gtg cgg gtg cgg atc tcc ccg gcc ggg gag gac      3564
Gly Ala Asp Glu Val Arg Val Arg Ile Ser Pro Ala Gly Glu Asp
    1175                1180                1185 acc gtg gcg ctc gcg gtg gcc gac ccc acc ggc cgc ccg gtg gcg      3609
Thr Val Ala Leu Ala Val Ala Asp Pro Thr Gly Arg Pro Val Ala
1190                1195                1200 acc gtc gag ggc ctg ctg ctg cgg aag atg acc ggc gat cag ctc      3654
Thr Val Glu Gly Leu Leu Leu Arg Lys Met Thr Gly Asp Gln Leu
    1205                1210                1215 agt ggc gcc cgc gcc gcg agc agc gag tcg ctg ttc cgg ctc gac      3699
Ser Gly Ala Arg Ala Ala Ser Ser Glu Ser Leu Phe Arg Leu Asp
1220                1225                1230 tgg ccc gcg ctg acc agc ctc gac cag ccc acc ccg ctg acc agg      3744
Trp Pro Ala Leu Thr Ser Leu Asp Gln Pro Thr Pro Leu Thr Arg
    1235                1240                1245 gcc gcg ctg gtc ggc gac gac ggg ctg gag gtc acc gag agc ctc      3789
Ala Ala Leu Val Gly Asp Asp Gly Leu Glu Val Thr Glu Ser Leu
1250                1255                1260 ttc gcg gcc ggg gtc cac ctg gag tcg tat gtg gac ctg gag tcg      3834
Phe Ala Ala Gly Val His Leu Glu Ser Tyr Val Asp Leu Glu Ser
    1265                1270                1275 ctg ggc gcg gcc gtc gac gcc ggt acg gcc gcc cca gcg gcg gtc      3879
Leu Gly Ala Ala Val Asp Ala Gly Thr Ala Ala Pro Ala Ala Val
1280                1285                1290 ctg gtc tcc tgc gcc gcc ggg ccc ggc gca ccg gcc gac gcg gta      3924
Leu Val Ser Cys Ala Ala Gly Pro Gly Ala Pro Ala Asp Ala Val
    1295                1300                1305 cgg gac tcc ctg cgc acc gcc ctg gag ctg gcc cag aac tgg tcg      3969
Arg Asp Ser Leu Arg Thr Ala Leu Glu Leu Ala Gln Asn Trp Ser
1310                1315                1320
```

```
              1310                1315                1320 gcc gat gag cgg ttc gcc gac tcc cgg ctg gtg ttc gtc acc cgt      4014
Ala Asp Glu Arg Phe Ala Asp Ser Arg Leu Val Phe Val Thr Arg
1325                1330                1335 ggc gcg gtg gcc acc gcg ccc gag gcg gag gtc gcc gat ctg ccg      4059
Gly Ala Val Ala Thr Ala Pro Glu Ala Glu Val Ala Asp Leu Pro
1340                1345                1350 ggc gcc gcc gtc tgg ggc ctg gtg cgc tcg gcg cag tcg gag aac      4104
Gly Ala Ala Val Trp Gly Leu Val Arg Ser Ala Gln Ser Glu Asn
1355                1360                1365 ccc gac cgg ttc acc ctc gtc gac ctc gac gag cac gag gag tcc      4149
Pro Asp Arg Phe Thr Leu Val Asp Leu Asp Glu His Glu Glu Ser
1370                1375                1380 gta cgg gcc ctt ccg gcg gtc ctc ccc tcc ggg gag ccg cag ctc      4194
Val Arg Ala Leu Pro Ala Val Leu Pro Ser Gly Glu Pro Gln Leu
1385                1390                1395 gcg ctg cgc gcc ggg cag ccg cac acc ccg cgg ctc gcc cgc gcc      4239
Ala Leu Arg Ala Gly Gln Pro His Thr Pro Arg Leu Ala Arg Ala
1400                1405                1410 cag ggg gcc acc ggc gcc acc cgt ccg ctg gac ccc gag ggc acc      4284
Gln Gly Ala Thr Gly Ala Thr Arg Pro Leu Asp Pro Glu Gly Thr
1415                1420                1425 gtg ctg atc acc ggc gcc acc ggt acg ctc ggc ggg ctg ctc gcc      4329
Val Leu Ile Thr Gly Ala Thr Gly Thr Leu Gly Gly Leu Leu Ala
1430                1435                1440 cgc cac ctg gtg acc cac cat ggc gtc cgc cat ctg ctg ctg acc      4374
Arg His Leu Val Thr His His Gly Val Arg His Leu Leu Leu Thr
1445                1450                1455 agc cgc cgg gga ccg gcc gcc gag gga gcc ggg cgg ctg cgc gag      4419
Ser Arg Arg Gly Pro Ala Ala Glu Gly Ala Gly Arg Leu Arg Glu
1460                1465                1470 gag ctg acc gag ctc ggc gcg atc gtg acc gtg gcg gcg tgc gac      4464
Glu Leu Thr Glu Leu Gly Ala Ile Val Thr Val Ala Ala Cys Asp
1475                1480                1485 acc gcc gac cgg gac gcc gtg gcc gac ctg gtg gcc cag gtg ccc      4509
Thr Ala Asp Arg Asp Ala Val Ala Asp Leu Val Ala Gln Val Pro
1490                1495                1500 gcc gac cac ccg ctg acc ggg gtg ttc cac acc gcc ggg gtg ctg      4554
Ala Asp His Pro Leu Thr Gly Val Phe His Thr Ala Gly Val Leu
1505                1510                1515 gac gac ggg gtg atc tcc tcg ctc acc ccc gag cgg ctg gac acg      4599
Asp Asp Gly Val Ile Ser Ser Leu Thr Pro Glu Arg Leu Asp Thr
1520                1525                1530 gtg ctg cgg ccc aag gtc gac gcc gca ctc cac ctc cac gag gcc      4644
Val Leu Arg Pro Lys Val Asp Ala Ala Leu His Leu His Glu Ala
1535                1540                1545 acc cgg gag ctg gac ctg gcc gcg ttc gtg ctc ttc tcc tcg gcc      4689
Thr Arg Glu Leu Asp Leu Ala Ala Phe Val Leu Phe Ser Ser Ala
1550                1555                1560 gcc gga gtg ctc ggc ggc gcg ggc cag ggc aac tac gcg gcc gcc      4734
Ala Gly Val Leu Gly Gly Ala Gly Gln Gly Asn Tyr Ala Ala Ala
1565                1570                1575 aac ggc ttc ctc gac gcc ttc gcc cag gcc cgc cgg gcc cag ggg      4779
Asn Gly Phe Leu Asp Ala Phe Ala Gln Ala Arg Arg Ala Gln Gly
1580                1585                1590 ctg ccc gcc cac tcc ctc gcc tgg ggg ctg tgg gcg cgg acc agc      4824
Leu Pro Ala His Ser Leu Ala Trp Gly Leu Trp Ala Arg Thr Ser
1595                1600                1605 gcg atg acc ggt acg gcg gac acg gcc ggg gcc gcc cgc tcg ggc      4869
```

```
Ala Met Thr Gly Thr Ala Asp Thr Ala Gly Ala Ala Arg Ser Gly
    1610            1615                1620 gtg gcc gcg ctc tcc tcc gaa cag ggc atg gaa ctc ctc gac acc      4914
Val Ala Ala Leu Ser Ser Glu Gln Gly Met Glu Leu Leu Asp Thr
    1625            1630                1635 gcc ctc gcc ctg gac acc ccg ctg ctg atc ccg atg cgg atc gac      4959
Ala Leu Ala Leu Asp Thr Pro Leu Leu Ile Pro Met Arg Ile Asp
    1640            1645                1650 ctc gcg gcg ctg cgg gcg ggc gcc gga tcc ggc tcg gta ccg ctg      5004
Leu Ala Ala Leu Arg Ala Gly Ala Gly Ser Gly Ser Val Pro Leu
    1655            1660                1665 ctg ctg cgc ggg ctg gtg cgg aca ccg gcg cgc cgg gcg ggc gcg      5049
Leu Leu Arg Gly Leu Val Arg Thr Pro Ala Arg Arg Ala Gly Ala
    1670            1675                1680 acc aca cgc ggc ggc tcg ccg ggc ggc ggc tcc gcg ctg cgg gaa      5094
Thr Thr Arg Gly Gly Ser Pro Gly Gly Gly Ser Ala Leu Arg Glu
    1685            1690                1695 cgg ctc gcc gcg ctc ccc gag gac gaa cag gac gcc gtg ctg gtg      5139
Arg Leu Ala Ala Leu Pro Glu Asp Glu Gln Asp Ala Val Leu Val
    1700            1705                1710 gaa ttg gtg tgc acg cag gtg gcc acc gtg ctc ggc cac ccg gac      5184
Glu Leu Val Cys Thr Gln Val Ala Thr Val Leu Gly His Pro Asp
    1715            1720                1725 ccg tcc gcc atc ggc ccg gcc cat gag ttc gtg gac tcc ggc ttc      5229
Pro Ser Ala Ile Gly Pro Ala His Glu Phe Val Asp Ser Gly Phe
    1730            1735                1740 gac tcg ctc acg gcg gtc gag ctg cgc aac cgg ctg aac gcg gcc      5274
Asp Ser Leu Thr Ala Val Glu Leu Arg Asn Arg Leu Asn Ala Ala
    1745            1750                1755 acc ggg ctg agg ctg ccc gcc acg ctc gtc ttc gac cat gag acg      5319
Thr Gly Leu Arg Leu Pro Ala Thr Leu Val Phe Asp His Glu Thr
    1760            1765                1770 ccc acc gat ctg gcc gcc cgg ctc cgc tcc gaa ctg gcc gcg gcc      5364
Pro Thr Asp Leu Ala Ala Arg Leu Arg Ser Glu Leu Ala Ala Ala
    1775            1780                1785 cgg cag tcg ggc ccc gcc gag cag acg ccc gcg ggc gcg ccg ccc      5409
Arg Gln Ser Gly Pro Ala Glu Gln Thr Pro Ala Gly Ala Pro Pro
    1790            1795                1800 gcc gcg gcg ggg gag tcc acc acg ctg agc acg ctg tac acc gag      5454
Ala Ala Ala Gly Glu Ser Thr Thr Leu Ser Thr Leu Tyr Thr Glu
    1805            1810                1815 gcg ttc gag acc ggg aag tgg aag gaa atc ttc gac ctg ctg cac      5499
Ala Phe Glu Thr Gly Lys Trp Lys Glu Ile Phe Asp Leu Leu His
    1820            1825                1830 gcc acg gcg gcg ctg cgg ccg cgg ttc agc gcc agc tcc gag ctg      5544
Ala Thr Ala Ala Leu Arg Pro Arg Phe Ser Ala Ser Ser Glu Leu
    1835            1840                1845 gag aag ctg ccg atg ccg gtc cgg ctc agc aag ggc ccg gcc gag      5589
Glu Lys Leu Pro Met Pro Val Arg Leu Ser Lys Gly Pro Ala Glu
    1850            1855                1860 cag cac ctg ttc tgc ttc tcc tcg tgc ctg gcg gtc gcg ggc atc      5634
Gln His Leu Phe Cys Phe Ser Ser Cys Leu Ala Val Ala Gly Ile
    1865            1870                1875 cac cag tac gcg cgg ttc gcg gcc tcg ctg cgg ggc cgg cgc gat      5679
His Gln Tyr Ala Arg Phe Ala Ala Ser Leu Arg Gly Arg Arg Asp
    1880            1885                1890 gtg tcg gcg ctc gcg ctg ccg ggc ttc ggc cgc ggt gaa ccc ctc      5724
Val Ser Ala Leu Ala Leu Pro Gly Phe Gly Arg Gly Glu Pro Leu
    1895            1900                1905
```

```
ccg gag acg gcg gac gcg gtg gtg gcc gcc cag gcc gag gcg gtg    5769
Pro Glu Thr Ala Asp Ala Val Val Ala Ala Gln Ala Glu Ala Val
    1910            1915                1920 gcg aag gcc gcc gac ggg cag ccg atc gtg ctc ctg ggc tcc tcg    5814
Ala Lys Ala Ala Asp Gly Gln Pro Ile Val Leu Leu Gly Ser Ser
1925            1930                1935 gcg ggc ggc tgg ttc gcc cac gcg gcg gcg gga cat ctg gag cgg    5859
Ala Gly Gly Trp Phe Ala His Ala Ala Ala Gly His Leu Glu Arg
    1940            1945                1950 atg ggc gtc cgg ccg acc gcg gtg gtc ctg gtg gac acc tac gtg    5904
Met Gly Val Arg Pro Thr Ala Val Val Leu Val Asp Thr Tyr Val
1955            1960                1965 ccc aag agc agc atc ctc aac cag ttc ggg ctc tcg ctc atg gac    5949
Pro Lys Ser Ser Ile Leu Asn Gln Phe Gly Leu Ser Leu Met Asp
    1970            1975                1980 ggg atg acc gag cgc gag ggc gtg ttc gtc acc atg gac gac gcc    5994
Gly Met Thr Glu Arg Glu Gly Val Phe Val Thr Met Asp Asp Ala
1985            1990                1995 cgg ctg tcg gcc atg ggc tgg tat ctc aac ctc ttc ggc agc tgg    6039
Arg Leu Ser Ala Met Gly Trp Tyr Leu Asn Leu Phe Gly Ser Trp
    2000            2005                2010 gac ccc gag ccg atc gag acc ccc acc ctc ctg gtg cgc gcg ctg    6084
Asp Pro Glu Pro Ile Glu Thr Pro Thr Leu Leu Val Arg Ala Leu
2015            2020                2025 gag ccg ctg tcc acc gga tcg ttg aag ctg gag gag ctg ccc gac    6129
Glu Pro Leu Ser Thr Gly Ser Leu Lys Leu Glu Glu Leu Pro Asp
    2030            2035                2040 tgg cgg tcc ttc tgg gag ctg ccg cac gac atc gtc gat gtg cgc    6174
Trp Arg Ser Phe Trp Glu Leu Pro His Asp Ile Val Asp Val Arg
2045            2050                2055 ggc aac cac ttc acc atg atg gag gac cac tcc ctc ccc acc gcc    6219
Gly Asn His Phe Thr Met Met Glu Asp His Ser Leu Pro Thr Ala
    2060            2065                2070 cag gcc atc gag gac tgg ctg gag cga ctg ccg cgc gac ggc gcc    6264
Gln Ala Ile Glu Asp Trp Leu Glu Arg Leu Pro Arg Asp Gly Ala
2075            2080                2085 tga                                                             6267
```

<210> SEQ ID NO 22
<211> LENGTH: 2088
<212> TYPE: PRT
<213> ORGANISM: Streptomyces sp. NRRL 30748

<400> SEQUENCE: 22

```
Val Ser Glu Ala Lys Leu Arg Asp Tyr Leu Lys Arg Val Thr Thr Asp
1               5                   10                  15

Leu His Arg Thr Arg Gln Arg Leu Gln Glu Ala Glu Ala Lys Asp His
                20                  25                  30

Glu Pro Ile Ala Ile Val Gly Met Ala Cys Arg Tyr Pro Gly Gly Val
            35                  40                  45

Ala Ser Pro Glu Asp Leu Trp Glu Leu Val Ala Asn Gly Arg Asp Ala
        50                  55                  60

Val Thr Glu Phe Pro Ala Asp Arg Gly Trp Asp Leu Glu Ala Leu Tyr
65                  70                  75                  80

Asp Pro Asp Pro Asp Lys Pro Gly Thr Ser Tyr Ala Arg Glu Gly Gly
                85                  90                  95

Phe Val Thr Asp Ala Asp His Phe Asp Pro Ala Phe Phe Gly Ile Ser
            100                 105                 110
```

-continued

```
Pro Arg Glu Ala Leu Ala Met Asp Pro Gln Gln Arg Leu Leu Leu Glu
        115                 120                 125

Thr Ala Trp Glu Ala Met Glu Arg Ala Gly Val Asp Pro Ala Thr Leu
130                 135                 140

Arg Gly Ser Arg Thr Gly Val Phe Ala Gly Val Met Tyr Gln Asp Tyr
145                 150                 155                 160

Ala Thr Arg Leu Arg Gln Val Pro Asp Val Glu Gly Tyr Val Gly
                165                 170                 175

Ser Gly Gly Ser Gly Ser Ile Ala Ser Gly Arg Ile Ala Tyr Thr Phe
                180                 185                 190

Gly Leu Glu Gly Pro Ala Val Thr Val Asp Thr Ala Cys Ser Ser Ser
        195                 200                 205

Leu Val Ala Leu His Leu Ala Ala Gln Ala Leu Arg Arg Gly Glu Cys
        210                 215                 220

Ser Leu Ala Leu Val Gly Gly Ser Met Val Met Ser Thr Pro Val Ala
225                 230                 235                 240

Phe Val Asp Phe Ser Arg Gln Arg Gly Leu Ala Ser Asp Gly Arg Cys
                245                 250                 255

Lys Ala Phe Ala Ala Ser Ala Asp Gly Thr Gly Trp Gly Glu Gly Val
            260                 265                 270

Gly Met Leu Leu Val Glu Arg Leu Ser Asp Ala Arg Arg Asn Gly His
        275                 280                 285

Gln Val Leu Ala Val Val Thr Gly Ser Ala Thr Asn Gln Asp Gly Ala
        290                 295                 300

Ser Ser Gly Leu Thr Ala Pro Asn Gly Pro Ser Gln Gln Arg Val Ile
305                 310                 315                 320

Arg Gln Ala Leu Ala Asp Ala Gly Leu Thr Ala Ala Asp Val Asp Ala
                325                 330                 335

Val Glu Ala His Gly Thr Gly Thr Pro Leu Gly Asp Pro Ile Glu Ala
            340                 345                 350

Gly Ala Leu Leu Ala Thr Tyr Gly Gln Asp Arg Pro Glu Asp Arg Pro
        355                 360                 365

Leu Trp Leu Gly Ser Leu Lys Ser Asn Ile Gly His Thr Gln Ala Ala
370                 375                 380

Ala Gly Val Gly Gly Val Ile Lys Thr Val Leu Ala Leu Arg His Gly
385                 390                 395                 400

Val Leu Pro Lys Thr Leu His Ala Asp Glu Pro Thr Pro Asn Val Asp
                405                 410                 415

Trp Glu Ser Gly Ala Val Arg Leu Leu Ala Glu Ala Arg Pro Trp Pro
            420                 425                 430

Glu Pro Glu Ala Glu Arg Pro Arg Arg Ala Ala Val Ser Ala Phe Gly
        435                 440                 445

Phe Ser Gly Thr Asn Ala His Val Ile Leu Glu Gln Ala Pro Ala Glu
        450                 455                 460

Glu Thr Ala Glu Glu Ala Ala Asp Glu Thr Pro Pro Asp Glu Thr Pro
465                 470                 475                 480

Ala Asp Thr Thr Pro Ala Thr Val Ser Asp Leu Val Pro Trp Pro Leu
                485                 490                 495

Ser Gly Arg Thr Glu Glu Ala Leu Arg Ala Gln Ala Ala Arg Leu Arg
            500                 505                 510

Ser Tyr Val Ala Gly Ala Pro Glu Pro Ser Pro Val Asp Ile Gly Tyr
        515                 520                 525

Ser Leu Ala Leu Thr Arg Ser Ala Phe Ala His Arg Ala Val Val Val
```

```
            530                 535                 540
Gly Ala Ser Arg Ala Glu Leu Leu Gly Glu Leu Asp Gln Leu Ala Ser
545                 550                 555                 560

Gly Val Thr Ser Gly Ala Val Ala Gly Ala Gly Lys Thr Ala Phe Leu
                565                 570                 575

Phe Thr Gly Gln Gly Ala Gln Arg Leu Gly Met Gly Arg Ala Leu His
                580                 585                 590

Thr Ala Phe Pro Val Phe Ala Ala Phe Asp Ala Val Cys Ala Glu
                595                 600                 605

Leu Asp Arg His Leu Asp Gly His Val Gly His Ala Val Arg Asp Val
610                 615                 620

Val Phe Gly Ala Asp Ala Glu Pro Leu Asp Arg Thr Leu Tyr Thr Gln
625                 630                 635                 640

Thr Gly Leu Phe Ala Val Glu Val Ala Leu Tyr Arg Leu Leu Glu Ser
                645                 650                 655

Trp Gly Val Thr Ala Asp Phe Leu Val Gly His Ser Val Gly Glu Leu
                660                 665                 670

Ala Ala Ala His Val Ala Gly Val Phe Ser Leu Glu Asp Ala Cys Ala
                675                 680                 685

Leu Val Ala Ala Arg Gly Arg Leu Met Asp Ala Leu Pro Ala Gly Gly
690                 695                 700

Ala Met Val Ser Leu Gln Thr Gly Glu Ala Glu Val Leu Pro His Leu
705                 710                 715                 720

Glu Gly Glu Glu Gly Gln Val Ser Leu Gly Ala Val Asn Gly Pro Ala
                725                 730                 735

Ala Thr Val Ile Ser Gly Glu Glu Lys Ala Val Leu Arg Ile Ala Asp
                740                 745                 750

Ala Val Gly Val Lys Ser Lys Arg Leu Arg Ile Gly Ile Ala Ala His
                755                 760                 765

Ser Pro Leu Val Asp Pro Met Leu Glu Glu Phe Ala Lys Val Ala Gly
                770                 775                 780

Glu Leu Thr Tyr Ala Thr Pro Arg Ile Ala Val Val Ser Asn Val Thr
785                 790                 795                 800

Gly Glu Ala Val Ala Glu Glu Leu Cys Ser Pro Asp Tyr Trp Val Arg
                805                 810                 815

His Val Arg Gln Pro Val Arg Phe Gln Asp Gly Val Arg Phe Leu Glu
                820                 825                 830

Asp Gln Gly Val Thr Arg Tyr Val Glu Val Gly Pro Ser Gly Val Leu
                835                 840                 845

Ser Val Met Gly Gln Glu Cys Val Ala Asp Pro Asp Ala Ala Phe
850                 855                 860

Val Pro Leu Leu Arg Lys Asp Arg Gly Glu Ala Glu Ser Leu Leu Ala
865                 870                 875                 880

Gly Val Gly Arg Val His Ala His Gly Gly Val Val Asp Trp Glu Gln
                885                 890                 895

Val Phe Ala Gly Arg Gly Ala Arg Val Glu Leu Pro Thr Tyr Ala
                900                 905                 910

Phe Gln Arg Gln Arg Tyr Trp Leu Asp Gly Ser Asp Arg Ala Gly Asp
                915                 920                 925

Val Thr Ser Ala Gly Leu Gly Ser Ala Gly His Pro Leu Leu Gly Ala
                930                 935                 940

Ala Val Glu Leu Ala Asp Ser Asp Gly Leu Val Leu Thr Gly Arg Leu
945                 950                 955                 960
```

-continued

Ser Leu Ala Ala Gln Pro Trp Leu Ala Asp His Ala Val Ser Gly Thr
            965                 970                 975

Val Leu Phe Pro Gly Thr Ala Phe Leu Glu Leu Ala Ile Gln Ala Gly
            980                 985                 990

Asp Gln Val Gly Cys Asp Gln Val Glu Glu Leu Thr Leu Gln Ala Pro
            995                 1000                1005

Leu Ile Leu Pro Ala Arg Gly Ala Leu Thr Leu Arg Val Thr Val
    1010                1015                1020

Gly Glu Pro Asp Glu Ser Gly Arg Arg Pro Leu Asn Val His Ser
    1025                1030                1035

Arg Pro Glu Gly Ala Gly Phe Gly Glu Pro Trp Thr Pro His Ala
    1040                1045                1050

Thr Gly Thr Leu Thr Thr Ala Thr Pro Asp Ala Pro Ala Glu Leu
    1055                1060                1065

Thr Ala Trp Pro Pro Ala Asp Ala Thr Glu Leu Asp Val Ser Asp
    1070                1075                1080

Met Tyr Glu Arg Tyr Ala Ala Gly Gly Phe Gly Tyr Gly Pro Ala
    1085                1090                1095

Phe Arg Gly Leu Arg Ala Ala Trp Leu Arg Gly Asp Glu Val Phe
    1100                1105                1110

Ala Glu Val Arg Leu Ala Gln Glu Gln Arg Pro Ala Ala Ala Gly
    1115                1120                1125

Tyr Gly Ile His Pro Ala Leu Leu Asp Ala Ser Leu His Gly Ile
    1130                1135                1140

Ala Leu Gly Thr Leu Phe Ala Gly Glu Asp Pro Glu Thr Ala Gln
    1145                1150                1155

Gly Arg Leu Pro Phe Ser Trp Thr Gly Val Ser Leu His Ala Ala
    1160                1165                1170

Gly Ala Asp Glu Val Arg Val Arg Ile Ser Pro Ala Gly Glu Asp
    1175                1180                1185

Thr Val Ala Leu Ala Val Ala Asp Pro Thr Gly Arg Pro Val Ala
    1190                1195                1200

Thr Val Glu Gly Leu Leu Leu Arg Lys Met Thr Gly Asp Gln Leu
    1205                1210                1215

Ser Gly Ala Arg Ala Ala Ser Ser Glu Ser Leu Phe Arg Leu Asp
    1220                1225                1230

Trp Pro Ala Leu Thr Ser Leu Asp Gln Pro Thr Pro Leu Thr Arg
    1235                1240                1245

Ala Ala Leu Val Gly Asp Asp Gly Leu Glu Val Thr Glu Ser Leu
    1250                1255                1260

Phe Ala Ala Gly Val His Leu Glu Ser Tyr Val Asp Leu Glu Ser
    1265                1270                1275

Leu Gly Ala Ala Val Asp Ala Gly Thr Ala Ala Pro Ala Ala Val
    1280                1285                1290

Leu Val Ser Cys Ala Ala Gly Pro Gly Ala Pro Ala Asp Ala Val
    1295                1300                1305

Arg Asp Ser Leu Arg Thr Ala Leu Glu Leu Ala Gln Asn Trp Ser
    1310                1315                1320

Ala Asp Glu Arg Phe Ala Asp Ser Arg Leu Val Phe Val Thr Arg
    1325                1330                1335

Gly Ala Val Ala Thr Ala Pro Glu Ala Glu Val Ala Asp Leu Pro
    1340                1345                1350

-continued

Gly Ala Ala Val Trp Gly Leu Val Arg Ser Ala Gln Ser Glu Asn
        1355                1360                1365

Pro Asp Arg Phe Thr Leu Val Asp Leu Asp Glu His Glu Glu Ser
1370                1375                1380

Val Arg Ala Leu Pro Ala Val Leu Pro Ser Gly Glu Pro Gln Leu
    1385                1390                1395

Ala Leu Arg Ala Gly Gln Pro His Thr Pro Arg Leu Ala Arg Ala
1400                1405                1410

Gln Gly Ala Thr Gly Ala Thr Arg Pro Leu Asp Pro Glu Gly Thr
    1415                1420                1425

Val Leu Ile Thr Gly Ala Thr Gly Thr Leu Gly Gly Leu Leu Ala
    1430                1435                1440

Arg His Leu Val Thr His His Gly Val Arg His Leu Leu Leu Thr
1445                1450                1455

Ser Arg Arg Gly Pro Ala Ala Glu Gly Ala Gly Arg Leu Arg Glu
    1460                1465                1470

Glu Leu Thr Glu Leu Gly Ala Ile Val Thr Val Ala Ala Cys Asp
1475                1480                1485

Thr Ala Asp Arg Asp Ala Val Ala Asp Leu Val Ala Gln Val Pro
    1490                1495                1500

Ala Asp His Pro Leu Thr Gly Val Phe His Thr Ala Gly Val Leu
1505                1510                1515

Asp Asp Gly Val Ile Ser Ser Leu Thr Pro Glu Arg Leu Asp Thr
    1520                1525                1530

Val Leu Arg Pro Lys Val Asp Ala Ala Leu His Leu His Glu Ala
    1535                1540                1545

Thr Arg Glu Leu Asp Leu Ala Ala Phe Val Leu Phe Ser Ser Ala
1550                1555                1560

Ala Gly Val Leu Gly Gly Ala Gly Gln Gly Asn Tyr Ala Ala Ala
1565                1570                1575

Asn Gly Phe Leu Asp Ala Phe Ala Gln Ala Arg Arg Ala Gln Gly
    1580                1585                1590

Leu Pro Ala His Ser Leu Ala Trp Gly Leu Trp Ala Arg Thr Ser
    1595                1600                1605

Ala Met Thr Gly Thr Ala Asp Thr Ala Gly Ala Ala Arg Ser Gly
    1610                1615                1620

Val Ala Ala Leu Ser Ser Glu Gln Gly Met Glu Leu Leu Asp Thr
    1625                1630                1635

Ala Leu Ala Leu Asp Thr Pro Leu Leu Ile Pro Met Arg Ile Asp
1640                1645                1650

Leu Ala Ala Leu Arg Ala Gly Ala Gly Ser Gly Ser Val Pro Leu
    1655                1660                1665

Leu Leu Arg Gly Leu Val Arg Thr Pro Ala Arg Arg Ala Gly Ala
    1670                1675                1680

Thr Thr Arg Gly Gly Ser Pro Gly Gly Gly Ser Ala Leu Arg Glu
    1685                1690                1695

Arg Leu Ala Ala Leu Pro Glu Asp Glu Gln Asp Ala Val Leu Val
    1700                1705                1710

Glu Leu Val Cys Thr Gln Val Ala Thr Val Leu Gly His Pro Asp
    1715                1720                1725

Pro Ser Ala Ile Gly Pro Ala His Glu Phe Val Asp Ser Gly Phe
    1730                1735                1740

Asp Ser Leu Thr Ala Val Glu Leu Arg Asn Arg Leu Asn Ala Ala

```
                1745                1750                1755

Thr Gly Leu Arg Leu Pro Ala Thr Leu Val Phe Asp His Glu Thr
    1760                1765                1770

Pro Thr Asp Leu Ala Ala Arg Leu Arg Ser Glu Leu Ala Ala Ala
    1775                1780                1785

Arg Gln Ser Gly Pro Ala Glu Gln Thr Pro Ala Gly Ala Pro Pro
    1790                1795                1800

Ala Ala Ala Gly Glu Ser Thr Thr Leu Ser Thr Leu Tyr Thr Glu
    1805                1810                1815

Ala Phe Glu Thr Gly Lys Trp Lys Glu Ile Phe Asp Leu Leu His
    1820                1825                1830

Ala Thr Ala Ala Leu Arg Pro Arg Phe Ser Ala Ser Ser Glu Leu
    1835                1840                1845

Glu Lys Leu Pro Met Pro Val Arg Leu Ser Lys Gly Pro Ala Glu
    1850                1855                1860

Gln His Leu Phe Cys Phe Ser Ser Cys Leu Ala Val Ala Gly Ile
    1865                1870                1875

His Gln Tyr Ala Arg Phe Ala Ala Ser Leu Arg Gly Arg Arg Asp
    1880                1885                1890

Val Ser Ala Leu Ala Leu Pro Gly Phe Gly Arg Gly Glu Pro Leu
    1895                1900                1905

Pro Glu Thr Ala Asp Ala Val Val Ala Ala Gln Ala Glu Ala Val
    1910                1915                1920

Ala Lys Ala Ala Asp Gly Gln Pro Ile Val Leu Leu Gly Ser Ser
    1925                1930                1935

Ala Gly Gly Trp Phe Ala His Ala Ala Ala Gly His Leu Glu Arg
    1940                1945                1950

Met Gly Val Arg Pro Thr Ala Val Val Leu Val Asp Thr Tyr Val
    1955                1960                1965

Pro Lys Ser Ser Ile Leu Asn Gln Phe Gly Leu Ser Leu Met Asp
    1970                1975                1980

Gly Met Thr Glu Arg Glu Gly Val Phe Val Thr Met Asp Asp Ala
    1985                1990                1995

Arg Leu Ser Ala Met Gly Trp Tyr Leu Asn Leu Phe Gly Ser Trp
    2000                2005                2010

Asp Pro Glu Pro Ile Glu Thr Pro Thr Leu Leu Val Arg Ala Leu
    2015                2020                2025

Glu Pro Leu Ser Thr Gly Ser Leu Lys Leu Glu Glu Leu Pro Asp
    2030                2035                2040

Trp Arg Ser Phe Trp Glu Leu Pro His Asp Ile Val Asp Val Arg
    2045                2050                2055

Gly Asn His Phe Thr Met Met Glu Asp His Ser Leu Pro Thr Ala
    2060                2065                2070

Gln Ala Ile Glu Asp Trp Leu Glu Arg Leu Pro Arg Asp Gly Ala
    2075                2080                2085
```

<210> SEQ ID NO 23
<211> LENGTH: 786
<212> TYPE: DNA
<213> ORGANISM: Streptomyces sp. NRRL 30748
<220> FEATURE:
<221> NAME/KEY: CDS
<222> LOCATION: (1)..(786)

<400> SEQUENCE: 23

```
atg gcg ttg ccc gtc acc gat gag agc ctg tgg ttc cgc agg ttc cat    48
Met Ala Leu Pro Val Thr Asp Glu Ser Leu Trp Phe Arg Arg Phe His
1               5                   10                  15 ccg cgc ccg gag gcc gag gtc agc ctg gtc tgc ctg ccg cac gcg gga    96
Pro Arg Pro Glu Ala Glu Val Ser Leu Val Cys Leu Pro His Ala Gly
            20                  25                  30 gga gcc gcc agc ttc tac ttc ccg atc tcc gag ctg ctg ccg ccg acc    144
Gly Ala Ala Ser Phe Tyr Phe Pro Ile Ser Glu Leu Leu Pro Pro Thr
        35                  40                  45 gtg gag gcg ctg gcc gtc cag tac ccg ggg cgg cag gac cgc cgc cat    192
Val Glu Ala Leu Ala Val Gln Tyr Pro Gly Arg Gln Asp Arg Arg His
50                  55                  60 gac gcg ccc atc gag gac atc cac gag atg gcg cgc gag atc tac gag    240
Asp Ala Pro Ile Glu Asp Ile His Glu Met Ala Arg Glu Ile Tyr Glu
65                  70                  75                  80 gcg ctg aag ccg ctc acg gca cac cgg ccg gtc gcg ctg ttc ggc cac    288
Ala Leu Lys Pro Leu Thr Ala His Arg Pro Val Ala Leu Phe Gly His
                85                  90                  95 agc atg ggc gcg agc gtc ggc ttc gag ctg gcc aga ctg ctc gaa ggg    336
Ser Met Gly Ala Ser Val Gly Phe Glu Leu Ala Arg Leu Leu Glu Gly
            100                 105                 110 gag ctg ggg acc gtg ccc gtg gcg ctc ttc gcc tcg ggc cgg ccc gcg    384
Glu Leu Gly Thr Val Pro Val Ala Leu Phe Ala Ser Gly Arg Pro Ala
        115                 120                 125 ccc tca cac cac cgg agc ctc ggc atc cac cgg cgc gac gac gcc ggg    432
Pro Ser His His Arg Ser Leu Gly Ile His Arg Arg Asp Asp Ala Gly
    130                 135                 140 ctc atc gcc gag ctc caa ctg gtc agc ggg acc gac tcg cgg atc ctc    480
Leu Ile Ala Glu Leu Gln Leu Val Ser Gly Thr Asp Ser Arg Ile Leu
145                 150                 155                 160 ggc gac gcc gaa ctg ctg cgg ctg gcc ctg ccc gcc atc cgc agc gac    528
Gly Asp Ala Glu Leu Leu Arg Leu Ala Leu Pro Ala Ile Arg Ser Asp
                165                 170                 175 tac aag gcg gcc gag acc tac gaa tac cgg ccc ggc gcc cgg ctg gcc    576
Tyr Lys Ala Ala Glu Thr Tyr Glu Tyr Arg Pro Gly Ala Arg Leu Ala
            180                 185                 190 tgc gac atc gtg ggg ctc acc ggt gac agc gac atc cgc gtc acc gcc    624
Cys Asp Ile Val Gly Leu Thr Gly Asp Ser Asp Ile Arg Val Thr Ala
        195                 200                 205 ggg gaa gtg gcg ggc tgg cgg gag cac acc tcg ggc tcc ttc cgg ctg    672
Gly Glu Val Ala Gly Trp Arg Glu His Thr Ser Gly Ser Phe Arg Leu
    210                 215                 220 gag gtc ttc tcc ggc ggc cac ttc tac ctg ggt gag cag aag gca gcg    720
Glu Val Phe Ser Gly Gly His Phe Tyr Leu Gly Glu Gln Lys Ala Ala
225                 230                 235                 240 gtg gcc gga gtc atc acg gac acc ctg cgg gcg gcc acc gcc cgc ccc    768
Val Ala Gly Val Ile Thr Asp Thr Leu Arg Ala Ala Thr Ala Arg Pro
                245                 250                 255 cga cga ccc atc gac tga                                            786
Arg Arg Pro Ile Asp
            260
```

<210> SEQ ID NO 24
<211> LENGTH: 261
<212> TYPE: PRT
<213> ORGANISM: Streptomyces sp. NRRL 30748

<400> SEQUENCE: 24

```
Met Ala Leu Pro Val Thr Asp Glu Ser Leu Trp Phe Arg Arg Phe His
1               5                   10                  15
```

```
Pro Arg Pro Glu Ala Glu Val Ser Leu Val Cys Leu Pro His Ala Gly
        20                  25                  30

Gly Ala Ala Ser Phe Tyr Phe Pro Ile Ser Glu Leu Leu Pro Pro Thr
            35                  40                  45

Val Glu Ala Leu Ala Val Gln Tyr Pro Gly Arg Gln Asp Arg His
 50                  55                  60

Asp Ala Pro Ile Glu Asp Ile His Glu Met Ala Arg Glu Ile Tyr Glu
 65                  70                  75                  80

Ala Leu Lys Pro Leu Thr Ala His Arg Pro Val Ala Leu Phe Gly His
                85                  90                  95

Ser Met Gly Ala Ser Val Gly Phe Glu Leu Ala Arg Leu Leu Glu Gly
            100                 105                 110

Glu Leu Gly Thr Val Pro Val Ala Leu Phe Ala Ser Gly Arg Pro Ala
            115                 120                 125

Pro Ser His His Arg Ser Leu Gly Ile His Arg Arg Asp Asp Ala Gly
        130                 135                 140

Leu Ile Ala Glu Leu Gln Leu Val Ser Gly Thr Asp Ser Arg Ile Leu
145                 150                 155                 160

Gly Asp Ala Glu Leu Leu Arg Leu Ala Leu Pro Ala Ile Arg Ser Asp
                165                 170                 175

Tyr Lys Ala Ala Glu Thr Tyr Glu Tyr Arg Pro Gly Ala Arg Leu Ala
            180                 185                 190

Cys Asp Ile Val Gly Leu Thr Gly Asp Ser Asp Ile Arg Val Thr Ala
            195                 200                 205

Gly Glu Val Ala Gly Trp Arg Glu His Thr Ser Gly Ser Phe Arg Leu
        210                 215                 220

Glu Val Phe Ser Gly Gly His Phe Tyr Leu Gly Glu Gln Lys Ala Ala
225                 230                 235                 240

Val Ala Gly Val Ile Thr Asp Thr Leu Arg Ala Ala Thr Ala Arg Pro
                245                 250                 255

Arg Arg Pro Ile Asp
            260

<210> SEQ ID NO 25
<211> LENGTH: 1254
<212> TYPE: DNA
<213> ORGANISM: Streptomyces sp. NRRL 30748
<220> FEATURE:
<221> NAME/KEY: CDS
<222> LOCATION: (1)..(1254)

<400> SEQUENCE: 25 atg cgt atc ctt ttc gcg acg gtg tcc gag aaa tcg cac ctg ttc acc       48
Met Arg Ile Leu Phe Ala Thr Val Ser Glu Lys Ser His Leu Phe Thr
 1               5                  10                  15 atg gtc ccg ctc gcc tgg tcg ctg gcc gcg gcc ggc cac gag gtg cat       96
Met Val Pro Leu Ala Trp Ser Leu Ala Ala Ala Gly His Glu Val His
            20                  25                  30 gtc gcc agc aat ccc gcg ctg acc gag tcc atc aag agc acc ggt ctg      144
Val Ala Ser Asn Pro Ala Leu Thr Glu Ser Ile Lys Ser Thr Gly Leu
        35                  40                  45 acg gcc gtc tcg gtc ggc aag gac cac aat ctc cac gag atg ctg acg      192
Thr Ala Val Ser Val Gly Lys Asp His Asn Leu His Glu Met Leu Thr
 50                  55                  60 cag aac cgc gag tcg ctg gag aac ccg ctc tcc gac tgg tcc acc ccg      240
Gln Asn Arg Glu Ser Leu Glu Asn Pro Leu Ser Asp Trp Ser Thr Pro
 65                  70                  75                  80
```

-continued

| | |
|---|---|
| gag ctc gat cag cac tcc tgg gaa cag gtg ctg atg aag ttc aag atc<br>Glu Leu Asp Gln His Ser Trp Glu Gln Val Leu Met Lys Phe Lys Ile<br>        85       90        95 | 288 |
| agc gtg atg ttc gcg tac cag acc tac aac gac tgc atg gtg cac gag<br>Ser Val Met Phe Ala Tyr Gln Thr Tyr Asn Asp Cys Met Val His Glu<br>     100        105        110 | 336 |
| ctg gtg gac tac gcc cgc cac tgg caa ccc gac ctg gtc atc tgg gac<br>Leu Val Asp Tyr Ala Arg His Trp Gln Pro Asp Leu Val Ile Trp Asp<br>     115        120        125 | 384 |
| ccg gtc agc tac gcg ggc ccg gtg gcc gcc cgg gtg gtg ggc gcc gcc<br>Pro Val Ser Tyr Ala Gly Pro Val Ala Ala Arg Val Val Gly Ala Ala<br>   130        135        140 | 432 |
| cac gcc cgg ctg ctg tgg tgc atc gac atc tac gcg aag atg cgt gag<br>His Ala Arg Leu Leu Trp Cys Ile Asp Ile Tyr Ala Lys Met Arg Glu<br>145        150        155        160 | 480 |
| gtg ttc ctg gcc cgc ctc gcc gaa cag ccc gag gag cgc cgc gag gac<br>Val Phe Leu Ala Arg Leu Ala Glu Gln Pro Glu Glu Arg Arg Glu Asp<br>     165        170        175 | 528 |
| ccg atg gcc gac tgg ctc ggt ggc atc ctc gcc cgc tac gac cgc acc<br>Pro Met Ala Asp Trp Leu Gly Gly Ile Leu Ala Arg Tyr Asp Arg Thr<br>   180        185        190 | 576 |
| ttc gac gag gag gtc gtg gtc ggc cag tgg acc atc gac cag atc ccc<br>Phe Asp Glu Glu Val Val Val Gly Gln Trp Thr Ile Asp Gln Ile Pro<br>     195        200        205 | 624 |
| acc agc ctc cag ctc ccg ctg tcg ctc cag cgg gtc ccg gtc cgc tat<br>Thr Ser Leu Gln Leu Pro Leu Ser Leu Gln Arg Val Pro Val Arg Tyr<br>   210        215        220 | 672 |
| ctg ccc tac aac ggc ccc tcc gac atc ccg gac tgg ctg cgc gag acc<br>Leu Pro Tyr Asn Gly Pro Ser Asp Ile Pro Asp Trp Leu Arg Glu Thr<br>225        230        235        240 | 720 |
| ccc gag cgg ccg cgg gtc gtg ctg acc tcc ggg gtc tcc gcg cgg gcc<br>Pro Glu Arg Pro Arg Val Val Leu Thr Ser Gly Val Ser Ala Arg Ala<br>     245        250        255 | 768 |
| gcc ctg ggc ggc acc ttc atg ccg gtg gcc gac atg atc gac acc ctg<br>Ala Leu Gly Gly Thr Phe Met Pro Val Ala Asp Met Ile Asp Thr Leu<br>   260        265        270 | 816 |
| ggg agc atg gac atc gag gtg gtg gcc gca ctg ccg ccc gag gag gtc<br>Gly Ser Met Asp Ile Glu Val Val Ala Ala Leu Pro Pro Glu Glu Val<br>     275        280        285 | 864 |
| gag gcg ctg gcg aag gtc ccc gcc aac acc cgt atc gtc gac ttc gtt<br>Glu Ala Leu Ala Lys Val Pro Ala Asn Thr Arg Ile Val Asp Phe Val<br>   290        295        300 | 912 |
| ccg ctg cac gcc ctg ctg ccc ggc gcc tcg gtc ctc atc cac cac ggc<br>Pro Leu His Ala Leu Leu Pro Gly Ala Ser Val Leu Ile His His Gly<br>305        310        315        320 | 960 |
| ggc ttc ggc tcc tgg ggc acc gca ctg gtc aac ggc gta ccg cag ttc<br>Gly Phe Gly Ser Trp Gly Thr Ala Leu Val Asn Gly Val Pro Gln Phe<br>     325        330        335 | 1008 |
| att ccc acc atc cgc tac gcc gac tgg tgg aac aag ggg acc agt ctg<br>Ile Pro Thr Ile Arg Tyr Ala Asp Trp Trp Asn Lys Gly Thr Ser Leu<br>   340        345        350 | 1056 |
| cac gag gcc ggt gcc gga ctc gtc gtc cac gcc tcg gag ttg acc gcc<br>His Glu Ala Gly Ala Gly Leu Val Val His Ala Ser Glu Leu Thr Ala<br>     355        360        365 | 1104 |
| gag gtg ctg cgg gag agc gtc gag cgg ctg ctg aag gac gcg tcg tac<br>Glu Val Leu Arg Glu Ser Val Glu Arg Leu Leu Lys Asp Ala Ser Tyr<br>   370        375        380 | 1152 |
| aag gag gcc gcc gag cgg ctg cgc gag gag aac ctg cgc acc ccc acc<br>Lys Glu Ala Ala Glu Arg Leu Arg Glu Glu Asn Leu Arg Thr Pro Thr<br>385        390        395        400 | 1200 |

```
ccg cac gat gtg gtg ccg gtg ctg gag aag ctc acc gtg gag cac ggc    1248
Pro His Asp Val Val Pro Val Leu Glu Lys Leu Thr Val Glu His Gly
            405                 410                 415 cga tga                                                             1254
Arg

<210> SEQ ID NO 26
<211> LENGTH: 417
<212> TYPE: PRT
<213> ORGANISM: Streptomyces sp. NRRL 30748

<400> SEQUENCE: 26

Met Arg Ile Leu Phe Ala Thr Val Ser Glu Lys Ser His Leu Phe Thr
1               5                   10                  15

Met Val Pro Leu Ala Trp Ser Leu Ala Ala Gly His Glu Val His
            20                  25                  30

Val Ala Ser Asn Pro Ala Leu Thr Glu Ser Ile Lys Ser Thr Gly Leu
        35                  40                  45

Thr Ala Val Ser Val Gly Lys Asp His Asn Leu His Glu Met Leu Thr
    50                  55                  60

Gln Asn Arg Glu Ser Leu Glu Asn Pro Leu Ser Asp Trp Ser Thr Pro
65                  70                  75                  80

Glu Leu Asp Gln His Ser Trp Glu Gln Val Leu Met Lys Phe Lys Ile
                85                  90                  95

Ser Val Met Phe Ala Tyr Gln Thr Tyr Asn Asp Cys Met Val His Glu
            100                 105                 110

Leu Val Asp Tyr Ala Arg His Trp Gln Pro Asp Leu Val Ile Trp Asp
        115                 120                 125

Pro Val Ser Tyr Ala Gly Pro Val Ala Ala Arg Val Gly Ala Ala
    130                 135                 140

His Ala Arg Leu Leu Trp Cys Ile Asp Ile Tyr Ala Lys Met Arg Glu
145                 150                 155                 160

Val Phe Leu Ala Arg Leu Ala Glu Gln Pro Glu Glu Arg Arg Glu Asp
                165                 170                 175

Pro Met Ala Asp Trp Leu Gly Gly Ile Leu Ala Arg Tyr Asp Arg Thr
            180                 185                 190

Phe Asp Glu Glu Val Val Gly Gln Trp Thr Ile Asp Gln Ile Pro
        195                 200                 205

Thr Ser Leu Gln Leu Pro Leu Ser Leu Gln Arg Val Pro Val Arg Tyr
    210                 215                 220

Leu Pro Tyr Asn Gly Pro Ser Asp Ile Pro Asp Trp Leu Arg Glu Thr
225                 230                 235                 240

Pro Glu Arg Pro Arg Val Val Leu Thr Ser Gly Val Ser Ala Arg Ala
                245                 250                 255

Ala Leu Gly Gly Thr Phe Met Pro Val Ala Asp Met Ile Asp Thr Leu
            260                 265                 270

Gly Ser Met Asp Ile Glu Val Val Ala Ala Leu Pro Pro Glu Glu Val
        275                 280                 285

Glu Ala Leu Ala Lys Val Pro Ala Asn Thr Arg Ile Val Asp Phe Val
    290                 295                 300

Pro Leu His Ala Leu Leu Pro Gly Ala Ser Val Leu Ile His His Gly
305                 310                 315                 320

Gly Phe Gly Ser Trp Gly Thr Ala Leu Val Asn Gly Val Pro Gln Phe
                325                 330                 335
```

```
Ile Pro Thr Ile Arg Tyr Ala Asp Trp Trp Asn Lys Gly Thr Ser Leu
            340                 345                 350

His Glu Ala Gly Ala Gly Leu Val Val His Ala Ser Glu Leu Thr Ala
            355                 360                 365

Glu Val Leu Arg Glu Ser Val Glu Arg Leu Leu Lys Asp Ala Ser Tyr
            370                 375                 380

Lys Glu Ala Ala Glu Arg Leu Arg Glu Glu Asn Leu Arg Thr Pro Thr
385                 390                 395                 400

Pro His Asp Val Val Pro Val Leu Glu Lys Leu Thr Val Glu His Gly
                405                 410                 415

Arg
```

```
<210> SEQ ID NO 27
<211> LENGTH: 597
<212> TYPE: DNA
<213> ORGANISM: Streptomyces sp. NRRL 30748
<220> FEATURE:
<221> NAME/KEY: CDS
<222> LOCATION: (1)..(597)

<400> SEQUENCE: 27
```

```
atg aag gtg cgc gag ctg gcg gtg tcc ggc gcc tac gag ttc agc ccg     48
Met Lys Val Arg Glu Leu Ala Val Ser Gly Ala Tyr Glu Phe Ser Pro
1               5                   10                  15 gac gtc cac cgg gac gag cgc ggc gcg ttc gtc gcc cac tac acc gaa     96
Asp Val His Arg Asp Glu Arg Gly Ala Phe Val Ala His Tyr Thr Glu
                20                  25                  30 tcg gcc ttc tcc gcg gcc gtc ggt cat ccg ctg cgc ctg ggc cag aac    144
Ser Ala Phe Ser Ala Ala Val Gly His Pro Leu Arg Leu Gly Gln Asn
            35                  40                  45 cac cac agc gtc tcc cgg cgc ggc acc gtc cgc ggg gtg cac tac gcg    192
His His Ser Val Ser Arg Arg Gly Thr Val Arg Gly Val His Tyr Ala
        50                  55                  60 gac gta ccc ccg ggg cag gcc aag atg gtg acc tgc gtc agc ggc gaa    240
Asp Val Pro Pro Gly Gln Ala Lys Met Val Thr Cys Val Ser Gly Glu
65                  70                  75                  80 ctc ctc gat gtg gtg gtg gac ttg cgg gtg ggc tcg ccc acc ttc ggc    288
Leu Leu Asp Val Val Val Asp Leu Arg Val Gly Ser Pro Thr Phe Gly
                85                  90                  95 cgc tgg gac agt gtg cgt ctt gac ccc gtc tcg tac cgg gcg gtg tat    336
Arg Trp Asp Ser Val Arg Leu Asp Pro Val Ser Tyr Arg Ala Val Tyr
            100                 105                 110 ctg gag gag ggc ctc ggc cac gca ttc atc gcg ctc cgg gac gac acg    384
Leu Glu Glu Gly Leu Gly His Ala Phe Ile Ala Leu Arg Asp Asp Thr
        115                 120                 125 gtg gcg gcc tac ctc aac tcg gag gag tac aac ccg ggc gcc gaa cac    432
Val Ala Ala Tyr Leu Asn Ser Glu Glu Tyr Asn Pro Gly Ala Glu His
130                 135                 140 gag atc gac ccc ttc gat ccc gcg ctc ggc ctg ccc tgg ccc aag gac    480
Glu Ile Asp Pro Phe Asp Pro Ala Leu Gly Leu Pro Trp Pro Lys Asp
145                 150                 155                 160 ctg gag tat ctg gtc tcc gag cgc gac cgg aac gcc ccc ggg ctg gcc    528
Leu Glu Tyr Leu Val Ser Glu Arg Asp Arg Asn Ala Pro Gly Leu Ala
                165                 170                 175 gcg gcc gaa cgg gcc ggt ctg ctg ccg tcc tac gag gtc tgc cgg gcg    576
Ala Ala Glu Arg Ala Gly Leu Leu Pro Ser Tyr Glu Val Cys Arg Ala
            180                 185                 190 ctg cac gcc cgg cgc ggc tga                                        597
Leu His Ala Arg Arg Gly
        195
```

<210> SEQ ID NO 28
<211> LENGTH: 198
<212> TYPE: PRT
<213> ORGANISM: Streptomyces sp. NRRL 30748

<400> SEQUENCE: 28

```
Met Lys Val Arg Glu Leu Ala Val Ser Gly Ala Tyr Glu Phe Ser Pro
1               5                   10                  15

Asp Val His Arg Asp Glu Arg Gly Ala Phe Val Ala His Tyr Thr Glu
            20                  25                  30

Ser Ala Phe Ser Ala Ala Val Gly His Pro Leu Arg Leu Gly Gln Asn
        35                  40                  45

His His Ser Val Ser Arg Arg Gly Thr Val Arg Gly Val His Tyr Ala
    50                  55                  60

Asp Val Pro Pro Gly Gln Ala Lys Met Val Thr Cys Val Ser Gly Glu
65                  70                  75                  80

Leu Leu Asp Val Val Asp Leu Arg Val Gly Ser Pro Thr Phe Gly
                85                  90                  95

Arg Trp Asp Ser Val Arg Leu Asp Pro Val Ser Tyr Arg Ala Val Tyr
                100                 105                 110

Leu Glu Glu Gly Leu Gly His Ala Phe Ile Ala Leu Arg Asp Asp Thr
            115                 120                 125

Val Ala Ala Tyr Leu Asn Ser Glu Glu Tyr Asn Pro Gly Ala Glu His
        130                 135                 140

Glu Ile Asp Pro Phe Asp Pro Ala Leu Gly Leu Pro Trp Pro Lys Asp
145                 150                 155                 160

Leu Glu Tyr Leu Val Ser Glu Arg Asp Arg Asn Ala Pro Gly Leu Ala
                165                 170                 175

Ala Ala Glu Arg Ala Gly Leu Leu Pro Ser Tyr Glu Val Cys Arg Ala
            180                 185                 190

Leu His Ala Arg Arg Gly
        195
```

<210> SEQ ID NO 29
<211> LENGTH: 915
<212> TYPE: DNA
<213> ORGANISM: Streptomyces sp. NRRL 30748
<220> FEATURE:
<221> NAME/KEY: CDS
<222> LOCATION: (1)..(915)

<400> SEQUENCE: 29

```
atg ccg ctg atc gag gtc agt aac ctg cgc aag gag tac cgc aat cac      48
Met Pro Leu Ile Glu Val Ser Asn Leu Arg Lys Glu Tyr Arg Asn His
1               5                   10                  15 gtg gcg gta cag gac gtg tcc ttc tcc gtg gag gag ggt gag atc ttc      96
Val Ala Val Gln Asp Val Ser Phe Ser Val Glu Glu Gly Glu Ile Phe
            20                  25                  30 ggc atc ctc ggc ccc aac ggg gcg ggc aag acc acc gcc gtg gag tgc     144
Gly Ile Leu Gly Pro Asn Gly Ala Gly Lys Thr Thr Ala Val Glu Cys
        35                  40                  45 atc gag ggc atg cgc aag cgc gac ggc ggc gag atc tcc gtg atg ggt     192
Ile Glu Gly Met Arg Lys Arg Asp Gly Gly Glu Ile Ser Val Met Gly
    50                  55                  60 ctc gac ccg ctg aag gac aag gac ctc gcc gag ctg cgc gag tcc atc     240
Leu Asp Pro Leu Lys Asp Lys Asp Leu Ala Glu Leu Arg Glu Ser Ile
65                  70                  75                  80
```

```
ggc atc cag ctc cag cag agc gaa ctg ccc ccc aag atg aag gtg tgg      288
Gly Ile Gln Leu Gln Gln Ser Glu Leu Pro Pro Lys Met Lys Val Trp
             85                  90                  95 gag gcg ctc gag ctc tac agc acc ttc tac cgc gac ccc gtc gac tgg      336
Glu Ala Leu Glu Leu Tyr Ser Thr Phe Tyr Arg Asp Pro Val Asp Trp
        100                 105                 110 cgc gag ctc atc aag gac tgg ggc ctg tcc gac aag gcg gac acg gcc      384
Arg Glu Leu Ile Lys Asp Trp Gly Leu Ser Asp Lys Ala Asp Thr Ala
    115                 120                 125 tac gga tcg ctg tcc ggc gga cag cag cag cgg ctg tcc atc gcg ctc      432
Tyr Gly Ser Leu Ser Gly Gly Gln Gln Gln Arg Leu Ser Ile Ala Leu
130                 135                 140 gcc ctc gtc ggc aag ccc agg atc gcc gtc ttc gac gag ctg acc acc      480
Ala Leu Val Gly Lys Pro Arg Ile Ala Val Phe Asp Glu Leu Thr Thr
145                 150                 155                 160 gcg ctc gac ccg cac gcc cgg cgc gag acc tgg aag ctg atc gag aag      528
Ala Leu Asp Pro His Ala Arg Arg Glu Thr Trp Lys Leu Ile Glu Lys
                165                 170                 175 gtc cgg gag cag gat gtg acc gtg ctg ctg gtc acc cac ttc atg gag      576
Val Arg Glu Gln Asp Val Thr Val Leu Leu Val Thr His Phe Met Glu
            180                 185                 190 gag gcc gag cgg ctc tgc gac cgg atc gcc atc atc gaa tcc ggc cgg      624
Glu Ala Glu Arg Leu Cys Asp Arg Ile Ala Ile Ile Glu Ser Gly Arg
        195                 200                 205 gtc gtc gcc ctc gac acc ccc tcc gga ctg gtg tcc cgg gtc gat gag      672
Val Val Ala Leu Asp Thr Pro Ser Gly Leu Val Ser Arg Val Asp Glu
    210                 215                 220 cag cag atc atc cgc ttc aag ccg tcc gtc ccg atg gac gac gag ctg      720
Gln Gln Ile Ile Arg Phe Lys Pro Ser Val Pro Met Asp Asp Glu Leu
225                 230                 235                 240 ctc acc tcg ctg ccc gag gtg agc agt gtg acc cgg tcc aag tcc cag      768
Leu Thr Ser Leu Pro Glu Val Ser Ser Val Thr Arg Ser Lys Ser Gln
                245                 250                 255 gtg acg gtg gtc ggc aag ggc aat gtc gtc tac gcc gtg atc tcc gtc      816
Val Thr Val Val Gly Lys Gly Asn Val Val Tyr Ala Val Ile Ser Val
            260                 265                 270 ctg gcc cgc aac cag atc gtg gcg aac gaa ctc cgc ctg gag cag gcg      864
Leu Ala Arg Asn Gln Ile Val Ala Asn Glu Leu Arg Leu Glu Gln Ala
        275                 280                 285 agt ctc gat gac gcc ttc gtc gcc ctg acc ggc tcc aag ccc gcc aac      912
Ser Leu Asp Asp Ala Phe Val Ala Leu Thr Gly Ser Lys Pro Ala Asn
    290                 295                 300 taa                                                                   915

<210> SEQ ID NO 30
<211> LENGTH: 304
<212> TYPE: PRT
<213> ORGANISM: Streptomyces sp. NRRL 30748

<400> SEQUENCE: 30

Met Pro Leu Ile Glu Val Ser Asn Leu Arg Lys Glu Tyr Arg Asn His
1               5                   10                  15

Val Ala Val Gln Asp Val Ser Phe Ser Val Glu Gly Glu Ile Phe
            20                  25                  30

Gly Ile Leu Gly Pro Asn Gly Ala Gly Lys Thr Thr Ala Val Glu Cys
        35                  40                  45

Ile Glu Gly Met Arg Lys Arg Asp Gly Gly Glu Ile Ser Val Met Gly
    50                  55                  60

Leu Asp Pro Leu Lys Asp Lys Asp Leu Ala Glu Leu Arg Glu Ser Ile
```

```
                65                  70                  75                  80
Gly Ile Gln Leu Gln Gln Ser Glu Leu Pro Pro Lys Met Lys Val Trp
                    85                  90                  95
Glu Ala Leu Glu Leu Tyr Ser Thr Phe Tyr Arg Asp Pro Val Asp Trp
                    100                 105                 110
Arg Glu Leu Ile Lys Asp Trp Gly Leu Ser Asp Lys Ala Asp Thr Ala
                    115                 120                 125
Tyr Gly Ser Leu Ser Gly Gly Gln Gln Arg Leu Ser Ile Ala Leu
        130                 135                 140
Ala Leu Val Gly Lys Pro Arg Ile Ala Val Phe Asp Glu Leu Thr Thr
145                 150                 155                 160
Ala Leu Asp Pro His Ala Arg Arg Glu Thr Trp Lys Leu Ile Glu Lys
                    165                 170                 175
Val Arg Glu Gln Asp Val Thr Val Leu Leu Val Thr His Phe Met Glu
                    180                 185                 190
Glu Ala Glu Arg Leu Cys Asp Arg Ile Ala Ile Ile Glu Ser Gly Arg
                    195                 200                 205
Val Val Ala Leu Asp Thr Pro Ser Gly Leu Val Ser Arg Val Asp Glu
                    210                 215                 220
Gln Gln Ile Ile Arg Phe Lys Pro Ser Val Pro Met Asp Asp Glu Leu
225                 230                 235                 240
Leu Thr Ser Leu Pro Glu Val Ser Ser Val Thr Arg Ser Lys Ser Gln
                    245                 250                 255
Val Thr Val Val Gly Lys Gly Asn Val Val Tyr Ala Val Ile Ser Val
                    260                 265                 270
Leu Ala Arg Asn Gln Ile Val Ala Asn Glu Leu Arg Leu Glu Gln Ala
                    275                 280                 285
Ser Leu Asp Asp Ala Phe Val Ala Leu Thr Gly Ser Lys Pro Ala Asn
                    290                 295                 300

<210> SEQ ID NO 31
<211> LENGTH: 738
<212> TYPE: DNA
<213> ORGANISM: Streptomyces sp. NRRL 30748
<220> FEATURE:
<221> NAME/KEY: CDS
<222> LOCATION: (1)..(738)

<400> SEQUENCE: 31 atg tcc ggg cgc acc aag ctc acc tac gtc gag agc aag ctg ttc ctg    48
Met Ser Gly Arg Thr Lys Leu Thr Tyr Val Glu Ser Lys Leu Phe Leu
1               5                   10                  15 cgc gat ccc acc gcg gtg ttc ttc gtc atc gcg ctg ccg atc atg ctg    96
Arg Asp Pro Thr Ala Val Phe Phe Val Ile Ala Leu Pro Ile Met Leu
                20                  25                  30 ctg gcc atc ttc cac ttc gtc acc acc aag tcc gac gac gac gcc gcc   144
Leu Ala Ile Phe His Phe Val Thr Thr Lys Ser Asp Asp Asp Ala Ala
            35                  40                  45 acc aag gcg tcg atg gcc gcg ttc gtc ccc gcg atg gcc atg tcg ctg   192
Thr Lys Ala Ser Met Ala Ala Phe Val Pro Ala Met Ala Met Ser Leu
        50                  55                  60 tgt ctg acg atg ctg gcc ctc aac ctg ctg ccc acg acc ctc gcg acc   240
Cys Leu Thr Met Leu Ala Leu Asn Leu Leu Pro Thr Thr Leu Ala Thr
65                  70                  75                  80 tac cgg gag aag ggc atc ctg cgg cgc atg gcc gcg agc ccc atc cac   288
Tyr Arg Glu Lys Gly Ile Leu Arg Arg Met Ala Ala Ser Pro Ile His
                85                  90                  95
```

```
ccg ggg aac ctg ctg ctc gcc cag ctc ttc atc aac ctg gtc acc gcg      336
Pro Gly Asn Leu Leu Leu Ala Gln Leu Phe Ile Asn Leu Val Thr Ala
            100                 105                 110 gcg gtc tcc gcg gtg ctg gtg ctc atc gtc ggc aag acc gcc ttc gac      384
Ala Val Ser Ala Val Leu Val Leu Ile Val Gly Lys Thr Ala Phe Asp
            115                 120                 125 acc aaa ctg ccc ggc gac gtc ccc gcc ttc ctg gtg agc ttc gtc ctg      432
Thr Lys Leu Pro Gly Asp Val Pro Ala Phe Leu Val Ser Phe Val Leu
        130                 135                 140 ggc acc tgg gcg ctg ttc tcc atc ggc ctg gtg atc gcg gcc gtg gcc      480
Gly Thr Trp Ala Leu Phe Ser Ile Gly Leu Val Ile Ala Ala Val Ala
145                 150                 155                 160 ccg agc agc aaa tcg gcc acc gcg atg ggc ctc tcc ctc ctc ttc ccc      528
Pro Ser Ser Lys Ser Ala Thr Ala Met Gly Leu Ser Leu Leu Phe Pro
                165                 170                 175 agc ctc ttc ttc ggc ggc gcg ttc ctc ccc aag gag gac ctg ccg gag      576
Ser Leu Phe Phe Gly Gly Ala Phe Leu Pro Lys Glu Asp Leu Pro Glu
            180                 185                 190 acg gtg tcc acc atc ggc gac tac acc ccg ctg ggc gcc gcg ctc cag      624
Thr Val Ser Thr Ile Gly Asp Tyr Thr Pro Leu Gly Ala Ala Leu Gln
            195                 200                 205 gcg ctg cgc gac tcc tgg gag aac cag tgg ccg cag acc ctg cac ctg      672
Ala Leu Arg Asp Ser Trp Glu Asn Gln Trp Pro Gln Thr Leu His Leu
        210                 215                 220 acc gtc ctc ggg gtg atc gcg gtt gcc gcc acc gcg gcc gcg gcc aag      720
Thr Val Leu Gly Val Ile Ala Val Ala Ala Thr Ala Ala Ala Ala Lys
225                 230                 235                 240 ctg ttc cgc tgg gag tga                                              738
Leu Phe Arg Trp Glu
            245

<210> SEQ ID NO 32
<211> LENGTH: 245
<212> TYPE: PRT
<213> ORGANISM: Streptomyces sp. NRRL 30748

<400> SEQUENCE: 32

Met Ser Gly Arg Thr Lys Leu Thr Tyr Val Glu Ser Lys Leu Phe Leu
1               5                   10                  15

Arg Asp Pro Thr Ala Val Phe Phe Val Ile Ala Leu Pro Ile Met Leu
            20                  25                  30

Leu Ala Ile Phe His Phe Val Thr Thr Lys Ser Asp Asp Ala Ala
        35                  40                  45

Thr Lys Ala Ser Met Ala Ala Phe Val Pro Ala Met Ala Met Ser Leu
    50                  55                  60

Cys Leu Thr Met Leu Ala Leu Asn Leu Leu Pro Thr Thr Leu Ala Thr
65                  70                  75                  80

Tyr Arg Glu Lys Gly Ile Leu Arg Arg Met Ala Ala Ser Pro Ile His
                85                  90                  95

Pro Gly Asn Leu Leu Leu Ala Gln Leu Phe Ile Asn Leu Val Thr Ala
            100                 105                 110

Ala Val Ser Ala Val Leu Val Leu Ile Val Gly Lys Thr Ala Phe Asp
            115                 120                 125

Thr Lys Leu Pro Gly Asp Val Pro Ala Phe Leu Val Ser Phe Val Leu
        130                 135                 140

Gly Thr Trp Ala Leu Phe Ser Ile Gly Leu Val Ile Ala Ala Val Ala
145                 150                 155                 160

Pro Ser Ser Lys Ser Ala Thr Ala Met Gly Leu Ser Leu Leu Phe Pro
```

```
                165                 170                 175
Ser Leu Phe Phe Gly Gly Ala Phe Leu Pro Lys Glu Asp Leu Pro Glu
            180                 185                 190

Thr Val Ser Thr Ile Gly Asp Tyr Thr Pro Leu Gly Ala Ala Leu Gln
            195                 200                 205

Ala Leu Arg Asp Ser Trp Glu Asn Gln Trp Pro Gln Thr Leu His Leu
            210                 215                 220

Thr Val Leu Gly Val Ile Ala Val Ala Ala Thr Ala Ala Ala Ala Lys
225                 230                 235                 240

Leu Phe Arg Trp Glu
                245

<210> SEQ ID NO 33
<211> LENGTH: 1263
<212> TYPE: DNA
<213> ORGANISM: Streptomyces sp. NRRL 30748
<220> FEATURE:
<221> NAME/KEY: CDS
<222> LOCATION: (1)..(1263)

<400> SEQUENCE: 33 gtg agc gcg tcc aag gac gac ggc gga cgg tgg gag cgg cac tcc gac    48
Val Ser Ala Ser Lys Asp Asp Gly Gly Arg Trp Glu Arg His Ser Asp
1               5                   10                  15 atc ctg ttc gga ggg ctg ccc tac ctt ctg ctg ttt ctg tcc acg gcc    96
Ile Leu Phe Gly Gly Leu Pro Tyr Leu Leu Leu Phe Leu Ser Thr Ala
                20                  25                  30 ctg agc ctg gtc cac ggc ccg ccc ccg gcc cgg cgg ctg ctc acc acg   144
Leu Ser Leu Val His Gly Pro Pro Pro Ala Arg Arg Leu Leu Thr Thr
            35                  40                  45 ctc ggc ctc gtg gcc gtg gcc gcc gtc tgg atc ctg ggc acc tac acc   192
Leu Gly Leu Val Ala Val Ala Ala Val Trp Ile Leu Gly Thr Tyr Thr
        50                  55                  60 ctg ccc acg ggc cgc cgc agc aga cag ccg tac ggc atg gcg cgc acg   240
Leu Pro Thr Gly Arg Arg Ser Arg Gln Pro Tyr Gly Met Ala Arg Thr
65                  70                  75                  80 gcc gtc tac ttc gcc ggg ctg ctc gcc ctc tcc gcc gcg ctg atg gcg   288
Ala Val Tyr Phe Ala Gly Leu Leu Ala Leu Ser Ala Ala Leu Met Ala
                85                  90                  95 cgg gac cag gtg ttc atg ctg ttc gcc gcc acc ggg ttc ctc cag gcg   336
Arg Asp Gln Val Phe Met Leu Phe Ala Ala Thr Gly Phe Leu Gln Ala
                100                 105                 110 ctg gtg ctg ctg ccg acc gtc tgg gcg ctg gtg tcc gtg gcg gcc acc   384
Leu Val Leu Leu Pro Thr Val Trp Ala Leu Val Ser Val Ala Ala Thr
            115                 120                 125 tcg ttc gtc gtc aat acc gtg ccg gac ggc ttc ccc cgg ccc acc acc   432
Ser Phe Val Val Asn Thr Val Pro Asp Gly Phe Pro Arg Pro Thr Thr
        130                 135                 140 ggc gcg gtg gtc ggc tat ctc gcc gcc atc gcc ttc cag acc gtg gtg   480
Gly Ala Val Val Gly Tyr Leu Ala Ala Ile Ala Phe Gln Thr Val Val
145                 150                 155                 160 atc ggc tgg atc aat ctg ctg tcg agc cgg ctc aac gaa cag cat cag   528
Ile Gly Trp Ile Asn Leu Leu Ser Ser Arg Leu Asn Glu Gln His Gln
                165                 170                 175 cgg cgc aaa cgc acc gtg gcc gaa ctc cgc tcc gcg ctc acc gag aac   576
Arg Arg Lys Arg Thr Val Ala Glu Leu Arg Ser Ala Leu Thr Glu Asn
                180                 185                 190 gcc gga ctc cac gcc cag ctg atc acc cag gcg cgc gag gcc gga gtg   624
Ala Gly Leu His Ala Gln Leu Ile Thr Gln Ala Arg Glu Ala Gly Val
            195                 200                 205
```

```
ctc gac gag cgc cag cgg atg gcg ggg gag atc cat gac acc ctc gcc    672
Leu Asp Glu Arg Gln Arg Met Ala Gly Glu Ile His Asp Thr Leu Ala
    210                 215                 220 cag ggg ctg gcc ggc atc atc cgg caa ctg gag gcc gcc gaa cac gcg    720
Gln Gly Leu Ala Gly Ile Ile Arg Gln Leu Glu Ala Ala Glu His Ala
225                 230                 235                 240 gag ggc gac cgc gag gtg tgg cgg cgc cat ctc gtc gct gcc aag gac    768
Glu Gly Asp Arg Glu Val Trp Arg Arg His Leu Val Ala Ala Lys Asp
                245                 250                 255 ctg gcc cgg gac agc ctg gcc gag gcg cgc cgt tcg gtc cag gcg ctc    816
Leu Ala Arg Asp Ser Leu Ala Glu Ala Arg Arg Ser Val Gln Ala Leu
            260                 265                 270 cgc ccc gag cga ctg gag tcc cgg acg ctg ccg gac gcc ttg gag tcg    864
Arg Pro Glu Arg Leu Glu Ser Arg Thr Leu Pro Asp Ala Leu Glu Ser
        275                 280                 285 ctg gcc gag ggg tgg tcg cag gag cgg gag ccg aag gcc gcg ttc gcg    912
Leu Ala Glu Gly Trp Ser Gln Glu Arg Glu Pro Lys Ala Ala Phe Ala
    290                 295                 300 acg aac ggg acc gcc atc ccg ctc cac gcc gag ctg gag gcc acg ctc    960
Thr Asn Gly Thr Ala Ile Pro Leu His Ala Glu Leu Glu Ala Thr Leu
305                 310                 315                 320 tac cgg gtg gcg cag gag gcg ctc gcc aac atc gcc aag cac gcc cgg    1008
Tyr Arg Val Ala Gln Glu Ala Leu Ala Asn Ile Ala Lys His Ala Arg
                325                 330                 335 gcg tcg aag gtg ggc atc acc ctg tcg tac atg gag gac gtg gtg gtc    1056
Ala Ser Lys Val Gly Ile Thr Leu Ser Tyr Met Glu Asp Val Val Val
            340                 345                 350 ctc gac gta ctc gac gac ggc gtc gga ttc gac ccc gcg gcc gcg gcg    1104
Leu Asp Val Leu Asp Asp Gly Val Gly Phe Asp Pro Ala Ala Ala Ala
        355                 360                 365 gcc gag gcc ggt gcc tcc ggc ggc cat ggc ctc ggg ctg gtg gcg atg    1152
Ala Glu Ala Gly Ala Ser Gly Gly His Gly Leu Gly Leu Val Ala Met
    370                 375                 380 cgg cgc cga ctg ggc cgg gtc gcc ggt acg ttg gac atc gaa agc gcc    1200
Arg Arg Arg Leu Gly Arg Val Ala Gly Thr Leu Asp Ile Glu Ser Ala
385                 390                 395                 400 cgt ggc gag ggc gcc gcc atc agc gcg gcc gtc ccc gtg atc ccc cag    1248
Arg Gly Glu Gly Ala Ala Ile Ser Ala Ala Val Pro Val Ile Pro Gln
                405                 410                 415 gaa gcc ggt gca tga                                                1263
Glu Ala Gly Ala
            420

<210> SEQ ID NO 34
<211> LENGTH: 420
<212> TYPE: PRT
<213> ORGANISM: Streptomyces sp. NRRL 30748

<400> SEQUENCE: 34

Val Ser Ala Ser Lys Asp Asp Gly Gly Arg Trp Glu Arg His Ser Asp
1               5                   10                  15

Ile Leu Phe Gly Gly Leu Pro Tyr Leu Leu Phe Leu Ser Thr Ala
            20                  25                  30

Leu Ser Leu Val His Gly Pro Pro Ala Arg Arg Leu Leu Thr Thr
        35                  40                  45

Leu Gly Leu Val Ala Val Ala Ala Val Trp Ile Leu Gly Thr Tyr Thr
    50                  55                  60

Leu Pro Thr Gly Arg Arg Ser Arg Gln Pro Tyr Gly Met Ala Arg Thr
65                  70                  75                  80
```

```
Ala Val Tyr Phe Ala Gly Leu Leu Ala Leu Ser Ala Ala Leu Met Ala
                85                  90                  95

Arg Asp Gln Val Phe Met Leu Phe Ala Ala Thr Gly Phe Leu Gln Ala
            100                 105                 110

Leu Val Leu Leu Pro Thr Val Trp Ala Leu Val Ser Val Ala Ala Thr
        115                 120                 125

Ser Phe Val Val Asn Thr Val Pro Asp Gly Phe Pro Arg Pro Thr Thr
    130                 135                 140

Gly Ala Val Val Gly Tyr Leu Ala Ala Ile Ala Phe Gln Thr Val Val
145                 150                 155                 160

Ile Gly Trp Ile Asn Leu Leu Ser Ser Arg Leu Asn Glu Gln His Gln
                165                 170                 175

Arg Arg Lys Arg Thr Val Ala Glu Leu Arg Ser Ala Leu Thr Glu Asn
            180                 185                 190

Ala Gly Leu His Ala Gln Leu Ile Thr Gln Ala Arg Glu Ala Gly Val
        195                 200                 205

Leu Asp Glu Arg Gln Arg Met Ala Gly Glu Ile His Asp Thr Leu Ala
    210                 215                 220

Gln Gly Leu Ala Gly Ile Ile Arg Gln Leu Glu Ala Ala Glu His Ala
225                 230                 235                 240

Glu Gly Asp Arg Glu Val Trp Arg Arg His Leu Val Ala Ala Lys Asp
                245                 250                 255

Leu Ala Arg Asp Ser Leu Ala Glu Ala Arg Arg Ser Val Gln Ala Leu
            260                 265                 270

Arg Pro Glu Arg Leu Glu Ser Arg Thr Leu Pro Asp Ala Leu Glu Ser
        275                 280                 285

Leu Ala Glu Gly Trp Ser Gln Glu Arg Glu Pro Lys Ala Ala Phe Ala
    290                 295                 300

Thr Asn Gly Thr Ala Ile Pro Leu His Ala Glu Leu Glu Ala Thr Leu
305                 310                 315                 320

Tyr Arg Val Ala Gln Glu Ala Leu Ala Asn Ile Ala Lys His Ala Arg
                325                 330                 335

Ala Ser Lys Val Gly Ile Thr Leu Ser Tyr Met Glu Asp Val Val Val
            340                 345                 350

Leu Asp Val Leu Asp Asp Gly Val Gly Phe Asp Pro Ala Ala Ala Ala
        355                 360                 365

Ala Glu Ala Gly Ala Ser Gly Gly His Gly Leu Gly Leu Val Ala Met
    370                 375                 380

Arg Arg Arg Leu Gly Arg Val Ala Gly Thr Leu Asp Ile Glu Ser Ala
385                 390                 395                 400

Arg Gly Glu Gly Ala Ala Ile Ser Ala Ala Val Pro Val Ile Pro Gln
                405                 410                 415

Glu Ala Gly Ala
            420

<210> SEQ ID NO 35
<211> LENGTH: 663
<212> TYPE: DNA
<213> ORGANISM: Streptomyces sp. NRRL 30748
<220> FEATURE:
<221> NAME/KEY: CDS
<222> LOCATION: (1)..(663)

<400> SEQUENCE: 35 atg agc gga aac acc cat ggc ggc gac acc ccc ggc ccc agc ccc atc     48
```

```
Met Ser Gly Asn Thr His Gly Gly Asp Thr Pro Gly Pro Ser Pro Ile
 1               5                  10                  15 cgt atc ctc atc gtc gac gac cac ccg gtg gtc cgc gac ggg ctg cgc         96
Arg Ile Leu Ile Val Asp Asp His Pro Val Val Arg Asp Gly Leu Arg
            20                  25                  30 ggg gtg ctg gag cgg gac ccc gac ttc acg gtg acc ggc gag gcc ggt        144
Gly Val Leu Glu Arg Asp Pro Asp Phe Thr Val Thr Gly Glu Ala Gly
        35                  40                  45 gac ggt gcc gag gcc gtc gaa ctg tac gag cga cag ccg gcc gat gtg        192
Asp Gly Ala Glu Ala Val Glu Leu Tyr Glu Arg Gln Pro Ala Asp Val
    50                  55                  60 gtc ctg atg gac ctg cgc atg ccc cgg atg ggc ggc gtg gag gcc atc        240
Val Leu Met Asp Leu Arg Met Pro Arg Met Gly Gly Val Glu Ala Ile
65                  70                  75                  80 aaa cgg ctg ctg cgc ggc gac ccc gag gcc cgg atc ctg gtg ctg acc        288
Lys Arg Leu Leu Arg Gly Asp Pro Glu Ala Arg Ile Leu Val Leu Thr
                85                  90                  95 acc tat gac acc gac agc gac gtc atg ggc gcc ctg gcc gcc ggg gcg        336
Thr Tyr Asp Thr Asp Ser Asp Val Met Gly Ala Leu Ala Ala Gly Ala
            100                 105                 110 acc ggc tat ctc ctc aag gac acc ccg cgc gag gag ctg acc cgc gcc        384
Thr Gly Tyr Leu Leu Lys Asp Thr Pro Arg Glu Glu Leu Thr Arg Ala
        115                 120                 125 gtg cga tcc gcc tcc tcg ggc cag tcc gtc ctc tcg ccc gcg gtc acc        432
Val Arg Ser Ala Ser Ser Gly Gln Ser Val Leu Ser Pro Ala Val Thr
    130                 135                 140 gga cgc gtt ctc ggc cag gta cgc aaa ccc acc cag ggc ccg ctg agc        480
Gly Arg Val Leu Gly Gln Val Arg Lys Pro Thr Gln Gly Pro Leu Ser
145                 150                 155                 160 gac cgt gaa ctc caa gtg ctc agg ctt atc gcg gac ggg gcc acg aat        528
Asp Arg Glu Leu Gln Val Leu Arg Leu Ile Ala Asp Gly Ala Thr Asn
                165                 170                 175 cga cag gcc gcg gcc gca ttg ttc atc agc cag gcc acc gtc aag acg        576
Arg Gln Ala Ala Ala Ala Leu Phe Ile Ser Gln Ala Thr Val Lys Thr
            180                 185                 190 cat ctt ctg cat gtc tac gag aaa ctc ggg gtg aag gat cgc gcg gca        624
His Leu Leu His Val Tyr Glu Lys Leu Gly Val Lys Asp Arg Ala Ala
        195                 200                 205 gcg gtc agc gag gcc cat aaa cga cat cta ttc gaa tga                    663
Ala Val Ser Glu Ala His Lys Arg His Leu Phe Glu
    210                 215                 220

<210> SEQ ID NO 36
<211> LENGTH: 220
<212> TYPE: PRT
<213> ORGANISM: Streptomyces sp. NRRL 30748

<400> SEQUENCE: 36

Met Ser Gly Asn Thr His Gly Gly Asp Thr Pro Gly Pro Ser Pro Ile
 1               5                  10                  15

Arg Ile Leu Ile Val Asp Asp His Pro Val Val Arg Asp Gly Leu Arg
            20                  25                  30

Gly Val Leu Glu Arg Asp Pro Asp Phe Thr Val Thr Gly Glu Ala Gly
        35                  40                  45

Asp Gly Ala Glu Ala Val Glu Leu Tyr Glu Arg Gln Pro Ala Asp Val
    50                  55                  60

Val Leu Met Asp Leu Arg Met Pro Arg Met Gly Gly Val Glu Ala Ile
65                  70                  75                  80

Lys Arg Leu Leu Arg Gly Asp Pro Glu Ala Arg Ile Leu Val Leu Thr
```

```
                  85                  90                  95
Thr Tyr Asp Thr Asp Ser Asp Val Met Gly Ala Leu Ala Ala Gly Ala
            100                 105                 110

Thr Gly Tyr Leu Leu Lys Asp Thr Pro Arg Glu Glu Leu Thr Arg Ala
            115                 120                 125

Val Arg Ser Ala Ser Ser Gly Gln Ser Val Leu Ser Pro Ala Val Thr
        130                 135                 140

Gly Arg Val Leu Gly Gln Val Arg Lys Pro Thr Gln Gly Pro Leu Ser
145                 150                 155                 160

Asp Arg Glu Leu Gln Val Leu Arg Leu Ile Ala Asp Gly Ala Thr Asn
                165                 170                 175

Arg Gln Ala Ala Ala Ala Leu Phe Ile Ser Gln Ala Thr Val Lys Thr
            180                 185                 190

His Leu Leu His Val Tyr Glu Lys Leu Gly Val Lys Asp Arg Ala Ala
            195                 200                 205

Ala Val Ser Glu Ala His Lys Arg His Leu Phe Glu
        210                 215                 220

<210> SEQ ID NO 37
<211> LENGTH: 966
<212> TYPE: DNA
<213> ORGANISM: Streptomyces sp. NRRL 30748
<220> FEATURE:
<221> NAME/KEY: CDS
<222> LOCATION: (1)..(966)

<400> SEQUENCE: 37
```

| | | | | | | | | | | | | | | | | |
|---|---|---|---|---|---|---|---|---|---|---|---|---|---|---|---|---|
| atg | ggc | cac | atc | cga | gat | cgg | cag | gcc | gtt | gtc | atc | ggc | ggc | acc | gga | 48 |
| Met | Gly | His | Ile | Arg | Asp | Arg | Gln | Ala | Val | Val | Ile | Gly | Gly | Thr | Gly | |
| 1 | | | | 5 | | | | | 10 | | | | | 15 | | |
| ttc | atc | ggg | cga | cat | atc | tgc | aga | gct | ctc | gcc | aag | cgc | gga | tat | gaa | 96 |
| Phe | Ile | Gly | Arg | His | Ile | Cys | Arg | Ala | Leu | Ala | Lys | Arg | Gly | Tyr | Glu | |
| | | | 20 | | | | | 25 | | | | | 30 | | | |
| gtc | ctg | gca | ata | gcg | aga | aaa | ccc | gcc | gaa | ccc | att | ccc | gga | gtc | gtc | 144 |
| Val | Leu | Ala | Ile | Ala | Arg | Lys | Pro | Ala | Glu | Pro | Ile | Pro | Gly | Val | Val | |
| | | | 35 | | | | | 40 | | | | | 45 | | | |
| ttt | ttg | gca | ctt | gac | gcg | gta | tcc | gcg | ccg | agc | gag | aac | atc | gtc | cgg | 192 |
| Phe | Leu | Ala | Leu | Asp | Ala | Val | Ser | Ala | Pro | Ser | Glu | Asn | Ile | Val | Arg | |
| | 50 | | | | | 55 | | | | | 60 | | | | | |
| gcc | gca | cag | tcc | gcc | gat | ctc | gtc | gtc | aac | gcc | gcg | ggc | gac | agc | tgg | 240 |
| Ala | Ala | Gln | Ser | Ala | Asp | Leu | Val | Val | Asn | Ala | Ala | Gly | Asp | Ser | Trp | |
| 65 | | | | | 70 | | | | | 75 | | | | | 80 | |
| gag | ggc | gac | gag | gcg | agc | atg | acg | gcc | tcg | cac | atc | ccg | ctc | gtg | gac | 288 |
| Glu | Gly | Asp | Glu | Ala | Ser | Met | Thr | Ala | Ser | His | Ile | Pro | Leu | Val | Asp | |
| | | | | 85 | | | | | 90 | | | | | 95 | | |
| cgg | ctg | gtg | gac | gcc | gtg | gcg | acc | ctc | ccc | agg | cga | ccg | cgc | ctg | gtc | 336 |
| Arg | Leu | Val | Asp | Ala | Val | Ala | Thr | Leu | Pro | Arg | Arg | Pro | Arg | Leu | Val | |
| | | | 100 | | | | | 105 | | | | | 110 | | | |
| cat | ctg | ggc | tcg | gtg | cac | gag | tac | ggc | ccc | gtc | ccc | gac | ggc | acg | gcc | 384 |
| His | Leu | Gly | Ser | Val | His | Glu | Tyr | Gly | Pro | Val | Pro | Asp | Gly | Thr | Ala | |
| | | | 115 | | | | | 120 | | | | | 125 | | | |
| atc | gcc | gag | gac | cac | ccc | acc | gcc | ccc | cgc | acc | ccc | tac | gcc | cgc | acc | 432 |
| Ile | Ala | Glu | Asp | His | Pro | Thr | Ala | Pro | Arg | Thr | Pro | Tyr | Ala | Arg | Thr | |
| | | | 130 | | | | | 135 | | | | | 140 | | | |
| aag | ctc | gtg | ggc | agc | cgg | atc | gtg | ctg | ggc | gcc | gcg | gac | gcg | ggc | cgt | 480 |
| Lys | Leu | Val | Gly | Ser | Arg | Ile | Val | Leu | Gly | Ala | Ala | Asp | Ala | Gly | Arg | |
| 145 | | | | | 150 | | | | | 155 | | | | | 160 | |
| atc | gac | ggc | tgc | gtg | ctg | cgc | gtc | acc | aac | gtc | tgc | gga | ccg | ggc | acc | 528 |
| Ile | Asp | Gly | Cys | Val | Leu | Arg | Val | Thr | Asn | Val | Cys | Gly | Pro | Gly | Thr | |

```
ccc cgg ggc agc ttc ctc ggg ctc gcc cac cgg ctg cgc cac acc      576
Pro Arg Gly Ser Phe Leu Gly Gly Leu Ala His Arg Leu Arg His Thr
            180                 185                 190 acc gag gac acc ccg ctc acc gtc acc ctc gtc gac gac cgg cgc gac  624
Thr Glu Asp Thr Pro Leu Thr Val Thr Leu Val Asp Asp Arg Arg Asp
        195                 200                 205 ttc atc gac gtc cgc gat gtc gcc gag gcc gtg gtg ctg gcc gcg agc  672
Phe Ile Asp Val Arg Asp Val Ala Glu Ala Val Val Leu Ala Ala Ser
    210                 215                 220 agc ccg gtg acc ggc cgg gtg ctc aac atc ggc cag ggc gac gcc ttc  720
Ser Pro Val Thr Gly Arg Val Leu Asn Ile Gly Gln Gly Asp Ala Phe
225                 230                 235                 240 agc atg cgc gaa ctg gcc ggg ctg ctg atc gcc gcc tcc cag gtc ccc  768
Ser Met Arg Glu Leu Ala Gly Leu Leu Ile Ala Ala Ser Gln Val Pro
                245                 250                 255 gac cgt ctg gtg cgc gag gag agc ggc gcc gtg cac agc aag ggc ggc  816
Asp Arg Leu Val Arg Glu Glu Ser Gly Ala Val His Ser Lys Gly Gly
            260                 265                 270 agc tgg acc cag gcc gac atc cgc ctc gcc cgg cgg ctc atg ggc tgg  864
Ser Trp Thr Gln Ala Asp Ile Arg Leu Ala Arg Arg Leu Met Gly Trp
        275                 280                 285 tcc ccg aag gtg gcc ctc aaa gaa tcc ctc cac gac ctg tgg gcc gcc  912
Ser Pro Lys Val Ala Leu Lys Glu Ser Leu His Asp Leu Trp Ala Ala
    290                 295                 300 tcc gcc act tcc agc cgg ccg gct gcc gcg gcg gcc cgt acc gaa gga  960
Ser Ala Thr Ser Ser Arg Pro Ala Ala Ala Ala Arg Thr Glu Gly
305                 310                 315                 320 cac tga                                                          966
His
```

<210> SEQ ID NO 38
<211> LENGTH: 321
<212> TYPE: PRT
<213> ORGANISM: Streptomyces sp. NRRL 30748

<400> SEQUENCE: 38

```
Met Gly His Ile Arg Asp Arg Gln Ala Val Val Ile Gly Gly Thr Gly
1               5                   10                  15

Phe Ile Gly Arg His Ile Cys Arg Ala Leu Ala Lys Arg Gly Tyr Glu
            20                  25                  30

Val Leu Ala Ile Ala Arg Lys Pro Ala Glu Pro Ile Pro Gly Val Val
        35                  40                  45

Phe Leu Ala Leu Asp Ala Val Ser Ala Pro Ser Glu Asn Ile Val Arg
    50                  55                  60

Ala Ala Gln Ser Ala Asp Leu Val Val Asn Ala Ala Gly Asp Ser Trp
65                  70                  75                  80

Glu Gly Asp Glu Ala Ser Met Thr Ala Ser His Ile Pro Leu Val Asp
                85                  90                  95

Arg Leu Val Asp Ala Val Ala Thr Leu Pro Arg Arg Pro Arg Leu Val
            100                 105                 110

His Leu Gly Ser Val His Glu Tyr Gly Pro Val Pro Asp Gly Thr Ala
        115                 120                 125

Ile Ala Glu Asp His Pro Thr Ala Pro Arg Thr Pro Tyr Ala Arg Thr
    130                 135                 140

Lys Leu Val Gly Ser Arg Ile Val Leu Gly Ala Ala Asp Ala Gly Arg
145                 150                 155                 160
```

-continued

```
Ile Asp Gly Cys Val Leu Arg Val Thr Asn Val Cys Gly Pro Gly Thr
            165                 170                 175

Pro Arg Gly Ser Phe Leu Gly Gly Leu Ala His Arg Leu Arg His Thr
        180                 185                 190

Thr Glu Asp Thr Pro Leu Thr Val Thr Leu Val Asp Asp Arg Arg Asp
    195                 200                 205

Phe Ile Asp Val Arg Asp Val Ala Glu Ala Val Leu Ala Ala Ser
210                 215                 220

Ser Pro Val Thr Gly Arg Val Leu Asn Ile Gly Gln Gly Asp Ala Phe
225                 230                 235                 240

Ser Met Arg Glu Leu Ala Gly Leu Leu Ile Ala Ala Ser Gln Val Pro
            245                 250                 255

Asp Arg Leu Val Arg Glu Glu Ser Gly Ala Val His Ser Lys Gly Gly
        260                 265                 270

Ser Trp Thr Gln Ala Asp Ile Arg Leu Ala Arg Arg Leu Met Gly Trp
    275                 280                 285

Ser Pro Lys Val Ala Leu Lys Glu Ser Leu His Asp Leu Trp Ala Ala
290                 295                 300

Ser Ala Thr Ser Ser Arg Pro Ala Ala Ala Ala Arg Thr Glu Gly
305                 310                 315                 320

His
```

<210> SEQ ID NO 39
<211> LENGTH: 987
<212> TYPE: DNA
<213> ORGANISM: Streptomyces sp. NRRL 30748
<220> FEATURE:
<221> NAME/KEY: CDS
<222> LOCATION: (1)..(987)

<400> SEQUENCE: 39

```
atg cag tac acc tat ctc ggc cgc acc gcc ctc aag gtg agc cga ctg      48
Met Gln Tyr Thr Tyr Leu Gly Arg Thr Ala Leu Lys Val Ser Arg Leu
1               5                   10                  15 tgc ctg ggc acc ctg aac ctc ggg gtg agg gcg agc gac gag gag agc      96
Cys Leu Gly Thr Leu Asn Leu Gly Val Arg Ala Ser Asp Glu Glu Ser
                20                  25                  30 cac gcg atc ctg gac acc gcc ctg gac cgc ggg gtc aac ttc atc gac     144
His Ala Ile Leu Asp Thr Ala Leu Asp Arg Gly Val Asn Phe Ile Asp
            35                  40                  45 acc gcc aac cag tac ggc tgg cag aag cac aag ggc tat acc gag gag     192
Thr Ala Asn Gln Tyr Gly Trp Gln Lys His Lys Gly Tyr Thr Glu Glu
        50                  55                  60 ttc ctc ggc ggc tgg ttc gcg gaa ggc ggc ggc cgg cgc gag aag gtc     240
Phe Leu Gly Gly Trp Phe Ala Glu Gly Gly Gly Arg Arg Glu Lys Val
65                  70                  75                  80 gtc ctg ggc acc aag gtc ttc aac gcg atg acc gac tgg ccc aat gac     288
Val Leu Gly Thr Lys Val Phe Asn Ala Met Thr Asp Trp Pro Asn Asp
                85                  90                  95 tcg ggg ctg tcc gcc cgg cac atc atc gcc tcc tgc gag gac tcg ctg     336
Ser Gly Leu Ser Ala Arg His Ile Ile Ala Ser Cys Glu Asp Ser Leu
            100                 105                 110 cgc cgg atg ggc acc gac tgg atc gat ctg ttc cag atg cac cac atc     384
Arg Arg Met Gly Thr Asp Trp Ile Asp Leu Phe Gln Met His His Ile
        115                 120                 125 gac cgc cac gcc ccg tgg gag gag gtg tgg cag gcg atg gag acg ctg     432
Asp Arg His Ala Pro Trp Glu Glu Val Trp Gln Ala Met Glu Thr Leu
    130                 135                 140
```

```
acc cgg cag ggc aag gtg cgc tac gtc ggc tcg tcc aac ttc gcc ggc      480
Thr Arg Gln Gly Lys Val Arg Tyr Val Gly Ser Ser Asn Phe Ala Gly
145                 150                 155                 160 tgg cac atc gcc gag gcc cag gag gcc gcg gcc cgc cgc cac ttc ctc      528
Trp His Ile Ala Glu Ala Gln Glu Ala Ala Ala Arg Arg His Phe Leu
                165                 170                 175 ggc atc gtc tcc gag cag agc gtg tac aac ctc gtc acc cgc cat atc      576
Gly Ile Val Ser Glu Gln Ser Val Tyr Asn Leu Val Thr Arg His Ile
            180                 185                 190 gaa ctg gag ctg atc ccc gcc gcc cag cgg tac ggg tcg ggg gtg ctc      624
Glu Leu Glu Leu Ile Pro Ala Ala Gln Arg Tyr Gly Val Gly Val Leu
        195                 200                 205 gcc tgg tcg ccg ctg cac ggc ggg ctc ctc agc ggg gcg ctg cgc aag      672
Ala Trp Ser Pro Leu His Gly Gly Leu Leu Ser Gly Ala Leu Arg Lys
    210                 215                 220 ctg gcc gag ggc acc gcg atg aag acc gcc cag ggc cgg gcc gcc cag      720
Leu Ala Glu Gly Thr Ala Met Lys Thr Ala Gln Gly Arg Ala Ala Gln
225                 230                 235                 240 gcg ctc gag gtc cac cgg gac gcc gtc gcc gcg tac gag aag ctg tgc      768
Ala Leu Glu Val His Arg Asp Ala Val Ala Ala Tyr Glu Lys Leu Cys
                245                 250                 255 gac ggc ctc ggc gcc gac ccg gcc gag gtg ggt ctt gcc tgg gtg atg      816
Asp Gly Leu Gly Ala Asp Pro Ala Glu Val Gly Leu Ala Trp Val Met
            260                 265                 270 gga cgc ccc ggc atc acc gcg ccg gtc atc ggg ccg cgc agc ctg gac      864
Gly Arg Pro Gly Ile Thr Ala Pro Val Ile Gly Pro Arg Ser Leu Asp
        275                 280                 285 cag ctg aca ggg gcc ttc aag gcc atg gag ctg acg ctg tcc gac gag      912
Gln Leu Thr Gly Ala Phe Lys Ala Met Glu Leu Thr Leu Ser Asp Glu
    290                 295                 300 gtg ctg gcc gaa ctg gac cgg ctg ttc ccg ccg atc ggc aac ggc ggc      960
Val Leu Ala Glu Leu Asp Arg Leu Phe Pro Pro Ile Gly Asn Gly Gly
305                 310                 315                 320 ccc ggg ccg gag gcg tgg gcg tgg tga                                  987
Pro Gly Pro Glu Ala Trp Ala Trp
                325
```

<210> SEQ ID NO 40
<211> LENGTH: 328
<212> TYPE: PRT
<213> ORGANISM: Streptomyces sp. NRRL 30748

<400> SEQUENCE: 40

```
Met Gln Tyr Thr Tyr Leu Gly Arg Thr Ala Leu Lys Val Ser Arg Leu
1               5                   10                  15

Cys Leu Gly Thr Leu Asn Leu Gly Val Arg Ala Ser Asp Glu Glu Ser
            20                  25                  30

His Ala Ile Leu Asp Thr Ala Leu Asp Arg Gly Val Asn Phe Ile Asp
        35                  40                  45

Thr Ala Asn Gln Tyr Gly Trp Gln Lys His Lys Gly Tyr Thr Glu Glu
    50                  55                  60

Phe Leu Gly Gly Trp Phe Ala Glu Gly Gly Arg Arg Glu Lys Val
65                  70                  75                  80

Val Leu Gly Thr Lys Val Phe Asn Ala Met Thr Asp Trp Pro Asn Asp
                85                  90                  95

Ser Gly Leu Ser Ala Arg His Ile Ile Ala Ser Cys Glu Asp Ser Leu
            100                 105                 110

Arg Arg Met Gly Thr Asp Trp Ile Asp Leu Phe Gln Met His His Ile
        115                 120                 125
```

```
Asp Arg His Ala Pro Trp Glu Glu Val Trp Gln Ala Met Glu Thr Leu
    130                 135                 140

Thr Arg Gln Gly Lys Val Arg Tyr Val Gly Ser Ser Asn Phe Ala Gly
145                 150                 155                 160

Trp His Ile Ala Glu Ala Gln Glu Ala Ala Ala Arg Arg His Phe Leu
                165                 170                 175

Gly Ile Val Ser Glu Gln Ser Val Tyr Asn Leu Val Thr Arg His Ile
            180                 185                 190

Glu Leu Glu Leu Ile Pro Ala Ala Gln Arg Tyr Gly Val Gly Val Leu
        195                 200                 205

Ala Trp Ser Pro Leu His Gly Gly Leu Leu Ser Gly Ala Leu Arg Lys
    210                 215                 220

Leu Ala Glu Gly Thr Ala Met Lys Thr Ala Gln Gly Arg Ala Ala Gln
225                 230                 235                 240

Ala Leu Glu Val His Arg Asp Ala Val Ala Ala Tyr Glu Lys Leu Cys
                245                 250                 255

Asp Gly Leu Gly Ala Asp Pro Ala Glu Val Gly Leu Ala Trp Val Met
            260                 265                 270

Gly Arg Pro Gly Ile Thr Ala Pro Val Ile Gly Pro Arg Ser Leu Asp
        275                 280                 285

Gln Leu Thr Gly Ala Phe Lys Ala Met Glu Leu Thr Leu Ser Asp Glu
    290                 295                 300

Val Leu Ala Glu Leu Asp Arg Leu Phe Pro Pro Ile Gly Asn Gly Gly
305                 310                 315                 320

Pro Gly Pro Glu Ala Trp Ala Trp
                325

<210> SEQ ID NO 41
<211> LENGTH: 1416
<212> TYPE: DNA
<213> ORGANISM: Streptomyces sp. NRRL 30748
<220> FEATURE:
<221> NAME/KEY: CDS
<222> LOCATION: (1)..(1416)

<400> SEQUENCE: 41 gtg ggc gtg gtg agc acg ctc cag gag cgg ctg atc cgc tcc gcc gcc      48
Val Gly Val Val Ser Thr Leu Gln Glu Arg Leu Ile Arg Ser Ala Ala
1               5                   10                  15 acc gtc gac agc tcg gtg acc ttg ctc gcc gac ttc cag cgc tgg ttc      96
Thr Val Asp Ser Ser Val Thr Leu Leu Ala Asp Phe Gln Arg Trp Phe
            20                  25                  30 cgc gag cgc gtc gac gcc gac gag tcc cgg atc gag atc atc ccg ttc     144
Arg Glu Arg Val Asp Ala Asp Glu Ser Arg Ile Glu Ile Ile Pro Phe
        35                  40                  45 gag gcg atg cgc ggc tgg gac ttc gcg ccg gac acc cac aac ctc gtc     192
Glu Ala Met Arg Gly Trp Asp Phe Ala Pro Asp Thr His Asn Leu Val
    50                  55                  60 cat gag acc ggc cgg ttc ttc acc gtc gag ggc atc cgg gtg cgg atg     240
His Glu Thr Gly Arg Phe Phe Thr Val Glu Gly Ile Arg Val Arg Met
65                  70                  75                  80 ccc ggg gcg ccg gtg gag gag tgg cgc cag ccg atc ctc cac cag ccg     288
Pro Gly Ala Pro Val Glu Glu Trp Arg Gln Pro Ile Leu His Gln Pro
                85                  90                  95 gag atc ggc atc ctg ggc gtc ctg gtc aag gac ttc gac ggc gta ccg     336
Glu Ile Gly Ile Leu Gly Val Leu Val Lys Asp Phe Asp Gly Val Pro
            100                 105                 110
```

-continued

| | | |
|---|---|---|
| cac ttc ctg atg cag gcc aag atg gag ccc ggt aac cac ggc gga ctc<br>His Phe Leu Met Gln Ala Lys Met Glu Pro Gly Asn His Gly Gly Leu<br>115                        120                   125 | 384 |
| cag ctg tcg ccc acc gtc cag gcc acc cgc agc aac tac acc cgg gtg<br>Gln Leu Ser Pro Thr Val Gln Ala Thr Arg Ser Asn Tyr Thr Arg Val<br>    130                     135                   140 | 432 |
| cac aag ggc cgg gcg gtg ccg tat ctg gag tac ttc cag cgg acg gaa<br>His Lys Gly Arg Ala Val Pro Tyr Leu Glu Tyr Phe Gln Arg Thr Glu<br>145                     150                   155                 160 | 480 |
| cgg cac cgg gtg ctc gcc gac gtc cgt cag tcg gag cag ggc agc tgg<br>Arg His Arg Val Leu Ala Asp Val Arg Gln Ser Glu Gln Gly Ser Trp<br>                   165                   170                 175 | 528 |
| ttc ttc cgc aag cgc aac cgc aac atg ctg gtc gag gtg gcg ccg gac<br>Phe Phe Arg Lys Arg Asn Arg Asn Met Leu Val Glu Val Ala Pro Asp<br>    180                     185                   190 | 576 |
| gtg gac gtc gag gtg cgc gac ggc ttc cgc tgg ctg acg ctg ggc cag<br>Val Asp Val Glu Val Arg Asp Gly Phe Arg Trp Leu Thr Leu Gly Gln<br>195                     200                   205 | 624 |
| ctg cac cat ctg ctg gcc gtg gag gac ctg gtg aac atg gac gcg cgc<br>Leu His His Leu Leu Ala Val Glu Asp Leu Val Asn Met Asp Ala Arg<br>    210                     215                   220 | 672 |
| agc gtc ctg gcc tgt ctg ccg cac tcc ccg ctg gac ccg gag gag acc<br>Ser Val Leu Ala Cys Leu Pro His Ser Pro Leu Asp Pro Glu Glu Thr<br>225                     230                   235                 240 | 720 |
| ttc ccg gcc acc gga tca cgc ggg acc gcg gag ccg gaa ccg ccg ggg<br>Phe Pro Ala Thr Gly Ser Arg Gly Thr Ala Glu Pro Glu Pro Pro Gly<br>                   245                   250                 255 | 768 |
| cgg cac gtc ctc cac cgc gac gcc gac atc ctc agc tgg atc acc gga<br>Arg His Val Leu His Arg Asp Ala Asp Ile Leu Ser Trp Ile Thr Gly<br>                  260                   265                 270 | 816 |
| ctg cgc acc gag cgc gag gtg ttc acc gag cgg ata ccg ctg cgg gag<br>Leu Arg Thr Glu Arg Glu Val Phe Thr Glu Arg Ile Pro Leu Arg Glu<br>            275                   280                 285 | 864 |
| acc acc ggc tgg cac cgc aac gcc cac cgc atc tcc cat gag agc gga<br>Thr Thr Gly Trp His Arg Asn Ala His Arg Ile Ser His Glu Ser Gly<br>    290                     295                   300 | 912 |
| cgc tac ttc agc gtg atg gcc gtg gac gtg acg gcg ggc ggc cgc gag<br>Arg Tyr Phe Ser Val Met Ala Val Asp Val Thr Ala Gly Gly Arg Glu<br>305                     310                   315                 320 | 960 |
| gtg ggt ggc tgg gcc cag ccc atg atc gag ccc cat gga ccg ggc gtg<br>Val Gly Gly Trp Ala Gln Pro Met Ile Glu Pro His Gly Pro Gly Val<br>                   325                   330                 335 | 1008 |
| gcc gcc ttt ctg ctg gcc tac gcc gac aag gtg ccg cat gtg ctg gtg<br>Ala Ala Phe Leu Leu Ala Tyr Ala Asp Lys Val Pro His Val Leu Val<br>    340                     345                   350 | 1056 |
| cag gcc cgc gcc gaa ccc ggc tac acg gac gtg gtg gaa ctg gcc ccc<br>Gln Ala Arg Ala Glu Pro Gly Tyr Thr Asp Val Val Glu Leu Ala Pro<br>            355                   360                 365 | 1104 |
| acc gtg cag tgc acc ccg cgc aac tac acc cat ctg ccc gag ggg gcc<br>Thr Val Gln Cys Thr Pro Arg Asn Tyr Thr His Leu Pro Glu Gly Ala<br>370                     375                   380 | 1152 |
| acg ccg ccg ttc ctc aag gag gtg gtg gag gca ccg gcc gac cgg gtg<br>Thr Pro Pro Phe Leu Lys Glu Val Val Glu Ala Pro Ala Asp Arg Val<br>385                     390                   395                 400 | 1200 |
| cgg ttc gac acc gtg ctc tcc gag gag ggc ggc cgc ttc ttc cac gcc<br>Arg Phe Asp Thr Val Leu Ser Glu Glu Gly Gly Arg Phe Phe His Ala<br>                   405                   410                 415 | 1248 |
| ttc aac cgc tat ctg gtc gtg gag acg gag atg agc gcc gtc ccc gag<br>Phe Asn Arg Tyr Leu Val Val Glu Thr Glu Met Ser Ala Val Pro Glu<br>    420                     425                   430 | 1296 |

```
gag ccg ccg cac tac cgc tgg atg gcg gtg cgt cag ctg ctc gac ctg    1344
Glu Pro Pro His Tyr Arg Trp Met Ala Val Arg Gln Leu Leu Asp Leu
        435                 440                 445 atc cgc cac agc cat tac gtc aac gtc gag gcg cgc acg ctc atc gcc    1392
Ile Arg His Ser His Tyr Val Asn Val Glu Ala Arg Thr Leu Ile Ala
    450                 455                 460 tgt ctg cac tcc ctg gcc gta tag                                    1416
Cys Leu His Ser Leu Ala Val
465                 470

<210> SEQ ID NO 42
<211> LENGTH: 471
<212> TYPE: PRT
<213> ORGANISM: Streptomyces sp. NRRL 30748

<400> SEQUENCE: 42

Val Gly Val Val Ser Thr Leu Gln Glu Arg Leu Ile Arg Ser Ala Ala
1               5                   10                  15

Thr Val Asp Ser Ser Val Thr Leu Leu Ala Asp Phe Gln Arg Trp Phe
            20                  25                  30

Arg Glu Arg Val Asp Ala Asp Glu Ser Arg Ile Glu Ile Ile Pro Phe
        35                  40                  45

Glu Ala Met Arg Gly Trp Asp Phe Ala Pro Asp Thr His Asn Leu Val
    50                  55                  60

His Glu Thr Gly Arg Phe Phe Thr Val Glu Gly Ile Arg Val Arg Met
65                  70                  75                  80

Pro Gly Ala Pro Val Glu Glu Trp Arg Gln Pro Ile Leu His Gln Pro
                85                  90                  95

Glu Ile Gly Ile Leu Gly Val Leu Val Lys Asp Phe Asp Gly Val Pro
            100                 105                 110

His Phe Leu Met Gln Ala Lys Met Glu Pro Gly Asn His Gly Gly Leu
        115                 120                 125

Gln Leu Ser Pro Thr Val Gln Ala Thr Arg Ser Asn Tyr Thr Arg Val
    130                 135                 140

His Lys Gly Arg Ala Val Pro Tyr Leu Glu Tyr Phe Gln Arg Thr Glu
145                 150                 155                 160

Arg His Arg Val Leu Ala Asp Val Arg Gln Ser Glu Gln Gly Ser Trp
                165                 170                 175

Phe Phe Arg Lys Arg Asn Arg Asn Met Leu Val Glu Val Ala Pro Asp
            180                 185                 190

Val Asp Val Glu Val Arg Asp Gly Phe Arg Trp Leu Thr Leu Gly Gln
        195                 200                 205

Leu His His Leu Leu Ala Val Glu Asp Leu Val Asn Met Asp Ala Arg
    210                 215                 220

Ser Val Leu Ala Cys Leu Pro His Ser Pro Leu Asp Pro Glu Thr
225                 230                 235                 240

Phe Pro Ala Thr Gly Ser Arg Gly Thr Ala Glu Pro Glu Pro Pro Gly
                245                 250                 255

Arg His Val Leu His Arg Asp Ala Asp Ile Leu Ser Trp Ile Thr Gly
            260                 265                 270

Leu Arg Thr Glu Arg Glu Val Phe Thr Glu Arg Ile Pro Leu Arg Glu
        275                 280                 285

Thr Thr Gly Trp His Arg Asn Ala His Arg Ile Ser His Glu Ser Gly
    290                 295                 300

Arg Tyr Phe Ser Val Met Ala Val Asp Val Thr Ala Gly Gly Arg Glu
```

```
                305                 310                 315                 320
Val Gly Gly Trp Ala Gln Pro Met Ile Glu Pro His Gly Pro Gly Val
                    325                 330                 335

Ala Ala Phe Leu Leu Ala Tyr Ala Asp Lys Val Pro His Val Leu Val
                340                 345                 350

Gln Ala Arg Ala Glu Pro Gly Tyr Thr Asp Val Val Glu Leu Ala Pro
                355                 360                 365

Thr Val Gln Cys Thr Pro Arg Asn Tyr Thr His Leu Pro Glu Gly Ala
    370                 375                 380

Thr Pro Pro Phe Leu Lys Glu Val Val Glu Ala Pro Ala Asp Arg Val
385                 390                 395                 400

Arg Phe Asp Thr Val Leu Ser Glu Gly Gly Arg Phe Phe His Ala
                405                 410                 415

Phe Asn Arg Tyr Leu Val Val Glu Thr Glu Met Ser Ala Val Pro Glu
                420                 425                 430

Glu Pro Pro His Tyr Arg Trp Met Ala Val Arg Gln Leu Leu Asp Leu
                435                 440                 445

Ile Arg His Ser His Tyr Val Asn Val Glu Ala Arg Thr Leu Ile Ala
                450                 455                 460

Cys Leu His Ser Leu Ala Val
465                 470

<210> SEQ ID NO 43
<211> LENGTH: 1341
<212> TYPE: DNA
<213> ORGANISM: Streptomyces sp. NRRL 30748
<220> FEATURE:
<221> NAME/KEY: CDS
<222> LOCATION: (1)..(1341)

<400> SEQUENCE: 43
```

| | | | | | | | | | | | | | | | | |
|---|---|---|---|---|---|---|---|---|---|---|---|---|---|---|---|---|
| atg | cag | gac | atc | atc | agc | gcc | gtg | ctg | gca | gag | gat | gcg | gtg | gcc | gcg | 48 |
| Met | Gln | Asp | Ile | Ile | Ser | Ala | Val | Leu | Ala | Glu | Asp | Ala | Val | Ala | Ala | |
| 1 | | | | 5 | | | | | 10 | | | | | 15 | | |
| gac | ttc | gcc | gcc | ttg | gac | ctt | ccc | gag | tcc | tat | cgg | ggc | gcg | gtg | atc | 96 |
| Asp | Phe | Ala | Ala | Leu | Asp | Leu | Pro | Glu | Ser | Tyr | Arg | Gly | Ala | Val | Ile | |
| | | | 20 | | | | | 25 | | | | | 30 | | | |
| ctc | aaa | gag | gag | tcc | gag | atg | ttc | gag | ggc | atg | gcc | acc | aag | gac | aag | 144 |
| Leu | Lys | Glu | Glu | Ser | Glu | Met | Phe | Glu | Gly | Met | Ala | Thr | Lys | Asp | Lys | |
| | | 35 | | | | | 40 | | | | | 45 | | | | |
| gac | ccc | cag | aag | tcg | ctc | cac | atc | cgc | gag | gtg | ccc | acc | ccc | gaa | ccg | 192 |
| Asp | Pro | Gln | Lys | Ser | Leu | His | Ile | Arg | Glu | Val | Pro | Thr | Pro | Glu | Pro | |
| | 50 | | | | | 55 | | | | | 60 | | | | | |
| ggc | ccg | ggt | gag | gcg | gtg | atc | gcg | gtc | atg | gcc | agc | gcg | atc | aac | tac | 240 |
| Gly | Pro | Gly | Glu | Ala | Val | Ile | Ala | Val | Met | Ala | Ser | Ala | Ile | Asn | Tyr | |
| 65 | | | | | 70 | | | | | 75 | | | | | 80 | |
| aac | acc | gtc | tgg | agc | gcc | atc | ttc | gag | ccg | ctc | ccg | acc | ttc | ggc | ttc | 288 |
| Asn | Thr | Val | Trp | Ser | Ala | Ile | Phe | Glu | Pro | Leu | Pro | Thr | Phe | Gly | Phe | |
| | | | | 85 | | | | | 90 | | | | | 95 | | |
| ctg | gag | cgc | tac | gcg | cgc | acc | gac | gac | ccc | gga | gcg | gcc | cgc | cac | gac | 336 |
| Leu | Glu | Arg | Tyr | Ala | Arg | Thr | Asp | Asp | Pro | Gly | Ala | Ala | Arg | His | Asp | |
| | | | 100 | | | | | 105 | | | | | 110 | | | |
| cgg | ccc | tac | cac | gtg | ctc | ggc | tcc | gac | ctg | gcc | ggt | gtg | gtg | ctg | cgc | 384 |
| Arg | Pro | Tyr | His | Val | Leu | Gly | Ser | Asp | Leu | Ala | Gly | Val | Val | Leu | Arg | |
| | | 115 | | | | | 120 | | | | | 125 | | | | |
| acc | ggg | ccc | ggg | gtg | cgc | cac | tgg | aag | ccg | ggc | gac | cgg | gtg | gtg | gcc | 432 |
| Thr | Gly | Pro | Gly | Val | Arg | His | Trp | Lys | Pro | Gly | Asp | Arg | Val | Val | Ala | |
| | 130 | | | | | 135 | | | | | 140 | | | | | |

```
cac tgc ctg tcc atc gaa ctg cgc tca ccg gac ggc cac gac gac tcc      480
His Cys Leu Ser Ile Glu Leu Arg Ser Pro Asp Gly His Asp Asp Ser
145                 150                 155                 160 atg ctc gac ccc gag cag cgc atc tgg ggc ttc gag acc aac tac ggc      528
Met Leu Asp Pro Glu Gln Arg Ile Trp Gly Phe Glu Thr Asn Tyr Gly
                165                 170                 175 ggg ctc gcc gag ctc tcg ctg gtc aag gcc aac cag ctg atg ccg atg      576
Gly Leu Ala Glu Leu Ser Leu Val Lys Ala Asn Gln Leu Met Pro Met
        180                 185                 190 ccc gcc cac ctc acc tgg gag gag gcc gcg tcc tcc ggc ctg gtc aac      624
Pro Ala His Leu Thr Trp Glu Glu Ala Ala Ser Ser Gly Leu Val Asn
                195                 200                 205 tcc acc gcg tac cgg cag ctc gtc tcc cgc aac ggc gcc cag atg aaa      672
Ser Thr Ala Tyr Arg Gln Leu Val Ser Arg Asn Gly Ala Gln Met Lys
    210                 215                 220 cag ggc gat gtg acc ctc atc tgg ggc gcg gcg ggt ggc ctc ggc tcg      720
Gln Gly Asp Val Thr Leu Ile Trp Gly Ala Ala Gly Gly Leu Gly Ser
225                 230                 235                 240 tac gcg acc cag ctg gcc gtc aac ggc ggg gcg atc ccg gtg tgc gtg      768
Tyr Ala Thr Gln Leu Ala Val Asn Gly Gly Ala Ile Pro Val Cys Val
                245                 250                 255 gtc tcc ggg cgg cgc aag gcc gaa ctc gtc cgc tcc atg ggg gcc gag      816
Val Ser Gly Arg Arg Lys Ala Glu Leu Val Arg Ser Met Gly Ala Glu
        260                 265                 270 ctg gtc atc gac cgg gcc gag gag ggc tat cgc ttc tgg aag gac gcg      864
Leu Val Ile Asp Arg Ala Glu Glu Gly Tyr Arg Phe Trp Lys Asp Ala
                275                 280                 285 acc acg ccc gac ccc cgg gag tgg aag cgc ttc ggg tcc cgg atc cgc      912
Thr Thr Pro Asp Pro Arg Glu Trp Lys Arg Phe Gly Ser Arg Ile Arg
    290                 295                 300 gaa ctc acc ggc ggc gac gac ccg gac atc gtc gtg gag cac ccc ggc      960
Glu Leu Thr Gly Gly Asp Asp Pro Asp Ile Val Val Glu His Pro Gly
305                 310                 315                 320 cgg gag acc ttc ggc gcc agt gtg ttc gtg gcg cgg cgc ggc gga acg     1008
Arg Glu Thr Phe Gly Ala Ser Val Phe Val Ala Arg Arg Gly Gly Thr
                325                 330                 335 atc gtc acc tgc gcc tcg acg tcc ggc tac cgc cac gag tac gac aac     1056
Ile Val Thr Cys Ala Ser Thr Ser Gly Tyr Arg His Glu Tyr Asp Asn
        340                 345                 350 cgc tat ctg tgg atg gcg ctc aag cgc atc atc ggc acc cac ttc gcc     1104
Arg Tyr Leu Trp Met Ala Leu Lys Arg Ile Ile Gly Thr His Phe Ala
                355                 360                 365 aac tac cgg gag gca tgg gcg gcc aac cgg ctg atc gag aag ggg atg     1152
Asn Tyr Arg Glu Ala Trp Ala Ala Asn Arg Leu Ile Glu Lys Gly Met
    370                 375                 380 gtg cac ccc acg ctc tcc aag gtc cat ccg ctc gag gcg gtc ggc acg     1200
Val His Pro Thr Leu Ser Lys Val His Pro Leu Glu Ala Val Gly Thr
385                 390                 395                 400 gcc acc cag gac gtc cac cgc aac cgc cac tcc ggg aag gtc ggc gtg     1248
Ala Thr Gln Asp Val His Arg Asn Arg His Ser Gly Lys Val Gly Val
                405                 410                 415 ctg tgc ctg gcc ccg gag gag ggg ctg ggg gta cgc gac ccg gag ctg     1296
Leu Cys Leu Ala Pro Glu Glu Gly Leu Gly Val Arg Asp Pro Glu Leu
        420                 425                 430 cgc gag cgc cat ctc ccg gcg atc aac cgc ttc cgc cgg gac tga         1341
Arg Glu Arg His Leu Pro Ala Ile Asn Arg Phe Arg Arg Asp
                435                 440                 445

<210> SEQ ID NO 44
<211> LENGTH: 446
```

```
<212> TYPE: PRT
<213> ORGANISM: Streptomyces sp. NRRL 30748

<400> SEQUENCE: 44

Met Gln Asp Ile Ile Ser Ala Val Leu Ala Glu Asp Ala Val Ala Ala
1               5                   10                  15

Asp Phe Ala Ala Leu Asp Leu Pro Glu Ser Tyr Arg Gly Ala Val Ile
                20                  25                  30

Leu Lys Glu Glu Ser Glu Met Phe Glu Gly Met Ala Thr Lys Asp Lys
            35                  40                  45

Asp Pro Gln Lys Ser Leu His Ile Arg Glu Val Pro Thr Pro Glu Pro
        50                  55                  60

Gly Pro Gly Glu Ala Val Ile Ala Val Met Ala Ser Ala Ile Asn Tyr
65                  70                  75                  80

Asn Thr Val Trp Ser Ala Ile Phe Glu Pro Leu Pro Thr Phe Gly Phe
                85                  90                  95

Leu Glu Arg Tyr Ala Arg Thr Asp Asp Pro Gly Ala Ala Arg His Asp
            100                 105                 110

Arg Pro Tyr His Val Leu Gly Ser Asp Leu Ala Gly Val Val Leu Arg
        115                 120                 125

Thr Gly Pro Gly Val Arg His Trp Lys Pro Gly Asp Arg Val Val Ala
130                 135                 140

His Cys Leu Ser Ile Glu Leu Arg Ser Pro Asp Gly His Asp Asp Ser
145                 150                 155                 160

Met Leu Asp Pro Glu Gln Arg Ile Trp Gly Phe Glu Thr Asn Tyr Gly
                165                 170                 175

Gly Leu Ala Glu Leu Ser Leu Val Lys Ala Asn Gln Leu Met Pro Met
            180                 185                 190

Pro Ala His Leu Thr Trp Glu Glu Ala Ala Ser Ser Gly Leu Val Asn
        195                 200                 205

Ser Thr Ala Tyr Arg Gln Leu Val Ser Arg Asn Gly Ala Gln Met Lys
210                 215                 220

Gln Gly Asp Val Thr Leu Ile Trp Gly Ala Ala Gly Gly Leu Gly Ser
225                 230                 235                 240

Tyr Ala Thr Gln Leu Ala Val Asn Gly Gly Ala Ile Pro Val Cys Val
                245                 250                 255

Val Ser Gly Arg Arg Lys Ala Glu Leu Val Arg Ser Met Gly Ala Glu
            260                 265                 270

Leu Val Ile Asp Arg Ala Glu Glu Gly Tyr Arg Phe Trp Lys Asp Ala
        275                 280                 285

Thr Thr Pro Asp Pro Arg Glu Trp Lys Arg Phe Gly Ser Arg Ile Arg
        290                 295                 300

Glu Leu Thr Gly Gly Asp Asp Pro Asp Ile Val Val Glu His Pro Gly
305                 310                 315                 320

Arg Glu Thr Phe Gly Ala Ser Val Phe Val Ala Arg Gly Gly Thr
                325                 330                 335

Ile Val Thr Cys Ala Ser Thr Ser Gly Tyr Arg His Glu Tyr Asp Asn
            340                 345                 350

Arg Tyr Leu Trp Met Ala Leu Lys Arg Ile Ile Gly Thr His Phe Ala
        355                 360                 365

Asn Tyr Arg Glu Ala Trp Ala Ala Asn Arg Leu Ile Glu Lys Gly Met
        370                 375                 380

Val His Pro Thr Leu Ser Lys Val His Pro Leu Glu Ala Val Gly Thr
385                 390                 395                 400
```

```
Ala Thr Gln Asp Val His Arg Asn Arg His Ser Gly Lys Val Gly Val
                405                 410                 415

Leu Cys Leu Ala Pro Glu Glu Gly Leu Gly Val Arg Asp Pro Glu Leu
            420                 425                 430

Arg Glu Arg His Leu Pro Ala Ile Asn Arg Phe Arg Arg Asp
        435                 440                 445

<210> SEQ ID NO 45
<211> LENGTH: 1053
<212> TYPE: DNA
<213> ORGANISM: Streptomyces sp. NRRL 30748
<220> FEATURE:
<221> NAME/KEY: CDS
<222> LOCATION: (1)..(1053)

<400> SEQUENCE: 45 atg ggc agc gag gcc ggg acg gag ccg ccg cgg cgc gtc acc atc agg      48
Met Gly Ser Glu Ala Gly Thr Glu Pro Pro Arg Arg Val Thr Ile Arg
1               5                   10                  15 gac gtg gca gcg cgg gcc ggg gtg tcc aag ggc gcg gtc tcg ctc gtc      96
Asp Val Ala Ala Arg Ala Gly Val Ser Lys Gly Ala Val Ser Leu Val
            20                  25                  30 ttc aac gac cgg ccc ggg gtc tcc cgg gcc acc cgg gac cgc atc ttc     144
Phe Asn Asp Arg Pro Gly Val Ser Arg Ala Thr Arg Asp Arg Ile Phe
        35                  40                  45 gcc gcc gcc cgg gag ctc ggc tgg tca ccc cat ctc tcc gcc cgg tcg     192
Ala Ala Ala Arg Glu Leu Gly Trp Ser Pro His Leu Ser Ala Arg Ser
    50                  55                  60 ctc tcc aac tcc cgc gtg gac acg gtc ggt ctg gcc atc gcc cgc ccg     240
Leu Ser Asn Ser Arg Val Asp Thr Val Gly Leu Ala Ile Ala Arg Pro
65                  70                  75                  80 gcc cgg acg ctg ggc ctc gag ccg tgg tcc atg gag ttc gtc tcg ggc     288
Ala Arg Thr Leu Gly Leu Glu Pro Trp Ser Met Glu Phe Val Ser Gly
                85                  90                  95 atc gag agc gtg ctg gtc gag cgc tcc tgc tcg ctg ctg cgg ctg         336
Ile Glu Ser Val Leu Val Glu Arg Ser Cys Ser Leu Leu Arg Leu
            100                 105                 110 gtc cgg gat gtg cgc gag gag atc gcg gtc cag gag gcg tgg tgg cgg     384
Val Arg Asp Val Arg Glu Glu Ile Ala Val Gln Glu Ala Trp Trp Arg
        115                 120                 125 ggg cgg cag atc ggc ggg tcc atc ctg gtc gat ctg cgg gac ggc gac     432
Gly Arg Gln Ile Gly Gly Ser Ile Leu Val Asp Leu Arg Asp Gly Asp
    130                 135                 140 ccc cgt gtc ccc gcg ctg cgg caa ctc ggc ctg ccc gcc gtg gtg gcc     480
Pro Arg Val Pro Ala Leu Arg Gln Leu Gly Leu Pro Ala Val Val Ala
145                 150                 155                 160 ggg cac ccc tcg ctg gcg gac ggg ttc acc tcg gtc tgg acg gac gac     528
Gly His Pro Ser Leu Ala Asp Gly Phe Thr Ser Val Trp Thr Asp Asp
                165                 170                 175 gcc acg gcc gtc acc gag gcg gtg cgc tat ctg gtg gcg ctg ggc cac     576
Ala Thr Ala Val Thr Glu Ala Val Arg Tyr Leu Val Ala Leu Gly His
            180                 185                 190 cgc cgg atc gcc cgg gtg ggc ggc gcc ccc ggg ctc ggg cac acc acg     624
Arg Arg Ile Ala Arg Val Gly Gly Ala Pro Gly Leu Gly His Thr Thr
        195                 200                 205 atc cgc aag gcc gcg ttc gag gcc gcc gta cgg gag gcg ggg ctg ggc     672
Ile Arg Lys Ala Ala Phe Glu Ala Ala Val Arg Glu Ala Gly Leu Gly
    210                 215                 220 gag ggt ccc acg gtg gcc acg gac ttc tcg ggc gag gag ggg gca cgg     720
Glu Gly Pro Thr Val Ala Thr Asp Phe Ser Gly Glu Glu Gly Ala Arg
```

```
                225                 230                 235                 240 gcc acc cgt gcc ctg ctg gcc tcg gcg gac cgg ccc acg gcg atc ctg         768
Ala Thr Arg Ala Leu Leu Ala Ser Ala Asp Arg Pro Thr Ala Ile Leu
                245                 250                 255 tac gac aac gac atc atg gcg gtg gcg ggc ctt tcg gtg gcc gcc gag         816
Tyr Asp Asn Asp Ile Met Ala Val Ala Gly Leu Ser Val Ala Ala Glu
            260                 265                 270 atg ggg ctg tcg gtg ccg gcc gat gta tcg ctg ctg gcc tgg gac gac         864
Met Gly Leu Ser Val Pro Ala Asp Val Ser Leu Leu Ala Trp Asp Asp
        275                 280                 285 tca cag ctg tgc cag ctg acg cac ccc acg ctc tcg gcg atg agc cac         912
Ser Gln Leu Cys Gln Leu Thr His Pro Thr Leu Ser Ala Met Ser His
    290                 295                 300 gat gtc ttc ggc tac ggg gcg cag gtg gcg cac cgc ctc ttc gag gtc         960
Asp Val Phe Gly Tyr Gly Ala Gln Val Ala His Arg Leu Phe Glu Val
305                 310                 315                 320 ctg ggc cag gcg gct ccc cgc gcc cat cag gcc ccc act ccg gcg ctc         1008
Leu Gly Gln Ala Ala Pro Arg Ala His Gln Ala Pro Thr Pro Ala Leu
                325                 330                 335 acc ccc cgg ggc agc acg gcc ccg cca cgt cgg cgc gag cca tga             1053
Thr Pro Arg Gly Ser Thr Ala Pro Pro Arg Arg Arg Glu Pro
                340                 345                 350

<210> SEQ ID NO 46
<211> LENGTH: 350
<212> TYPE: PRT
<213> ORGANISM: Streptomyces sp. NRRL 30748

<400> SEQUENCE: 46

Met Gly Ser Glu Ala Gly Thr Glu Pro Pro Arg Arg Val Thr Ile Arg
1               5                   10                  15

Asp Val Ala Ala Arg Ala Gly Val Ser Lys Gly Ala Val Ser Leu Val
                20                  25                  30

Phe Asn Asp Arg Pro Gly Val Ser Arg Ala Thr Arg Asp Arg Ile Phe
            35                  40                  45

Ala Ala Ala Arg Glu Leu Gly Trp Ser Pro His Leu Ser Ala Arg Ser
        50                  55                  60

Leu Ser Asn Ser Arg Val Asp Thr Val Gly Leu Ala Ile Ala Arg Pro
65                  70                  75                  80

Ala Arg Thr Leu Gly Leu Glu Pro Trp Ser Met Glu Phe Val Ser Gly
                85                  90                  95

Ile Glu Ser Val Leu Val Glu Arg Ser Cys Ser Leu Leu Leu Arg Leu
            100                 105                 110

Val Arg Asp Val Arg Glu Glu Ile Ala Val Gln Glu Ala Trp Trp Arg
        115                 120                 125

Gly Arg Gln Ile Gly Gly Ser Ile Leu Val Asp Leu Arg Asp Gly Asp
    130                 135                 140

Pro Arg Val Pro Ala Leu Arg Gln Leu Gly Leu Pro Ala Val Val Ala
145                 150                 155                 160

Gly His Pro Ser Leu Ala Asp Gly Phe Thr Ser Val Trp Thr Asp Asp
                165                 170                 175

Ala Thr Ala Val Thr Glu Ala Val Arg Tyr Leu Val Ala Leu Gly His
            180                 185                 190

Arg Arg Ile Ala Arg Val Gly Gly Ala Pro Gly Leu Gly His Thr Thr
        195                 200                 205

Ile Arg Lys Ala Ala Phe Glu Ala Ala Val Arg Glu Ala Gly Leu Gly
    210                 215                 220
```

```
Glu Gly Pro Thr Val Ala Thr Asp Phe Ser Gly Glu Gly Ala Arg
225                 230                 235                 240

Ala Thr Arg Ala Leu Leu Ala Ser Ala Asp Arg Pro Thr Ala Ile Leu
            245                 250                 255

Tyr Asp Asn Asp Ile Met Ala Val Ala Gly Leu Ser Val Ala Ala Glu
            260                 265                 270

Met Gly Leu Ser Val Pro Ala Asp Val Ser Leu Leu Ala Trp Asp Asp
            275                 280                 285

Ser Gln Leu Cys Gln Leu Thr His Pro Thr Leu Ser Ala Met Ser His
290                 295                 300

Asp Val Phe Gly Tyr Gly Ala Gln Val Ala His Arg Leu Phe Glu Val
305                 310                 315                 320

Leu Gly Gln Ala Ala Pro Arg Ala His Gln Ala Pro Thr Pro Ala Leu
                325                 330                 335

Thr Pro Arg Gly Ser Thr Ala Pro Pro Arg Arg Arg Glu Pro
            340                 345                 350

<210> SEQ ID NO 47
<211> LENGTH: 897
<212> TYPE: DNA
<213> ORGANISM: Streptomyces sp. NRRL 30748
<220> FEATURE:
<221> NAME/KEY: CDS
<222> LOCATION: (1)..(897)

<400> SEQUENCE: 47 aat acg act cac tat agg gag agg atc ccg gtc ggc tgg gcc acc gcc      48
Asn Thr Thr His Tyr Arg Glu Arg Ile Pro Val Gly Trp Ala Thr Ala
1               5                   10                  15 gac cgg atg cgc cgc aat atg cgg atc gcc acc cgc cac acg gtg ggc      96
Asp Arg Met Arg Arg Asn Met Arg Ile Ala Thr Arg His Thr Val Gly
                20                  25                  30 tcg ctg gcc cgg gag acc ttc tgg agc cgg ggc gcg atc ctg tgg ggc     144
Ser Leu Ala Arg Glu Thr Phe Trp Ser Arg Gly Ala Ile Leu Trp Gly
            35                  40                  45 ccg gcc ggt ccg gtc cgc tac cag ctg cgg ccg gcg ccc ggc ggc acc     192
Pro Ala Gly Pro Val Arg Tyr Gln Leu Arg Pro Ala Pro Gly Gly Thr
        50                  55                  60 ccc gct ccc ccg ccc gac ggc ggc gac ccg gac tat ctc cac cgt gag     240
Pro Ala Pro Pro Pro Asp Gly Gly Asp Pro Asp Tyr Leu His Arg Glu
65                  70                  75                  80 ctg gcg atg cgg ctg tcc acc ggc gac atc gcc ttc gag ctg tgt gtg     288
Leu Ala Met Arg Leu Ser Thr Gly Asp Ile Ala Phe Glu Leu Cys Val
                85                  90                  95 cag cgc tat ctg gac gac cgc cgc acc ccg gtc gag gac ggt tcg gtg     336
Gln Arg Tyr Leu Asp Asp Arg Arg Thr Pro Val Glu Asp Gly Ser Val
            100                 105                 110 gag tgg cgg gag agc gac gcg ccg gtg gtc ccg gtc gcg gtg ctc acc     384
Glu Trp Arg Glu Ser Asp Ala Pro Val Val Pro Val Ala Val Leu Thr
        115                 120                 125 gtg ccg cgc cag gac ctg gac ggc gcc cgg gcc cgg tcg gct gcc cgc     432
Val Pro Arg Gln Asp Leu Asp Gly Ala Arg Ala Arg Ser Ala Ala Arg
    130                 135                 140 cgg gtc gag caa ctg gcg ttc aac ccc tgg cac acc acc gag gag ttc     480
Arg Val Glu Gln Leu Ala Phe Asn Pro Trp His Thr Thr Glu Glu Phe
145                 150                 155                 160 cgt ccg ctc ggc aac ctc aac cgg gcc cgc aag gcc gcg tac gag gcc     528
Arg Pro Leu Gly Asn Leu Asn Arg Ala Arg Lys Ala Ala Tyr Glu Ala
                165                 170                 175
```

```
gcc gcg gcg cac cgg ctc ggc ctg cgc gtc ccc gcc gcc gag cag cgg      576
Ala Ala Ala His Arg Leu Gly Leu Arg Val Pro Ala Ala Glu Gln Arg
            180                 185                 190 ccc acc gcg cca ctg ccc gtc ccg gtg cgc gcc gcc ctc gac ctg ccg      624
Pro Thr Ala Pro Leu Pro Val Pro Val Arg Ala Ala Leu Asp Leu Pro
        195                 200                 205 gta cgc gcc gcc ctc gac ctg ccg gtg cgg gcg gcc ttc gag ctg gtc      672
Val Arg Ala Ala Leu Asp Leu Pro Val Arg Ala Ala Phe Glu Leu Val
    210                 215                 220 gac cgc tgt gtg ccc tgg cat cgg ctg ccg gcc ccg ctg ggg ctg ctc      720
Asp Arg Cys Val Pro Trp His Arg Leu Pro Ala Pro Leu Gly Leu Leu
225                 230                 235                 240 aac ccg gcc gcg ctg ggc cgg acg ctg cgc cgg ctc ggc ctc gtc gag      768
Asn Pro Ala Ala Leu Gly Arg Thr Leu Arg Arg Leu Gly Leu Val Glu
                245                 250                 255 ggg gac cac aca ccc gag gcg ccg cag cgc ccc gcc acg gcc ggg gag      816
Gly Asp His Thr Pro Glu Ala Pro Gln Arg Pro Ala Thr Ala Gly Glu
            260                 265                 270 agc ccc cgg gtg gcg cgc tcg tac gac gcc ccg acc agc gat ccc gcc      864
Ser Pro Arg Val Ala Arg Ser Tyr Asp Ala Pro Thr Ser Asp Pro Ala
        275                 280                 285 gtg gcg ctg ccc ggg gcg tcg tcc ctg tcc tga                          897
Val Ala Leu Pro Gly Ala Ser Ser Leu Ser
    290                 295

<210> SEQ ID NO 48
<211> LENGTH: 298
<212> TYPE: PRT
<213> ORGANISM: Streptomyces sp. NRRL 30748

<400> SEQUENCE: 48

Asn Thr Thr His Tyr Arg Glu Arg Ile Pro Val Gly Trp Ala Thr Ala
1               5                   10                  15

Asp Arg Met Arg Asn Met Arg Ile Ala Thr Arg His Thr Val Gly
            20                  25                  30

Ser Leu Ala Arg Glu Thr Phe Trp Ser Arg Gly Ala Ile Leu Trp Gly
        35                  40                  45

Pro Ala Gly Pro Val Arg Tyr Gln Leu Arg Pro Ala Pro Gly Gly Thr
    50                  55                  60

Pro Ala Pro Pro Asp Gly Gly Asp Pro Asp Tyr Leu His Arg Glu
65                  70                  75                  80

Leu Ala Met Arg Leu Ser Thr Gly Asp Ile Ala Phe Glu Leu Cys Val
                85                  90                  95

Gln Arg Tyr Leu Asp Asp Arg Arg Thr Pro Val Glu Asp Gly Ser Val
            100                 105                 110

Glu Trp Arg Glu Ser Asp Ala Pro Val Val Pro Val Ala Val Leu Thr
        115                 120                 125

Val Pro Arg Gln Asp Leu Asp Gly Ala Arg Ala Arg Ser Ala Ala Arg
    130                 135                 140

Arg Val Glu Gln Leu Ala Phe Asn Pro Trp His Thr Thr Glu Glu Phe
145                 150                 155                 160

Arg Pro Leu Gly Asn Leu Asn Arg Ala Arg Lys Ala Ala Tyr Glu Ala
                165                 170                 175

Ala Ala Ala His Arg Leu Gly Leu Arg Val Pro Ala Ala Glu Gln Arg
            180                 185                 190

Pro Thr Ala Pro Leu Pro Val Pro Val Arg Ala Ala Leu Asp Leu Pro
        195                 200                 205
```

```
Val Arg Ala Ala Leu Asp Leu Pro Val Arg Ala Phe Glu Leu Val
    210                 215                 220

Asp Arg Cys Val Pro Trp His Arg Leu Pro Ala Pro Leu Gly Leu Leu
225                 230                 235                 240

Asn Pro Ala Ala Leu Gly Arg Thr Leu Arg Arg Leu Gly Leu Val Glu
                245                 250                 255

Gly Asp His Thr Pro Glu Ala Pro Gln Arg Pro Ala Thr Ala Gly Glu
            260                 265                 270

Ser Pro Arg Val Ala Arg Ser Tyr Asp Ala Pro Thr Ser Asp Pro Ala
    275                 280                 285

Val Ala Leu Pro Gly Ala Ser Ser Leu Ser
290                 295

<210> SEQ ID NO 49
<211> LENGTH: 63201
<212> TYPE: DNA
<213> ORGANISM: Streptomyces sp. NRRL 30748

<400> SEQUENCE: 49
agggttttcc cagtcacgac ggatcccctg agcctgggcc acacagccgc cgggacccgg      60
gcgcctggtg tcacgcccgt gacgagccgt gatcctccag cctgaccggc ggcaggaact     120
cgctcagcag ggtgcggtgc caccaggccc ggtggcccg ccgctccgcc cggtggtga      180 agcggtagag atacagccgc gcccgcagat gggtgggcgg cgtccccggg aagggggttgg    240 tccgcagcag cttcaccgtc gcccggtcgt tgaccagca cttgccgatc agcggggtga     300
accaggaccc ggcgtagccc ggtgagagcc ccgcgaacca catcatccag tccagccgca    360
gatggtacgg ggcgtactgg cgcggcaacc ggcgcacatc gcccggcttg ccccggaact    420
catagtcccg ccagaccgtg tccggggtga ggaccgcctc gtcggtgccc tggatcacca    480
cctcctgccg gctgcggttg acgctgccga acgcccgta ggtgttggcc aggtgcagcg     540
gattgaagga gaagttcatc agctgacggc ccgacagcag attgcgggcc ggccagtagc    600
tgagcaccag caccaggacg gtggcggcca gcaccaccgc ctcgtaccag accggggag     660 cggcgaggtc cggcggcccg ggcagcccca gcacctccgc ggcccggcgc ccgtcgaccg    720
ccgggagcgc cagcaggatg gtcagccagt tgagccagga gaagttgccc gaggtcacca    780
gccacaactg ggtgaccacg acgatccccg cggccacgcc ggcgaccggc tgcggagtga    840
acagcaccac gggcacgatc agctgcgcca catggttggc cgccgcctcc acccggtgca    900
gcggcttcgg cagatggtgg aagtaccagc tcagcggccc cggcatcggc tgggtctcat    960
ggtggtagta cagacaggtc aggtcccgcc agcagcggtc cccacggatc ttgatcagcc   1020
cggcgccgaa ctccacccgg aacagcagcc agcgcgtcag ccacaggatg agcacgggtg   1080
gcgcggtgtg ctcattgccc aggaacacgg cgaggaaccc cgactccagc agcagggtct   1140
cccagccgaa gccgtaccac acctgcccca cgttgacgat cgacagatac agcagccaca   1200
gcaccagcca cgccaccatc gcgaccgcca gcggcgcccg gtcgccgcc cccaccagca   1260 gcgcggccga cagcgcggcc cccagccagg cgcagcaggc gaagaaccgg tcggagtagt   1320
gcagctggaa caggctgggc gagcggcgga acggcacccg gtccaggaag cgcggcaccg   1380
gcgtcagccc ccgctcgccg agtagcgccc gcccctgccg ggccgccacc agaaaggcga   1440
tcagatagac ggcggccagc ccccgttgga agaccagccg gctcagccag tagtcggatg   1500
aggtgaacca ctccatgggg accgctccct gggccggtgc gccttcggcc tgtatgtatc   1560
```

```
cggtaccacc tccgacgggt gcccgtcatc cgccgggtca tacggcggac cgggttcatt    1620
cggtaggggg cctagggggg tgatgggtta ggggttatcg gtgccgtgcc cggtccgtag    1680
cgtcaaagcc cggcatggat ccggagggaa ccacccaatg cttcttctcg agcaccgccg    1740
caccccgcga acagcgacga cagcgatggc accggcgacg gcggcggtgg ccgcgcgggc    1800
cgggagatcc agatgaccga gcagccggtc cggacatccg gcgggcggcc catcgggatc    1860
ctcggcaccg gctcgtatct gcccgccgag accgtgtcca acgagctggt ggccgagcgc    1920 gcggggggtga ccccggactg gatctcggcg aagaccggga tccaccgccg ccgttacgcc    1980
gccgaccacg aggccacctc cgatctggcc gtggaggccg cccgcgccgc cctcgcggac    2040
gccgggatcg gcgccgatca gctcggctgg atcgtggtgg ccacctcgac ccccgatcac    2100
ccccagcccg ccaccgcctg tctggtgcag caccggatcg gcgcgaccgg cgccgccgcc    2160
ttcgacctca acgcggtctg cagcggcttt gtcttcgccc tggtgacggc ggccgggctg    2220
ctgtccgccg gtccggcgc ccccgccccg tacgccttgg tgatcggcgc cgatgtctac    2280
tcccgcatca tcgaccgcac cgaccggcgg accgccgtgc tcttcggcga cggggccggg    2340
gcggtggtgc tcggacccgt gcgtcccggc tacggcctca gcggatcgct gctcaccagc    2400
gacggcgcgc tccatgagct gatcgaggtg acggcgggcg gcagccgtgt cccggcgtcg    2460
gagaagaccc tcgccgacgg gggccacttc ttccggatgc ggggccgcgc ggtcagcgaa    2520
tacgtcctgg ccgagctgcc gcgcgcgata gggcgcctgc tggccgcgca ccgcacggac    2580
cccgcgagcg tggaccactt catcccccat caggccaatg tgtgctgct ggccaaggcg    2640 cttccggacc tcggactgcc gcgggcgcgc actcatctga cggtggccga gcacggcaac    2700
accagcgccg cctccatccc gctggcgctc gacgacgccc ggcggcaggg cgtgttcggc    2760
gacggggagt tgctgctgct ggccggtttc ggcggcggga tgtcgctcgg cgccgcgctg    2820
ctcatatggc aggacggcca ccgcggtccg tgaccaaccc aaggtcccag ccagcgaaag    2880
gactcatcgg catggcacag cgcttcccca ccgtcgcggt gttcgggctc ggcaccaccg    2940
gccgccacct cgtggacgcc ctggtccgcg gtggccggcg ggtgatcgcc gtggagcggg    3000
acgaaccggc cctgcgacgt ggccgggcgg aggtgaccgc gcccgattcc gcagtcgaat    3060
tcaccaccga cccggcggcc gccgcccggg ccgatctggt ggtcgaggcg gtccccgaac    3120
ggctggagac caagctcggg ctgctcgccc gcgcccacgc cgactgcccg ccggagacgg    3180
tgttcgccac cacgaccacc ggcctcccgg tgaccgagat cgccgtcggc tccgggcgga    3240
ccgaccgcac ggtgggggctg cacctcttcc cgctgggccc cgaccgcgag cagccggcgg    3300
tggaggtggt gggcaccccg ctcaccgcgg acgcggtcct ggccgacgtc cgggaactca    3360
tacgcgacct gggccggatc ccggtgcggg tggccgaccg gccgggcttc gtcggggggcg    3420 cgctcaccat ggcgtacctc aacaacgcgg tggccatgta cgagcggcgc tacgcctcgc    3480
gcgacagcat cgacaccgcc atgaccctcg gctgcggact gccgatgggg ccgctggccc    3540
agctggacgc catgggtctg gacaccgcgc gggactccct ggaggcgctg tacgagcgca    3600
ccggcgatcc gcggtacgcg cccgcgccca ccctggccca tatggtgacc gccggtctgc    3660
tcggggtgaa ggcgggccgc ggcttctacg agtacggggc gggcggcgcg gcgccgggcg    3720
gggcgacgga cggcctgggc gagcccgtac cggcccgcgc ggtgcggcgg atcgggtgg    3780 tgggctcggg cacgatggcc gtcggcatcg cggaggtgtg cgcgcgctcc ggctatccga    3840
cggtgctggt ggcccggagc gagatgcgcg cgaaggaggc cacggccgcc gtggagcgct    3900
cgctggagcg cggagtgcgg cgcggcaagc tggcgcccga gctgctcacc gaggcgatgg    3960
```

```
gccggctgac cgcgggctgt gaactccagg ccctcggcgc ctgcgatctg gtggtcgagg   4020
ccgtggcgga ggacatcgac gtcaagcggg ccgtcttcgc cgatctggac cgggtgtgcg   4080
caccgggtgc ggtgctcgcc acctccacct ccagcctgcc cgtgatcgag tgcgcgatgg   4140
cgacgcggcg gcccgaggac gtcatcggga tgcacttctt caaccccgcc ccggtgatgc   4200
ggctggtcga ggtggtgcac accgtgctga cctccaagga ggcgctcggc acggcccacg   4260
cggtggccgc ggcgctcggc aagcgcgcgg tggactgccc cgaccgggcc ggtttcatcg   4320
tcaacgccct gctcttcccc tatctgaaca gcgcggtggc gatgctcgag gagggctggg   4380
ccaccgccga tgacatcgat acggtgatgg cggccggtca gggctatccg atgggcccgc   4440
tgcggctgct ggatgtgatc ggtctggatg tctcgctcgc catccagcgc actctgtacg   4500
gcaccttccg ggatccggcc ctgaccccgg cgcgccatct ccggcggctg gtcgaggcgg   4560
gccacctggg ccgcaagggc gggaggggc tgcacctcca cgagcgatag cggcgggcca   4620 cgggggatg ccggggccgg ggacacacct ccccggcccc ggcatccgta tggccgcggc   4680
gatgacaggg ggtgcgcaga tgccactgcg atagtccaac ggcgaggtgt gtggctccgg   4740
aattcatcgg caagggaata ggtatgccga ccctctgtcc gctttatggc atgagaattc   4800
ccggcgaatc gcttgcggtt accagtggca acagacataa gcaccgcatt ggcgatcaaa   4860
acgggcaaat aaatgttcga gacggatcct cggagccctc tgtgtatgac cacttagtgt   4920
cggagtcaag gatgtcggga gctttcccgg gtacggctag ggggtctcgt gtatgctggc   4980
ccttccgaac aaatgcccac gtgaacgggg gtggcgcagg ttgtcagggt gtcggtgcac   5040
ttcggcttca acgtgttgcc ccaggtaggg gcgtcccgcc cgcctcgctt ttgtcgagcg   5100
ttgggcagtc cgctcagaat tggtaattcg ttaacgatga ttttacgtgc ggcgatggtg   5160
gcgtgaccgg tgggcgtata gcttgctggg aggcgttcga actgccgtga gcagtgcttc   5220
gcgtcgcatt cggggtgcg agcaatggtg ttttcatcgg ccagagccag acaattcgac   5280
gcgcaattcg agagacttcg gcgggcattt tccagatgcc tgtccggaga ggcgggcatc   5340
gtgctcgtcg agggtgcggt cggttgtggc aagacccata cgctggaagc cgtcacggcc   5400
catgcggcga aggccggagc ccttgtcctc aaggcatacg gaacctcggc cgaccgggcc   5460
ccgctcggca cactgcgcca gctcctggac tcgccccggc tgcccagggc gaccgccgac   5520
cagctgcgcc gggcactcga ccacggcgcc ctcgacgccg caccgccccg ggaaacccct   5580
ggtggcgacc ccgtcggcgc gaaccccacc catgtccagg gagcccggga gttccgtgcc   5640
gcactccatg aactcgcctc ccgtgaaccg gtggtgatct gcgtcgacga actccagctc   5700
gtcgacgcgc cgtcacttca gtacctgctg tacctggcga cccgttcgcg ctccgccaaa   5760
ctcctcatgg tgttcgcaca ggcgacggac agcgaacgac aagacgcggt cttcaatacc   5820
gaactgctgc gccagcccaa tttccagcgg ctgcggctgg aacggctgtc ctgggatgag   5880
acggcacatc tgctcaccac tcgtctggga cttccggatt ccaccgatgt ggcctacacc   5940
tggtatgagg tgagcggcgg taatccgttg ttgctacgcg cggtgataga cgattaccgc   6000
accgcggggg cgcccccacg gcgcagccgc gcagtggagc ccgtggtggg cgacatgttt   6060
gtgcaggccg tgctcacctg cgtctaccgc agcgggcgca ccgtctcccg gctggccgag   6120
ggaatcgcgc tgctcggtgc gtccgcctcc ctcgaactcc tcggcggct gctgcgcatc   6180 ggccccgccg gaaccgccg cggagtcgcc gcgctggacg cggcggggct cgtcgacggt   6240
ctggccttcc gccacccgta tgtcgaggcc gcggtgctgg aggacatgga ccccgaggtc   6300
```

```
cggctggaca tgaaccgccg cgccgccgtc ctgctgcacc agggcggcgg ggcgaccctc   6360
gccgtggccc gccatctgct cgcggcccag gccgcggacg agccctgggg ggtgccgctg   6420
ctgcgggacg ccgcgcagca ggcgctcgcc gaggacgacg ccaagctggc ggtggcctgt   6480
ctggagctgg cgtacgcggc ctgcgcggac gaggagctgc gcgccggcat caggatcggc   6540
accgccggga tcatgtggcg gctcaacccc tcggcgtccg agcggatgct ggaggagccg   6600
ctggccgcgc tgtgcgccga ccggctgccc gcctcccata tcgggcggct gatcgagctg   6660
ttgctcgccc acggccggat cgaggaggcg cgcggcgcga tcggccggct caacgccgtg   6720
atgagcaacg cggggcccac ttcgatgtcc cagttccggc tgaccgcccg ctgggcccag   6780
gagtccggtg cgtcggaccg ggcccccggg ccacggcgc gccagggcga ggacggcggc   6840
gccctccgtg cgcagctcag atcccgcaga cccttcgcgc tgtcgacgat cacggcggcg   6900
ttcagcggct tcttcggccg cggggggacc gaggagtcgc cggtggccgc ggcggagaag   6960
gtgctcgatg tctcgccgct caccgacgcc accttcgagc ccatcgtcaa ctcggtgaac   7020
gcgctggtgt acgcgggccg cccggacaag gcggcgccgt ggtgcgacgc gctgatggag   7080
gaggccgagc ggcgccgggc gccgggctgg cgggccatct tcgcctcgat ccgcgccgaa   7140
atcgccctgc ggcagggcaa tctcgtggag tcggcggcct atgcgaccat cgccctggag   7200
atcgttcccg gccgcgacgg aagcgtcttc atcggcggcc ccctggccag ccagatcctg   7260
gcgtacacgg agatgggcaa gcacgacgcg gcggcgcggc atctgagccg cccggtcccc   7320
gaggcgctgt tcaagagcat ctacggactg ggctacaccc gcgccgcgg ccgctactac   7380
ctggccacca accgcatcaa cgcggcgctc ggcgaattcc tcatggccgg ccggctcgcc   7440
cagctgtggg agctcgacca gccggcgctg ctgccctggc gctcggacgc cgccgaggca   7500
tggctggagc tcggcgaccg ggagaaggcc gccaacctgg tctccgagca gctggccagg   7560
aacggcgccg gggactcccg ggtccgtggc gtctccctgc ggttactggc cgcggcgggc   7620
gacatcgaga accggtcccg gctgctcggc caggccgtcg aggagctgca gtgctccggc   7680
gaccgcctgg agctggcccg ggcgctggac gatctgggac gtacgctgcg cggatccggg   7740
gagctggggc gggccgacgc catcatgggc cgggcctggc ggatggccaa ggagtgcggc   7800
gccgaggagc tgtgcgcccg catccgtctc gactcgggtc tggaggcccg cgatccacgg   7860
ccggtggtgc gaccggtgtc cgcaccgctc ggcccgaagc cggcggtgcc gccgtccctg   7920
ggcaccaagc tcagcgaatc cgaggccgg gtggccgccc tggcggtgga cggttatacg   7980
aaccgggaaa tagccgccag cctgttcatc accatcagca cggtggaaca gcatttgacg   8040
cgggtgtacc gcaagctgaa tatcaggagc cggcagcagc tgccgaccgc gctccgggcc   8100
caggtggacg aaatcgcctg agcgaagacg gggatcgcct gagcgaagac ggggcgatg   8160
ccccgcggaa ggggtggcca cacgcggcca cccctgttcc atgcccaccc ctgattaccc   8220
ccctatagcc gcgacagacc tggagcccgg gctgaccgcg ttgatagctt ctggccgcat   8280
gaagggcata gtcctcgccg gaggaagcgg tacccgactg catcctttga cacatgcggt   8340
gtcgaagcag atccttcccg tctacaacaa accgatgatc tattaccgc tgtcggtgct   8400
catgctcggc ggcgtcaggg aaatccagat catctcgacc ccgctccatg tggagctgtt   8460
ccgcgcgctt ctcggcgacg gcggccgact gggtctttcg atcgagtacg ccgagcagcc   8520
cgaggccaat ggaatcgccg aggcattcat catcggagcc gagttcatcg gcgatgacca   8580
ggtggcgctg gtcctcggcg acaatatctt ccacgggccc ggattctcga agatgctgca   8640
ccatgaggca aaccatgtcg acggctgtgt gctcttcggc tacggagtca aggaccccga   8700
```

```
gcgctacggt gtcggggaaa tggatgagca gggccggctg atctccttgg aggagaagcc   8760
gaccgccccc aaatccaatc tggcgatcac cggtctgtat ctctacgaca acgacgtcgt   8820
ggacatcgcc aagaacgtac ggccctccgc gcgcggcgaa ctggagatca ccgacgtcaa   8880
ccgcgtctat ctggaacgcg aaaagccag actggtgggg ctcggccgcg gattcgcctg    8940
gctggacact ggaacccatg actcactgct ccaggcgggc cagtatgtgc agcttctgga   9000
gcagcgccag ggagtgcgga tcgcctgtct cgaggagata gccttccgca tggggttcat   9060
cgacgccgcc gcctgttatg agctcggtgc ggagctcagc aagacggact acggacaata   9120
tctgatggat atcgcgggcc aataaccgct gaagggttgt ctccagtgcg catagttgtg   9180
accggcggcg cgggcttcat cggctcccac ttcgtccggc agaccctgac aggggcgtac   9240
gcggcctggg cggacgccca ggtcgtggtg gtcgacaagc tcacctacgc gggcaacgag   9300
gccaacctgg ccgaggtcgc ggacagcccc cggctgcgct tcgtgcgcgg tgacatctgc   9360
gacggcgagc tcgtcggcga actgctgcgg gacaccgatc tggtggtcca cttcgccgcg   9420
gaatcacatg tcgaccgctc gatatccggc gccgaggaat tcgtgcgcac caatgtcctg   9480
ggcacccaca ccctcctcaa cgcggccgcg aacgcggagg tcggaaagtt cgtccacatc   9540
tccacggacg aggtctacgg ctccatcgaa aacggctcct ggagcgagga ggaaccctc   9600
gaacccaact cgccgtattc cgcctccaag gcgtcctccg atctgctggc ccgggccttc   9660
caccgcaccc acggactgcc cgtctgtgtg accgctgct ccaacaacta cggcccgtac   9720
caacaccccg agaaggtcat accgctcttc gtcaccaacc tcatgacgg caaaccggtg   9780
ccgctctacg gcgacggcgg aaatgtccgg gactggctgc atgtggacga ccactgccgc   9840
ggtatcgccc tggtcgccga aacggccgc ccggagagg tctacaacat cggcggcggc    9900
accgaactga ccaatctgga actcacggaa cggctgctcg aactgctcgg cgccgaccgg   9960
tccctgatcg agcgggtgcc cgaccgcaag ggccatgacc gccgttactc ggtggacatc   10020
acaaaaatct ccactgaact cggctaccgc ccccagatgt cgttcgagaa cggcctcgcg   10080
gaaaccgcca gtggtacat gacacaccgc ggttggtggg aaccgctcaa gaagatgtga    10140
ccaccccta cagcaagggtt aggggtggat gcggttaggg gtggttgagt cgactcccgc   10200
cccataccgt cgacttccgg atcatggtca gtccagtcgc gtcgtaatct caactgagag   10260
aagagtctga ggtcgtgatg tcggagaact ccctggtgcg tgacgggcac atcgcggtcg   10320
tcggtatggc atgtcgcgtg ccgggcgcat cgaccccgga tgagttccgg cagttgctgc   10380
gcaatggaga gagtgccatc acggagatcc cggcggaccg gtatgccgat gagctccggg   10440
acgcgggtat tcgattcggc gggttcgtcg aaagggcagc cgagttcgat ccggagttct   10500
tcgggatttc accccgagag gcacgggcga tggacccca gcagcggctc gcgctggaac    10560
tgtgctggga ggccctggaa aacgccggac tcgtcccggc gagactcgag gcagccgca    10620
ccggcgtctt catcggcgcc atcgccgacg actacgcggc cctggtccac cgcggcgaac   10680
ccgccgccat cacccagcac accctcaccg ggctgaaccg cggcatcatc gccaaccggg   10740
tctcctacgc cctcgggctg cgcggcccga gcgtcgccgt ggacaccggg cagtcgtcct   10800
ccctggccgc cgtgcacctg gcctgcgaga gcctgcggcg cggcgagacc gagaccgccg   10860
tcgcgggcgg cgtccagctc aacctcgccc cgacggctt catcgccgcc tcccggttcg   10920
gcgcgctctc cccggacggc cgctccttca ccttcgacgc ccgggccaat ggctatgtgc   10980
gcggcgaggg cggcggcctc gtcgtgctca agcggctgcc ggacgcgctg cgcgacggcg   11040
```

```
acccggtgct gtgtgtgatc cgcggttccg acgccaacaa cgacggcggc ggcgacagcc   11100
tcaccacccc cgcggcccac gggcaggagg ccatgctgcg cgccgcctac gagcgcgccg   11160
gggtcgaccc cgcccgggtc cagtacgtcg aactgcacgg caccggcacc aaggtcggcg   11220
acccggtcga ggccgtggcg ctgggcgcgg tcctcggcgc gggccgggcg gacggcgcgc   11280
cgctgcgggt cggctccgcc aagacgaacg tgggccacct cgaaggcgcg gccgggatca   11340
ccggtctcat caagacggtg ctctcgctcg cccaccggga gctgttcccg agcctcaacc   11400
accagacgcc gaaccccgcg atcccctgg acaccctggg cctgacggtc cagaccgccc   11460
tcgacgactg ggccccgcag gcggacaccc cacggctcgc gggcgtcagc tcgttcggca   11520
tgggcggcac caatgtgcac atggtgctgg aggaggcacc cgccgacgac ccggccgcgg   11580
aacgccgac ggccctcgac acggtgccgt gggtgctctc ggcccgtacc gagggcgcgt   11640
tgcgggccca gcggagcgg ctgcggtcgt atgtgggggc gcggccggag ttggatccgg   11700
tggatgtggg ttactcgctg gcgttgaccc ggtccgcttt cggtcaccgc gcggcggtcg   11760
tcggccgcaa ctgtggggag ctgttgagcg gtcttgagca gctcgccgcg ggtgtggtcc   11820
cgggcgcggt ggctgacgag gagggcagga cggcgtttct gttcactggt cagggtgctc   11880
aacggctggg tatgggcgg gggttgtatt cggcgtttcc ggtgttcgcg gtgtcgttcg   11940
acgaggtgtg cgcggagctg gaccgtcatc tggatggttc ggtgggggag gtggtgttcg   12000
gcgaggatgc cgaggcgttg gatcggacgg tgttcactca ggccgggctg ttcgctttgg   12060
aggtgggct gttccggctg gtggagtcgt ggggtctggc gccggattc ctggtggggc   12120
attcggtggg ggagttggcg gccgcccatg tggcgggggt gttttcgctg gaggacgcct   12180
gtgcgctggt ggcggcgcgt ggtcggctga tgcaggcgct gcccggcggt ggtgcgatgg   12240
tgtcgctgaa ggctccggag gccgaggtgc tgccgcatct ggccggttac gaggaccggg   12300
tgagcgttgc ggcggtcaat ggcccgtcgg cgaccgtgat ctccggtgag gagtcggcgg   12360
tgctcgcggt ggcggaggcg gtgggggtca agagcaagcg gctgagcgtc tcgcatgcct   12420
ttcactcgcc gctgatggag gggatgctgg ctgcgttcgc cgaggtggcg gccgggatcg   12480
cctacgccac gccaggcatc gcgatcgtct cgaacgtgac gggcgagttg gcggggagg   12540
aggtgtgctc gccggagtac tgggtgcgcc atgtgcgtca ggcggtgcgc ttcgggatg   12600
gcatacggtt cctcgagacc cagggcgtca cccgctttgt ggagctcgga cccgcggtg   12660
tgctctccgc catgggccag gaatgcgtct ccggcccggc cgcgttcgta cctctgttgc   12720
gcaaggaccg cgaggagacc gaggcgctgc tctccggtgt cgcccaggtg cacgctcacg   12780
gtggcgaggt ggactgggag gcggtgttcg ccgggcgcgg tgcgcatcgg gtggagctgc   12840
ccacatacgc cttccagcgg cagcgctact ggctggacac cgacctcccc ggcaccgagg   12900
acgccgccac cgatgaaccc ctctcctggc gcgaggagtt cgcggccctg accgactccg   12960
ccgagcgcga gcgcgtggcg ctggagctgg tccgtacgca caccgcctgg gtcctgggct   13020
ctccgggacc cgacgccgtc gaccccgaga agatcttcaa ggacctcggc ttcgactcgc   13080
tgatgtccgt cgagctgtgc aacctcctca gcaccgccac cggaacgcgg ctcgccggga   13140
ccgtcctctt cgaccacccc acccgctgg ccctctccca ccacctccgg gaggtggtgg   13200
tgggcactcg gccggtcgtg gccccgcgcc cggccgccac ccggaccgtc accacgggcg   13260
acgacgaccc gatcgccatc gtggcgatga gctgccgcct ccccggaggg gtgcgcaccc   13320
ccgagcagct gtgggagctg gtcagcgagg gccgggacgc catcgccggc ttccccgcca   13380
accggggctg ggacctcgag gggctctacg acccggaccc ggcccgccac ggcaccagct   13440
```

```
atgtgcgcga gggcggattc ctctacgagg cggaccagtt cgacccggcc ttcttcggca    13500
tcagccccg  cgaggcccag gcgatggacc cccagcagcg gctgctgatg gagaccgcgt    13560
gggaggcgtt cgagcgcgcc gggatcgacc ccaccacgct caagggcagt gacgcgggtg    13620
tcttcgtcgg cgccatgccg caggactacg gccccggat  ggacgaggcg tcggaagggt    13680
tcgagggcta tctgctgacc ggtggcacca ccagtgtcgc ctccggccgg atcgcctaca    13740
cctgggggct cgagggcccg gcggtcaccg tcgacacggc ctgctcgtcc tcgctggtgg    13800
ccctgcacat ggccgtacgg tcgctgcgcc agggcgagtg ctcgctggcg ctggccggcg    13860
gcgccaccgt gatgtccagc cccgggatct tcgtggagct gagccgccag aaggcgctgt    13920
cgccggacgg ccgctgcaag gcgttctcgt ccgacgccga cggcaccggc tggggcgagg    13980
gcgtgggcat ggtgctgctg gagcggctgt cggacgcgcg gcgcaacggc caccaggtgc    14040
tggcgctggt ccgtggttcc gccaccaacc aggacggcgc gagcaacgga ctcaccgccc    14100
cgagcggccc ggcccagcag cgggtcatcc ggcaggcgct ggccgacgcg gggctgagca    14160
cggccgatgt ggacgcggtc gaggcacacg gcaccggcac ctcgctcggc gaccccatcg    14220
aggcgggcgc gctgctggcc acctacgcc  aggaccgcgc cggggaccgg ccgctgtggc    14280
tgggctcgct gaagtccaac gtcggccacc cccaggcggc ggcgggcgtg gccggtgtca    14340
tcaagatggt gctggcgctg cgccacggcg tgctgcccca gaccctgcac gtacacgagc    14400
cctcgccgca tgtcgactgg tcgtccgggg ccgtggagct gctgaccgag tcccggccgt    14460
ggccggagcc cgagagcgag cggccgcgcc gcgcgggcgt gtcgtccttc ggcatcagcg    14520
gtaccaacgc acacgccatc ctggagcagg cccggccga  accggccgcc ggccacgacg    14580
cgccgcgccc ggcggccccg gagctgcccg tgctgccctg ggtgctgtcc gggcgcaccg    14640
aacaggccct gcgcacccgg gccgagcagt gcggaaccga gctggccgac cacccccggca   14700
ccgacctcgc cgcgctcggc cacgccctcg ccaccacccg cacggccttc ggccaccggg    14760
cggtggtcct cggccgggac ccggagcggc tcctgacgg  cctcggcgcg ctcgcgcagg    14820
gcaccccggc gccccacgtg gtccagggca cggcgggcgg ccggcggaag accgtgttcg    14880
tcttccccgg acagggctcg cagtggatcg ggatggcact tccgctgtgg gacgcctcgc    14940
ccgtcttcgc ggagcggctg gaggagtgcg ccgacgccct ggagccgttc ctggactggt    15000
cgttgcgcga tgtgctgcgc ggcgagccgg gcgccccgtc gctgtcccgt atcgacgtgg    15060
tgcagcccgc gctgttcgcg gtgatggtgt gctggcggc  gctgtggcgc agtcacggcg    15120
tcgaaccggc cgcggtggtc ggccattcgc agggcgagat cgccgccgcg tacgtggccg    15180
gagggctttc gctccaggac gccgccaagg tggtggcccg gcgcagccag gcatgggccg    15240
agctgagcgg caagggcggc atgctctcgg tgctcgcgtc ggccgggacg gtcgcggagc    15300
ggctgcggcc gtggagcgaa cggctcggca tcgccgccgt caacagcccc gccaccgtga    15360
ccgtctccgg cgacccggag gccctggacg ccttcatggc cgagctcgcc gccgacgggg    15420
tgaagtcccg ccgggtgccg ggcgtggaca ccgccggaca ctccccgcag gtcgacgggt    15480
tgcgcgagcg gctgctgcgc gaggtggcgg gggtacggcc gcgcccctcg cggatcgcgt    15540
actactccac ggtgaccggc gggccgctgg acaccaccga gctggacacc gactactggt    15600
accggaacat gcgcgagccg gtggacttcg agcgggccac ccgggcgctg ctggccgacg    15660
gccacacggc gttcatcgaa tgcgccccgc accccatgct cgccatgtcg ctccagcaga    15720
ccatcgagga cgcgggcgga aacgccgccg tcgtcggcac gctgcgccgg gacgagggcg    15780
```

```
gcccggagcg cttcgcgggc tcgttcgccg aggcgtacgt ccagggtgtc gaaccgtcgt   15840
gggacaccgt gttcggggc gcgccggggc gcggtgagcg tgccctggag ctgccgacgt   15900
atccgttcca gcggcagcgg tactggctgg acaagccggt cgcggcgagc gatgtggcgg   15960
cggccggact cgacgcggcc gggcatccgc tgctcggcgc ggcggtcccg ctggccgggg   16020
cggacgacca cctgttcacc ggccggatct ccgcacagga ccacccctgg ctcaccgagc   16080
gcaccggact cgacgcggcc gtgctgcccg gcagcgccct cgccgaactg gcgatccgcg   16140
cgggcgacca ggtcggctgc gaccggatcg gggaactgtc cctggacgcg ccgctggtac   16200
tgcccgagaa gggtgccgcg gtgatccagg tgcgtatcgg cgccccggac gacgagggct   16260
cgcgcgccct cagcgtccac gcgcgcgccg agggcgccga cgccgacgag ccgtggacgc   16320
ggtacgccac ggcggtcctg ggcatgggtg ctccggccgc cgacgtcggc ctcgtcgcgt   16380
ggcccccggc cgacgccgtc ccggcggagg tggcgggagg cgccgtcgcg gcctggcggc   16440
tcggtgagga cctctacgtc gaggtcgggc tgaccgaggc cgaggaggcc gacgccgggc   16500
gctacggact gcacccggcg ctgctggagt cggcgctcga cgcggtggag accccgggcg   16560
acggtggcgg gtcgtggctg gccgccgtat ggagtggtgt cgccctgcac gccacgggcg   16620
ccacggcgct gcgggtgcgg ctgacgccga cgggtcccga tgcgtacgcg gtcgtcgcgg   16680
ccgacctgag cggtgccccg gtggcctcgg tggaccggct cgtgctgcgc gcggtggaca   16740
cgcccgaacc gatcggcggc cgctccgccc tccacccgtc gctgttccgg ctggagtggc   16800
ccgcggtgtc cgccgcggac accaccgcga ccgcgcctcc ggcgacctgg gcggtgctcg   16860
gcgacgaccc gctcgggctc tccgcggccg tggacgcggg gccgtacgac gagacggcgg   16920
atgcgccgga cgcggtcctg gtgccgtgcg tcgcgggagt cgacggcgat gtggcggagg   16980
cggcccacgc ggccacccac cgagcgcttg cgctgatcca gcgctggacc tccgatgacc   17040
gcctcgcctc ctcccggctg gtgttcctca cccgcggcgc ggtcgcgggt gccccggtg   17100 aagaggtccc ggacgtggcc cacggcgccg tatggggcct ggtgcgctcg cccagtcgg   17160 aacaccccgg ccgcttcgtc ctcgtcgacc tcgacgccga gccggagtcg gtgaccgctc   17220
tcccggccgc ggtggcttct ggcgaacctc agtgcgcggt acgcgaggga ctggtgaggg   17280
tgccccggct ggggcgggtg gcgaggggga cggggccgc cgaggccacc gcgcccgg   17340 ccaccgggct cgccgacggc caccgaccgc tggacccga aggcaccgtt ctcatcaccg   17400
gcgccaccgg gaccctcggc gggctcgtcg cccgccatct ggtggccgag catggcgtac   17460
ggcatctgct gctggtcagt cggcgtgggc ccgcggccga cggtatgggc gaactccgct   17520
ccgagctggc cgagttggga gccaccgtca ccgtcgccgc ctgcgatgcc gccgaccggg   17580
aggcgctcgc cgggcttctc ggcgcgatac ccgccgcgca tccgctgacc gccgtgatcc   17640
acgcggcggg tgtgctcgac gacgcgtcg tggacgcgct gaaccccgag cggctcgacc   17700
gcgtgctgcg gcccaaggtc gacgccgcgt ggaatctgca cgagctgacc gcggggcacg   17760
acctgtccgc gttcgtgctc tactcctccg tcgtcgccac catcggcaac gccggacagg   17820
ccaactacgc cgccgccaac gccttcctgg actcgctcgc ccagcaccgc agggcccgtg   17880
gcctggccgc ccagtccctc gcctgggggcc tgtgggagca gcgcagcggc atgagcgggc   17940
atctggacga cgccgatgtg cggcgcatgg cgcgctccgg catccgtccg ctgcccagcg   18000
cggagggcat ggaactcttc gacgccgcgc gggaggcggg cgatgccacg ctcgtacccg   18060
tccggctcga cctcgccgat ctgcgcaagc gcgccgcgag caccgccgcc acccccggcc   18120
aggacgccgt accggcccat ctgcgcggcc tggtccggac accggtccgc cgcgtcgtac   18180
```

```
gggccggtgg cggaggcggg gccgcggaga gcgacgagag ctcgttcggg cggcggctgg    18240
ccgccctgcc gacggccgac cgggacccgt tcctgctgga cctggtgcgg gaacacgcgg    18300
cgggcgtgct ggggctcgcc gccccggacg acatcgaggc cacccgcgcc ttccgcgagg    18360
tcggtttcga ctccctgacc gccgtggagt tgcgcaaccg gctgggcgcc gccaccgggc    18420
tgcggctgcc gaccactctc ctcttcgact acccgacccc cgccgtgctg gtggaccact    18480
tgcggcgcga ggcactgggc gagcaggcgg aagtggcggc cgtggtggcc gccgtccgcc    18540
ccgccgacga cgatccgatc gccatcgtgg ccatgagctg ccggctgccc ggcggggtcc    18600
gcggccccga ggatctgtgg gagctggtgg cggacggtcg cgatgtgatc tcgaccttcc    18660
cgaccgaccg cggctggaac gtcgaggagc tctacgaccc caaccccgat acgccgggca    18720
ggagttacgc caaggaaggc ggtttcctct acgacgccta cgacttcgac cccgagttct    18780
tcgggatctc gccgcgcgag gcgctggcca tggacccgca gcagcggctg ctgctggaga    18840
cctcctggga ggcgctggag cgcgccggga tcgacccgca ctccacgaag ggcagcacgg    18900
cgggcgtgtt catcggctcc accgccagg actacgcctc gcggctgggc gagatccccg    18960
aggacatgga ggggtatctg ctgaccggca aggccgccag cgtggtctcc ggccgcatcg    19020
cctactccct cggctgggag ggcccggcgc tcaccatcga caccgcgtgc tcctcctccc    19080
tggtcgccat ccaccaggcg gcgcaggcgc tgcgccaggg cgagtgctcg atggcgctgg    19140
cgggtggcac gacgatgatg tcgacgccga gtctgttcat cgagttcagc aggcagcgcg    19200
ggctcgcccc tgacgccgg tcgaaggcgt tctcctcgga caccgacggc accagctggg    19260
gcgagggcgt cagcatggtg ctcctggagc ggctgtccga cgcgcgggcg aacggccatg    19320
aggtgctggc gctggtgtgt ggctcggccg tcaaccagga cggcgccagc aacggcctca    19380
ccgcccccaa cggcccctcc cagcagcggg tgatccggca ggcgctggcg aacgccgggc    19440
tgtcggccgc cgaggtggac gccgtcgagg cgcacggcac cggcaccacg ctcggtgacc    19500
cgatcgaggc ccaggccatc ctcgccacct acggccaggg ccgggaggca gaacggccgc    19560
tgcggctggg cgcgttgaag tccaacatcg gccacaccca gggcgcggcc ggcggcgcgg    19620
gagtcatcaa gatggtcatg gcgatgcgcc acggcctgct gcccaggacg ctccacgtca    19680
aggagcccac cccgcatgtg gactggacgg ccggggccgt cgagctgctg accgaggcca    19740
gggagtggcc cgcgggcgag cgggtgcggc gcgccggggt gtccgccttc ggcatcagcg    19800
gcaccaacgc ccacctcatc ctggaggaac cgcccgccgc cccggccacc gaaccggcca    19860
ccgaacctga tccggagtcg gagccgacgg tgcgcaccga tgtggtgccg tggatggtgt    19920
ccgggcgtac cgagggcgcg ttgcgggccc aggcggagcg gctgcggtcg tatgtggggg    19980
cgcggccgga gttggatccg gtggatgtgg gttactcgct ggcgctgacc cggtccgcct    20040
tcggtcaccg cgcggcggtc gtcggccgcg accgtgggga gctgttgagc ggtcttgagc    20100
agctcgccgc gggtgtggtc ccgggcgcgg tggctgacga cgagggcagg acggcgtttc    20160
tgttcactgg tcagggtgct caacggctgg gtatggggcg ggggttgtat tcggcgtttc    20220
cggtgttcgc ggtggcgttc gatgaggtgt gcgcggagct ggaccgtcat ctggatggtt    20280
cggtggggga ggtggtgttc ggcgaggatg ccgaggcgtt ggatcggacg gtgttcactc    20340
aggccgggct gttcgctttg gaggtggggc tgttccggct ggtggagtcg tggggtctgg    20400
tgccggattt tctggtgggg cattcggtgg gggagttggc ggccgcccat gtggcggggg    20460
tgttttcgct ggaggacgcc tgtgcgctgg tggcggcgcg tggtcggctg atgcaggcgc    20520
```

```
tgcccggcgg tggtgcgatg gtgtcgctga aggctccgga ggccgaggtg ctgccgcatc   20580
tggccggtta cgaggaccgg gtgagcgttg cggcggtcaa tggcccggtg gcgaccgtga   20640
tctccggtga ggagtcggcg gtgctcgcgg tggcggaggc ggtgggggtg aggagtaagc   20700
ggctgagcgt ctcgcatgcc tttcactcgc cgctgatgga ggggatgctg gccgagttcg   20760
ccgaggtggc gggccggatc ggctactccg caccgcgcat ggcgatcgtc tcgaacctca   20820
cgggcgagtt ggcgggggat gaggtgtgct cgccggagta ctgggtgcgc catgtgcgtc   20880
aggcggtgcg cttcggggat ggcatacggt tcctcgagac ccagggcgtc acccgctttg   20940
tggagctcgg acccgcgggt gtgctctccg ccatgggccg cgagtgcgtc tctggtccgg   21000
ccgcgttcgt acctctgttg cgcaaggacc gcgaggagac cgaggcgctg ctctccggtg   21060
tcgcccaggt gcacgctcac ggtggcgagg tggactggga ggcggtgttc gccgggcgcg   21120
gtgcgcagcg ggtggagctg cccacatacg ccttccagcg gcagcgctac tggttcgacc   21180
ccgccacgcc gggaacgccg accgccgcca ccacggacac gtcctccgtg gaggcccgtt   21240
tctgggaggc ggtcgagcgc gaggacctgg aggcgctgac caccaccctg gagatcgacc   21300
agcaggcgcg gctcggcgac ctgctgcccg cgctctcctc ctggcgccgg gccagagcg   21360
accgcgccac cgtggactcc tggcgctacc ggatcacctg gtccccgacg gccgtcgaag   21420
agcgtacggc gctgctgtcc ggcatctggt gggtggccgt accggagggc cgggcggacg   21480
gcgcggggat cgccgccgtg gcggccgccc tcgaccggcg ggggcgcgc gtcgtgcccc   21540
tcaccgtggc cacgaccggc cgtgacgcgc tcgccgcgcg gctgcgccac gaggcggata   21600
ccggtggcac accggccggt gtgctctcgc tgctcgccct cgacgacggt ccacaccccg   21660
aacacggtgc gctcagcacc ggtctggccc tcaacgtcgg gctgatccag cgctgggcg   21720
acgcggggat cgccgccccg ctgtggctcg ccaccaccgg cgccgtctcg gtgagcggat   21780
ccgatccgct cggcagcccc gcacaggcgc ccacctgggg cctcggccgg gtcgtggccc   21840
tggagcaccc gcagcggtgg ggcggtctga tcgacctccc cggggacctc gacgaacgga   21900
cggcggaccg gctgtgcgcc gcgctctccg gcatcgccgg cggcagcggc ccggaggacc   21960
aactcgccct ccgtgacgcc ggggtgttcg tccgacggct ggtccgggcg ccgctgcgca   22020
caccgggccg ggagagctgg aagccgcatg gcaccgtgct gatcaccggg gcaccggtg   22080
ggctcggcgc ccaggtcgcc cgctggctgg cccgctccgg tgccgaacac ctcgtgctca   22140
ccagccgccg tggcatcgcg gcgcccggcg ccgccggact gcgcgacgag ctgatcgcgc   22200
tgggcgaggg cggtgtccgg gtgacggtgg cggcgtgcga cgtccgcgac cgtgacgagg   22260
tggcggcgct gctgcgccgg atcaccaccg ggggcgaccc ggtgcacgcc gtcttccacg   22320
ccgcgggcgt cgtggagttc tcccagctcg ccgacagtac ggtggccgac ttcgcggaga   22380
tggccgacgg caaggtgctg ggcgccgccc atctggacgc gttgctggac caggaccacc   22440
tcgaggcgtt cgtgctcttc tcgtccatcg ccgccacctg ggggagcggc gggcagagcg   22500
cctacgcggc cgccaacgcc cacctggacg ccctcgccga gcaccgcgag gcacgcggcc   22560
tccccgccac ctcggtggcc tggggtccgt gggccgacca cggcatgatc gagcacggcg   22620
aggtggcgga gcacctcagc cgccgtggac tccccgcgat ggcaccggag ttggccgtgg   22680
ccgcgctgag cgaggcgctg cacaccgcg agacctcgct cgtcctcgcc gatgtgcgct   22740
gggaccgctt cgtccccggc ttcaccgcgg cgcgccccg gccgctgatc ggcgagctgc   22800
cggaggtgcg cgatgccctc gccaccaccg cggcccccga caccaccggt ccggacgacg   22860
tggcggacac cttcctggcg ggcctcgcgg gcctgtcggg cgaggacctg gaccgggccc   22920
```

```
tgcgggacct ggtgcacgcc caggcggcgg ccgtactcgg ccactcctcg tccgacgcgg    22980
tcgccggcgg ccgcccgttc aaggagctgg gcttcgactc gctcaccgcc gtcgaactgc    23040
gcaaccggct ggccgcggtc accggactcg acctgcccgc caccctcgtc ttcgactatc    23100
cggcgcccgc gccactggcc gagtacctgc gcggcgagct gccgtcggcc cgcccggcgg    23160
acgcgcgcac cctcttcgac gacctggacc ggtgggagtc cgcgctgccg gagctgatgg    23220
ccgaggacgg ggtgcgggag cggctgacgg ggcggctgaa cgacctcatg gcgaagttgg    23280
gcggcacgcc cggggaacac accggcgggc cgtcccccga caccggcctc ctctccgcta    23340
ccgccgacga ggtcttcgac ttcatcgaca acgaattcgg ggcttcctga tggcgaacga    23400
gaacgaagag aaactcctca cctacctcaa gcgggtctcc tccgacctca agcaggcgcg    23460
tgaccggctg gagcggatcg aggccgacga gcggagccg atcgccatcg tctcgatggg    23520
ctgccggttc cccggcggtg tccgctcgcc ggaggacctg tggcggctgg tggccgaggg    23580
ccgggacgcg atctcggagt tccccgccaa ccgcggctgg gacgtcgagg gactctacga    23640
ccccgacccg ggccggtccg gcacctgcaa caccccgcgag gcggcttcg tccacgacgc    23700 cgaccagttc gacccggcct tcttcggcat ctccccgcgc gaggcgctgg ccatggaccc    23760
acagcagcgg ctgctgctgg aggtgtcctg ggaggcgatc gagcgcgcgg gcatcgaccc    23820
gctctcgctg aagggcacca gggccggggt ctatgtgggg ctcgcctcgt tccagtacgg    23880
cggggacccg cagtacgccc cgcagagcgt cgagggccat ctgctgatcg gtaatgtctc    23940
cagcgtggcc tccggccgga tctcctacac cctcggcctc gagggaccgg ccatcaccct    24000
ggacaccgcg tgctcgtcct cgctggtgac catgcatctg gcggcccagg cgctgcgtcg    24060
cggcgaatgc tcgctggcgc tggccggagg ggtggcggtg atggccaccc cgggtgtctt    24120
cgtcgagttc agccatcagc gcggactggc cgccaacggc cgctgcaagt ccttcgccgc    24180
gggcgccgac ggcaccggct ggggcgaggg ggcgggcatg gtgctgctgg agcggctgtc    24240
cgacgcccgc cgcaacggcc accccgtcct cgccgtgctg cgctccagcg ccatgaacca    24300
ggacggcgcg agcaacggcc tcgccgcgcc caacggcccg gcccagcgcc gggtcatcga    24360
ggcggcgctg actgccgccg ggctcacggt ggacgacgtc gacgccgtcg aggcccatgg    24420
cacgggcacg gcgctcggcg atccgatcga ggcgggcgcg ctgctcgcca cgtacggcaa    24480
gggccgcacc tccggccatc cgctgtggct cggctcgctc aagtccaaca tcggccacac    24540
ccaggcggcg gccggggtcg gcggggtcat caagacggtg atggccctgc ccacgggac    24600 gctgccgagg acactccatg tcgagcgggc gtccccgggc gtcaactggt cctccggcgc    24660
ggtcgagttg ctgaccgagg cccgggagtg gcccgagcgt ggccgtccgc gccgcgccgg    24720
ggtgtccgcg ttcggggtga gcggcaccaa cgcccatgtc atcctcgaac aggccccggc    24780 cgaggggag gacgacgaag aaggcgcccc cgccctggac gggaccgcgc tcggtggctc    24840
cgccgtcccc tgggcgctct ccggcaggag cgaagcggcc ctgcgggcgc aggcggagcg    24900
gctgctggcg catctgaacg agcgccccga ggtgtcccg gccgatgtcg gccactcact    24960
cgccaccgga cggtcggcct tcgaataccg cgccgcggtg gtgggcgcgg accggcccca    25020
actgctgggc caacttgagg cgttggcctc cggtggggtc tccgcaggtg tggtgcgtgg    25080
cgagggagtc acgcggccg atgcccgtcc ggtgttcgtg tttccggggc aggggtcgca    25140
gtgggtgggg atggcggtgg agttgctgga ttcgtcgccg gtgttcgcgg gtcggttggc    25200
ggagtgtgag gtggcgctgt cggggtttgt ggactggtcg ttgagtggtg tgttgcgggg    25260
```

```
tgaggggccg gggttggggc ggtggatgt ggtgcagccg gcgttgtggg cggtgatggt    25320
gtcgttggcg gaggtgtggc gtgcgtgtgg ggtgacgcct gccgctgtgg tggggcattc    25380
gcagggggag atcgcggcgg cggtggtggc gggtgcgctg tcgttggagg acggggcacg    25440
ggtcgtcgcg ctgcggtcgc aggccatcgg acgggctg gccggacacg gcggcatgat    25500
gtccgtgtcg ctcccggtcg aggaggtgcg ggagcggatc gccgcctggg aggggcgtat    25560
ctccgtggcg gccgtcaacg gccccggcgc ggtggtcgtc tccggcgaac cggaggcgct    25620
gcgtgaactc caggcggagt gcgaggccga ggacgtacgg gcgaagctga tcccggtgga    25680
ctacgcctcg cactcggcgc aggtggagaa gatccacgac gagctgctgc ggatcctcgc    25740
ccccatccgg ccgcgcacct cgcggatcgt cttccactcg accgtcaccg gtgaacccct    25800
ggacaccgct gggctcgacg ccgcctactg ggcgcgcaac cttcgggaga gcgtacagct    25860
cgaagcggcc acccgggcgc tgctcaccag cggccaccgg ctgttcgtgg aggtgagccc    25920
gcaccccgtg ctggccgcgg ccatcgaggc caccgtcgag gccgccgagg gctcggccgc    25980
cgtcatcggc accctgcgcc gcgaggaggg cggccccgag cggatgctgc tctcgctcgc    26040
ccagggctac gtccatggcg cggaggtgga ctggcggggg ctgttcgccg ggcggggagc    26100
gaggcgcgtc gaccttccca cgtacgcgtt ccagcgcgcc cgctactggg tcgagccccg    26160
gaccgggccc gccgaggcgg ccaccggccc ggcggaggcg gagttctgga ccgcggtcga    26220
gaaggccgac ctggacacgc tgacggcgac actgggcgcg gacgccgacg cgccgctcag    26280
cgaggtgctt ccgctgctct cgtcgtggcg gtcccggctg agcgaccagg cggagctcga    26340
cgcctggcgc taccgcatcg gctggcaacc gctcgacggc cggcggaccc ccacgctccc    26400
gggccgcctg ctggtggcgg tgcccaccga ggcccgcgcc actgataccg aggccatcac    26460
cgccgggctc gccgcgctcg gcgtcgaggt cgtccccgtg cgcatcggcc cggacgacac    26520
cgaccgcgcc cggctcgcca cccgtatcac cgaggccctc ggggacaccg gggcgcccgg    26580
cggcgtggtg tccctcctcg ctctcgacga agcaccgcac ccggaacacc ccgaggtgcc    26640
caccgggttc gccaccaccc tcgacctggt gcgggcgctg ggcgaggcgg gcgtcgacgc    26700
gccgctgtgg tgtgtcaccc gtggcgccgt gtccgccagt ggcgccgacc gtctcggagc    26760
ccccgcgcag gccctcgtct ggggcctggg cggtgcggtc gccctggagc atccgcagcg    26820
ctggggcggg ctggtcgatc tgcccgggac gctcgacgag ggcgccctcc gggcgctcgc    26880
ccgcgccctg accggccagg acggcgaaaa ccagctggcc atccgcgcct cgggcaccct    26940
cgcccggcgg ctccggcggg ccggggccgg ccgctccggt gagcgctggc agcccgcgcg    27000
caccgtcctg atcaccggcg gcaccggtgg cgtcggcgcc cagatcgccc gtggactggt    27060
cgacgagggc gccgagcacg tggtgctcat cagccgccgt ggccccagg ccccggcgc    27120
ggccgagctg gaggccgaac tgaccgagcg cggcgcccgg gtgaccgtcg ccgcatgcga    27180
tgtggccgac cgcgaggcgc tggcacacct gctgaaccag gtcacccacg acggcgcgga    27240
ccacccgctc accgccgtgg tgcacgccgc gggcgcgctg gacgacgcca ccgtggacgc    27300
gctcaccccc gagcggatcg aggccgtact gcgccccaag gtggcggcg cgcgccatct    27360
gcacgagctc acccgggacc tggacctgga cctcgacgcg ttcgtcctga tctcctcgat    27420
cgccggcacc gtgggcgccg ccggccaggg caactacgcg gcggccagcg cgtatctcga    27480
cgcgctcgcc cagctgcgcc gcgcggacgg tctgcccgcc acctcggtgg cctggagtgc    27540
ctgggcgggc ggcggaatga tcgacggcga ggtggcggac cagctgcgac gccgtggcgc    27600
gccgcccatc gacggcgtac gggcgctgga actgctgcgg cagacggtcg cgcagagcga    27660
```

```
tggcttcctc gtcgcggccg acatcgattg gggccgtttc gccccgccc tgtccgccac    27720
ccgcccgttg ccgctgctcg ccgacctccc cgaggcgggc ggcaccttgc aggatccggc   27780
cggagcggag cgggaggagg ccggtggcgc cgccgcgctg cgcacgcggc tcgcggagct   27840
cagcccggcc gaccgccaca ccgccctcgt ggagctggtg agcgagcagg cggccgcggc   27900
cctcggctac gccgacgcgg gcgcgttcga gaccggacgg gccttcaagg agctgggctt   27960
cgactcgctg accgccgtcg atctgcgcaa ccggctgaac gccgccaccg gactccggct   28020
gccggtcacc ctcgtcttcg actacccgac cgccgacgac ctcgccgtgc tgctgcggga   28080
ggaactcctg ccatcgggcg gggagcccgt ggacaccgtg gcgctcgccg agctcgaccg   28140
cgtccagtcc accctcgccg ccctggagct ggacgacatc gaatcggcca ccgacgacga   28200
gatgttcgag ctgctcgacg ggatgttcga gctgctgggc cgggatctga cggccccatg   28260
aaccgccgcg ccaccgcccc ggccgccacc gacgttccgg ccctcttgag gagctgacga   28320
ccatggacaa cgagaagaag ctgcgcgact acctcaagcg ggccaccggc cacctccgcg   28380
ccgcacaccg ccggatccag gagttgcagg ccccgagcc catcgccatc gtggcgatga   28440
actgccgcta cgcgggcgac atccggtccc ccgaggacct gtggcaggcc gtggccgaag   28500
gccgggacgg catgggcgac ttcccggccg accgggctg ggacctgccg aacctcttcg   28560
acccggaccc ggaccgcgag ggccgcacct acgcccgcca gggcggattc ctccaggacg   28620
tggaccagtt cgaccggcg ttcttcggca tctccgccg cgaggccctc accatggacc   28680
cgcagcagcg gctgctgctg gaagtggtgt gggagacctt cgaacgggcc ggaatcgatc   28740
cgggcaccct gcgcgcgagc gacaccggca tcttcatggg cgccaccgac ttcgactacg   28800
cccgtgatct gaccgagctc cccgaggggc tcgagggcca gatgtccatg ggggcctcgg   28860
gcgccatcct ctccggccgg gtcgcctaca ccctggggct ggagggcccg gccgtcacgg   28920
tcgacaccat gtgctcgtcc tcgctggtgg cactgcacat ggcgtgccag gcgctgcgcc   28980
agggcgactg ctcgatggcg ctcaccggcg gcaccaccgt gatgtccacg ccgagcggtt   29040
tcatcgagtt cagccgccag cgtgcgctgt ccacctcctc ccgctgccag gcgttctcct   29100
cgacggccga cggcaccgcc tggggcgagg gcgtcggggt gctgctgctg aacggctct   29160
cggacgcccg ccgcaacggc cacaccgtgc tcgcggtggt ccgcggcagc gccatcaacc   29220
aggacggcgc cagcaacggc ctcaccgcgc ccaacggccg ggcccagcag cgggtgatcc   29280
gccaggcgct ggccaacgcc accctgtccg ggaccgatgt ggacgtggtc gaggcacacg   29340
gcacgggaac gtcgctgggc gaccccatcg aggcgaacgc cctgctggcc acgtacggca   29400
ggaaccgccc ggccgaccgg ccgctctggc tcggctcgct gaagtccaac atcggccaca   29460
cggccgccgc cgcggggtc ggcggtgtga tcaagatggt gcaggcgatc cgccacgggg   29520
tgctgcccag caccctgcac atccaggagc cgtcgcccaa cgtggactgg acctcgggcg   29580
ccgtcgaact gctcaccgag gccggccgt ggccggagac cgggcgggtc cgccgcgccg   29640
gggtgtccgc cttcggcgcc agcggcacca atgcccacgc catcatcgag caggccccg   29700
aggccaccgg accggcggac acttcaaccg agggcgtggc accgtgggt ggcgcggcgg   29760
tgccgtgggt gctgtcggcc aagaccgagt cgggtctgcg cggcaggcg gagcggttgc   29820
tggcacgcct cgcggagggt ccggagccgt ccccggcgga cgtgggcttc tcgctggcca   29880
ccacccgcgc ccgcttcgac caccgcgcgg tggtggtagg tggcggcgtc gaggacttcc   29940
gcgccgggct gacggcgctc acccgggccg agcccggtgg cctggtggcc cagggcgtgg   30000
```

```
cgggccacgc cgggaagccg gtgttcgtgt ttccggggca ggggtcgcag tgggtgggga  30060
tggcggtgga gttgctggat tcgtcgccgg tgttcgcggg tcgttggcg gagtgtgagg  30120
tggcgctgtc ggggttcgtg gactggtcgt tgagtggtgt gttgcggggt gagggtccgg  30180
ggttggagcg ggtggatgtg gtgcagccgg cgttgtgggc ggtgatggtg tcgttggcgg  30240
aggtgtggcg tgcgtgtggg gtgacgcctg ccgctgtggt ggggcattcg caggggagga  30300
tcgcggcggc ggtggtggcg ggtgcgctgt cgttggagga cggggcgcgg gtggtggcgc  30360
tgcgctcgca ggccatcgga cgtgggctgg cggggcgtgg ggggatgatg tccgtcgccg  30420
agggcgccga tcgggtgcgg gagcgcatca ccgcctgggg cggtcgtata tcggtggcgg  30480
cggtcaacgg tccgggctcg atcgtggtgt ccggtgaccc ggaggcgctg cgtgaactcc  30540
aggcggagtg cgaggccgag gacgtacggg cgaagctgat cccggtggac tacgcgtccc  30600
actcggccca tgtggaagcg ctccgcgagg agttgctcga cctgctcgcc ccgatccgcc  30660
cgcgcacctc ggacatcacc ttccactcca ccgtcacggg cacccccctg gacaccgcgg  30720
atctggacgc cgggtactgg tacaccaatc tgcgggagac ggtcgagctg gagtcggcgg  30780
tgcgggccct gtcggccgcc gggttcggca cgttcctgga gatgtcgccg catccggtgc  30840
tgacgatgcc gctccaggcg accgccgagg acgccgtggt cgtgggctcg ctgcggcgtg  30900
acgagggcgg tccggagcgg ttcctggcct cgctgggcga ggcgttcgtc cggggcgtgg  30960
ccgtcgactg ggccgcggtg ttcgccgggc tgggcgcgtc cgtggtggaa ctgcccacgt  31020
acgccttcca gcggcagcgc tactggctgg agcggcccgc ggcgcaggcg ccgccaccg   31080
ggggcgaccc ggtggacgcc gagttctggg acgccgtcga gcgcgaggac ctggccgcgc  31140
tgaccgccgc gctggaggtg gacgccgacg aggggcggtc gtcgctgcgg accgtgctcc  31200
cggcgctgtc ctcctggcgg cgcggccgcc gcgagcggtc cgtactcgac tcctggcgct  31260
accacgtcac ctggaaccgg gtgccggacc cggcctctgc ggccctgacc ggcacctggc  31320
tgctcgcggt cccggccgga agcctcgtcg acacccccgc cggacacctc ggcaccgagc  31380
tcgtcgacgc cgtacgcggc ggcctggaga cccacggcgc cacggtcgtc accgtcgagg  31440
tggccgaggc cgaccgcgcc gcggtcgccg cgcggctcgc cgaggccacc gcccgggcca  31500
ccccggccgg ggtgctctca ctgctcgggc tccccgacgc accgcacccc gcacacgcgg  31560
gcgtgcccat gggactcgcg ctcaccctcg ccctcgtcca ggccctcggc gacacggggg  31620
tggacgcccc gctgtggctg gccaccgtg cggcgtgtc cgtcggcggc accgacgccc  31680
tcggcagccc cgcccaggcg gccgtatggg gccttggccg ggtcgccgct ctcgaacacc  31740
cccagcgctg gggcggcatg gtcgacctgc cggacaccgt cgacggccgg gtgaccaccc  31800
ggctgtgcgc cgcgctcgcg gccgcctcg atgacgagga ccagctggcc ctgcggtcct  31860
ccggggtgtt cgtccggcgg ctggtacggg ccgcggagca ccgggggagc ggccccgtgt  31920
ggagccccga gggcaccgtg ctgctcaccg gcggcaccgg tggcgtcggc gcccagatcg  31980
cccgccggct ggcccaggcc ggtgccgaac acctggtgct caccagccgc cggggccccg  32040
acgccccgcg cgcggacaag ctcaaggccg aactgaccga gctcggcgcc aaggtcaccg  32100
tggccgcgtg cgatgtggcc gaccgcgccg cgctggaggc gctcgtacgg aaggtggagg  32160
ccgagggccc gccgatccgt tccgtactgc acatcgccgg tgccggtgtg ctcgtcccgc  32220
tcgccgacac cgatctggcg gagttcgcgg acacggcgga ggccaaggtc gcgggcgcgg  32280
cgaacctgga cgcgctcttc gacgggaca cgctcgactc cttcgtgctc ttctcctcca  32340
tctcggccgt ctggggcagt ggcgaacacg gcgcgtacgc cgccgccaac gcctatctcg  32400
```

```
acgggctggc cgagcaccgc cgggcccgcg ggctcaccgc cacctcggtg gtgtggggca   32460
tctggagccc cgaggagggc gggatggccg ccaacctcgc cgaggagcaa ctgcgcggcc   32520
ggggcatccc gttcatgtcc ccccggctcg ccatcgacgc gttctggcag gtgatggagc   32580
gggacgagac cgtggtcgtg gtcgccgacg tggactggga gcggttcgtc cccgtcttca   32640
cctcggcccg gaccagcccg ctcatcggcc aggtgcccga cgtggcgcgg atcctcgcgg   32700
ccgacgccga caccggacg gacacgaccc gcgagtcctc ctcgctgcgc gaccggctgg   32760
ccgagttggc cccggcggac cggcaggcgg cagtgctgtc gctggtgcgc tcgcagatcg   32820
ccaccgtcct cggctactcc ggccccgagg ccgtcgacgc cacgcgcgcc ttccgcgagc   32880
tgggcttcga ctccctgagc gccgtcgacc tgcgcaaccg cctgggcacc gccaccgggc   32940
tccgcttccc cgtcaccgtc gtcttcgact acccgagcgc ggaggagctc gccggacaca   33000
tcggcgccga actcttcccc gacgacaccg ccgccaccgc cctcgacccc gaagaggcca   33060
acgtccgcag ggcgttgacc tccatcccgc tgctccggct ccgcgaatcc ggactgctgg   33120
acgagctgct gcggctggcc ggttcccacg accccgccac cgcaccggcg gacgaggagc   33180
ccgccgagtc catcgacgac ctggacgtgg atgacctcgt gcgcatggcc tacgacaaga   33240
acgacctctg acgagactcg actgcggagc tgacaatggc aaacccaacc gacaagatcg   33300
ttggcgcgct gcgggagtct ctgaaggaga ccgaacggct gcgccgggtc aatcagcaac   33360
tcaccgccgc ctcccgggaa cccatcgcca tcgtggcgat gagctgccgc taccccggcg   33420
atgtgcgcgg ccccgaggac ctgtgggagc tggtcaccgg cgggcgcgac gccatctccg   33480
ggttccccgg caaccgcggc tgggacctgg agaacctcta cgacccggac cccgaccggc   33540
agggcaccgt ctacgccacc gagggcggat tcctccacga cgccgaccag ttcgaccccg   33600
ccttcttcgg catctcgccc cgcgaggcca ccgtgatgga cccgcagcag cggctgctgc   33660
tggagacctc ctgggaggcg ttcgagcgcg ccggaatcga tccggcggcg ctgcgcggca   33720
gcaagaccgg catcttcgtg ggcgccgcct accagggcta catccccgac tggccccata   33780
tgcccgaggg tctcgagggc cacctggtca cgggcatctc cgcgagcatc atgtccggcc   33840
gcgtcgccta caccctgggc ctggagggcc cggccgtcac catcgacacc gcctgctcgt   33900
cctcgctggt cgccctccac ctggcctgcc agtcgctgcg ccaggcgac tgctcgctcg   33960 ccctcgcggg cggcgccgcc gtgatgggcg cccgatggg gctcatcggc ttcgcccggc   34020
agcgcggact ggcgcaggac ggccgctgca aggcgttcgc cgaggggggcc gacggcatgg   34080 gcctcggcga gggcgtcggc atgctgctgc tggaacgcct ctcggacgcg cggcgcaacg   34140
gccacgaggt gctggccgtg gtgcgcggct cggccgtcaa ccaggacggc gccagcaacg   34200
gcctcaccgc ccccaacggc cgctcccagc agcgggtgat ccgccaggcg ctcgccaacg   34260
ccgcgctcac ggcggagcag atcgacgcgg tcgaggccca cggcaccggc acccgctgg   34320 gcgaccgat cgaggcgggc gcgctgctcg ccacgtacgg gaaggaccgc gcggcggacc   34380
gacccgtgct gatcggctcg ctgaagtcca acatcggcca tccgcaggcc gccggcggtg   34440
tcggcggtgt catcaagatg gtgcaggcca tgcgccacgg cctgctgccc aggacactcc   34500
acgccgagga gcgctcctcg cggatcgact ggtcggcggg ggcggtggaa ctgctgaccg   34560
aggccaggga gtggccgcgc ggcgaggaac cccgccgggc cgccgtctcg gccttcgggg   34620
ccagtggcac caatgtgcac accatcctcg aggatgcgcc cgaggaggag ctttcggaga   34680
ccgcggccga gggggacgcc ccggtgggcg ggggagtggt gccgtgggtg ctgtcggcga   34740
```

```
agagcgcggc gggtctgcgg gcgcaggccg agcggctgct gacgcatgtc accgcgcgcc   34800
ccgggctgtc cccggccgat gtcggccact cgctcgccac cacccgtggc cgcttcgacc   34860
accgcgcgct cgtcctgggc ggcggccgcg acgagctgat cgacgcactg ggcgcactgg   34920
cgtcgggcgg cgagtccccg cgtgtggtgc gtggcgaggg agtcacggcg gccgatgccc   34980
gtccggtgtt cgtgtttccg gggcaggggt cgcagtgggt ggggatggcg gtggagttgc   35040
tggattcgtc gccggtgttc gcgggtcggt tggcggagtg tgaggtggcg ctgtcggggt   35100
ttgtggagtg gtcgttgagt ggtgtgttgc ggggtgaggg tccggggttg gagcgggtgg   35160
atgtggtgca gccggcgttg tgggcggtga tggtgtcgtt ggcggaggtg tggcgtgcgt   35220
gtggggtgac gcctgccgct gtggtggggc attcgcaggg ggagatcgcg gcggcggtgg   35280
tggcgggtgc gctgtcgttg gaggacgggg cgcgggtggg ggcgctgcgg tcgcaggcca   35340
tcggacgcgg gctggcgggg cgtgggggga tgatgtccgt cgccgagggc gccgattggg   35400
tgcgggagcg catcaccgcc tggggtggtc gtatatcggt ggcggcggtc aacggtccgg   35460
gctcgatcgt ggtgtccggt gacccggagg cgctgcgtga actccaggcg gagtgcgagg   35520
ccgaggacgt acgggcgaag ctgatcccgg tggactacgc gtcccactcg gcccatgtcg   35580
aggagttgcg cgatgaactc ctcgacgtcc tggccccgat cgccccgcgc cgcgccgagg   35640
tgccgttctg ctcgacggtc accgcgacca ccatcgacac caccgactc gacgcgggt    35700
actggtacac caatctgcgg gagacggtcg agctggagtc ggcggtgcgg gccctgtcgg   35760
ccgccgggtt cggcacgttc ctggagatgt cgccgcatcc ggtactgacc atgccgctcc   35820
aggcgaccgc cgaggacgcc gtggtcgtgg gctcgctgcg gcgtgacgag ggcggtccgg   35880
agcggttcct ggcctcgctg ggcgaggcgt tcgtccgggg cgtggccgtc gactgggcgg   35940
cggtgtgcgc cgggtccacg gtcgtggaac tgccgacgta cgccttccag cggcagcgct   36000
actggctcga aggctcctcc gcacccgccg aaggcgcggc ggtggacgcg gacttctggg   36060
acgccgtgga gcgcgaggac ctgaccgcgc tggccgccgc gctggaggtg gacgccgagg   36120
agtcgtccct ggccatggtg gttcggcgc tggccgcatg gcgccgggcg cgccgtgagc    36180
ggtccgtgct cgactcctgg cgctaccagg tcacctggaa gccctgggc gacgccctca    36240
cctccgccca cgaccggtcg tcggccggtg cgacctggct gatcgccgcg cccgccggag   36300
cgccggaggg cccgcgtgtc gcggaggcgc tgcgggaacg cggcgccgg gtgcggctgg     36360
tggagctgac cgaagcggac gccgtacgcg aggcgctcgc ccgcgggctc ggcgaggcca   36420
cggccgatac gccaccgacc gctgtgctct cgctcctcgc gctcgccgag gacccgtacc   36480
gcgcgggcac ggcgcagccg ctcggccttg ccctcaacct cgccctcctc caggcgctct   36540
tcgacaccgg ggccgatgtc ccggtgtggt acgccacgcg cggcgcggtg tccgtgggcc   36600
gcgcggacgc gctggaccat ccgctgcagg cgctcagctg gggcctgggc cggatcgcgg   36660
cggtggagta cccgcggtgc cggggcggtc tggtggatct gcccggcact ctcgacgacc   36720
gtgccgtcgc gcggctgtgc ggtgtgctcg cgggccggct gaccgacgag gaccaggtcg   36780
cggtgcgcgc ctccgggtc cacgggcgca ggctggtcag ggcctcggcg caccggccg     36840
acgccaccgc gccgtggcgg ccgcgcggca ccgtgctggt caccggaggc accggcggcc   36900
tgggcgccca tgtggcgcgc tggctggccc ggggcggcgc cgaacacctg gtgctctcca   36960
gccgccgggg ccccgacgcc cccggagcgg ccgaactcgc cgacgggata agggagtcgg   37020
gggtccgggt gaccgtggcc gcgtgcgacg ccgccgaccg cgacgcgctg gccgacctcc   37080
tcgccacgct ggacgccgac gaggcaccgc tcgacgcggt cgtccacacc gcgggcgtcc   37140
```

```
tggacgacgg ggtgctcgac accctcaccc ccgagcgcgc cgacggggtg ctgcgcccga   37200
aggtggacgc ggcgctccat ctgcacgagc tcacccggga ccgcgagctg tccgccttcg   37260
tgctcttctc ctccttcgcg ggcacgctcg gcggtcccgg ccagggcagc tacgcggccg   37320
ccaacgcctt cctcgacgcg ctcgcacacg cccgccgcgc ccagggcctc cccgccacct   37380
ccgtggcctg gggcgcgtgg tccggcgcg ggctggtgga cgaggccgtc caggcgcggc   37440
tgcgcgccac cggtatgccc gcgatggcac ccgacctggc gatcgccgcc tccagcgcg   37500 ccctggacgt ggccgacacc catgtggccg tggccgatgt cgagtgggac cggctcatcg   37560
ccgccacgcc ctccctggac ggggccgccg tgctcggcga actccccgac gcgcgacggg   37620
cggaggtggc ggccgcgacc acgggcgagg aggacacccc gctgagccag cggctggccg   37680
ggctgtcgcc gcaggaggcc gaggaggcgc tggccgacct cgtcagcgcc gaagtggccg   37740
ccgcgctcgg ctacgccgac accgcggcgg tcgaggccgg gcgggccttc gcgcgagctgg  37800 gcttcgactc gctgaccgcc gtcgatctgc gcaaccggct gaacgcggcc accgggctgc   37860
ggctgccggt caccctcgtc ttcgactacc cgaccgtcgc cgcgctggcc cgcttcctgc   37920
tcgccgagag cggtgccggt gaaaccgcgg ccaccgcccc ggcgggcccg gtgcccgccg   37980
ccgtcgcggt ggacgacgac ccgatcgcca tcgtggccat gagctgccgc ctccccggcg   38040
gggtgaccac ccccgaggag ctgtggcggc tgttgatgga tggccgggac gccatctcgg   38100
acttccccac cgaccgcggc tgggacatcg agggccacta cgaccccgac cccgacaagc   38160
cgggcacgtt ctacgccacc ggcggtggtt cctccacca ggccgaccac ttcgaccccg   38220
agttcttcgg gatctccccg cgcgaggcgc tcgccatcga ccccccagcag cggctgctgc   38280 tggagaccag ctgggagacg ttcgagcggg ccggatcga cccggcctcg gtgaagggca   38340
cccaggccgg agtcttcatc ggcgccagct acaacgacta cggctcgcgc ttcacccgcg   38400
cacccgagga gttcgagggc tatctggcca ccggcagcgc cagcagcgtg gcgtccgggc   38460
gcatctcgta caccttcggc ctcgaagggc ccgcggtcac cgtggacacc gcctgctcgt   38520
cctcgctggt cgccctccac caggcggccc aggcgctgcg ccaggggag tgctcgctgg   38580 cgctcgcggg cggtgtcgtg gtgatgtcca cgctggacac cttcatcgag ttcagcaggc   38640
agcgggccat ggcccccgac ggccgctgca aggcgttctc ggcggccgcc gacgcgcgcc   38700
gatgggccga gggcgtcggc atgctgctgc tggagcggct ctccgacgcg cgggcgaacg   38760
gccatgaggt gctggcgctg gtgcgtggct cggccgtcaa ccaggacggc gccagcaacg   38820
gcctcaccgc ccccaacggc ccctcccagc agcgggtgat ccgccaggcg ctggccggtg   38880
cgggcctgtc ggccgccgat gtggacgcgg tcgagaccca tggcaccggc accggctcg   38940 gcgacccat cgaggcgcag gccctgatgg ccacctacgg ccaggggcgg gacgccgacc   39000
ggccgctgtg gctgggcgcg ctgaagtcca acatcggcca cacccaggcc gcttcgggcg   39060
tcgccgggat catcaagacg gtgctggcgc tgcgacacgg cgtgctgccc aagaccctcc   39120
acgccgatga cgcgctcgcc gacgtggact ggtcggccgg tgcggtggag ctgctgaccg   39180
aggcccggga gtggcccgag acgggacggc cgcggcgcgc gggcgtgtcc gccttcggcg   39240
tcagcggcac gaacgtccat gtggtgctgg agcagggccc cgagcacacc gcgccggtgg   39300
ccgagcggac ggtcgactcg gacgtggtgc cgtgggtgct ctccgcgcgc ggcgagaccg   39360
cgctgcgggc gcaggccggg cggctgcgtg cccgtctgga ggagcggccg gagctgcgcc   39420
cggtggacgt cggctacgcg ctggcgacgg gccgctcggc cttcggccac cgcgccgtgg   39480
```

```
tcgtcggcgc ggagcgggag gaactgctgc ggggactcgc ggaactggcc tcggggacgg    39540
cgcgggagac ggtggccgac gccggtagga cggccttcct gttcaccggg cagggtgctc    39600
aacggctcgg catgggacgg gagttgtacg acgcgttccc ggtgttcgcg gcggcgttcg    39660
acgcggtgtg cgccgagctg gaccgccatc tggacggctc ggtgcgcgag gtggtgttcg    39720
gcggggacgc ggagccgctg aaccggaccg tgttcaccca gaccgcgctg ttcgccctcg    39780
aagtggcgct gtaccggctg gtcgagtcct ggggtctgcg cccggacttc ctggtcggcc    39840
actcggtggg cgagctggcg gccgcccatg tggccggggt gttctcgctg gaggacgcgt    39900
gtgcgctggt ggcggcccgg ggccggctga tgcaggcgct gccggagggc ggtgcgatgg    39960
tgtcgctcca ggcggccgag gccgatgtgc tgccacatct cgaaggccac gaggaccggg    40020
tgagcgtggc ggcggtcaac gggccgcggg cgaccgtcat ctccggtgac gaggacaccg    40080
tcctgcggat cgcggaggcg accggggcca gagcaagcg gctcaccgtc tcccacgcct    40140
tccactcgcc gctgatggac gccatgctcg cggagttcgg cacggtggcc accgggatcg    40200
gctactccac accgcgcatc gcggtggtct ccaatgtcac cggtgaggcg gcgggcgagg    40260
agctgtgctc gcccgagtac tggggtgcgcc acgtccgccg tgcggtgcgc ttcggggacg    40320
gcatccgctt cctcgccgag cggaatgtga cccgcttcgt cgagatcggc cggccggtgt    40380
gctctccgcc atggggccag gagtgcctgg ccgaggccgg caccgagacc gacatcgaca    40440
ccgagaccgc gttcgtcccg ctgctgcgca aggaccgcag cgaggccgag tcgctgctgg    40500
ccggggtggg ccgggtgcac gcccacggtg gcgcggtgga ctgggagcag gtgttcgcgg    40560
gccgtggcgc ccgccgggtg gagctgccga cgtacgcctt ccagcggcag cgctactggc    40620
tggacgcgcc cgccaccgtg ggcgatgtgg cctcggccgg tctcggcgcc gcgggcatc    40680
cgctgctggg cgcggccgtc gaactcgccg acagcgacgg cctggtgctc accgggcggc    40740
tgtccacgcg cggccagccc tggctggccg accacgcggt ctccggtgtg gtcctcttcc    40800
ccggcaccgc cttcctggag ctcgccatcc aggccgggga ccgggtgggc tgcgaccgcg    40860
tcgacgagct gaccctccag cgcgccgctca tcctgcccga gcgcggcgcc gtcaccctgc    40920
aactggtggt ggacccgccc gaggaggacg gccgtcgcgc cctgaacgtc tactcccgcc    40980
ccgaggacac gaacggtgag ccgccgtgga cccggcacgc cacgggtgtg ctggcggccg    41040
gtgccgccga gggctcgtac gacctgggcg gggcgtggcc ccgccgggc gccgagccga    41100
tcgaggtcga ggacctgtac gagcggttcg cggcggcgg cttcggctac ggcccgtcgt    41160
tccagggggct gcgcgcggcc tggctgcgcg gcgacgaggt gttcgccgag gtacggctgg    41220
cgcaggagca gcagtccgcc gccaccgcct acggcctgca ccccgccctg ctggacgccg    41280
cgctgcacac catcgcgctc ggcccgatgc tccaggcggg cgaggccgg ttgccgttct    41340
cctggaccgg ggtgacgctg cacgcctccg gggccggtga ggtacgggtg cggctcacgc    41400
cgagcggcac cgacacggtg gccctgacgg tggcggacac catcgacgg ccggtggcca    41460
ccgtcgaatc cctggtgttg cgcaagcggc ccgaacggct cggcgacgcc gccaccggcg    41520
gcgactcgct ctaccggctc gactgggtgg ccgccgacac ctccgcggcg acgcccgaac    41580
aaccctccgg gcactgggcc ctgctcggcg acgacgactt caagctggtc ggactcgatg    41640
tgcacacata cccgaacctg gaggcgctgc ccgccgaccc ggccgccgtg cccgccaccg    41700
tactggtgcc ctgcgcaccg gagcccagg gcgtggccga cgccgtacgg gccgcgaccc    41760
accgggcgct gacgctgctc cgggcctggc tgaccgagga ccggttcgcc gactcccgcc    41820
tggtgttcat cacccgggc gcggtggcca ccacacccgg cgcggacgta cccgatctgg    41880
```

```
cgcacgccgc cgtatggggc ctggtgcgct ccgcgcagtc ggagaacccc gaccggttcg   41940
tgctcgtcga cctcgacgag caggaggaat cggcgctcgc cctgccgacc gcgctcgccc   42000
tggacgagcc tcaactcgct gtgcgccagg gggacatcgt ggtggccagg ctcgccacca   42060
cccccgtccc cgacaccgcc ccgcccgcct gggaccccga gggcacggtg ctggtcaccg   42120
gggccaccgg caccatcggc ggggtcatcg cccgccatct ggtggccgag ggcggagtgc   42180
ggcatctgct gctcacgagc cgccgtggcc cggacgccga gggcgcggcc gaactccacg   42240
cggaacttgc ggagttgggc gcccaggtca ccctcgccgc ctgcgatgtg gccgaccggg   42300
aggcgctggc cgcgctgctg gccaccgtcc ccgccgcaca tccgctgacc gccgtcgtgc   42360
acacggcggg cgtcctggac gacggtgtgg tctcctcgct cacccccgag cggctggaca   42420
cggtgctgcg gcccaaggtc gacgccgcgc tcaccctgca cgagctgacc cgcgacctgg   42480
acctgtccgc gctcgtcctg ttctcgtcca tcgccggcac cttcggcgga atgggccagg   42540
gcaactacgc ggcggccaac gccttcctcg acgccttcgc ccagcactgc cgcgcccagg   42600
ggcggcccgt ccagtcacac gcgtgggggc tgtgggccca gcgcagcgag atgaccggca   42660
agctggaggg cgccgatctg aaccggctgg cgcgcggtgg catcgtcccg ttctcctcgg   42720 cggacgcgc cgggctcttc gacgccgcac gcgccgtgga ctccgccgtc gtgctgccga   42780
tgcgcctgga caccgcgggg ctcggagccc ggtccggtga cgtaccggcg ctgctgcgcg   42840
ggctggtgag ggccgcgccc gccaccaggc ccgcccggcg gacggccgcc ggagccgggg   42900 ccgccccccgc gcggcccgag gggctcaagc agcatctgac gagcctgccg gaggccgagc   42960
gcggccggtt cctgctggac ctggtccgca ccaccgtggc cggggtgctg ggcttcgact   43020
cggtggcggc cgtcgaggcg gagcgcggtc tgctggacct cggcttcgac tcgctcaccg   43080
cggtcgagct ccgtaaccaa ctcggcaagg ccaccggccg gcgcctgccg gtgaccctgc   43140
tcttcgacta ccccacctcc acggcgatcg ccgcgtatct ggaagcggaa atcgccccgg   43200
aggcattcac cgccgcgtcg atgaccttcc ccgaactcga cgccctggaa agcaacctgg   43260
ccaaggtcgc cgtcgacgac gaggcgcgca ccacgctcgc ctcgcgcctg caagacctgc   43320
tggtacggct cggccaaggc ccggaggacg cggaggacgc ggtcgccggc cgcatcgacg   43380
ccgcctcgga cgacgagatc ttcgacttca tcgagaacga actcggcctg tagtgcacgg   43440
agttggaatt catagagatg ggcggtaaac ggtgagcgag gcaaaactcc gcgactacct   43500
caagcgagtg accacggatc tgcaccgcac tcgccagcgc ctccaggagg ccgaggcaaa   43560
ggaccacgag cccatcgcca tcgtcgggat ggcctgccgc taccccggtg gcgtggcctc   43620 gccgaggac ctgtgggagc tggtggccaa cggccgggac gcggtcaccg agttccccgc   43680
cgaccggggc tgggacctcg aggccctcta cgacccggac ccggacaagc cggggacgag   43740
ctatgcgcgc gaaggcggct tcgtcaccga cgccgaccac ttcgaccccg ccttcttcgg   43800
catctccccg cgccgaggccc tcgccatgga cccgcagcag cggctgctgc tggagaccgc   43860
gtgggaggcc atgagcgggc cggggtgga cccggccacg ctgcgcggca gccgcaccgg   43920
ggtcttcgcg ggcgtgatgt accaggacta cgcgacccgg ctgcgtcagg tgcccgacga   43980
tgtcgagggg tacgtcggca gcggtggctc cggcagcatc gcctccggcc gtatcgccta   44040
caccttcggt ctcgaagggc ccgcggtcac cgtggacacc gcctgctcgt cctcgctggt   44100
ggccctgcac ctcgccgcac aggcgctgcg cggggggag tgctccctgg ccctggtcgg   44160 cggggtcgatg gtgatgtcca caccggtggc cttcgtggac ttcagccgcc agcgcgggct   44220
```

```
cgcctccgac ggccgctgca aggcgttcgc cgcctccgcc gacggcaccg gctggggcga    44280
gggcgtgggc atgctgctcg tggagcggct gtcggatgcg cggcgcaacg gccaccaggt    44340
gctcgcggtc gtcacgggct ccgccaccaa ccaggacggc gccagcagcg ggctgaccgc    44400
ccccaacggc ccctcccagc agcgcgtcat ccggcaggca ctggccgacg ccgggctcac    44460
cgcggccgat gtggacgcgg tcgaggccca cggcaccggc accccgctcg gcgaccccat    44520
cgaggcgggc gcgctgctcg ccacctacgg ccaggaccgc cccgaggacc ggccgctgtg    44580
gctcggctcg ctgaagtcca acatcggcca cacccaggcc gccgcgggcg tcggagggggt   44640 catcaagacg tgtgctggcgc tgcgccacgg cgtgctgccc aagaccctgc acgccgacga    44700
gccgacgccc aacgtggact gggagtcggg cgcggtacgg ctgctggccg aggcccggcc    44760
gtggcccgag ccgaggccg aacgcccgcg ccgcgccgcc gtgtccgcct tcggcttcag    44820
cggcaccaac gcccatgtga tcctggagca ggcccccgcc gaggagaccg cggaggaggc    44880
cgccgacgag acaccccgg atgagactcc cgcggacacc acgcccgcca ccgtgtccga    44940
cctggtgccg tggccgctgt cggggcggac cgaggaggcc ctgcgggccc aggccgcgcg    45000
gctgcggtcc tacgtggcgg gcgcgcccga gccgtccccc gtggacatcg gctactcgct    45060
ggcgctcacc cgctccgcct tcgcccaccg tgcggtggtc gtgggagcga gccgtgccga    45120
actgctcggt gagctcgacc agttggcctc cggtgtcacc tccggcgcgg tggccggtgc    45180
gggcaagacg gcgttcctgt tcaccgggca gggcgcacag cggctcggca tgggacgcgc    45240
cctgcatacc gccttcccgg tcttcgccgc cgcgttcgac gccgtctgcg ccgagctcga    45300
ccgccacttg gacggccatg tcgggcacgc ggtgcgggac gtggtcttcg gcgcggacgc    45360
cgaaccgctc gaccggaccc tctacaccca gaccggtctc ttcgccgtcg aggtggcgct    45420
gtaccggctg ctggagtcct ggggcgtgac cgcggacttc ctggtcggcc actcggtggg    45480
cgagctggcg gcgcccatg tggcgggcgt gttctcgctg gaggacgcct gtgcgctggt    45540
ggcggcccgg ggccggctga tggacgcgct gcccgccgga ggcgcgatgg tgtcgctgca    45600
gaccggcgag gccgaggtgc tgccccatct ggagggcgag gagggccagg tgtcgctggg    45660
cgcggtcaac ggcccggcgg ccacggtgat ctccggcgag gagaaggccg tcctgcggat    45720
cgcggacgcg gtcggcgtca agagcaagcg gctgcggatc ggtatcgcgg cccattcgcc    45780
gctggtggac cccatgctgg aggagttcgc caaggtcgcc ggtgaactga cctacgccac    45840
cccccggatc gcggtggtgt ccaatgtgac cggagaggcg gtcgccgagg agctgtgctc    45900
gccggattac tgggtgcgcc atgtgcgcgca gccggtgcgg ttccaggacg gggtgcggtt    45960
cctcgaggac cagggcgtga cccgctatgt ggaggtcggc ccgtccggtg tgctgtccgt    46020
gatgggccag gagtgcgtcg ccgaccccga cgccgccgcg ttcgtcccgc tgctgcgcaa    46080
ggaccgtggc gaggccgagt cgctgctggc cggggtgggc cgggtgcacg cccacggtgg    46140
cgtggtggac tgggagcagg tgttcgcggg ccgtggcgcc cgccgggtgg agctgcccac    46200
gtacgccttc cagcggcagc gctactggct cgacggctcg gaccgggcgg gcgatgtgac    46260
ctcggcgggg ctgggctcgg ccgggcatcc gctgctgggc gccgctgtcg aactcgccga    46320
cagcgacggc ctggtgctca ccgggcggct gtccctggcc gcccagccct ggctggccga    46380
tcacgccgtc tccggcacgg tcctcttccc cggcaccgcg ttcctcgagc tcgcgatcca    46440
ggccggtgac caggtcggct gcgaccaggt cgaggagctg accctccagg cgccgctgat    46500
cctccccgcg cgtggcgcgc tcaccctccg ggtgaccgtc ggcgaacccg acgagagcgg    46560
acggcgcccg ctgaacgtcc actcccgccc cgagggcgcc gggttcggcg agccgtggac    46620
```

```
cccgcacgcc accggcacgc tcaccaccgc cacaccggat gccccgccg agctgaccgc    46680 gtggcctccg gcggacgcca ccgaactcga cgtcagcgac atgtacgagc ggtacgcggc    46740
gggcggcttc ggctacggcc cggccttccg gggcctgcgc ccgcctggc tgcgcggcga    46800 cgaggtgttc gccgaggtgc ggctggccca ggagcagcgg ccggccgccg ccgggtacgg    46860
gatccacccg gccctgctcg acgcctccct gcacggcatc gcgctcggca ccctcttcgc    46920
cggggaggac cccgagacgg cgcaggggcg gttgccgttc tcctggaccg gggtgtcgct    46980
gcacgccgcc ggggccgacg aggtgcgggt gcggatctcc ccggccgggg aggacaccgt    47040
ggcgctcgcg gtggccgacc ccaccggccg cccggtggcg accgtcgagg gcctgctgct    47100
gcggaagatg accggcgatc agctcagtgg cgcccgcgcc gcgagcagcg agtcgctgtt    47160
ccggctcgac tggcccgcgc tgaccagcct cgaccagccc accccgctga ccagggccgc    47220
gctggtcggc gacgacgggc tggaggtcac cgagagcctc ttcgcggccg ggtccacct    47280 ggagtcgtat gtggacctgg agtcgctggg cgcggccgtc gacgccggta cggccgcccc    47340
agcggcggtc ctggtctcct gcgccgccgg gccggcgca ccggccgacg cggtacggga    47400
ctccctgcgc accgcctgg agctggccca gaactggtcg gccgatgagc ggttcgccga    47460 ctccggctg gtgttcgtca cccgtggcgc ggtggccacc gcgcccgagg cggaggtcgc    47520
cgatctgccg ggcgccgccg tctggggcct ggtgcgctcg gcgcagtcgg agaaccccga    47580
ccggttcacc ctcgtcgacc tcgacgagca cgaggagtcc gtacgggccc ttccggcggt    47640
cctcccctcc ggggagccgc agctcgcgct gcgcgccggg cagccgcaca ccccgcggct    47700
cgcccgcgcc caggggggcca ccggcgccac ccgtccgctg gaccccgagg gcaccgtgct    47760
gatcaccggc gccaccggta cgctcggcgg gctgctcgcc cgccacctgg tgacccacca    47820
tggcgtccgc catctgctgc tgaccagccg ccggggaccg gccgccgagg gagccgggcg    47880
gctgcgcgag gagctgaccg agctcggcgc gatcgtgacc gtggcggcgt gcgacaccgc    47940
cgaccgggac gccgtggccg acctggtggc ccaggtgccc gccgaccacc cgctgaccgg    48000
ggtgttccac accgccgggg tgctggacga cggggtgatc tcctcgctca ccccccgagcg    48060 gctggacacg gtgctgcggc ccaaggtcga cgccgcactc cacctccacg aggccacccg    48120
ggagctggac ctgccgcgt tcgtgctctt ctcctcggcc gccggagtgc tcggcggcgc    48180
gggccagggc aactacgcgg ccgccaacgg cttcctcgac gccttcgccc aggcccgccg    48240
ggcccagggg ctgcccgccc actccctcgc ctggggctg tgggcgcgga ccagcgcgat    48300
gaccggtacg gcggacacgg ccggggccgc ccgctcgggc gtggccgcgc tcctcccga    48360 acagggcatg gaactgctcg acaccgccct cgccctggac accccgctgc tgatcccgat    48420
gcggatcgac ctcgcggcgc tgcgggcggg cgccggatcc ggctcggtac cgctgctgct    48480
gcgcgggctg gtgcggacac cggcgcgccg ggcgggcgcg accacacgcg gcggctcgcc    48540
gggcggcggc tccgcgctgc gggaacggct cgccgcgctc cccgaggacg aacaggacgc    48600
cgtgctggtg gaattggtgt gcacgcaggt ggccaccgtg ctcggccacc cggaccgtc    48660 cgccatcggc ccggcccatg agttcgtgga ctccggcttc gactcgctca cggcggtcga    48720
gctgcgcaac cggctgaacg cggccaccgg gctgaggctg cccgccacgc tcgtcttcga    48780
ccatgagacg cccaccgatc tggccgcccg gctccgctcc gaactggccg cggcccgga    48840 gtcgggcccc gccgagcaga cgcccgcggg cgcgccgccc gccgcggcgg gggagtccac    48900
cacgctgagc acgctgtaca ccgaggcgtt cgagaccggg aagtggaagg aaatcttcga    48960
```

-continued

```
cctgctgcac gccacggcgg cgctgcggcc gcggttcagc gccagctccg agctggagaa   49020
gctgccgatg ccggtccggc tcagcaaggg cccggccgag cagcacctgt tctgcttctc   49080
ctcgtgcctg gcggtcgcgg gcatccacca gtacgcgcgg ttcgcggcct cgctgcgggg   49140
ccggcgcgat gtgtcggcgc tcgcgctgcc gggcttcggc cgcggtgaac ccctcccgga   49200
gacggcggac gcggtggtgg ccgcccaggc cgaggcggtg gcgaaggccg ccgacgggca   49260
gccgatcgtg ctcctgggct cctcggcggg cggctggttc gcccacgcgg cggcgggaca   49320
tctggagcgg atgggcgtcc ggccgaccgc ggtggtcctg gtggacacct acgtgcccaa   49380
gagcagcatc ctcaaccagt tcgggctctc gctcatggac gggatgaccg agcgcgaggg   49440
cgtgttcgtc accatggacg acgcccggct gtcggccatg ggctggtatc tcaacctctt   49500
cggcagctgg accccgagc cgatcgagac ccccaccctc ctggtgcgcg cgctggagcc   49560
gctgtccacc ggatcgttga agctggagga gctgcccgac tggcggtcct tctgggagct   49620
gccgcacgac atcgtcgatg tgcgcggcaa ccacttcacc atgatggagg accactccct   49680
ccccaccgcc caggccatcg aggactggct ggagcgactg ccgcgcgacg gcgcctgacc   49740
cgcccggaca cccgtagagg cgccctcccc gcatcagata aggaatgacg accatggcgt   49800
tgcccgtcac cgatgagagc ctgtggttcc gcaggttcca tccgcgcccg gaggccgagg   49860
tcagcctggt ctgcctgccg cacgcgggag gagccgccag cttctacttc ccgatctccg   49920
agctgctgcc gccgaccgtg gagcgctgg ccgtccagta cccggggcgg caggaccgcc   49980
gccatgacgc gcccatcgag gacatccacg agatggcgcg cgagatctac gaggcgctga   50040
agccgctcac ggcacaccgg ccggtcgcgc tgttcggcca cagcatgggc gcgagcgtcg   50100
gcttcgagct ggccagactg ctcgaagggg agctggggac cgtgcccgtg gcgctcttcg   50160
cctcgggccg gcccgcgccc tcacaccacc ggagcctcgg catccaccgg cgcgacgacg   50220
ccgggctcat cgccgagctc caactggtca gcgggaccga ctcgcggatc ctcggcgacg   50280
ccgaactgct gcggctggcc ctgcccgcca tccgcagcga ctacaaggcg ccgagacct   50340
acgaataccg gccggcgcc cggctggcct gcgacatcgt ggggctcacc ggtgacagcg   50400
acatccgcgt caccgccggg gaagtggcgg gctggcggga gcacacctcg ggctccttcc   50460
ggctggaggt cttctccggc ggccacttct acctgggtga gcagaaggca gcggtggccg   50520
gagtcatcac ggacaccctg cgggcggcca ccgcccgccc ccgacgaccc atcgactgag   50580
agagaaaccg acgatgcgta tccttttcgc gacggtgtcc gagaaatcgc acctgttcac   50640
catggtcccg ctcgcctggt cgctggccgc ggccggccac gaggtgcatg tcgccagcaa   50700
tcccgcgctg accgagtcca tcaagagcac cggtctgacg gccgtctcgg tcggcaagga   50760
ccacaatctc cacgagatgc tgacgcagaa ccgcgagtcg ctggagaacc cgctctccga   50820
ctggtccacc ccggagctcg atcagcactc ctgggaacag gtgctgatga agttcaagat   50880
cagcgtgatg ttcgcgtacc agacctacaa cgactgcatg gtgcacgagc tggtggacta   50940
cgcccgccac tggcaacccg acctggtcat ctgggacccg gtcagctacg cgggcccggt   51000
ggccgccgg gtggtgggcg ccgcccacgc ccggctgctg tggtgcatcg acatctacgc   51060
gaagatgcgt gaggtgttcc tggcccgcct cgccgaacag cccgaggagc gccgcgagga   51120
cccgatggcc gactggctcg gtggcatcct cgcccgctac gaccgcacct cgacgagga   51180
ggtcgtggtc ggccagtgga ccatcgacca gatccccacc agcctccagc tcccgctgtc   51240
gctccagcgg gtcccggtcc gctatctgcc ctacaacggc ccctccgaca tcccggactg   51300
gctgcgcgag acccccgagc ggccgcgggt cgtgctgacc tccggggtct ccgcgcgggc   51360
```

```
cgccctgggc ggcaccttca tgccggtggc cgacatgatc gacaccctgg ggagcatgga    51420
catcgaggtg gtggccgcac tgccgcccga ggaggtcgag gcgctggcga aggtccccgc    51480
caacacccgt atcgtcgact tcgttccgct gcacgccctg ctgcccggcg cctcggtcct    51540
catccaccac ggcggcttcg gctcctgggg caccgcactg gtcaacggcg taccgcagtt    51600
cattcccacc atccgctacg ccgactggtg gaacaagggg accagtctgc acgaggccgg    51660
tgccggactc gtcgtccacg cctcggagtt gaccgccgag gtgctgcggg agagcgtcga    51720
gcggctgctg aaggacgcgt cgtacaagga ggccgccgag cggctgcgcg aggagaacct    51780
gcgcaccccc accccgcacg atgtggtgcc ggtgctggag aagctcaccg tggagcacgg    51840
ccgatgaagg tgcgcgagct ggcggtgtcc ggcgcctacg agttcagccc ggacgtccac    51900
cgggacgagc gcggcgcgtt cgtcgcccac tacaccgaat cggccttctc cgcggccgtc    51960
ggtcatccgc tgcgcctggg ccagaaccac acagcgtct cccggcgcgg caccgtccgc    52020
ggggtgcact acgcggacgt accccgggg caggccaaga tggtgacctg cgtcagcggc    52080
gaactcctcg atgtggtggt ggacttgcgg gtgggctcgc ccaccttcgg ccgctgggac    52140
agtgtgcgtc ttgaccccgt ctcgtaccgg gcggtgtatc tggaggaggg cctcggccac    52200
gcattcatcg cgctccggga cgacacggtg gcggcctacc tcaactcgga ggagtacaac    52260
ccgggcgccg aacacgagat cgacccctttc gatcccgcgc tcggcctgcc ctggcccaag    52320
gacctggagt atctggtctc cgagcgcgac cggaacgccc ccgggctggc cgcggccgaa    52380
cgggccggtc tgctgccgtc ctacgaggtc tgccgggcgc tgcacgcccg gcgcggctga    52440
gccggcgggg acgccccggc gcggctgacc cggcccggct gacctccatc caccgatcgg    52500
ttgatgcggc cgatcggccg gtcggtggag gaaggatcag cccggtgggc agccgatggg    52560
ccgatccccc ggggatatcc gcttcctacg gtggaagagt gagagaaccg agcgaggagg    52620
acccgggccg atgccgctga tcgaggtcag taacctgcgc aaggagtacc gcaatcacgt    52680
ggcggtacag gacgtgtcct tctccgtgga ggagggtgag atcttcggca tcctcggccc    52740
caacggggcg ggcaagacca ccgccgtgga gtgcatcgag ggcatgcgca gcgcgacgg    52800 cggcgagatc tccgtgatgg gtctcgaccc gctgaaggac aaggacctcg ccgagctgcg    52860
cgagtccatc ggcatccagc tccagcagag cgaactgccc cccaagatga aggtgtggga    52920
ggcgctcgag ctctacagca ccttctaccg cgaccccgtc gactggcgcg agctcatcaa    52980
ggactggggc ctgtccgaca aggcggacac ggcctacgga tcgctgtccg gcggacagca    53040
gcagcggctg tccatcgcgc tcgccctcgt cggcaagccc aggatcgccg tcttcgacga    53100
gctgaccacc gcgctcgacc cgcacgcccg gcgcgagacc tggaagctga tcgagaaggt    53160
ccgggagcag gatgtgaccg tgctgctggt cacccacttc atggaggagg ccgagcggct    53220
ctgcgaccga atcgccatca tcgaatccgg ccgggtcgtc gccctcgaca ccccctccgg    53280
actggtgtcc cgggtcgatg agcagcagat catccgcttc aagccgtccg tcccgatgga    53340
cgacgagctg ctcacctcgc tgcccgaggt gagcagtgtg accggtcca agtcccaggt    53400 gacggtggtc ggcaagggca atgtcgtcta cgccgtgatc tccgtcctgg cccgcaacca    53460
gatcgtggcg aacgaactcc gcctggagca ggcgagtctc gatgacgcct tcgtcgccct    53520
gaccggctcc aagcccgcca actaaagccg ccgaggagac ttctgccatg tccgggcgca    53580
ccaagctcac ctacgtcgag agcaagctgt tcctgcgcga tcccaccgcg gtgttcttcg    53640
tcatcgcgct gccgatcatg ctgctggcca tcttccactt cgtcaccacc aagtccgacg    53700
```

```
acgacgccgc caccaaggcg tcgatggccg cgttcgtccc cgcgatggcc atgtcgctgt    53760
gtctgacgat gctggccctc aacctgctgc ccacgacccg cgcgacctac cgggagaagg    53820
gcatcctgcg gcgcatggcc gcgagcccca tccaccgggg gaacctgctg ctcgcccagc    53880
tcttcatcaa cctggtcacc gcggcggtct ccgcggtgct ggtgctcatc gtcggcaaga    53940
ccgccttcga caccaaactg cccggcgacg tccccgcctt cctggtgagc ttcgtcctgg    54000
gcacctgggc gctgttctcc atcggcctgg tgatcgcggc cgtggcccccg agcagcaaat   54060
cggccaccgc gatgggcctc tccctcctct tccccagcct cttcttcggc ggcgcgttcc    54120
tccccaagga ggacctgccg gagacggtgt ccaccatcgg cgactacacc ccgctgggcg    54180
ccgcgctcca ggcgctgcgc gactcctggg agaaccagtg gccgcagacc ctgcacctga    54240
ccgtcctcgg ggtgatcgcg gttgccgcca ccgcggccgc ggccaagctg ttccgctggg    54300
agtgaggtga gcgcgtccaa ggacgacggc ggacggtggg agcggcactc cgacatcctg    54360
ttcggagggc tgccctacct tctgctgttt ctgtccacgg ccctgagcct ggtccacggg    54420
ccgcccccgg cccggcggct gctcaccacg ctcggcctcg tggccgtggc cgccgtctgg    54480
atcctgggca cctacaccct gcccacgggc cgccgcagca cagccgta cggcatggcc      54540
cgcacggccg tctacttcgc cgggctgctc gccctctccg ccgcgctgat ggcgcgggac    54600
caggtgttca tgctgttcgc cgccaccggg ttcctccagg cgctggtgct gctgccgacc    54660
gtctgggcgt cggtgtccgt ggcggccacc tcgttcgtcg tcaataccgt gccggacggc    54720
ttccccccggc ccaccaccgg cgcggtggtc ggctatctcg ccgccatcgc cttccagacc   54780
gtggtgatcg gctggatcaa tctgctgtcg agccggctca acgaacagca tcagcggcgc    54840
aaacgcaccg tggccgaact ccgctccgcg ctcaccgaga acgccggact ccacgcccag    54900
ctgatcaccc aggcgcgcga ggccggagtg ctcgacgagc gccagcggat ggcggggggag   54960
atccatgaca ccctcgccca ggggctggcc ggcatcatcc ggcaactgga ggccgccgaa    55020
cacgcggagg gcgaccgcga ggtgtggcgg cgccatctcg tcgctgccaa ggacctggcc    55080
cgggacagcc tggccgaggc gcgccgttcg gtccaggcgc tccgcccccga gcgactggag   55140
tcccggacgc tgccggacgc cttggagtcg ctggccgagg ggtggtcgca ggagcgggag    55200
ccgaaggccg cgttcgcgac gaacgggacc gccatcccgc tccacgccga gctggaggcc    55260
acgctctacc gggtggcgca ggaggcgctc gccaacatcg ccaagcacgc ccgggcgtcg    55320
aaggtgggca tcaccctgtc gtacatggag gacgtggtgg tcctcgacgt actcgacgac    55380
ggcgtcggat tcgaccccgc ggccgcgcg ccgaggccg tgcctccgg cggccatggc       55440
ctcgggctgg tggcgatgcg gcgccgactg ggccgggtcg ccggtacgtt ggacatcgaa    55500
agcgcccgtg gcgagggcgc cgccatcagc gcggccgtcc ccgtgatccc ccaggaagcc    55560
ggtgcatgag cggaaacacc catggcggcg acacccccgg ccccagcccc atccgtatcc    55620
tcatcgtcga cgaccaccccg gtggtccgcg acgggctgcg cggggtgctg gagcgggacc   55680
ccgacttcac ggtgaccggc gaggccggtg acggtgccga ggccgtcgaa ctgtacgagc    55740
gacagccggc cgatgtggtc ctgatggacc tgcgcatgcc ccggatgggc ggcgtggagg    55800
ccatcaaacg gctgctgcgc ggcgacccccg aggcccggat cctggtgctg accacctatg   55860
acaccgacag cgacgtcatg ggcgcccctgg ccgccggggc gaccggctat ctcctcaagg   55920
acaccccgcg cgaggagctg acccgcgccg tgcgatccgc ctcctcgggc cagtccgtcc    55980
tctcgccccg ggtcaccgga cgcgttctcg gccaggtacg caaacccacc cagggcccgc    56040
tgagcgaccg tgaactccaa gtgctcaggc ttatcgcgga cggggccacg aatcgacagg    56100
```

```
ccgcggccgc attgttcatc agccaggcca ccgtcaagac gcatcttctg catgtctacg   56160
agaaactcgg ggtgaaggat cgcgcggcag cggtcagcga ggcccataaa cgacatctat   56220
tcgaatgaca ccgcaggtcg gggccgtgat aggggtgccc gatagggggtg gacgagggta   56280
ggggttgttc cgctcgaagc ggcgccaata cggtggcgat atgggccaca tccgagatcg   56340
gcaggccgtt gtcatcggcg gcaccggatt catcggcga catatctgca gagctctcgc   56400
caagcgcgga tatgaagtcc tggcaatagc gagaaaaccc gccgaaccca ttcccggagt   56460
cgtcttttg gcacttgacg cggtatccgc gccgagcgag aacatcgtcc gggccgcaca   56520
gtccgccgat ctcgtcgtca acgccgcggg cgacagctgg gagggcgacg aggcgagcat   56580
gacggcctcg cacatcccgc tcgtggaccg gctggtggac gccgtggcga ccctccccag   56640
gcgaccgcgc ctggtccatc tgggctcggt gcacgagtac ggccccgtcc ccgacggcac   56700
ggccatcgcc gaggaccacc ccaccgcccc ccgcaccccc tacgcccgca ccaagctcgt   56760
gggcagccgg atcgtgctgg gcgccgcgga cgcgggccgt atcgacggct gcgtgctgcg   56820
cgtcaccaac gtctgcggac cgggcacccc ccggggcagc ttcctcggcg ggctcgccca   56880
ccggctgcgc cacaccaccg aggacacccc gctcaccgtc accctcgtcg acgaccggcg   56940
cgacttcatc gacgtccgcg atgtcgccga ggccgtggtg ctggccgcga gcagcccggt   57000
gaccggccgg gtgctcaaca tcggccaggg cgacgccttc agcatgcgcg aactggccgg   57060
gctgctgatc gccgcctccc aggtccccga ccgtctggtg cgcgaggaga gcggcgccgt   57120
gcacagcaag ggcggcagct ggacccaggc cgacatccgc ctcgcccggc ggctcatggg   57180
ctggtccccg aaggtggccc tcaaagaatc cctccacgac ctgtgggccg cctccgccac   57240
ttccagccgg ccggctgccg cggcggcccg taccgaagga cactgatgca gtacacctat   57300
ctcggccgca ccgcccctcaa ggtgagccga ctgtgcctgg gcaccctgaa cctcggggtg   57360
agggcgagcg acgaggagag ccacgcgatc ctggacaccg ccctggaccg cggggtcaac   57420
ttcatcgaca ccgccaacca gtacggctgg cagaagcaca agggctatac cgaggagttc   57480
ctcggcgggt ggttcgcgga aggcggcggc cggcgcgaga aggtcgtcct gggcaccaag   57540
gtcttcaacg cgatgaccga ctggcccaat gactcggggc tgtccgcccg gcacatcatc   57600
gcctcctgcg aggactcgct gcgccggatg ggcaccgact ggatcgatct gttccagatg   57660
caccacatcg accgccacgc cccgtgggag gaggtgtggc aggcgatgga gacgctgacc   57720
cggcagggca aggtgcgcta cgtcggctcg tccaacttcg ccggctggca catcgccgag   57780
gcccaggagg ccgcggcccg ccgccacttc ctcggcatcg tctccgagca gagcgtgtac   57840
aacctcgtca cccgccatat cgaactggag ctgatccccg ccgcccagcg gtacggggtc   57900
ggggtgctcg cctggtcgcc gctgcacggc gggctgctca gcggggcgct gcgcaagctg   57960
gccgagggca ccgcgatgaa gaccgcccag ggccggccg cccaggcgct cgaggtccac   58020
cgggacgccg tcgccgcgta cgagaagctg tgcgacggcc tcgcgccga cccggccgag   58080
gtgggtcttg cctgggtgat gggacgcccc ggcatcaccg cgccggtcat cgggccgcgc   58140
agcctggacc agctgacagg ggccttcaag gccatggagc tgacgctgtc cgacgaggtg   58200
ctggccgaac tggaccggct gttcccgccg atcggcaacg gcggcccgg ccggaggcg   58260
tgggcgtggt gagcacgctc caggagcggc tgatccgctc cgccgccacc gtcgacagct   58320
cggtgacctt gctcgccgac ttccagcgct ggttccgcga gcgcgtcgac gccgacgagt   58380
cccggatcga gatcatcccg ttcgaggcga tgcgcggctg ggacttcgcg ccggacaccc   58440
```

```
acaacctcgt ccatgagacc ggccggttct tcaccgtcga gggcatccgg gtgcggatgc    58500
ccggggcgcc ggtggaggag tggcgccagc cgatcctcca ccagccggag atcggcatcc    58560
tgggcgtcct ggtcaaggac ttcgacggcg taccgcactt cctgatgcag gccaagatgg    58620
agcccggtaa ccacggcgga ctccagctgt cgcccaccgt ccaggccacc cgcagcaact    58680
acacccgggt gcacaagggc cgggcggtgc cgtatctgga gtacttccag cggacggaac    58740
ggcaccgggt gctcgccgac gtccgtcagt cggagcaggg cagctggttc ttccgcaagc    58800
gcaaccgcaa catgctggtc gaggtggcgc cggacgtgga cgtcgaggtg cgcgacggct    58860
tccgctggct gacgctgggc cagctgcacc atctgctggc cgtggaggac ctggtgaaca    58920
tggacgcgcg cagcgtcctg gcctgtctgc cgcactcccc gctggacccg gaggagacct    58980
tcccggccac cggatcacgc gggaccgcgg agccggaacc gccggggcgg cacgtcctcc    59040
accgcgacgc cgacatcctc agctggatca ccggactgcg caccgagcgc gaggtgttca    59100
ccgagcggat accgctgcgg gagaccaccg gctggcaccg caacgcccac cgcatctccc    59160
atgagagcgg acgctacttc agcgtgatgg ccgtggacgt gacggcgggc ggccgcgagg    59220
tgggtggctg ggcccagccc atgatcgagc ccatggacc gggcgtggcc gcctttctgc    59280
tggcctacgc cgacaaggtg ccgcatgtgc tggtgcaggc ccgcgccgaa cccggctaca    59340
cggacgtggt ggaactggcc cccaccgtgc agtgcacccc gcgcaactac acccatctgc    59400
ccgaggggc cacgccgccg ttcctcaagg aggtggtgga ggcaccggcc gaccgggtgc    59460
ggttcgacac cgtgctctcc gaggagggcg gccgcttctt ccacgccttc aaccgctatc    59520
tggtcgtgga gacggagatg agcgccgtcc ccgaggagcc gccgcactac cgctggatgg    59580
cggtgcgtca gctgctcgac ctgatccgcc acagccatta cgtcaacgtc gaggcgcgca    59640
cgctcatcgc ctgtctgcac tccctggccg tatagggggg cgcctagggg gcgccacctg    59700
ggcggagcta ggggttattc ggatcgtggc cgctgccata gcctccggga cacagagtgc    59760
ccggagcggt acatcggagg acatgtcatg caggacatca tcagcgccgt gctggcagag    59820
gatgcggtgg ccgcggactt cgccgccttg gaccttcccg agtcctatcg gggcgcggtg    59880
atcctcaaag aggagtccga gatgttcgag ggcatggcca ccaaggacaa ggaccccag    59940
aagtcgctcc acatccgcga ggtgcccacc cccgaaccgg gccgggtga ggcggtgatc    60000
gcggtcatgg ccagcgcgat caactacaac accgtctgga gcgccatctt cgagccgctc    60060
ccgaccttcg gcttcctgga gcgctacgcg cgcaccgacg accccggagc ggcccgccac    60120
gaccggccct accacgtgct cggctccgac ctggccggtg tggtgctgcg caccgggccc    60180
ggggtgcgcc actggaagcc gggcgaccgg gtggtggccc actgcctgtc catcgaactg    60240
cgctcaccgg acgccacga cgactccatg ctcgaccccg agcagcgcat ctggggcttc    60300
gagaccaact acggcgggct cgccgagctc tcgctggtca aggccaacca gctgatgccg    60360
atgcccgccc acctcacctg ggaggaggcc gcgtcctccg gcctggtcaa ctccaccgcg    60420
taccggcagc tcgtctcccg caacggcgcc cagatgaaac agggcgatgt gaccctcatc    60480
tggggcgcgg cgggtggcct cggctcgtac gcgacccagc tggccgtcaa cggcggggcg    60540
atcccggtgt gcgtggtctc cgggcggcgc aaggccgaac tcgtccgctc catggggcc    60600
gagctggtca tcgaccgggc cgaggagggc tatcgcttct ggaaggacgc gaccacgccc    60660
gacccccggg agtggaagcg cttcgggtcc cggatccgcg aactcaccgg cggcgacgac    60720
ccggacatcg tcgtggagca ccccggccgg gagaccttcg cgccagtgt gttcgtggcc    60780
cggcgcggcg gaacgatcgt cacctgcgcc tcgacgtccg gctaccgcca cgagtacgac    60840
```

```
aaccgctatc tgtggatggc gctcaagcgc atcatcggca cccacttcgc caactaccgg    60900
gaggcatggg cggccaaccg gctgatcgag aaggggatgg tgcacccccac gctctccaag   60960 gtccatccgc tcgaggcggt cggcacggcc acccaggacg tccaccgcaa ccgccactcc   61020
gggaaggtcg gcgtgctgtg cctggccccg gaggaggggc tgggggtacg cgacccggag   61080
ctgcgcgagc gccatctccc ggcgatcaac cgcttccgcc gggactgaac cggttcaacg   61140
ggtgtcatgg ctcgcgccga cgtggcgggg ccgtgctgcc ccgggggggtg agcgccggag   61200 tgggggcctg atgggcgcgg ggagccgcct ggcccaggac ctcgaagagg cggtgcgcca   61260
cctgcgcccc gtagccgaag acatcgtggc tcatcgccga gagcgtgggg tgcgtcagct   61320
ggcacagctg tgagtcgtcc caggccagca gcgatacatc ggccggcacc gacagcccca   61380
tctcggcggc caccgaaagg cccgccaccg ccatgatgtc gttgtcgtac aggatcgccg   61440
tgggccggtc cgccgaggcc agcagggcac gggtggcccg tgcccctcc tcgcccgaga    61500 agtccgtggc caccgtggga ccctcgccca gccccgcctc ccgtacggcg gcctcgaacg   61560
cggccttgcg gatcgtggtg tgcccgagcc cggggcgcc gcccaccgg gcgatccggc     61620 ggtggcccag cgccaccaga tagcgcaccg cctcggtgac ggccgtggcg tcgtccgtcc   61680
agaccgaggt gaacccgtcc gccagcgagg ggtgcccggc caccacgcg ggcaggccga    61740 gttgccgcag cgcggggaca cggggtcgc cgtcccgcag atcgaccagg atggacccgc    61800
cgatctgccg cccccgccac cacgcctcct ggaccgcgat ctcctcgcgc acatcccgga   61860
ccagccgcag cagcagcgag caggagcgct cgaccagcac gctctcgatg cccgagacga   61920
actccatgga ccacggctcg aggcccagcg tccgggccgg gcgggcgatg ccagaccga    61980 ccgtgtccac gcgggagttg gagagcgacc gggcggagag atgggggtgac cagccgagct   62040 cccgggcggc ggcgaagatg cggtcccggg tggcccggga accccgggc cggtcgttga    62100 agacgagcga gaccgcgccc ttggacaccc cggcccgcgc tgccacgtcc ctgatggtga   62160
cgcgccgcgg cggctccgtc ccggcctcgc tgcccatgcc accgctcccc gccgtccgtc   62220
ccctgtggac cgccacacga tagcgcgtcg ataaaccggt ccagtcgggc gcggtccgct   62280
cggggaaact cgggtgcggc ggtcaggaca gggacgacgc cccgggcagc gccacggcgg   62340
gatcgctggt cggggcgtcg tacgagcgcg ccacccgggg gctctccccg gccgtggcgg   62400
ggcgctgcgg cgcctcgggt gtgtggtccc cctcgacgag gccgagccgg cgcagcgtcc   62460
ggcccagcgc ggccgggttg agcagcccca gcggggccgg cagccgatgc cagggcacac   62520
agcggtcgac cagctcgaag gccgcccgca ccggcaggtc gagggcggcg cgtaccggca   62580
ggtcgagggc ggcgcgcacc gggacgggca gtggcgcggt gggccgctgc tcggcggcgg   62640
ggacgcgcag gccgagccgg tgcgccgcgg cggcctcgta cgcggccttg cgggcccggt   62700
tgaggttgcc gagcggacgg aactcctcgg tggtgtgcca ggggttgaac gccagttgct   62760
cgacccggcg ggcagccgac cgggcccggg cgccgtccag gtcctggcgc ggcacggtga   62820
gcaccgcgac cgggaccacc ggcgcgtcgc tctcccgcca ctccaccgaa ccgtcctcga   62880
ccggggtgcg gcggtcgtcc agatagcgct gcacacacag ctcgaaggcg atgtcgccgg   62940
tggacagccg catcgccagc tcacggtgga gatagtccgg gtcgccgccg tcggcgggg    63000 gagcgggggt gccgccgggc gccggccgca gctggtagcg gaccggaccg gccgggcccc   63060
acaggatcgc gccccggctc cagaaggtct cccgggccag cgagcccacc gtgtggcggg   63120
tggcgatccg catattgcgg cgcatccggt cggcggtggc ccagccgacc gggatcctct   63180
```

| | |
|---|---|
| ccctatagtg agtcgtatta t | 63201 |

<210> SEQ ID NO 50
<211> LENGTH: 22
<212> TYPE: DNA
<213> ORGANISM: unknown
<220> FEATURE:
<223> OTHER INFORMATION: synthetic

<400> SEQUENCE: 50

| | |
|---|---|
| csggsgssgc sggsttcats gg | 22 |

<210> SEQ ID NO 51
<211> LENGTH: 24
<212> TYPE: DNA
<213> ORGANISM: unknown
<220> FEATURE:
<223> OTHER INFORMATION: synthetic

<400> SEQUENCE: 51

| | |
|---|---|
| gggwrctggy rsggsccgta gttg | 24 |

<210> SEQ ID NO 52
<211> LENGTH: 21
<212> TYPE: DNA
<213> ORGANISM: unknown
<220> FEATURE:
<223> OTHER INFORMATION: synthetic

<400> SEQUENCE: 52

| | |
|---|---|
| gasctsggsy tsgactcsct m | 21 |

<210> SEQ ID NO 53
<211> LENGTH: 21
<212> TYPE: DNA
<213> ORGANISM: unknown
<220> FEATURE:
<223> OTHER INFORMATION: synthetic

<400> SEQUENCE: 53

| | |
|---|---|
| sgasgarcas gcsgtgtcsa c | 21 |

<210> SEQ ID NO 54
<211> LENGTH: 18
<212> TYPE: DNA
<213> ORGANISM: unknown
<220> FEATURE:
<223> OTHER INFORMATION: synthetic

<400> SEQUENCE: 54

| | |
|---|---|
| gcggtgagtt gctgattg | 18 |

<210> SEQ ID NO 55
<211> LENGTH: 18
<212> TYPE: DNA
<213> ORGANISM: unknown
<220> FEATURE:
<223> OTHER INFORMATION: synthetic

<400> SEQUENCE: 55

| | |
|---|---|
| gacctggacg tggatgac | 18 |

ELAIOPHYLIN BIOSYNTHETIC GENE CLUSTER

This application claims the priority of U.S. provisional patent application Ser. No. 60/627,752, filed Nov. 14, 2004, the contents of which is incorporated herein.

FIELD OF THE INVENTION

Background of the Invention

Compounds produced by living organisms as part of primary or secondary metabolic processes, are a rich source of bioactive molecules. The polyketide family of compounds encompasses a wide range of molecules with an equally wide range of biological activities. Examples of the diversity of polyketide secondary metabolites include the immunosuppressive macrolactone rapamycin, the antibacterial aromatic polyketide tetracycline, the antifungal polyene amphotericin, the cytotoxic enediyne calicheamicin and the antiparasitic macrocyclic lactone nemadectin.

The polyketide elaiophylin is a unique macrodiolide produced by several Streptomyces species. Elaiophylin itself possesses a myriad of activities including antibacterial, antihelmintic, anticancer and immunosuppressive activity.

Elaiophylin, although interesting in and of itself, is also often produced along with a number of other polyketides by many Streptomyces species as an undesirable co-product. In one such strain, Streptomyces sp. NRRL 30748, elaiophylin is co-produced with nigericin and meridamycin. Meridamycin is of interest to due to its neuroprotective and neuroregenerative properties. However, due to the similar chemical properties of elaiophylin and meridamycin, it is problematic to separate the two polyketides by standard chromatographic techniques.

Biosynthetically, elaiophylin is quite interesting, as it is formed from two linear polyketide precursors which, when dimerized, produce a cyclic polyketide that possesses a unique $C_2$ symmetry that is only found in a small group of polyketides. Understanding the mechanism by which this unique dimerization occurs could facilitate the rational design of novel cyclic polyketides also possessing $C_2$ symmetry. Cloning the elaiophylin biosynthetic cluster would enable the examination of the dimerizing enzyme as well as the modification of the other biosynthetic genes to produce novel elaiophylin analogs. The present invention fulfills these needs.

SUMMARY OF THE INVENTION

The present invention provides an isolated nucleic acid comprising the elaiophylin biosynthetic gene cluster of Streptomyces sp. NRRL 30748 (SEQ ID NO:49) or at least 70% nucleic acid identity with SEQ ID NO:49. The invention further provides an isolated nucleic acid that encodes an open reading frame (orf) of the elaiophylin gene cluster of Streptomyces sp. NRRL 30748. In an embodiment of the invention, the nucleic acid encodes a polypeptide having the amino acid sequence of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, or SEQ ID NO:48. In a preferred embodiment, the nucleic acid comprises the sequence of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, or the complement thereof.

The invention also provides vectors and host cells comprising the nucleic acids. In a preferred embodiment, the host cell is prokaryotic. In one embodiment, the invention provides a cosmid containing DNA isolated from Streptomyces sp. NRRL 30748, that contains the complete elaiophylin biosynthetic cluster. Methods for the isolation of such DNA and for the manipulation of such DNA to alter the formation of the elaiophylin compound are also provided. Also provided are probes and primers for identification and amplification of elaiophylin biosynthetic cluster nucleic acids. The probes and primers are useful for, for example, hybridization and DNA amplification. In certain embodiments, the probes and primers are degenerate. In one embodiment of the invention, a method is provided for identifying a nucleic acid in an organism that encodes a polyketide synthase using a probe or primer corresponding to a polyketide synthase of Streptomyces sp. NRRL 30748.

The invention provides proteins and polypeptide comprising the amino acid sequence of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, or SEQ ID NO:48, and variants thereof.

In an embodiment of the invention, a method is provided for producing elaiophylin. In a preferred embodiment, Streptomyces sp. NRRL 30748 is incubated in a culture medium under conditions suitable for expression of elaiophylin, and elaiophylin is recovered. In another embodiment, a method is provided for producing other bioactive molecules of interest from a host in which elaiophylin production has been disrupted. In a particular embodiment, the bioactive molecule is meridamycin and the host is a streptomycete in which a polyketide synthase of the elaiophylin biosynthetic cluster has been disrupted.

The invention also provides a polyketide synthase (PKS) module having a novel thioesterase domain capable of catalyzing polyketide chain termination wherein a cyclic polyketide with $C_2$ symmetry is produced from a linear polyketide precursor. The thioesterase domain or the complete PKS that contains the thioesterase domain can be incorporated into a heterologous polyketide biosynthetic cluster to make other cyclic polyketides.

DETAILED DESCRIPTION OF THE INVENTION

Figure 1:
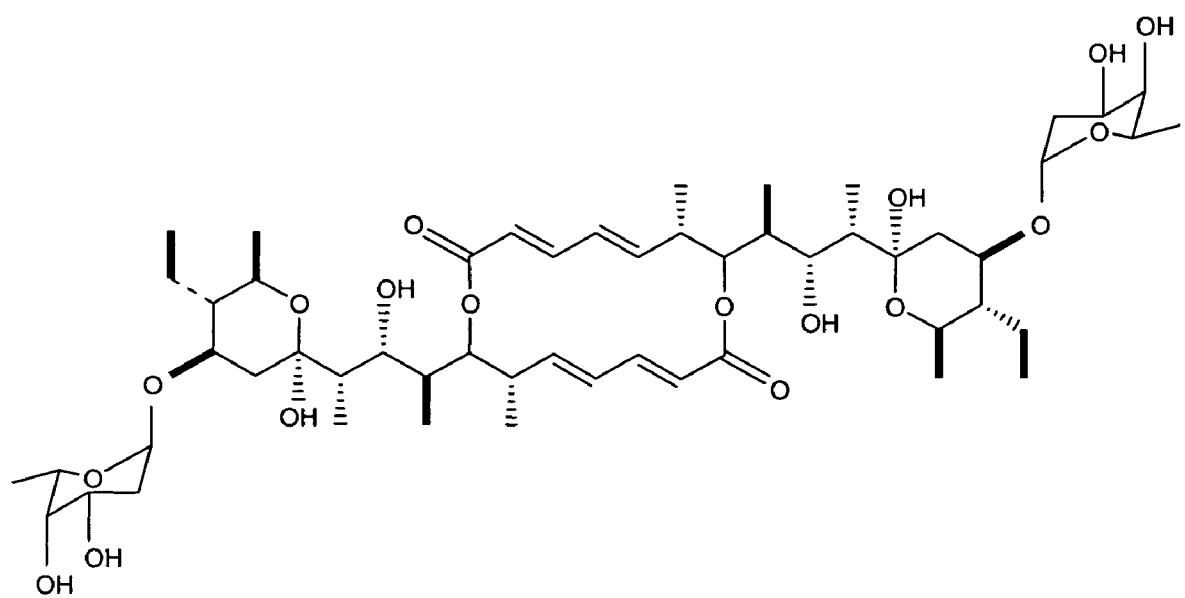
FIG. 1 depicts the chemical structure of elaiophylin.
Figure 2:
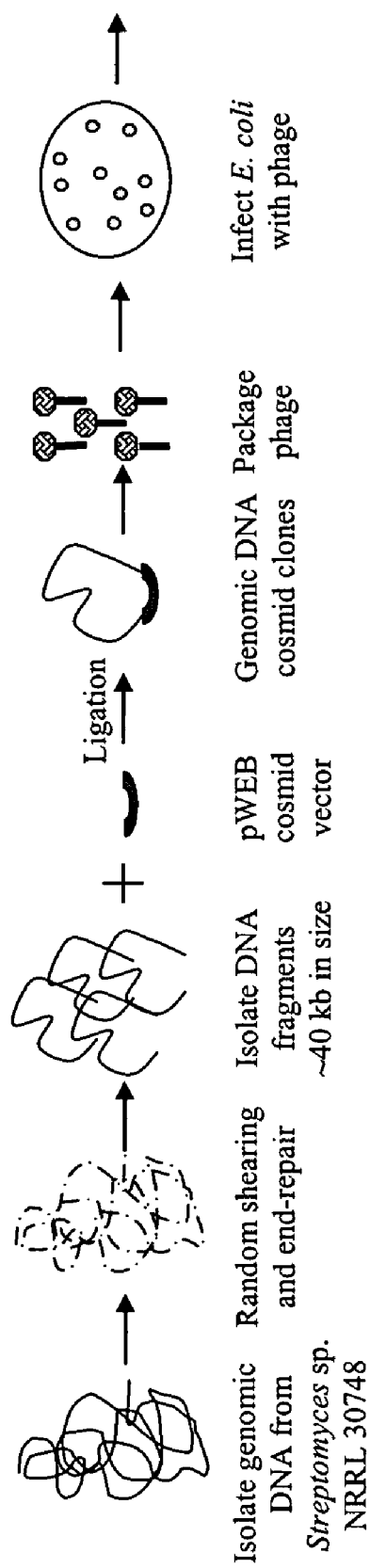
FIG. 2 is a flow chart describing the methods used to identify the elaiophylin biosynthetic gene cluster.

Polyketides are synthesized by the sequential head-to-tail decarboxylative condensation of short carboxylate extender units such as malonic acid to a starter unit such as acetic or benzoic acid. The diversity of polyketide-derived structures found in nature is accomplished by several factors. One is simply the length of the initial carbon chain. Further complexity is generated by the use of a variety of starter units. The incorporation of alternative extender carboxylates such as methylmalonate, methoxymalonate and ethylmalonate also contributes to the structural diversity of polyketides. Modification of the carbonyl functions adds to the complexity, as the initial β-ketone can be reduced to a variable extent. Finally, additional complexity is accomplished via cyclization of the linear polyketide chain.

Polyketide metabolites are produced by enzymes referred to as polyketide synthases (PKSs). Most PKSs can be classified as belonging to one of three general classes: type I, type II or type III. Type I or "modular" PKSs are large multifunctional enzymes composed of multiple discrete domains, each responsible for catalyzing a single reaction of the polyketide biosynthetic process. The individual domains are grouped into functional units referred to as modules. A minimal module is capable of incorporating a single carboxylate unit into the growing polyketide chain and is composed of three domains: an acyl-CoA:acyl-carrier protein transferase (AT) domain, an acyl-carrier protein (ACP) domain and a ketosynthase (KS) domain. The AT domain selects the appropriate acyl-CoA ester and catalyzes the transfer of the α-carboxylated extender to the phosphopantetheine thiol of the ACP. The KS domain catalyzes the formation of a C—C bond via decarboxylative condensation between the KS-bound growing polyketide chain and the ACP-bound extender unit, thereby extending the growing polyketide chain by two carbons.

The extended polyketide chain, bound to the ACP, can next be transferred to the following KS for another round of chain extension, or the ACP-bound polyketide can undergo a variety of postcondensation modifications. The first possible modification, catalyzed by a β-ketoreductase domain (KR), reduces the β-carbonyl resulting from the condensation reaction to a hydroxyl. The second possible modification, catalyzed by a dehydratase domain (DH), reduces the β-OH group introduced by the KR to an alkane. The third possible modification, catalyzed by an enoyl reductase domain (ER), further reduces the alkane produced by the DH to an alkene.

Generally a "loading module" initiates polyketide biosynthesis. A loading module is usually composed of an AT and ACP domain, although in some cases it also includes a KS domain. In cases where a KS is present, it is generally referred to as a KS$^Q$, the superscript letter indicating that the KS is not functional due to an active site mutation where the essential cysteine residue is replaced by a glutamine. Polyketide synthesis is initiated by the AT of the loading domain selecting a specific acyl-CoA and transferring the acyl-group as a thiol ester to the ACP of the loading domain. Once the loading domain is primed with an initiating acyl-thiol ester, the acyl group is transferred to the active site cysteine of the KS of the first extender module, which catalyzes the decarboxylative condensation of the KS-bound acyl group with the acyl group loaded on the ACP of the same module, thereby generating a new acyl-ACP that has a backbone two carbon units longer than the loading unit. At this point the β-carbonyl produced as a result of the condensation reaction can be reduced to a varying extent, as described above, depending on the domain composition of the following module.

The growing polyketide chain is then transferred from the ACP of the first extender module to the KS of the next module, and the process is repeated. Once the carbon chain has undergone it's final extension, the linear polyketide chain is released from the terminal ACP (and often cyclized as well) either by the action of a thioesterase, which can be a domain present at the end of the last extender module or a discrete gene, or via intramolecular cyclization facilitated via an internal nucleophile that attacks the carbonyl of the polyketide-ACP linkage. Generally, the organization of modules of a PKS are consistent with the order of acyl group incorporation and modification in the polyketide structure, thus polyketide synthesis is said to be "co-linear." The co-linear nature of type I PKSs allows the prediction of the product of a PKS based upon the primary amino acid sequence of the enzyme. Additionally, the non-iterative modular nature of type I PKSs enables one to make discrete changes to the structure of a polyketide by altering single domains of the PKS. For example a hydroxyl group of particular polyketide could be changed to a ketone by inactivating the ketoreductase responsible for reducing the original ketone.

The present invention provides an isolated nucleic acid molecule comprising a gene cluster for elaiophylin, a variant or a fragment thereof. An elaiophylin gene cluster is a nucleic acid that encodes the genes and regulatory elements for the biosynthesis of elaiophylin.

In accordance with the present invention, there is provided an isolated nucleic acid molecule which encodes the entire pathway for the biosynthesis of elaiophylin, including polyketide biosynthetic genes and sugar biosynthetic genes that are linked to the polyketide biosynthetic genes. The gene cluster encodes a complex of five polyketide synthases and additional enzymes that work together to produce elaiophylin, which cannot be easily generated by conventional synthetic chemistry. The nucleic acid molecule may be DNA isolated from *Streptomyces* sp., and is preferably isolated from the strain of *Streptomyces* known as *Streptomyces* sp. NRRL 30748, deposited at the Agricultural Research Service Culture Collection (NRRL, 1815 North University Street, Peoria, Ill., 61064). The nucleotide sequence of the elaiophylin biosynthetic gene cluster of *Streptomyces* sp. NRRL 30748 is given by SEQ ID NO:49. The deposit was made under the terms of the Budapest Treaty. The preferred nucleic acid comprises 24 open reading frames spanning approximately 63 kb of contiguous DNA. Table 1 provides a list of open reading frames (orfs) identified in the elaiophylin gene cluster and their predicted function in the biosynthesis of elaiophylin. Also provided by the invention are isolated nucleic acids that comprise open reading frames as provided in Table 1.

TABLE 1

Open Reading Frames of the Elaiophylin Gene Cluster

| orf | Start/Stop (bp) | SEQ ID NO | Length (aa) | SEQ ID NO | Function |
|---|---|---|---|---|---|
| 1 | 71-1516c | 1 | 481 | 2 | Unknown |
| 2 | 1813-2853 | 3 | 346 | 4 | 3-oxoacyl-acyl carrier protein synthase |
| 3 | 2892-4610 | 5 | 572 | 6 | Hydroxylacyl-CoA dehydrogenase |
| 4 | 5248-8121 | 7 | 957 | 8 | LuxR family transcriptional regulator |
| 5 | 8279-9145 | 9 | 288 | 10 | TDP-glucose synthase |
| 6 | 9166-10140 | 11 | 324 | 12 | TDP-glucose-4,6-dehydratase |
| 7 | 10296-23390 | 13 | 4364 | 14 | Polyketide synthase |
| 8 | 23390-28261 | 15 | 1623 | 16 | Polyketide synthase |
| 9 | 28323-33251 | 17 | 1642 | 18 | Polyketide synthase |
| 10 | 33276-43433 | 19 | 3385 | 20 | Polyketide synthase |
| 11 | 43472-49738 | 21 | 2088 | 22 | Polyketide synthase |
| 12 | 49794-50579 | 23 | 261 | 24 | Type II thioesterase |
| 13 | 50594-51847 | 25 | 417 | 26 | Glycosyltransferase |
| 14 | 51844-52440 | 27 | 198 | 28 | 4-keto-6-deoxyglucose-3,5-epimerase |
| 15 | 52631-53545 | 29 | 304 | 30 | ABC transporter (ATPase domain) |
| 16 | 53568-54305 | 31 | 245 | 32 | ABC transporter (permease domain) |
| 17 | 54307-55569 | 33 | 420 | 34 | Two component regulator (sensor/kinase) |
| 18 | 55566-56228 | 35 | 220 | 36 | Two component regulator (effector domain) |
| 19 | 56321-57286 | 37 | 321 | 38 | NDP-hexose-4-ketoreducatase |
| 20 | 57286-58272 | 39 | 328 | 40 | NDP-hexose-2,3-enoylreductase |
| 21 | 58260-59675 | 41 | 471 | 42 | NDP-hexose-2,3-dehydratase |
| 22 | 59788-61128 | 43 | 446 | 44 | Crotonyl-CoA reductase |
| 23 | 61145-62197c | 45 | 350 | 46 | LacI family transcriptional regulator |
| 24 | 62303-end | 47 | 298 | 48 | hypothetical protein (partial) |

The invention further provides nucleic acids that specifically hybridize (or specifically bind) under stringent hybridization conditions to SEQ ID NO:1, SEQ ID NO:3, SEQ ID NO:5, SEQ ID NO:7, SEQ ID NO:9, SEQ ID NO:1, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47 or SEQ ID NO:49. Also contemplated are nucleic acids that would specifically bind to the aforementioned sequences but for the degeneracy of the nucleic acid code. The nucleic acids may be of sufficient length to encode a complete protein (e.g., a complete orf).

The nucleic acids further include probes and primers. In certain embodiments, the probes or primers may be degenerate. Further, in accordance with their use, probes and primers may be single or double stranded. Probes and primers include, for example, oligonucleotides that are at least about 12 nucleotides in length, preferably at least about 15 nucleotides in length, and more preferably at least about 18 nucleotides in length, and further include PCR amplification products that might be generated using primers of the invention.

Hybridization under stringent conditions refers to conditions under which a probe will hybridize preferentially to its target subsequence, and to a lesser extent to, or not at all to, other sequences. It also will be understood that stringent hybridization and stringent hybridization wash conditions in the context of nucleic acid hybridization experiments such as southern and northern hybridizations are sequence dependent, and are different under different environmental parameters. It is well known in the art to adjust hybridization and wash solution contents and temperatures such that stringent hybridization conditions are obtained. Stringency depends on such parameters as the size and nucleotide content of the probe being utilized. See Sambrook et al. and other sources for general descriptions and examples. Another guide to the hybridization of nucleic acids is found in Tijssen (1993) Laboratory Techniques in Biochemistry and Molecular Biology—Hybridization with Nucleic Acid Probes, part I, chapter 2, Overview of principles of hybridization and the strategy of nucleic acid probe assays, Elsevier, N.Y.

Preferred stringent conditions are those that allow a probe to hybridize to a sequence that is more than about 90% complementary to the probe and not to a sequence that is less than about 70% complementary. Generally, stringent hybridization and wash conditions are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Increased stringency may be obtained, for example, by selecting conditions equal to the $T_m$ for a particular probe.

An example of stringent hybridization conditions for hybridization of complementary nucleic acids which have more than 100 complementary residues on a filter in a Southern or northern blot is 50% formamide with 1 mg of heparin at 42° C., with the hybridization being carried out overnight. An example of highly stringent wash conditions is 0.15 M NaCl at 72° C. for about 15 minutes. An example of stringent wash conditions is a 0.2 times SSC wash at 65° C. for 15 minutes (see, Sambrook et al. (1989) Molecular Cloning—A Laboratory Manual (2nd ed.) Vol. 1-3, Cold Spring Harbor Laboratory, Cold Spring Harbor Press, NY, for a description of SSC buffer). Often, a high stringency wash is preceded by a low stringency wash to remove background probe signal. An example of a medium stringency wash for a duplex of, e.g., more than 100 nucleotides, is 1 times SSC at 45° C. for 15 minutes. An example of a low stringency wash for a duplex of, e.g., more than 100 nucleotides, is 4-6 times SSC at 40° C. for 15 minutes. In general, a signal to noise ratio of 2 times (or higher) than that observed for an unrelated probe in the particular hybridization assay indicates detection of a specific hybridization.

Nucleic acids which do not hybridize to each other under stringent conditions are still substantially identical if the polypeptides which they encode are substantially identical. This occurs, e.g., when a copy of a nucleic acid is created using the maximum codon degeneracy permitted by the genetic code. Accordingly, nucleotide sequences of the invention include sequences of nucleotides that are at least about 70%, preferably at least about 80%, and more preferably at least about 90% identical to SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47 or SEQ ID NO:49 or fragments thereof that are at least about 50 nucleotides, more preferably at least about 100 nucleotides in length.

The present invention is also directed to methods of producing one or more proteins of the elaiophylin biosynthetic pathway. Such proteins may be produced by expressing one or more nucleotide sequences comprising SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47 or SEQ ID NO:49 in a host cell. For example, one or more of the aforementioned nucleic acid sequences can be operably linked to regulatory control nucleic acid sequences to affect expression of the nucleic acid sequences, and incorporated into a vector for expression in a host cell.

Control elements useful in the present invention include promoters, optionally containing operator sequences and ribosome binding sites. In certain embodiments, constitutive expression may be desired. Other regulatory sequences may also be desirable, such as those which allow for regulation of expression of the nucleic acid sequence relative to the growth of the host cell. Regulatory sequences are known to those of skill in the art, and examples include those which cause the expression of a gene to be turned on or off in response to a chemical or physical stimulus, including the presence of a regulatory compound. Other types of regulatory elements may also be present in the vector, for example, enhancer sequences. Various expression vectors are known in the art, e.g., cosmids, Pls, YACs, BACs, PACs, HACs.

Selectable markers can also be included in the recombinant expression vectors. A variety of markers are known which are useful in selecting for transformed cell lines and generally comprise a gene whose expression confers a selectable phenotype on transformed cells when the cells are grown in an appropriate selective medium. Such markers include, for example, genes that confer antibiotic resistance or sensitivity to the plasmid.

The vectors described above can be inserted in any prokaryotic or eukaryotic cell suitable for protein expression. Preferred host cells are those of species or strains (e.g., bacterial strains) that naturally express elaiophylin. Examples of host cells include, but are not limited to, *Actinomyces, Streptomyces, Micromonospora*, and the like. In one embodiment, the proteins are expressed in *E. coli*. Recovery of the gene expression products can be accomplished according to standard methods well known to those of skill in the art. Thus, for example, the proteins can be expressed with a convenient tag to facilitate isolation (e.g., a $His_6$ tag). Other standard protein purification techniques are suitable and well known to those of skill in the art. When the entire elaiophylin gene cluster is expressed, elaiophylin can be recovered. By selecting certain orfs for expression, the cyclic polyketide core of elaiophylin can be produced. By expressing variants of certain orfs for expression (see below), elaiophylin related compounds can be produced. Related compounds may have modifications to the polyketide core and/or attached sugar moieties.

One may also desire to use a nucleic acid molecule comprising SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47 or SEQ ID NO:49 or a fragment thereof as a probe to, for example, identify other organisms capable of producing elaiophylin or related polyketide containing compounds. One may use the nucleotide sequences as a probe by any suitable method, including a method similar to that described in the Examples below. As described herein, a dNDP-glucose-4,6-dehydratase (DH) probe was used to identify cosmid clones of *Streptomyces* sp. NRRL 30748 that might contain an elaiophylin synthetic cluster. Similarly, the nucleic acids of the invention can be used to identify orfs of an elaiophylin biosynthetic gene cluster in other organisms. Other organisms generally include organisms that produce secondary metabolites, such as, for example, fungi, *bacillus*, pseudomonads, myxobacteria and cyanobacteria. Preferably, the nucleic acids are used to identify genes of an organism of the order *Actinomyces*, preferably *Streptomyces*.

The present invention also provides substantially pure proteins and polypeptides. The term "substantially pure" as used herein in reference to a given protein or polypeptide means that the protein or polypeptide is substantially free from other biological macromolecules. For example, the substantially pure polypeptide is at least 75%, 80%, 85%, 95%, or 99% pure by dry weight. Purity can be measured by any appropriate standard method known in the art, for example, by column chromatography, polyacrylamide gel electrophoresis, or HPLC analysis.

Proteins and polypeptides of the invention are those encoded by the orfs of an elaiophylin biosynthetic gene cluster. In preferred embodiments, the proteins and polypeptides are those comprising SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, or SEQ ID NO:48.

It will also be appreciated that proteins or polypeptides of the invention further include proteins having substantially the same amino acid sequence as the aforementioned preferred proteins and polypeptides. Substantially the same amino acid sequence is defined herein as a sequence with at least about 70%, preferably at least about 80%, and more preferably at least about 90% homology, as determined by the FASTA search method in accordance with Pearson and Lipman (Proc. Natl. Acad. Sci. USA 85, 2444-8 (1988)), including sequences that are at least about 70%, preferably at least about 80%, and more preferably at least about 90% identical.

Such proteins will have the same or similar activities to those of *Streptomyces* sp. NRRL 30748, particularly where there are conservative amino acid substitutions. A conservative amino acid substitution is defined as a change in the amino acid composition by way of changing one or more amino acids of a peptide, polypeptide or protein, or fragment thereof. The substitution is of amino acids with generally similar properties (e.g., acidic, basic, aromatic, size, positively or negatively charged, polarity, non-polarity) such that the substitutions do not substantially alter relevant peptide, polypeptide or protein characteristics (e.g., charge, isoelectric point, affinity, avidity, conformation, solubility) or activity. Typical conservative substitutions are selected within groups of amino acids, which groups include, but are not limited to:

(1) hydrophobic: methionine (M), alanine (A), valine (V), leucine (L), isoleucine (I);

(2) hydrophilic: cysteine (C), serine (S), threonine (T), asparagine (N), glutamine (Q);

(3) acidic: aspartic acid (D), glutamic acid (E);

(4) basic: histidine (H), lysine (K), arginine (R);

(5) aromatic: phenylalanine (F), tyrosine (Y) and tryptophan (W);

(6) residues that influence chain orientation: gly, pro.

The invention also provides methods for fermenting and cultivating *Streptomyces* sp. NRRL 30748. Cultivation may be carried out in a wide variety of liquid culture media. Media which are useful for the elaiophylin production include an assimilable source of carbon, such as dextrin, sucrose, molasses, glycerol, etc.; an assimilable source of nitrogen, such as protein, protein hydrolysate, polypeptides, amino acids, corn steep liquor, etc.; and inorganic anions and cations, such as potassium, sodium, ammonium, calcium, sulfate, carbonate, phosphate, chloride, etc. Trace elements such as boron, molybdenum, copper, etc., are supplied as impurities of other constituents of the media.

According to the invention, an elaiophylin biosynthetic gene cluster of a host can be cloned by generating a library of nucleic acids from the host and identifying the members of that library that contain nucleic acids that encode protein components of the elaiophylin biosynthetic pathway. For example, in one embodiment a nucleic acid probe from a dNDP-4,6-dehydratase gene can be used. In another embodiment, a nucleic acid probe from a polyketide synthase gene can be used. If an entire elaiophylin biosynthetic gene cluster is not present in the identified library member, other library members containing adjacent or overlapping nucleic acids of the host can then be obtained.

Where it is desired to obtain a recombinant plasmid containing all or part of an orf nucleic acids of the invention can be cloned or subcloned by methods disclosed herein or otherwise known in the art. For example, orfs or portions thereof can be obtained by PCR amplification of elaiophylin biosynthetic gene cluster gene sequences using primers designed according to sequences disclosed herein. Of course, alternative methods of obtaining such recombinant clones are well known in the art and may be used.

The invention permits specific changes to be made to individual orfs, either by site directed mutagenesis, deletion, or replacement to modify the elaiophylin polyketide core in ways that would be difficult by chemical methods.

According to the invention, vectors carrying such recombinant DNA may be introduced into an elaiophylin producing strain to disrupt such production, or to provide for production of a related antibiotic. In one embodiment, a vector is provided that carries a portion of an elaiophylin gene cluster orf. Upon homologous recombination of the exogenous orf into the elaiophylin host, the endogenous orf is interrupted, and elaiophylin production is halted. Alternatively, the endogenous elaiophylin gene cluster orf may be interrupted by homologous recombination of a nucleotide sequence into which a mutation or deletion has been introduced. In a preferred embodiment, a polyketide synthase encoding sequence is interrupted.

Similarly, a vector comprising a modified orf can be recombined into an endogenous elaiophylin gene cluster in order that a modified antibiotic is produced. For example, a polyketide synthase module can be recombined that results in addition or inactivation of a ketoreductase domain. (See, e.g., Example 4) In another embodiment, the acetyltransferase (AT) substrate specificity of a polyketide synthase module can be changed. Active site residues are known for ATs of other PKS clusters with differing substrate specificities. (See, Lau et al., 1999, Biochemistry 38:1643-51; Haydock et al., 1995 FEBS Lett., 374:246-48.)

Figure 4:
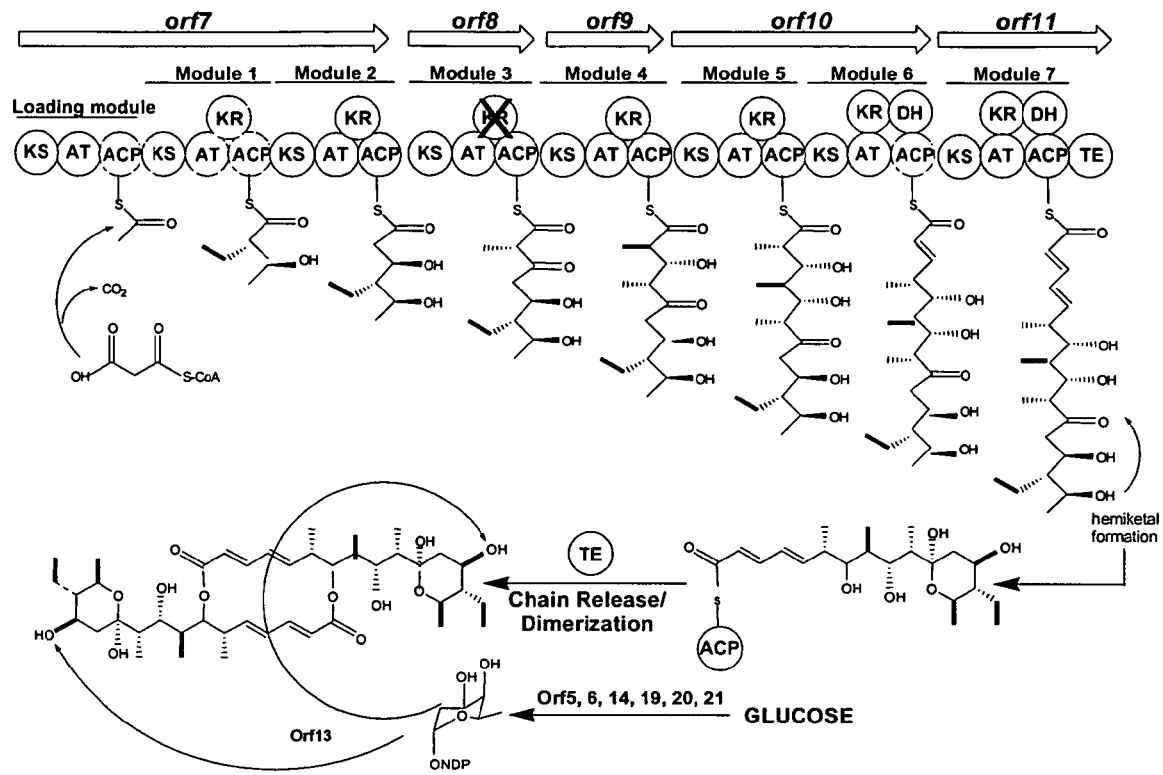
FIG. 4 is a pictorial representation of the biosynthesis of elaiophylin by the novel PKS described herein. Functional domains: KS=extender module ketosynthase; AT=acyltransferase; ACP=acyl-carrier protein; KR=ketoreductase; DH=dehydratase; TE=thioreductase.

In another embodiment of the invention, novel cyclic polyketides can be created by incorporation of the thioesterase (TE) domain of orf11 or all of orf11 into a heterologous polyketide biosynthetic gene cluster. The novel polyketide synthase encoded by orf11 (SEQ ID NOs:21 and 22) of *Streptomyces* sp. NRRL 30748 includes a TE domain that catalyzes a polyketide chain termination reaction wherein a cyclic polyketide with $C_2$ symmetry is produced from a linear polyketide precursor. (See, FIG. 4). The TE of orf11 can accordingly be used for chain termination and cyclization of polyketides made by other organisms. The TE domain of orf11 is recognizable by its homology with other TE domains, which are approx 230 amino acids in size, and have an invariant G×S×G domain as well as a GdH domain at the C-terminus of the domain. (See, e.g., Donadio et al., 1992, Gene 111:51-60; NCBI Conserved Domain Database, CD: COG3319.1, COG3319: Thioesterase domains of type I polyketide synthases or non-ribosomal peptide synthetases.)

Further, the invention provides a method of accomplishing such gene transfers in order to produce such recombinants. According to the invention, a portion of orf8 was subcloned into a plasmid that was propagated in an *E. coli* host. In order to facilitate transfer from *E. coli* into *Streptomyces* and selection in *Streptomyces*, an oriT/apramycin resistance cassette was incorporated into the plasmid. In a similar manner, all or part of any orf can be cloned, optionally modified, and recombined into the elaiophylin biosynthetic cluster of *Streptomyces* sp. NRRL 30748 or other organism.

By providing the genes involved in elaiophylin production and a means for modifying the genes in a host, the invention enables disruption of elaiophylin production in a host organism. Such disruption is particularly useful for the production and isolation of other secondary metabolites that are coproduced with elaiophylin and which may be difficult to separate from elaiophylin. For example, in the *Streptomyces* strain particularly disclosed herein, elaiophylin is coproduced with nigericin and meridamycin, and the separation of meridamycin from elaiophylin is problematic. To simplify meridamycin purification from fermentation broths of *Streptomyces* sp. NRRL 30748, elaiophylin production was eliminated via a gene disruption of one of the PKSs involved in elaiophylin biosynthesis. In other circumstances, where separation of a desired biologically active compound from elaiophylin may not be difficult, it can nevertheless be cost effective to disrupt elaiophylin production.

EXAMPLES

The following examples further illustrate the invention, but should not be construed to limit the scope of the invention in any way. It is to be understood and expected that variations in the principles of the invention herein disclosed may be made by one skilled in the art and it is intended that such modifications are to be included within the scope of the present invention.

Detailed descriptions of conventional methods, such as those employed in the construction of vectors and plasmids, the insertion of genes encoding polypeptides into such vectors and plasmids, the introduction of plasmids into host cells, and the expression and determination thereof of genes and gene products can be obtained from numerous publications, including Sambrook, J et al., Molecular Cloning: A Laboratory Manual, $2^{nd}$ ed., Cold Spring Harbor Laboratory Press (1989). All references mentioned herein are incorporated in their entirety.

Example 1

DNA Isolation

DNA isolation from *Streptomyces* sp. NRRL 30748—Isolation of genomic DNA was based on a modification of that described by Hopwood et al. (1985). Approximately 1 ml of a frozen mycelia glycerol stock was inoculated into a 25 mm×150 mm seed tube containing 10 ml of MYM media (4 g/l maltose, 4 g/l yeast extract, 10 g/l malt extract, pH 7.0) and 2-6 mm glass beads. The culture was grown at 28° C. and 200 rpm for 5 days. The cells were then pelleted by centrifugation at 3000×g for 10 min. The supernatant was discarded and the pellet was suspended in 300 µl of $T_{50}$-$E_{20}$ (Tris 50 mM-EDTA-20 mM) containing 5 mg/ml lysozyme and 0.1 mg/ml RNase and incubated at 37° C. for 1 hr with gentle mixing every 15 min. 50 µl of 10% SDS was then added and the sample was thoroughly mixed. Next 85 µl of 5 mM NaCl was added and the sample was again thoroughly mixed. The sample was then extracted with 400 µl phenol/chloroform/isoamyl alcohol (50/49/1). After vortexing the sample thoroughly, it was centrifuged at 10,000×g for 20 min at room temperature. Following centrifugation, the aqueous phase was removed and placed in a new microcentrifuge tube. An equal volume of room temperature isopropanol was added to the sample and thoroughly mixed by inversion. The sample was let stand at room temperature for 5 min. The sample was then centrifuged at 12,000×g for 30 min at 4° C. The isopropanol was carefully poured out of the tube and the DNA pellet rinsed with 1 ml of cold 70% ethanol. After being let stand in ice for 5 min the 70% ethanol was poured out of the tube and the DNA was air dried for 10 minutes. The DNA was dissolved in 0.3 ml of sterile water. DNA integrity and concentration was estimated by agarose gel electrophoresis.

DNA isolation from *Escherichia coli*—Plasmid DNA and small-scale cosmid DNA preparations were performed using the Qiaprep Spin MiniPrep Kit (Qiagen Inc, Valecia, Calif., USA) according to the manufacturer's specifications.

Cosmid DNA was isolated using the Qiagen Large Construct Kit (Qiagen Inc, Valecia, Calif., USA) according to the manufacturer's specifications.

Example 2

*Streptomyces* sp. NRRL 30748 Genomic Library Construction

A *Streptomyces* sp. NRRL 30748 genomic library was constructed using the pWEB Cosmid Cloning Kit (Epicentre Technologies, Madison, Wis., USA) according to the manufacturers specifications. The general library construction protocol was as follows. 10 µg of genomic DNA was randomly sheared by passing the genomic DNA through a Hamilton HPLC/GC syringe into 30-45 kb fragments. Following shearing, the fragmented DNA was end-repaired to produce blunt-ended fragments using the end-repair enzyme mix contained in the kit. The sheared and end-repaired DNA was then separated on a 1% low melting point agarose gel using linear T7 DNA (~40 Kb) to serve as a molecular weight marker. Genomic DNA approximately equal in size to the T7 DNA was cut from the gel and the DNA was eluted from the agarose. The purified DNA was then ligated into the pWEB vector. Following ligation, the ligated insert DNA was packaged into lambda phage particles using the MaxPlax Lambda Packaging Extracts provided with the pWEB cosmid cloning kit. The phage extract was then titered to determine the colony-forming units per milliliter. Upon determining the titer of the phage extract an appropriate amount of extract was used to infect *E. coli* EPI100 host cells and the infected cells were plated on Difco Luria agar plates containing 50 µg/ml of kanamycin to give a cell density of approximately 200 colonies per plate.

Example 3

Library Screening

Elaiophylin contains the 2,6-deoxysugar L-oliose which is attached to the polyketide core via an ether linkage. As it was likely that a dNDP-D-glucose-4,6-dehydratase (DH) catalyzed a step in the biosynthesis of this sugar, and that the gene encoding the enzyme would be clustered with other genes required to produce elaiophylin, a DH probe was generated by PCR using primers dehydra1 (5'-CSGGSGSSGCSGGST-TCATSGG-3'; SEQ ID NO:50) and dehydra2 (5'-GGG-WRCTGGYRSGGSCCGTAGTTG-3'; SEQ ID NO:51) (Decker et al. (1996)) to amplify a DH gene fragment from the genomic DNA of *Streptomyces* sp. NRRL 30748. PCR was conducted using JumpStart REDTaq Ready Mix PCR Reaction Mix (Sigma-Aldrich Corp, St. Louis, Mo.) according to the manufacturer's specifications. The primers were used at a final concentration of 0.5 µM. The PCR was performed on a Biometra T gradient thermocycler. The starting denaturing temperature was 96° C. for 4 min. The following 30 cycles were as follows: denaturing temperature 96° C. (45 sec), annealing temperature 66° C. (45 sec), extension temperature 72° C. (3 min). At the end, the final extension temperature was 72° C. for 10 min. The ~500 bp amplicon was cloned into pCR2.1 using the TOPO TA Cloning Kit (Invitrogen Corp, Carlsbad, Calif.) following the manufacturers recommendations. A portion (2.5 µl) of the cloning reaction was used to transform *E. coli* TOP10 cells (Invitrogen Corp, Carlsbad, Calif.) which were subsequently plated on Difco Luria Agar containing 50 µg/ml kanamycin, 40 µg/ml X-gal and 0.2 mM IPTG to facilitate blue/white screening of recombinant clones. Ten white colonies were picked and their plasmid DNA isolated. Sequencing of these clones revealed a single DH gene fragment. The DH fragment containing clones are designated pBWA33.

The *Streptomyces* sp. NRRL 30748 genomic library was screened by colony hybridization using the DH fragment cloned in pBWA33. Recombinant colony DNA of the genomic library cosmid clones were transferred to Nytran SuPerCharge nylon membrane discs (Schleicher & Schuell BioScience, Inc., Keene, N.H.) as described by Sambrook and Russell (2001). The DH probe was prepared using PCR and primers dehydra1 and dehydra2 to amplify the insert of pBWA33. The amplified 530 bp PCR product was separated by agarose gel electrophoresis and labeled with [$\alpha$-$^{32}$P]dCTP (3000 Ci/mmol Amersham Bioscience, Piscataway, N.J.) using the Megaprime DNA Labeling kit according to the manufacturer's specifications (Amersham Bioscience, Piscataway, N.J.).

The nylon membrane on which the DNA samples were immobilized was washed in 6×SSC, then placed in a hybridization bottle with prewarmed (65° C.) prehybridization solution (6×SSC/5×Denhardt's reagent/0.5% (w/v) SDS and 100 µg/ml of denatured, sheared herring sperm DNA) and "prehybridized" for 2 h. The denatured probe was then added, and hybridization proceeded overnight at 65° C. The following day the membrane was washed once with prewarmed (65° C.) 2×SSC/0.1% SDS (Wash Solution 1) for 1 h and once with prewarmed (65° C.) 1×SSC/0.1% SDS (Wash Solution 2) for 1 h. The nylon membrane was then wrapped in Saran wrap and exposed to Kodak X-omat AR film for 4 h. The exposed films were developed using a Kodak X-omat 2000A processor.

Five colonies were identified: pBB6, pBB15, pBB33, pBB34, pBB44. These colonies were picked and grown in Difco Luria Broth containing 50 µg/ml kanamycin. The cosmid DNA was purified from the cultures and cut with NcoI. The restriction digests were separated by agarose gel electrophoresis and the DNA was transferred to a Nytran SuPerCharge nylon membrane as described by Sambrook and Russell (2001). To identify cosmids that contained polyketide-associated DH genes the membrane was next probed with a polyketide-specific probe (provided by Dr. Min He). The probe was generated by amplifying a PKS fragment using the following primers: ACP sense (5'-GASCTSGG-SYTSGACTCSCTM-3'; SEQ ID NO:52); KS antisense (5'-SGASGARCASGCSGTGTCSAC-3'; SEQ ID NO:53). The amplification was performed using Streptomyces sp. NRRL 30748 genomic DNA template and PCR conditions identical to those described above. These primers were designed to amplify a fragment of PKS genes spanning the ACP and KS domains of adjacent modules. The amplified product was examined by agarose gel electrophoresis and the amplified product was excised from the gel and eluted from the agarose. The purified DNA was labeled and used to probe the nylon membrane as previously described. Four cosmids hybridized to the ACP-KS probe: pBB6, pBB15, pBB33, pBB34.

Example 4

Figure 3:
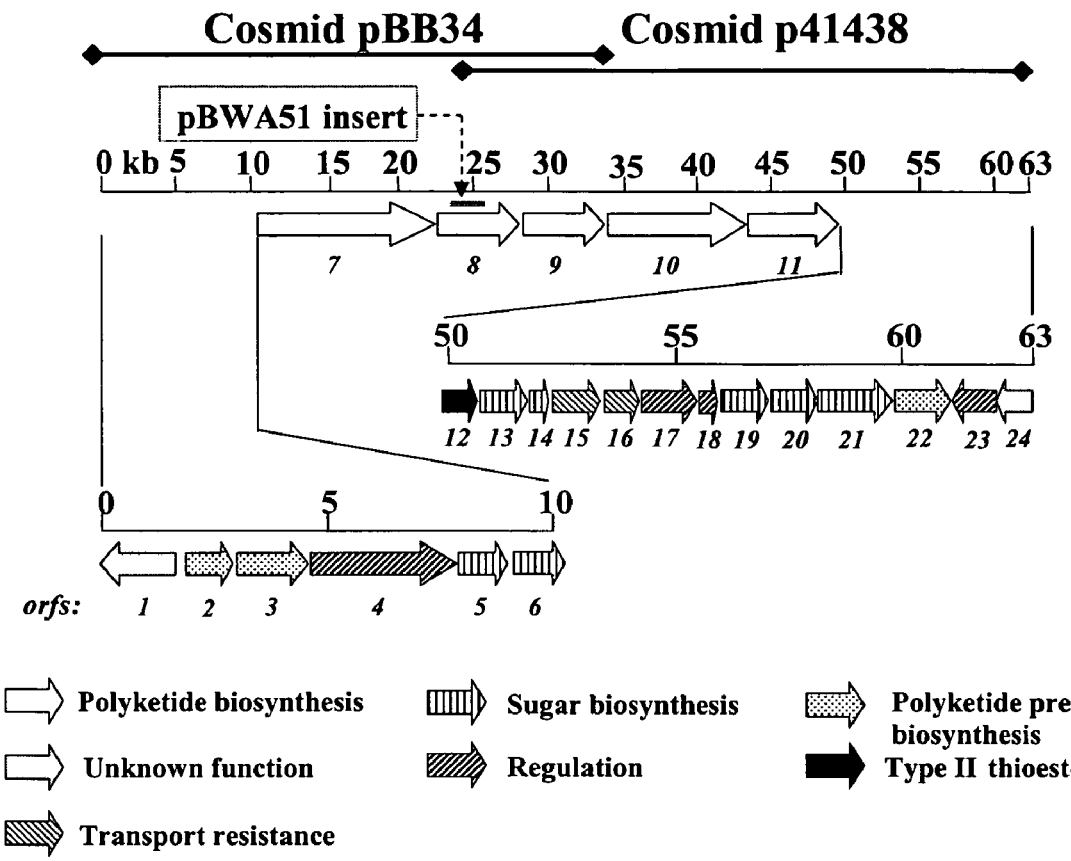
FIG. 3 shows the organization of the elaiophylin biosynthetic gene cluster. Orf designations correspond to Table 1. A DNA segment used to interrupt elaiophylin synthesis is depicted above orf8.

Isolation and characterization of complete elaiophylin biosynthetic cluster.—Sequence analysis of pBB34 indicated that the 5 prime portion of the elaiophylin cluster had been cloned. To identify the 3 prime portion of the cluster a probe was generated from the 3 prime end of pBB34 using the following primers: BB34pr1FWD (5'-GCGGTGAGTTGCT-GATTG-3'; SEQ ID NO:54) and BB34pr1REV (5'-GAC-CTGGACGTGGATGAC-3'; SEQ ID NO:55). PCR amplification using these primers and pBB34 DNA as template was performed as described above. The 169 bp PCR product was used to screen the Streptomyces sp. NRRL 30748 genomic library as described above. Two cosmid clones were identified (p41438 and p41439) and the cosmid DNA was isolated. End sequencing revealed that p41438 overlapped pBB34 by 10,790 bp. Cosmid p41438 was subsequently completely sequenced. Analysis of the full sequence of p41438 indicated that the cosmid did indeed overlap with pBB34. The total DNA sequence contained in pBB34 and p41438 was 63.2 kb. Analysis of the gene encoded by the 63.2 kb of DNA indicated that all of the genes necessary for the biosynthesis of elaiophylin had been cloned. The organization of the elaiophylin gene cluster is depicted in FIG. 3. The functions of proteins encoded by the open reading frames, numbered 1-24 as in Table 1, were identified by comparison to GenBank sequence deposits.

The AT domain substrate specificity for each PKS module (FIG. 4, modules 1-7 of PKSs encoded by orfs 7-11) was determined by comparison to active site residues of ATs of other PKS clusters with known substrate specificity. The predicted substrate specificity (Table 2) corresponds to the structure of elaiophylin.

TABLE 2

Substrate specificity of PKS modules

| Module | AT active site motif residues | AT predicted substrate specificity |
|---|---|---|
| AT-Loading | QQGHSVGRFHNHV | Malonate |
| AT-Module 1 | QQGHSQGRGHTNV | Ethylmalonate |
| AT-Module 2 | QQGHSVGRFHNHV | Malonate |
| AT-Module 3 | QQGHSQGRSHHAV | Methylmalonate |
| AT-Module 4 | QQGHSQGRSHTNV | Methylmalonate |
| AT-Module 5 | QQGHSQGRSHTNV | Methylmalonate |
| AT-Module 6 | QQGHSVGRFHNHV | Malonate |
| AT-Module 7 | QQGHSVGRAHNHV | Malonate |

Based on the structure of elaiophylin, a KR domain was not expected in PKS module 3, as the ketone group introduced by the chain extension catalyzed by module 2 is required for hemiketal formation. A comparison of the amino acid sequence of a putative KR domain in PKS module 3 (KR3) to KR domains of other proteins is provided in Table 3. Only the characteristic Rossmann fold and the catalytic residues are shown, along with the spacing of the catalytic residues. Examination of the elaiophylin KR3 amino acid sequence indicates a N to S substitution at the last catalytic residue. Other catalytic residues are identical with similar spacings. The elaiophylin Rossmann fold sequence compares favorably with the corresponding sequences of other KR domains.

TABLE 3

Comparison of KR domains

| | Rossman fold sequence | catalytic residues (amino acid spacing) | | | | | | | | |
|---|---|---|---|---|---|---|---|---|---|---|
| Amphotericin KR15 | GTVLVTGGTG | (101) | K | (23) | S | (12) | Y | (3) | N |
| Nystatin KR15 | GTVLLTGGTG | (101) | K | (23) | S | (12) | Y | (3) | N |
| Amphotericin KR3 | GTVLITGGTG | (101) | K | (23) | S | (12) | Y | (3) | N |
| Amphotericin KR5 | GTVLVTGGTG | (100) | K | (23) | S | (12) | Y | (3) | N |
| Pimaricin KR1 | GTVLVTGGTG | (100) | K | (23) | S | (12) | Y | (3) | N |
| Nystatin KR12 | GTVLITGGTG | (100) | K | (23) | S | (12) | Y | (3) | N |

TABLE 3-continued

Comparison of KR domains

| | Rossman fold sequence | catalytic residues (amino acid spacing) | | | | | | | |
|---|---|---|---|---|---|---|---|---|---|
| Pimaricin KR8 | GTVLVTGGTG | (100) | K | (23) | S | (12) | Y | (3) | N |
| Eyrthromycin KR1 | GTVLVTGGTG | (100) | K | (23) | S | (12) | Y | (3) | N |
| Elaiophylin KR3 | GTVLITGGTG | (103) | K | (25) | S | (12) | Y | (3) | S |

Example 5

Disruption of Elaiophylin Biosynthesis pBB34 DNA was digested with NcoI (New England Biolabs) and subcloned into NcoI digested pUC120. The resulting clones were end sequenced using the M13 forward and M13 reverse sequencing primers. One clone, p34983, contained a 1.7 kb insert whose sequence was similar to several type I PKSs (as determined by BlastX analysis).

Figure 5:
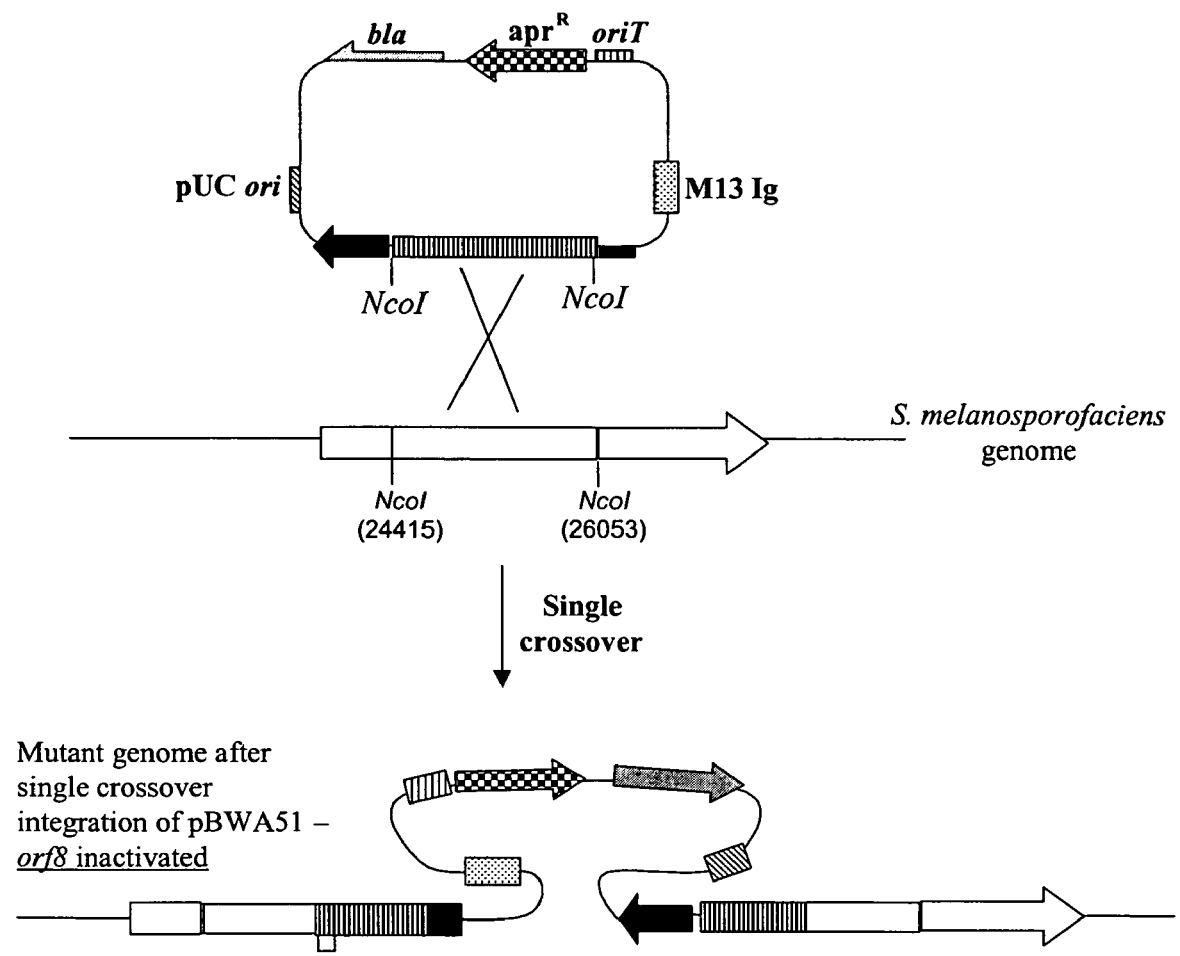
FIG. 5 is a diagrammatic illustration of the inactivation of the elaiophylin cluster via disruption of the polyketide synthase (PKS) encoded by orf8. pUC ori=pUC plasmid origin of replication; bla=ampicillin resistance; apr$^R$=ampramycin resistance; oriT=RK2 plasmid origin of transfer; M13 Ig=M13 phage intergenic region; lacZ=β-galactosidase.

The p34983 plasmid was used to disrupt elaiophylin biosynthesis. First, an apramycin resistance gene/oriT cassette was cloned into the vector backbone of p34983 yielding pBWA51. The oriT sequence (from the RK2 plasmid) allows conjugal transfer of pBWA51 from E. coli to Streptomyces sp. NRRL 30748, whereas the apramycin resistance gene facilitates the selection of streptomycete exconjugants. Streptomycetes are not sensitive to ampicillin (the selectable marker present in pUC120).

pBWA51 was used to transform E. coli ET12567/pUZ8002. pBWA51 could then be transferred from E. coli to Streptomyces sp. NRRL 30748 via intergeneric conjugation. The conjugation method was identical to that described by Kieser et al. (2000) except the conjugation mixture of E. coli and Streptomyces sp. NRRL 30748 spores was plated on R6 media. The conjugation plates were incubated at 37° C. for 16 hrs and then were overlaid with 1 mL of water containing 0.5 mg/ml apramycin and 0.5 mg/ml nalidixic acid. The plates were then incubated at 30° C. for 7 days. Two Streptomyces sp. NRRL 30748 exconjugants were isolated. Because the pBWA51 plasmid does not contain a replication origin that is functional in streptomycetes, both apramycin resistant exconjugants were expected to be the result of a single crossover integration of pBWA51 into the putative elaiophylin PKS gene cluster at a site containing DNA homologous to the 1.7 kb NcoI fragment contained in pBWA51 (FIG. 5).

Both exconjugants were fermented under elaiophylin producing conditions. Several loop fulls of the wild type and mutant cultures were inoculated into seed tubes containing two glass beads and 10 ml of seed media (WSB4YESS: 5 g/l WGE80M wheat hydrolysate (DMV International), SE50MAF soy hydrolysate (DMV International), 3 g/l yeast extract (Difco), 20 g/l soluble starch (Difco) pH 7.0) and grown at 26° C./200 rpm for 2-3 days. 0.25 ml of these cultures were used to inoculated a second stage seed which was 25 ml of WSB4YESS in a 250 ml flask. The second stage seed was grown for 48 hrs and then 1 ml was used to inoculate 25 ml of 14-10 fermentation media (dextrose 10 g/l, soy flour 15 g/l, NaCl 2 g/l, $CaCO_3$ 1 g/l) in a 250 ml flask. Each culture was fermented at 26° C./200 rpm in triplicate. 1 ml samples were taken from each fermentation on day 5 and 7.

Figure 6:
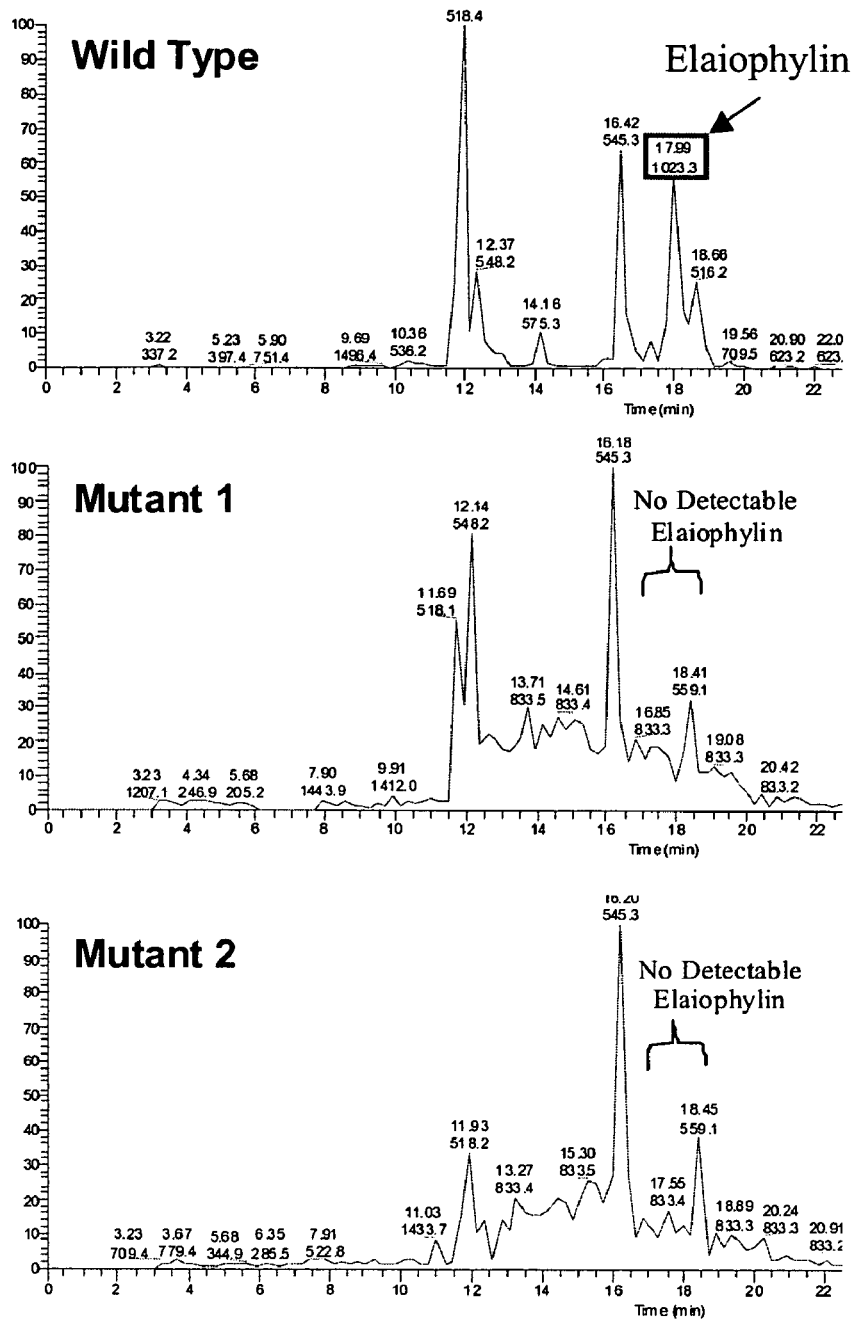
FIG. 6 provides LC/MS analysis of fermentation broths of two orf8 disruption mutants compared to the wild type elaiophylin producer.

Extraction of the samples was performed as follows. 2 ml of 95/5 ethyl acetate/methanol was added to 1 ml of fermentation sample and vortexed for 5 min. The sample was then centrifuged at 4,000 rpm for 25 min. After the spin, the liquid in the tube had separated into two phases. 0.75 ml was carefully removed from the upper phase and put in a new tube. An equal volume of methanol was then added to the 0.75 ml sample. Extracts processed this way were analyzed by LC/MS using the following parameters. Samples were analyzed on an Agilent 1100 system coupled with a Thermo-Finnigan LCQ Deca mass spectrometer. The samples were chromatographed using 5 to 95% B in A over 25 minutes with a flow rate of 0.8 ml/min on a YMC ODS-A column (4.5×100 mm) (A=$H_2O$/0.025% formic acid; B=MeCN/0.025% formic acid). Ionization was achieved by electrospray ionization. Analysis of the fermentation broths by LC/MS indicated that no elaiophylin was produced by the two single crossover mutants (FIG. 6). Additionally, disruption of elaiophylin production did not have any significant effect on meridamycin titers. These results indicated that the DNA contained in cosmid pBB34 is involved in elaiophylin biosynthesis.

I claim:

1. A strain of *Streptomyces* in which a polyketide synthase gene encoding a polypeptide having the amino acid sequence of SEQ ID NO:14 within an elaiophylin gene cluster is disrupted by the recombinant substitution of said polyketide synthase gene with a nucleic acid sequence comprising a modified version of said polyketide synthase gene encoding a disrupted variant of the amino acid sequence of SEQ ID NO:14, whereby the production of elaiophylin by said *Streptomyces* strain is eliminated.

2. A method of improving the recovery of meridamycin coproduced with elaiophylin by a strain of *Streptomyces*, the method comprising:
   culturing a strain of *Streptomyces* in a culture medium under conditions suitable for expression of meridamycin and
   recovering meridamycin from the culture medium,
   wherein a polyketide synthase gene of the elaiophylin gene cluster of said *Streptomyces* strain that encodes the amino acid sequence of SEQ ID NO:14 is disrupted, such that production of elaiophylin by said *Streptomyces* strain is eliminated.

3. A method of producing the *Streptomyces* strain of claim 1 wherein a nucleic acid encoding a polypeptide having the amino acid sequence of SEQ ID NO:14 is substituted by a nucleic acid sequence comprising a modified version of said polyketide synthase gene that encodes a disrupted amino acid sequence of SEQ ID NO:14, the method comprising:
   providing a host cell containing a plasmid which comprises said substituting nucleic acid sequence and a selectable marker wherein said plasmid allows conjugal transfer of said substituting nucleic acid into a *Streptomyces* spore and wherein said spore can be selected based on the selectable marker, contacting the host cell with spores of the *Streptomyces*, and selecting the exconjugants.

* * * * *

UNITED STATES PATENT AND TRADEMARK OFFICE
CERTIFICATE OF CORRECTION

PATENT NO.        : 7,595,187 B2
APPLICATION NO.   : 11/274683
DATED             : September 29, 2009
INVENTOR(S)       : Bradley A. Haltli It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 523 days.

Signed and Sealed this

Twenty-eighth Day of September, 2010

David J. Kappos
*Director of the United States Patent and Trademark Office*